US012060425B2

(12) United States Patent
Wu et al.

(10) Patent No.: US 12,060,425 B2
(45) Date of Patent: Aug. 13, 2024

(54) HIGH AFFINITY ANTIBODIES TO PD-1 AND LAG-3 AND BISPECIFIC BINDING PROTEINS MADE THEREFROM

(71) Applicant: SHANGHAI EPIMAB BIOTHERAPEUTICS CO., LTD., Shanghai (CN)

(72) Inventors: Xuan Wu, Shanghai (CN); Shiyong Gong, Shanghai (CN); Chengbin Wu, Shanghai (CN)

(73) Assignee: SHANGHAI EPIMAB BIOTHERAPEUTICS CO., LTD., Shanghai (CN)

( * ) Notice: Subject to any disclaimer, the term of this patent is extended or adjusted under 35 U.S.C. 154(b) by 643 days.

(21) Appl. No.: 17/051,834

(22) PCT Filed: Apr. 30, 2019

(86) PCT No.: PCT/CN2019/085164
§ 371 (c)(1),
(2) Date: Oct. 30, 2020

(87) PCT Pub. No.: WO2019/210848
PCT Pub. Date: Nov. 7, 2019

(65) Prior Publication Data
US 2021/0188980 A1 Jun. 24, 2021

(30) Foreign Application Priority Data
May 3, 2018 (WO) ................ PCT/CN2018/085468

(51) Int. Cl.
*C07K 16/28* (2006.01)
*A61K 39/00* (2006.01)

(52) U.S. Cl.
CPC .... *C07K 16/2818* (2013.01); *A61K 2039/505* (2013.01); *C07K 2317/31* (2013.01); *C07K 2317/515* (2013.01); *C07K 2317/522* (2013.01); *C07K 2317/565* (2013.01)

(58) Field of Classification Search
CPC ............................................... C07K 16/2818
See application file for complete search history.

(56) References Cited

U.S. PATENT DOCUMENTS

| | | | |
|---|---|---|---|
| 5,006,309 A | 4/1991 | Khalil et al. |
| 5,063,081 A | 11/1991 | Cozzette et al. |
| 5,089,424 A | 2/1992 | Khalil et al. |
| 5,294,404 A | 3/1994 | Grandone et al. |
| 5,714,350 A | 2/1998 | Co et al. |
| 5,955,264 A | 9/1999 | Seed et al. |
| 6,350,861 B1 | 2/2002 | Co et al. |
| 6,579,676 B1 | 6/2003 | Seed et al. |
| 6,984,488 B1 | 1/2006 | Gershoni et al. |
| 7,419,821 B2 | 9/2008 | Davis et al. |
| 7,498,420 B2 | 3/2009 | Michaud et al. |
| 7,682,833 B2 | 3/2010 | Miller et al. |
| 7,838,638 B2 | 11/2010 | Allan et al. |
| 7,854,930 B2 | 12/2010 | Goetsch et al. |
| 8,628,773 B2 | 1/2014 | Guo |
| 8,722,859 B2 | 5/2014 | Miller et al. |
| 8,802,375 B2 | 8/2014 | Sampson et al. |
| 2002/0004587 A1 | 1/2002 | Miller et al. |
| 2002/0137134 A1 | 9/2002 | Gerncross |
| 2004/0018577 A1 | 1/2004 | Emerson Campbell et al. |
| 2004/0018590 A1 | 1/2004 | Gerncross |
| 2005/0042664 A1 | 2/2005 | Wu et al. |
| 2005/0074821 A1 | 4/2005 | Wild et al. |
| 2005/0100546 A1 | 5/2005 | Jakobovits et al. |
| 2005/0180972 A1 | 8/2005 | Wahl et al. |
| 2005/0250185 A1 | 11/2005 | Murphy et al. |
| 2006/0160164 A1 | 7/2006 | Miller et al. |
| 2006/0206947 A1 | 9/2006 | Scallon et al. |
| 2006/0235208 A1 | 10/2006 | Lazar et al. |
| 2007/0065912 A1 | 3/2007 | Carson et al. |
| 2007/0071675 A1 | 3/2007 | Wu et al. |
| 2008/0269467 A1 | 10/2008 | Allen et al. |
| 2009/0055944 A1 | 2/2009 | Korman et al. |
| 2009/0155275 A1 | 6/2009 | Wu et al. |

(Continued)

FOREIGN PATENT DOCUMENTS

| | | | |
|---|---|---|---|
| CN | 107840887 A | 3/2018 |
| CN | 107614013 A | 1/2019 |

(Continued)

OTHER PUBLICATIONS

Office Action and Search Report dated May 4, 2022, issued in RU Application No. 2020139447 (13 pages).
International Patent Application No. PCT/CN2019/085164, filed Apr. 30, 2019, by Shanghai EpimAb Biotherapeutics Ltd.: International Search Report and Written Opinion, mailed Aug. 8, 2019 (14 pages).
Alam et al.+B128:B250, (2016) "Inflammatory Process in Alzheimer's and Parkinson's Diseases: Central Role of Cytokines," Curr. Pharm. Design, 22(5): 541-548.
Almagro et al., (2008) "Humanization of antibodies," *Frontiers in Bioscience-Landmark*. 13(5); 1619-1633.
Alsaab et al., (2017) "PD-I and PD-LI Checkpoint Signaling Inhibition for Cancer Immunotherapy: Mechanism, Combinations, and Clinical Outcome," *Frontiers in Pharmacology*, 8: Article 561 (doi: 10.3389/fphar.2017.00561).

(Continued)

*Primary Examiner* — Gregory S Emch
*Assistant Examiner* — Ashley H. Gao
(74) *Attorney, Agent, or Firm* — FINNEGAN, HENDERSON, FARABOW, GARRETT & DUNNER, LLP

(57) ABSTRACT

High-affinity antibodies recognizing Programmed Death Ligand-1 (PD-1) and Lymphocyte Activation Gene 3 protein (LAG-3) are disclosed. Binding sites from humanized anti-PD-1 and anti-LAG-3 antibodies are incorporated into a Fabs-in-Tandem Immunoglobulin format without significant loss of binding affinity, and the resultant bispecific, multi-valent binding proteins are able to bind to both PD-1 and LAG-3 simultaneously. Such bispecific FIT-Ig binding proteins are useful for treatment of cancer.

21 Claims, 13 Drawing Sheets

Specification includes a Sequence Listing.

(56) References Cited

U.S. PATENT DOCUMENTS

| | | |
|---|---|---|
| 2009/0162360 A1 | 6/2009 | Klein et al. |
| 2009/0226443 A1 | 9/2009 | Filvaroff et al. |
| 2009/0252683 A1 | 10/2009 | Kischel et al. |
| 2009/0311253 A1 | 12/2009 | Ghayur et al. |
| 2010/0076178 A1 | 3/2010 | Ghayur et al. |
| 2010/0260668 A1 | 10/2010 | Ghayur et al. |
| 2012/0301400 A1 | 11/2012 | Williams et al. |
| 2012/0321626 A1 | 12/2012 | Zhou |
| 2013/0058937 A1 | 3/2013 | Auer et al. |
| 2013/0066054 A1 | 3/2013 | Humphreys et al. |
| 2013/0078249 A1 | 3/2013 | Ast et al. |
| 2014/0056897 A1 | 2/2014 | Buelow et al. |
| 2014/0194599 A1 | 7/2014 | Pass et al. |
| 2015/0093387 A1 | 4/2015 | Wu et al. |
| 2016/0017045 A1 | 1/2016 | Liu et al. |
| 2016/0120999 A1 | 5/2016 | Shen et al. |
| 2016/0289341 A1 | 10/2016 | Wu |
| 2017/0137517 A1 | 5/2017 | Bowman et al. |
| 2017/0247456 A1 | 8/2017 | Freeman et al. |
| 2017/0327590 A1* | 11/2017 | Lowy ............... A61P 35/04 |
| 2017/0335007 A1 | 11/2017 | Chen et al. |
| 2018/0002423 A1* | 1/2018 | Wang ............... C07K 16/2827 |
| 2018/0194845 A1 | 7/2018 | De Goeij et al. |
| 2019/0085075 A1 | 3/2019 | La Motte-Mohs et al. |
| 2019/0256602 A1 | 8/2019 | Campbell et al. |
| 2019/0345252 A1 | 11/2019 | Kinsella et al. |
| 2021/0040197 A1 | 2/2021 | Tong et al. |

FOREIGN PATENT DOCUMENTS

| | | |
|---|---|---|
| EP | 1 176 195 | 1/2002 |
| EP | 2 443 154 B1 | 12/2013 |
| EP | 2 654 789 B1 | 5/2018 |
| JP | 2003-531588 A | 10/2003 |
| JP | 2007-501013 A | 1/2007 |
| JP | 2010-535032 A | 11/2010 |
| JP | 2012-522527 | 9/2012 |
| JP | 2012-530088 A | 11/2012 |
| JP | 2013-538204 | 10/2013 |
| JP | 2014-504860 A | 2/2014 |
| JP | 2014-526895 A | 10/2014 |
| JP | 2015-505319 A | 2/2015 |
| JP | 2017-506215 A | 3/2017 |
| JP | 2017-516489 A | 6/2017 |
| KR | 10-2015-0014551 | 2/2015 |
| RU | 2339696 C2 | 11/2008 |
| RU | 2433831 C2 | 11/2011 |
| RU | 2011121419 A | 12/2012 |
| RU | 2494107 C2 | 9/2013 |
| RU | 2012121189 A | 11/2013 |
| TW | 201613962 A | 4/2016 |
| TW | 201702265 A | 1/2017 |
| TW | 201803906 A | 2/2018 |
| WO | WO 1999/054342 A1 | 10/1999 |
| WO | WO 2001/077342 A1 | 10/2001 |
| WO | WO 2002/072636 A2 | 9/2002 |
| WO | WO 2003/016466 A2 | 2/2003 |
| WO | WO 2003/035835 A2 | 5/2003 |
| WO | WO 2005/016382 A1 | 2/2005 |
| WO | WO 2005/095457 A2 | 10/2005 |
| WO | WO 2005/117973 A2 | 12/2005 |
| WO | WO 2006/121168 A1 | 11/2006 |
| WO | WO 2009/018386 A1 | 2/2009 |
| WO | WO 2009/080253 A1 | 7/2009 |
| WO | WO 2009/095478 A1 | 8/2009 |
| WO | WO 2010/000721 A1 | 1/2010 |
| WO | WO 2010/112193 A1 | 10/2010 |
| WO | WO 2010/115589 A1 | 10/2010 |
| WO | WO 2010/145792 A1 | 12/2010 |
| WO | WO 2011/117330 A1 | 9/2011 |
| WO | WO 2012/025525 A1 | 3/2012 |
| WO | WO2012/085132 A1 | 6/2012 |
| WO | WO 2012/121775 A1 | 9/2012 |
| WO | WO 2013/026831 A1 | 2/2013 |
| WO | WO 2013/104804 A2 | 7/2013 |
| WO | WO 2013/150043 A1 | 10/2013 |
| WO | WO 2014/083178 A1 | 6/2014 |
| WO | WO 2014/144357 A1 | 9/2014 |
| WO | WO 2014/161845 A1 | 10/2014 |
| WO | WO 2014/167022 A1 | 10/2014 |
| WO | WO 2015/016559 A1 | 2/2015 |
| WO | WO 2015/087279 A1 | 6/2015 |
| WO | WO 2015/103072 A1 | 7/2015 |
| WO | WO 2015/134411 A1 | 9/2015 |
| WO | WO 2015/138920 A1 | 9/2015 |
| WO | WO 2015/175375 A1 | 11/2015 |
| WO | WO 2015/176033 | 11/2015 |
| WO | WO 2015/193352 A1 | 12/2015 |
| WO | WO 2016/020309 A1 | 2/2016 |
| WO | WO 2016/028672 A1 | 2/2016 |
| WO | WO 2016/044224 A1 | 3/2016 |
| WO | WO 2016/079081 A1 | 5/2016 |
| WO | WO 2017/019846 A1 | 2/2017 |
| WO | WO 2017/024515 A1 | 2/2017 |
| WO | WO 2017/089334 A1 | 6/2017 |
| WO | WO 2017/133540 A1 | 8/2017 |
| WO | WO2017/136820 | 8/2017 |
| WO | WO 2017/220569 A1 | 12/2017 |
| WO | WO 2018/069500 A2 | 4/2018 |
| WO | WO 2019/027935 A1 | 2/2019 |
| WO | WO 2019/068907 A1 | 4/2019 |
| WO | WO 2019/096900 A1 | 5/2019 |

OTHER PUBLICATIONS

Aoki et al., (2005) "Endothelial Progenitor Cell Capture by Stents Coated With Antibody Against CD34," *J. Am. Coll. Cardiol.*, 45(10): 1574-1579.

Apantaku et al., (2000) "Breast cancer diagnosis and screening," *Am Fam Physician*. 62(3):596-602.

Arancio et al., (2004) "RAGE potentiates Aβ-induced perturbation of neuronal function in transgenic mice," *EMBO J.*, 23: 4096-4105.

Arndt et al., (1999) "A Bispecific Diabody That Mediates Natural Killer Cell Cytotoxicity Against Xenotransplantated Human Hodgkin's Tumors," *Blood*, 94: 2562-2568.

Arndt et al., (2003) "Bispecific Diabodies for Cancer Therapy," *Methods Mal. Biol.*, 207: 305-321.

Atwell et al., (1997) "Stable Heterodimers from Remodeling the Domain Interface of a Homodimer using a Phage Display Library," *J. Mal. Biol.*, 270: 26-35.

Baker et al., (2011) "NF-KB, inflammation and metabolic disease," *Cell Metab.*, 13(1): 11-22 (doi:10.1016/j.cmet.2010.12.008).

Bargou et al., (2008) "Tumor Regression in Cancer Patients by Very Low Doses of a T-Cell-Engaging Antibody," *Science*, 321: 974-977.

Bastid et al., "ENTPD1/CD39 is a promising therapeutic target in oncology," *Oncogene*, 32(24):1743-1751 (2013).

Belikov (2007) "Connection between chemical structure, properties of substances and their action on organism," *Pharmaceutical Chemistry*, Chapter 2.6 Moscow, MEDpress-inform, 27-29.

Belyaeva et al., (2007) "Autoantibodies to cirtullinated antigens for diagnosis and prediction of clinical course in early rheumatoid arthritis," [in Russian]. *Meditsinskaya immunologiya*, 9(1):77-84.

Bernett et al., "Multiple Bispecific Checkpoint Combinations Promote T Cell Activation," Xencor, Inc., 2016.

Blackburn et al., (2009) "Coregulation of CD8+ T cell exhaustion by multiple inhibitory receptors during chronic viral infection," *Nature Immunology*, vol. 10, No. 1, 29-37.

Blake et al., (2014) "Role of IL-17 and IL-22 in autoimmunity and cancer," *Actas Dermo-Sifiliogr.*, 105(Supl. 1): 41-50.

Bonnefoy et al., "CD39: A complementary target to immune checkpoints to counteract tumor-mediated immunosuppression," *OncoImmunology*, 4:5, e1003015 (2015).

Bornemann et al., (2001) "Aβ-Induced Inflammatory Processes in Microglia Cells of APP23 Transgenic Mice," *Am. J. Pathol.*, 158(1): 63-73.

Bostrom et al., (2009) "Variants of the Antibody Herceptin That Interact with HER2 and VEGF at the Antigen Binding Site," *Science*, 323: 1610-1614.

(56) References Cited

OTHER PUBLICATIONS

Bour-Jordan et al., (2011) "Intrinsic and extrinsic control of peripheral T-cell tolerance by costimulatory molecules of the CD28/B7 family," *Immunol Rev*, 241(1), 180-205.
Boyce et al., (2005) "No audible wheezing: nuggets and conundrums from mouse asthma models," *J. Exp. Med.*, 201(12): 1869-1873.
Brand, (2005) "Rodent Models of Rheumatoid Arthritis," *Comparative Medicine*, 55(2): 114-122.
Breder et al. "Panitumumab (vectibix) in chemoresistant metastatic colorectal cancer treatment. Retrospective clinical trial of chemotherapy department", Oncological Coloproctology, 2013, No. 1, pp. 41-51.
Brennan et al., (1985) "Preparation of Bispecific Antibodies by Chemical Recombination of Monoclonal Immunoglobulin G1 Fragments," Science, 229: 81-83.
Brinkmann et al., (2017) "The making of bispecific antibodies," *mAbs*, 9(2): 182-212 http://dx.doi.org/10.1080/19420862.2016.1268307.
Buras et al., (2005) "Animal Models of Sepsis: Setting the Stage," *Nat. Rev. Drug Discovery*, 4: 854-865.
Burke et al., (2006) "Zotarolimus (ABT-578) eluting stents," *Adv. Drug Del. Rev.*, 58: 437-446.
Burmester et al., (2013) "Emerging cell and cytokine targets in rheumatoid arthritis," *Nat. Rev. Rheumatol.* (doi: 10.1038/nrrheum.2013.168).
Calandra et al., (2000) "Protection from septic shock by neutralization of macrophage migration inhibitory factor," *Nature Med.*, 6(2): 164-170.
Camisaschi et al., (2010) "LAG-3 Expression Defines a Subset of CD4+ CD25 High Foxp3+ Regulatory T Cells That are Expanded at Tumor Sites," *Journal of Immunology*, 184:6545-6551.
Canfield et al., (1991) "The Binding Affinity of Human IgG for its High Affinity Fc Receptor Is Determined by Multiple Amino Acids in the CH2 Domain and Is Modulated by the Hinge Region," *J. Exp. Med,*. 173(6): 1483-1491.
Carter et al. (2002) "PD-1:PD-L inhibitory pathway affects both CD4+ and CD8+ T cells and is overcome by IL-2," *Eur J. Immunol*, 32, 634-643.
Castoldi et al., (2013) "A novel bispecific EGFR/Met antibody blocks tumor-promoting phenotypic effects induced by resistance to EGFR inhibition and has potent antitumor activity," *Oncogene*, 32(50): 5593-5601 XP055129019, ISSN:0950-9232, DOI: 10.1038/onc.2013.245.
Chalmin et al., "Stat3 and Gfi-1 Transcription Factors Control Th17 Cell Immunosuppressive Activity via the Regulation of Ectonucleotidase Expression," *Immunity*, 36:362-373 (2012).
Chemnitz et al., (2004) "SHP-1 and SHP-2 Associate with Immunoreceptor Tyrosine-based Switch Motif of Programmed Death 1 Upon Primary Human T Cell Stimulation but Only Receptor Ligation Prevents T Cell Activation", *Journal of Immunology*, 173:945-954.
Chen et al., (2015) "Upregulation of Pd—Li by EGFR Activation Mediates the Immune Escape in EGFR-Driven NSCLC: Implication for Optional Immune Targeted Therapy for NSCLC Patients with EGFR Mutation," *Journal of Thoracic Oncology*, 10(6): 910-923.
Co et al., (1993) "Genetically engineered deglycosylation of the variable domain increases the affinity of an anti-CD33 monoclonal antibody," *Mal. Immunol.*, 30(15): 1361-1367.
Coffman et al., (2005) "Nonhuman primate models of asthma," *J. Exp. Med.*, 201(12): 1875-1879.
Coloma et al., (1997) "Design and production of novel tetravalent bispecific antibodies," *Nature Biotechnol.*, 15: 159-163.
Cuesta et al., "Multivalent antibodies: when design surpasses evolution," *Trends in Biotechnology*, 28 (2010) 355-362.
Curran et al., (2010) "PD-I and CTLA-4 combination blockade expands infiltrating T cells and reduces regulatory T and myeloid cells within B16 melanoma tumors," *Proc. Natl. Acad. Sci. USA*, 107: 4275-4280.

Dahlen et al., (2018) "Bispecific antibodies in cancer immunotherapy," *Therapeutic Advances in Vaccines and Immunotherapy*, 6(1) 3-17.
Day et al., (2006) "PD-1 expression on HIV-specific T cells is associated with T-cell exhaustion and disease progression," *Nature*, vol. 443, 350-354.
De Genste et al., (2006) "Antibody repertoire development in camelids," *Dev Comp Immunol* 2006; 30:187-98.
Deaglio S. and Robson S.C., "Ectonucleotidases as Regulators of Purinergic Signaling in Thrombosis, Inflammation, and Immunity," *Adv. Pharmacol.*, 61:301-332 (2011).
Deane et al., (2003) "RAGE mediates amyloid-peptide transport across the blood-brain barrier and accumulation in brain," *Nature Med.*, 9(7): 907-913.
Decision of Grant mailed on Dec. 17, 2021 in RU Application No. 2018129878, citing Breder et al.
Descotes, (1992) "Immunotoxicology of Immunomodulators," *Develop. Biol. Standard*, 77: 99-102.
Deyev et al, "Multivalency: the hallmark of antibodies used for optimization of tumor targeting by design," *BioEssays*, 30:904-918, 2008.
Dhimolea et al., (2012) "Poster Sessions," *mAbs*, 4(1), p. 14-16. doi:10.4161/mabs.19908, p. 16.
Diamond et al., (1984) "Somatic mutation of the T15 heavy chain gives rise to an antibody with autoantibody specificity," *Proc. Natl. Acad. Sci.* USA 81:5841-5844.
Dickson, (2002) "Molecular Mechanisms of Axon Guidance," *Science*, 298: 1959-1964.
DiGiammarino et al., (2011) "Ligand association rates to the inner-variable-domain of a dual-variable domain immunoglobulin are significantly impacted by linker design," *mAbs*, 3(5): 487-494.
Domeniconi et al., (2005) "Overcoming inhibitors in myelin to promote axonal regeneration," *J. Neurolog. Sciences*, 233: 43-47.
Dong et al., (2011) "A stable IgG-like bispecific antibody targeting the epidermal growth factor receptor and the type I insulin-like growth factor receptor demonstrates superior anti-tumor activity," *mAbs* 3: 273-288.
Doppalapudi et al., (2010) "Chemical generation of bispecific antibodies," *Proc. Natl. Acad. Sci. USA*, 107: 22611-22616.
Durocher et al., (2002) "High-level and high-throughput recombinant protein production by transient transfection of suspension-growing human 293-EBNAI cells," *Nucl. Acids Res.*, 30(2e9): 1-9.
Dwyer et al., "CD39 and control of cellular immune responses," *Purinergic Signal*, 3:171-180 (2007).
Economides et al., (2003) "Cytokine traps: multi-component, high-affinity blockers of cytokine action," *Nature Med.*, 9(1): 47-52.
Eltzschig et al., "Central Role of Sp1-regulated CD39 in hypoxia/ischemia protection," *Blood*, 113: 224-232 (2009).
Enjyoji et al., "Targeted disruption of cd39/ATP diphosphohydrolase results in disordered hemostasis and thromboregulation," *Nat. Med.*, 5:1010-1017 (1999).
EPO Communication dated Aug. 9, 2017, enclosing Extended European Search Report, which includes (pursuant to Rule 62 EPC) the supplementary European search report, and the European search opinion dated Jul. 28, 2017, issued in corresponding EP Application No. 14 87 7308.8.
European Application No. 17748342.7, by Epimab Biotherapeutics, Inc., Examination Report, dated Feb. 8, 2021 (7 pages).
European Application No. 17841965, Supplemental European Search Report, dated Mar. 23, 2020. (10 pgs.).
European Search Report (parital supplementary) and provisional search opinion issued Oct. 15, 2019, in counterpart European Application No. EP 17748342.7.
Extended European Search Report and Search Opinion issued Feb. 18, 2020, in counterpart European Application No. EP 17748342.7 (16 pgs.).
Extended European Search Report and Search Opinion issued Mar. 16, 2022, in European Application No. EP 19833932.7 (8 pgs.).
Fan et al., (2015) "Bispecific antibodies and their applications," *J. Hematol. Oneal.*, 8, 130 (doi: 10.1186/s13045-015-0227-0).
Finotto et al., (2005) "Asthmatic changes in mice lacking T-bet are mediated by IL-13," *Int. Immunol.*, 17(8): 993-1007.

(56) References Cited

OTHER PUBLICATIONS

Freeman et al., (2000) "Engagement of the PD-1 Immunoinhibitory Receptor by a Novel B7 Family Member Leads to Negative Regulation of Lymphocyte Activation," *J. Exp. Med.*, vol. 192, No. 7, 1027-1034.

Gall et al., (2005) "T cells armed with anti-CD3×anti-CD20 bispecific antibody enhance killing of CD20+ malignant B cells and bypass complement-mediated rituximab resistance in vitro," *Experimental Hematology*, v.33, No. 4, p. 452-459. doi:10.1016/j.exphem.2005.01.007.

Genain et al., (1997) "Creation of a model for multiple sclerosis in *Callithrix jacchus* marmosets," *J. Mal. Med.*, 75(3): 187-197.

Genovese et al., (2005) "Abatacept for Rheumatoid Arthritis Refractory to Tumor Necrosis Factor a Inhibition," *N. Engl. J. Med.*, 353: 1114-1123.

Giege et al., (1999) "Chapter 1, in Crystallization of Nucleic Acids and Proteins, a Practical Approach, 2nd ed., Ducruix and Giege, eds.," *Oxford University Press* pp. 1-16.

Glennie et al., (1987) "Preparation and Performance of Bispecific F(ab' y)2 Antibody Containing Thioether-LinkedFab'yFragments," *J. Immunol.*, 139(7): 2367-2375.

Goldspiel et al., (1993) "Human Gene Therapy," *Clin. Pharm.*, 12: 488-505.

Gong et al., (2017) "Fabs-in-tandem immunoglobulin is a novel and versatile bispecific design for engaging multiple therapeutic targets," *MAbs*, 9(7):1118-1128.

Gong et al., (2019) "Generation of Fabs-in-tandem immunoglobulin molecules for dual-specific targeting," *Methods.*, 154:87-92.

Gracie et al., (1999) "A proinflammatory role for IL-18 in rheumatoid arthritis," *J. Clin. Invest.*, 104(10): 1393-1401.

Griffin et al., (2000) "Blockade of T Cell Activation Using a Surface-Linked Single Chain Antibody to CTLA-4 (CD152)," *J. Immunol.*, 164: 4433-4442.

Griffin et al., (2012) "IL-17 and TNF-α Sustain Neutrophil Recruitment during Inflammation through Synergistic Effects on Endothelial Activation," *J. Immunol.*, 188(12): 6287-6299.

Grosso et al., (2007) "LAG-3 regulates CD8+ T cell accumulation and effector function in murine self- and tumor-tolerance systems," *Journal of Clinical Investigation*, vol. 117, No. 11, 3383-3392.

Hannier et al., (1998) "CD3/TCR Complex-Associated Lymphocyte Activation Gene-3 Molecules Inhibit CD3/TCR Signaling," *J Immunol*, 161:4058-4065.

Harriman et al., (1999) "Summary of clinical trials in rheumatoid arthritis using infliximab, an anti-TNFα treatment," *Ann. Rheum. Dis.*, 58: (Suppl. I) 161-164.

Hart et al., (2001) "Preclinical efficacy and safety of mepolizumab (SB-240563), a humanized monoclonal antibody to IL-5, in cynomolgus monkeys," *J. Allergy Clin. Immunol.*, 108(2): 250-257.

Hildebrand et al., (2006) "Surface coatings for biological activation and functionalization of medical devices," *Surface & Coatings Technology*, 200: 6318-6324.

Holliger et al., (1993) "'Diabodies': Small bivalent and bispecific antibody fragments," *Proc. Natl. Acad. Sci. USA*, 90: 6444-6448.

Holliger et al., (1997) "Diabodies: small bispecific antibody fragments," *Cancer Immunol. Immunother.*, 45: 128-130.

Huang et al., (2004) "Role of LAG-3 in Regulatory T Cells," *Immunity*, vol. 21, 503-513.

Huard et al., (1997) "Characterization of the major histocompatibility complex class II binding site on LAG-3 protein," *Immunology, Proc. Natl. Acad. Sci. USA*, vol. 94, 5744-5749.

Huston et al., (1988) "Protein engineering of antibody binding sites: recovery of specific activity in an antidigoxin single-chain Fv analogue produced in *Escherichia coli*," *Proc. Natl. Acad. Sci. USA*, 85: 5879-5883.

Hwang et al., (2002) "Cutting Edge: Targeted Ligation of CTLA-4 In Vivo by Membrane-Bound Anti-CTLA-4 Antibody Prevents Rejection of Allogeneic Cells," *J. Immunol.*, 163: 633-637.

International Search Report and Written Opinion issued in PCT/US17/16691, dated Jul. 19, 2019 (17 pgs.).

International Search Report and Written Opinion issued in PCT/US2014/072336, mailed Apr. 28, 2015 (13 pgs.).

International Search Report and Written Opinion issued in PCT/US2017/046875, mailed Dec. 28, 2017 (19 pgs.).

International Search Report and Written Opinion issued in PCT/US2019/040762, mailed Dec. 3, 2019 (15 pgs.).

International Search Report and Written Opinion issued in PCT/CN2019/110593, mailed Jul. 9, 2020 (14 pgs.).

Ito et al., (2003) "Transfer of Severe Experimental Autoimmune Encephalomyelitis by IL-12- and IL-18-Potentiated T Cells is Estrogen Sensitive," *J. Immunol.*, 170(9): 4802-4809.

Jacobsen et al., (2017) "Engineering an IgG Scaffold Lacking Effector Function with Optimized Developability," *J Biol Chem.*, 292(5): 1865-1875.

Jain et al., "Engineering antibodies for clinical applications," *Trends in Biotechnology*, vol. 25, No. 7, 2007, 307-316.

Jakob et al., (2013) "Structure reveals function of the dual variable domain immunoglobulin (DVD-Ig™) molecule," *mAbs*, 5(3): 358-363.

Janelsins et al., (2005) "Early correlation of microglial activation with enhanced tumor necrosis factor-alpha and monocyte chemoattractant protein-I expression specifically within the entorhinal cortex of triple transgenic Alzheimer's disease mice," *J. Neuroinflammation*, 2(23): 1-12.

Jarantow et al., (2015) "Impact of Cell-surface Antigen Expression on Target Engagement and Function of an Epidermal Growth Factor Receptor c-MET Bispecific Antibody," *J. Biol. Chem.*, 290(41): 24689-24704.

Jefferis, (2005) "Glycosylation of recombinant antibody therapeutics," *Biotechnol. Prag.*, 21: 11-16.

Jin et al., (2008) "MetMAb, the one-armed 5D5 anti-c-Met antibody, inhibits orthotopic pancreatic tumor growth and improves survival," *Cancer Res.*, 68(11):4360-4368.

Johansson et al., (2006) "Efficient expression of recombinant human monoclonal antibodies in *Drosophila* S2 cells," *J. Immunol. Meth.*, 318: 37-46; Genbank supplement pp. 1-2, DOI: 10.1016/j.jim.2006.08.017.

Johnson, et al., (2010) "Effector cell recruitment with novel Fv-based dual-affinity re-targeting protein leads to potent tumor cytolysis and in vivo B-cell depletion," *J. Mal. Biol.*, 399: 436-449.

Jones, (2000) "Rovelizumab—ICOS Corp," *Idrugs : the Investigational Drugs Journal*, 3(4):442-446.

Kadomatsu et al., (2010) "Angiopoietin-like proteins: emerging targets for treatment of obesity and related metabolic diseases," *FEBS J.*, 278: 559-564.

Kanda et al., (2007) "Establishment of a GDP-mannose 4,6-dehydratase (GMD) knockout host cell line: a new strategy for generating completely non-fucosylated recombinant therapeutics," *J. Biotechnol.*, 130(3):300-310.

Kapojos et al., "Enhanced ecto-apyrase activity of stimulated endothelial or mesangial cells is downregulated by glucocorticoids in vitro," *Eur. J. Pharmacol.*, 501:191-198 (2004).

Karnezis et al., (2004) "The neurite outgrowth inhibitor Nogo A is involved in autoimmune-mediated demyelination," *Nature Neurosci.*, 7: 736.

Karni et al., (2002) "IL-18 is linked to raised IFN-y in multiple sclerosis and is induced by activated CD4+ T cells via CD40-CD40 ligand interactions," *J. Neuroimmunol.*, 125: 134-140.

Karshtedt et al (2011) "Limits on Hard-to-Reproduce Inventions: Process Elements and Biotechnology's Compliance with the Enablement Requirement," *HastingsSci.&Tech.LJ*,3(1): 109-155.

Kipriyanov et al., (1999) "Bispecific Tandem Diabody for Tumor Therapy with Improved Antigen Binding and Pharmacokinetics," *J. Mal. Biol.*, 293: 41-56.

Klein et al., (2012) "Progress in overcoming the chain association issue in bispecific heterodimeric IgG antibodies," *mAbs*, 4(6): 653-663.

Klein et al., (2016) "The use of CrossMAb technology for the generation of bi- and multispecific antibodies," *mAbs*, 8(6): 1010-1020.

Klein, (2002) "Aβ toxicity in Alzheimer's disease: globular oligomers (ADDLs) as new vaccine and drug targets," *Neurochem. Int.*, 41: 345-352.

(56) References Cited

OTHER PUBLICATIONS

Klooster et al., Generation of immuno-modulatory receptor binding bispecific antibodies to modulate tumor immunity (B088), Merus N.V., Sep. 23, 2016.
Klyubin et al., (2005) "Amyloid protein immunotherapy neutralizes A oligomers that disrupt synaptic plasticity in vivo," *Nature Med.*, 11: 556-561.
Kontermann et al., (2015) "Bispecific Antibodies," *Drug Discovery Today*, 20(7): 838-847.
Kontermann, (2005) "Recombinant bispecific antibodies for cancer therapy," *Acta Pharmacologica Sinica*, 26(1): 1-9.
Koopmans et al., (2018) "A novel bispecific antibody for EGFR-directed blockade of the PD-1/PD-L1 immune checkpoint," *Oncoimmunology*, 7(8):e1466016 (11 pages).
Kriangkum et al., (2001) "Bispecific and bifunctional single chain recombinant antibodies," *Biomol. Eng.*, 18: 31-40.
Latchman et al., (2001) "PD-L2 is a second ligand for PD-1 and inhibits T cell activation," *Nature Immunology*, 2(3) 261-268.
Leung et al., (2000) "Combined Effects of IL-12 and IL-18 on the Induction of Collagen-Induced Arthritis," *J. Immunol.*, 164(12): 6495-6502.
Li et al., (2013) "Bispecific Antibody to ErbB2 Overcomes Trastuzumab Resistance through Comprehensive Blockade of ErbB2 Heterodimerization," *Cancer Res.*, 73(21): 6471-6483.
Lindhofer et al., (1995) "Preferential species-restricted heavy/light chain pairing in rat/mouse quadromas. Implications for a single-step purification of bispecific antibodies," *J. Immunol.*, 155: 219-225.
Lloyd et al., (2001) "Mouse Models of Allergic Airway Disease," *Adv. Immunol.*, 77: 263-295.
Lu et al., (2002) "Fab-scFv fusion protein: an efficient approach to production of bispecific antibody fragments," *J. Immunol. Methods*, 267: 213-226.
Lu et al., (2004) "Simultaneous blockade of both the epidermal growth factor receptor and the insulin-like growth factor receptor signaling pathways in cancer cells with a fully human recombinant bispecific antibody," *J. Biol. Chem.*, 279(4): 2856-2865.
Lu et al., (2005) "A Fully Human Recombinant IgG-like Bispecific Antibody to Both the Epidermal Growth Factor Receptor and the Insulin-like Growth Factor Receptor for Enhanced Anti tumor Activity," *The Journal of Biological Chemistry*, vol. 280, No. 20, Issue of May 20, pp. 19665-19672.
Lublin, "Relapsing experimental allergic encephalomyelitis an autoimmune model of multiple sclerosis," *Springer Semin. Immunopathol.*, 8: 197-208 (1985).
Luster et al., (1994) "Use of animal studies in risk assessment for immunotoxicology," *Toxicology*, 92(1-3): 229-243.
Mack et al., (1995) "A small bispecific antibody construct expressed as a functional single-chain molecule with high tumor cell cytotoxicity," *Proc. Natl. Acad. Sci. USA*, 92: 7021-7025.
Macon-Lemaitre et al., (2005) "The negative regulatory function of the lymphocyte-activation gene-3 co-receptor (CD223) on human T cells," *Immunology*, 115, 170-178.
Makwana et al., (2005) "Molecular mechanisms in successful peripheral regeneration," *FEBS J.*, 272: 2628-2638.
Mariuzza et al., (1987) "The structural basis of antigen-antibody recognition" *Ann. Rev. Biophys. Chem.* 16:139-159.
Marques et al., (2005) "Mediation of the cytokine network in the implantation of orthopedic devices," Chapter 21, In Biodegradable Systems in Tissue Engineering and Regenerative Medicine, (Reis et al., eds.) *CRC Press LLC*, pp. 377-397.
Martin et al., (2000) "Genetic and Hormonal Risk Factors in Breast Cancer," *Journal of the National Cancer Institute*, vol. 92, No. 14: pp. 1126-1135.
Marvin et al., (2005) "Recombinant approaches to IgG-like bispecific antibodies," *Acta Pharmacologica Sinica*, 26(6): 649-658.
Masliah et al., (2005) "Effects of cx-Synuclein Immunization in a Mouse Model of Parkinson's Disease," *Neuron*, 46: 857-868.
McDonnell et al., (2001) "TNF Antagonism," *In New Drugs for Asthma, Allergy and COPD Prog Respir Res.*, vol. 31, (Hansel et al., eds.) pp. 247-250.

McGee et al., (2003) "The Nogo-66 receptor: focusing myelin inhibition of axon regeneration," *Trends Neurosciences*, 26(4): 193-198.
Merchant et al., (1998) "An efficient route to human bispecific IgG," *Nature Biotechnol.*, 16: 677-681.
Merck KGaA, F-Star shake on immune-oncology bispecifics, 2017, *Nature Biotechnology*, 35(7). 601.
Miller et al., (2003) "Design, Construction, and In Vitro Analyses of Multivalent Antibodies," *J. Immunol.*, 170: 4854-4861.
Milstein et al., (1983) "Hybrid hybridomas and their use in immunohistochemistry," *Nature*, 305: 537-540.
Miossec et al., (2012) "Targeting IL-17 and TH17 cells in chronic inflammation," *Nature Reviews Drug Discovery*, v.11, p. 763-776.
Mizumoto et al., "CD39 is the dominant Langerhans cell-associated ecto-NTPDase: Modulatory roles in inflammation and immune responsiveness," *Nat. Med.*, 8:358-365 (2002).
Mizushima et al., (1990) "pEF-BOS, a powerful mammalian expression vector," *Nucl. Acids Res.*, 18(17): 5322.
Moores et al., (2016) "A Novel Bispecific Antibody Targeting EGFR and cMet Is Effective against EGFR Inhibitor-Resistant Lung Tumors," *Cancer Res.*, 76(13): 3942-3953 XP055431654, us ISSN: 0008-5472, DOI: 10.1158/0008-5472.CAN-15-2833.
Morgan et al., (1993) "Human Gene Therapy," *Annu. Rev. Biochem.*, 62:191-217.
Mulligan, (1993) "The Basic Science of Gene Therapy," *Science*, 260: 926-932.
Nakanishi et al., (2001) "Interleukin-IS Regulates Both THI and TH2 Responses," *Annu. Rev Immunol.*, 19: 423-474.
Nelson, (2005) "The Dualistic Nature of Immune Modulation In Alzheimer's Disease: Lessons from the Transgenic Models," *Curr. Pharm. Des.*, 11: 3335-3352.
Neuberger, et al., (1985) "A hapten-specific chimaeric IgE antibody with human physiological effector function," *Nature 314*, 268-270 https://doi.org/10.1038/314268a0.
Nomi et al., (2007) "Clinical Significance and Therapeutic Potential of the Programmed Death-1 Ligand/Programmed Death-1 Pathway in Human Pancreatic Cancer," *Clin Cancer Res*, 13(7), 2151-2157.
Office Action in Japanese Patent Application No. 2019-208956 issued on Jul. 7, 2021.
Office Action and Search Report dated Jul. 2, 2021 issued in Russian Application No. 2020142965.
Office Action and Search Report, dated Nov. 30, 2020 in Russian Application No. 2019103230 citing Yarilin (16 pgs.).
Office Action dated Jul. 30, 2021, in Russian Application No. 2019103230/10, citing Belyaeva et al. (12 pgs.).
Office Action Decision to Refuse Grant dated Sep. 25, 2020, in Russian Application No. 2016129959 for Epimab Biotherapeutics, Inc., filed Dec. 24, 2014, citing Belikov.
Ohigashi et al., (2005) "Clinical Significance of Programmed Death-1 Ligand-1 and Programmed Death-1 Ligand-2 Expression in Human Esophageal Cancer," *Clin Cancer Res*, 11(8), 2947-2953.
Ohno et al., (1985) "Antigen-binding specificities of antibodies are primarily determined by seven residues of VH," *Proc. Natl. Acad. Sci. USA*, 82:2945-2949.
Oike et al., (2009) "Angiopoietin-Like Proteins—Potential Therapeutic Targets for Metabolic Syndrome and Cardiovascular Disease," *Cir. J.*, 73: 2192-2197.
Okamoto et al., (2014) "Rituximab for Rheumatoid Arthritis," *N. Engl. J. Med.*, 351: 1909.
Okazaki et al., (2007) "PD-1 and PD-1 ligands: from discovery to clinical application," *International Immunology*, 19(7), 813-824.
Owens et al., (1995) "The Immunology of Multiple Sclerosis and Its Animal Model, Experimental Allergic Encephalomyelitis," *Neural. Clin.*, 13(1): 51-73.
Padilla et al., (2005) "IL-13 Regulates the Immune Response to Inhaled Antigens," *J. Immunol.*, 174(12): 8097-8105.
Pardoll, (2012) "The blockade of immune checkpoints in cancer immunotherapy," *Nat. Rev. Cancer*, 12: 252-264.
Parry et al., (2005) "CTLA-4 and PD-1 Receptors Inhibit T-Cell Activation by Distinct Mechanisms," *Molecular and Cellular Biology*, vol. 25, No. 21, 9543-9553.
Partial Supplementary European Search report from related European Application No. 19796462.0 dated Aug. 10, 2022 (21 pages).

(56) References Cited

OTHER PUBLICATIONS

Pauli et al., (2014) "*Staphylococcus aureus* infection induces protein A-mediated immune evasion in humans," *J. Exp. Med.*, 211: 2331-2339; Genbank supplement pp. 1-2, DOI: 10.1084/jem. 20141404.
Peipp et al., (2002) "Bispecific antibodies targeting cancer cells," *Biochem. Soc. Trans.*, 30(4): 507-511.
Peng, (2004) "Experimental Use of Murine Lupus Models," *Methods Mol. Med.*, 102: 227-272.
Peterson et al., (2018) "Macrophage-Targeted Therapeutics for Metabolic Disease," *Trends Pharmacol. Sci.* 39(6):536-546 (doi.org/10.1016/j.tips.2018.03.001).
Pluckthun et al., (1997) "New protein engineering approaches to multivalent and bispecific antibody fragments," *Immunotechnology*, 3: 83-105.
Presta, (2008) "Molecular engineering and design of therapeutic antibodies," *Curr. Opin. Immunol.*, 20: 460-470.
ProSpec-Tany TechnoGene Ltd.: "TNF a Human" [Content pp. 3 pp.] Retrieved Sep. 10, 2013 from <http://www.prospecbio.com/english/PrintContentPage.aspx>.
Qi et al., (2019) "Conventional and Chemically Programmed Asymmetric Bispecific Antibodies Targeting Folate Receptor," *Front Immunol.*, 10:1994 (13 pages).
Ridgway et al., (1996) "Knobs-into-holes' engineering of antibody CH3 domains for heavy chain heterodimerization," *Protein Eng.*, 9(7): 617-621.
Riechmann et al., (1988) "Reshaping human antibodies for therapy," *Nature*, 332: 323-327.
Riethmuller, (2012) "Symmetry breaking: bispecific antibodies, the beginnings, and 50 years on," *Cancer Immun.*, 12: 12-18.
Riley, (2009) "PD-1 signaling in primary T cells", *Immunol Rev*, 229(1):114-125.
Robinson, (1993) "Gene therapy—proceeding from laboratory to clinic," *Trends Biotechnol.*, 11(5): 155.
Rudikoff et al., (1982) "Single amino acid substitution altering antigen-binding specificity," *Proc. Natl. Aca. Sci. USA*, 79:1979-1983.
Satta et al., (2013) "Redirection of T-cell effector functions for cancer therapy: bispecific antibodies and chimeric antigen receptors," *Future Oneal.*, 9(4): 527-539 DOI: http://dx.doi.org/10.2217/fon.12.203.
Schaefer et al., (2011) "Immunoglobulin domain crossover as a generic approach for the production of bispecific IgG antibodies," *Proc. Natl. Acad. Sci. USA*, 108: 11187-11192.
Sela-Culang et al., (2013) "The structural basis of antibody-antigen recognition," *Frontiers in Immunology*, 4(302):1-13.
Sfikakis et al., (2005) "Rituximab anti-B-cell therapy in systemic lupus erythematosus: pointing to the future," *Curr. Opin. Rheumatol.*, 17: 550-557.
Shan et al., (2009) "The Angiopoietin-like Proteins ANGPTL3 and ANGPTL4 Inhibit Lipoprotein Lipase Activity through Distinct Mechanisms," *J. Biol. Chem.*, 284(3): 1419-1424.
Shepherd et al., (2005) "Novel 'inflammatory plaque' pathology in presenilin-1 Alzheimer's disease," *Neuropathol. Appl. Neurobiol.*, 31: 503-511.
Shields et al., (2002) "Lack of Fucose on Human IgG 1 N-Linked Oligosaccharide Improves Binding to Human FcγRIII and Antibody-dependent Cellular Toxicity," *J. Biol. Chem.*, 277(30): 26733-26740.
Smith et al., "Cloning, sequencing, and expression of a human brain ecto-apyrase related to both the ecto-ATPases and CD39 ecto-apyrases," *Biochim. Biophys. Acta*, 1386: 65-78 (1998).
Snibson et al., (2005) "Airway remodelling and inflammation in sheep lungs after chronic airway challenge with house dust mite," *Clin. Exp. Allergy* 35: 146-152.
Solomon, (2004) "Alzheimer's Disease and Immunotherapy," *Curr. Alzheimer. Res.*, 1: 149-163.
Spiess et al., (2015) "Alternative Molecular Formats and Therapeutic Applications for Bispecific Antibodies," *Mol. Immunol*, 67: 95-106.
Staerz et al., (1985) "Hybrid antibodies can target sites for attack by T cells," *Nature*, 314: 628-631.
Stagg et al., "Anti-CD73 antibody therapy inhibits breast tumor growth and metastasis," *Proc. Natl. Acad. Sci USA*, 107(4):1547-1552 (2010).
Stamper et al., (2001) "Crystal structure of the B7-1/CTLA-4 complex that inhibits human immune responses," *Nature*, 410: 608-611.
Stanglmaier et al., (2008) "Bi20 (FBTA05), a novel trifunctional bispecific antibody (anti-CD20×anti-CD3), mediates efficient killing of B-cell lymphoma cells even with very low CD20 expression levels," *Int. J. Cancer*, 123(5): 1181-1189.
Steinman et al., (2005) "Virtues and pitfalls of EAE for the development of therapies for multiple sclerosis," *Trends Immunol.*, 26(11):565-571.
Stubenrauch et al., (2010) "Impact of Molecular Processing in the Hinge Region of Therapeutic IgG4 Antibodies on Disposition Profiles in Cynomolgus Monkeys," *Drug Metab. Dispos.*, 38: 84-91.
Sung et al., (2015) "Dual-Affinity Re-Targeting Proteins Direct T Cell-Mediated Cytolysis of Latently HIV Infected Cells," *J. Clin. Invest.*, 125(11): 4077-4090.
Tang et al., (2015) "The association between PD-LI and EGER status and the prognostic value of PD-LI in advanced non-small cell lung cancer patients treated with EGFR-TKis," *Oncotarget*, 6(16): 14209-14219.
Teng et al., (2005) "Nogo Signaling and Non-Physical Injury-Induced Nervous System Pathology," *J. Neurosci. Res.*, 79: 273-278.
T'Hart et al., (2005) "Suppression of Ongoing Disease in a Non-human Primate Model of Multiple Sclerosis by a Human-Anti-Human IL-12p40 Antibody," *J. Immunol.*, 175(7): 4761-4768.
TNF tumor necrosis factor [*Homo sapiens* (human)]—Gene ID: 7124, updated on Jul. 28, 2013 (16 pgs.), National Center for Biotechnology Information. U.S. National Library of Medicine. Jul. 30, 2013 <http://www.ncbi.nlm.nih.gov/gene/7124>.
Tolstoshev, (1993) "Gene Therapy, Concepts, Current Trials and Future Directions," *Annu. Rev. Pharmacol. Toxicol.*, 32: 573-596.
Trautmann et al., (2006) "Upregulation of PD-1 expression on HIV-specific CD8+ T cells leads to reversible immune dysfunction," *Nature Medicine*, vol. 12, No. 10, 1198-1202.
Tsushima et al., (2006) "Predominant expression of B7-H1 and its immunoregulatory roles in oral squamous cell carcinoma," *Oral Oncology*, 42, 268-274.
Tuohy et al., (1999) "Spontaneous Regression of Primary Autoreactivity during Chronic Progression of Experimental Autoimmune Encephalomyelitis and Multiple Sclerosis," *J. Exp Med.*, 189(7): 1033-1042.
Turnis et al., (2015) "Inhibitory receptors as targets for cancer immunotherapy," *Eur J Immunol*, 45(7), 1892-1905.
Umana et al., (1999) "Engineered glycoforms of an antineuroblastoma IgG 1 with optimized antibodydependent cellular cytotoxic activity," *Nature Biotechnol.*, 17: 176-180.
Vajdos et al., (2002) "Comprehensive Functional Maps of the Antigen-binding Site of an Anti-ErbB2 Antibody Obtained with Shotgun Scanning Mutagenesis," *J. Mal. Biol.*, 320: 415-428.
Van Der Neut Kolfschoten et al., (2007) "Anti-Inflammatory Activity of Human IgG4 Antibodies by Dynamic Fab Arm Exchange," *Science*, 317: 1554-1557.
Vivier et al., (1997) "Immunoreceptor tyrosine-based inhibition motifs", *Immunology Today*, vol. 18, No. 6, 286-291.
Von Merren et al., (2003) "Monoclonal Antibody Therapy For Cancer," *Annu. Rev. Med.*, 54: 343-369.
Wallick et al., (1988) "Glycosylation of a VH Residue of a Monoclonal Antibody Against α(I-->6) Dextran Increases Its Affinity for Antigen," *J. Exp. Med.*, 168: 1099-1109.
Wang et al., (2017) "A Human Bi-specific Antibody against Zika Virus with High Therapeutic Potential," *Cell*, 171: 229-241.
Weiner et al., (1995) "Phase I trial of 2BI, a bispecific monoclonal antibody targeting c-cerbB-2 and Fe gamma RIii," *Cancer Res.*, 55: 4586-4593.
Workman et al., (2003) "The CD4-related molecule, LAG-3 (CD223), regulates the expansion of activated T cells," *Eur. J. Immunol.*, 33, 970-979.

(56) References Cited

OTHER PUBLICATIONS

Wörn et al., (2001) "Stability engineering of antibody single-chain Fv fragments," *J Mol Biol.*, 305(5):989-1010.
Wright et al.,(1991) "Antibody variable region glycosylation: position effects on antigen binding and carbohydrate structure," *EMBO J.*, 10(10): 2717-2723.
Wu et al., (1991) "Delivery systems for gene therapy," *Biotherapy*, 3: 87-95.
Wu et al., (1996) "Tumor localization of anti-CEA single-chain Fvs: improved targeting by non-covalent dimers," *Immunotechnology*, 2(1): 21-36.
Wu et al., (2006) "Drug/device combinations for local drug therapies and infection prophylaxis," *Biomaterials*, 27: 2450-2467.
Wu et al., (2007) "Simultaneous targeting of multiple disease mediators by a dual-variable-domain immunoglobulin," *Nature Biotechnol.*, 25(11): 1290-1297.
Wu et al., (2015) "Fab-based bispecific antibody formats with robust biophysical properties and biological activity," *mAbs, Landes Bioscience US*, 7(3): 470-482 XP009185560, ISSN: 1942-0870, DOI: 10.1080/19420862.2015.1022694.
Xing et al., (2015) "A site of varicella-zoster virus vulnerability identified by structural studies of neutralizing antibodies bound to the glycoprotein complex gHgL," *Proc. Natl. Acad. Sci. USA*, 112: 6056-6061; Genbank supplement pp. 1 3, DOI: 10.1073/pnas.1501176112.
Xu et al., (2004) "Recombinant DNA vaccine encoding multiple domains related to inhibition of neurite outgrowth: a potential strategy for axonal regeneration," *J. Neurochem.*, 91: 1018-1023.
Xu et al., (2015) "Production of bispecific antibodies in "knobs-into-holes" using a cell-free expression system," *mAbs*, 7(1): 231-242.
Yarilin, (1999) "Foundations of Immunology," *Moscow, Meditsina* 172-174.
Yarilin, (1999) "Foundations of Immunology," *Moscow, Meditsina* 354-358.
Yegutkin et al., Metabolism of circulating ADP in the bloodstream is mediated via integrated actions of soluble adenylate kinase-1 and NTPDase1/CD39 activities, *FASEB. J.*, 26:3875-3883 (2012).
Yoshinaga et al., (2008) "Ig L-chain shuffling for affinity maturation of phage library-derived human anti-human MCP-1 antibody blocking its chemotactic activity," *J. Biochem.*, 143:593-601.
Zapata et al., (1995) "Engineering linear F(ab')2 fragments for efficient production in *Escherichia coli* and enhanced antiproliferative activity," *Protein Eng.*, 8(10): 1057-1062.
Zhao et al. (2018) "Combating of non-small-cell lung cancer (NSCLC) through EGFR/PD-L1 bispecific antibody generated by Lock-and-Key method," *Journal of Clinical Oncology*, vol. 36, No. 15_suppl, pp. 1-4, XP055901534.
Zimmermann H., "Two novel families of ectonucleotidases: molecular structures, catalytic properties and a search for function," *Trends Pharmacol. Sci.*, 20:231-236 (1999).
Zocher et al., (2004) "A Bispecific Single-Chain Antibody Fusion Protein for Targeted Depletion of Autoreactive B Cells via Unstimulated Human T Lymphocytes," *Mal. Immunol.*, 41(5): 511-518.
Zola et al., (2005) "CD molecules 2005: human cell differentiation molecules," *Blood*, 106: 3123-3126.
International Search Report and Written Opinion issued in PCT/CN2019/085164, mailed Aug. 8, 2019 (16 pgs.).
Office Action in Japanese Patent Application No. 2021-510507 issued on Apr. 4, 2023.

* cited by examiner

A

B

A

B ize: 4px;">: 4px;">## HIGH AFFINITY ANTIBODIES TO PD-1 AND LAG-3 AND BISPECIFIC BINDING PROTEINS MADE THEREFROM

RELATED APPLICATIONS

This application is a national stage application under 35 U.S.C. § 371 of PCT/CN2019/085164, filed Apr. 30, 2019, which designated the U.S. and claims the benefit of PCT/CN2018/085468, filed May 3, 2018. The entire contents of the foregoing applications are incorporated herein by reference.

SEQUENCE LISTING

This application contains a Sequence Listing which has been submitted electronically in ASCII format and is incorporated herein by reference in its entirety. The ASCII copy, created on Mar. 12, 2024, is named "15491.0005-00000 Replacement-Corrected Sequence Listing.txt" and is 429,008 bytes in size.

FIELD OF THE INVENTION

The present invention relates to new antibodies recognizing Programmed Cell Death Protein 1 (PD-1), new antibodies recognizing Lymphocyte-Activation Gene 3 protein (LAG-3), and bispecific PD-1/LAG-3 binding proteins such as FIT-Ig binding proteins made using those antibodies. The antibodies and bispecific binding proteins are useful for treatment of immunological diseases and hematological cancers.

BACKGROUND OF THE INVENTION

Programmed Cell Death Protein 1 (PD-1)

Programmed Cell Death Protein 1 (PD-1, CD279) is a member of the CD28 family of receptors, which includes CD28, CTLA-4, ICOS, PD-1, and BTLA. Expression of PD-1 is frequently found in immune cells such as T cells, B cells, monocytes and natural killer (NK) cells. PD-1 and like family members are type I transmembrane glycoproteins containing an immunoglobulin-like domain resembling an Ig variable domain that is responsible for ligand binding and a cytoplasmic tail that is responsible for the binding of signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif). Vivier et al., *Immunol. Today*, 18:286-291 (1997) and Chemnitz et al., *J. Immunol.*, 173:945-954 (2004).

Two cell surface glycoprotein ligands for PD-1 have been identified, Programmed Death Ligand 1 (PD-L1, CD274, 87-H1) and PD-L2(CD273, B7-DC), and have been shown to induce intracellular signal transduction that inhibits CD3- and CD28-mediated T cell activation. Riley, *Immunol. Rev.*, 229:114-125 (2009). This downregulation of T cell activation in turn results in reduction of T cell proliferation, IL-2 secretion, IFN-γ secretion, and secretion of other growth factors and cytokines. Freeman et al., *J. Exp. Med.*, 192:1027-1034 (2000); Latchman et al., *Nat. Immunol.*, 2:261-8 (2001); Carter et al., *Eur. J. Immunol*, 32:634-43 (2002); Ohigashi et al., *Clin. Cancer Res.*, 11:2947-53 (2005). Signaling via the PD-1/PD-L1 interaction is believed to serve critical, non-redundant functions within the immune system, by negatively regulating T cell responses. This regulation is involved in T cell development in the thymus, in regulation of chronic inflammatory responses, and in maintenance of both peripheral tolerance and immune privilege. The critical nature of these functions is exemplified in PD-1-deficient mice, which exhibit an autoimmune phenotype. PD-1 deficiency in C57BL/6 mice results in chronic progressive lupus-like glomerulonephritis and arthritis. In Balb/c mice, PD-1 deficiency leads to severe cardiomyopathy due to the presence of heart-tissue-specific self-reacting antibodies.

Following T cell stimulation, PD-1 recruits the tyrosine phosphatase SHP-2 to the ITSM motif within its cytoplasmic tail, leading to the dephosphorylation of effector molecules such as CD3-ζ, PKC-θ and ZAP70 that are involved in the CD3 T cell signaling cascade. The mechanism by which PD-1 down-modulates T cell responses is similar to but distinct from that of CTLA-4, as both molecules regulate an overlapping set of signaling proteins. Parry et al., *Mol Cell Biol.*, 25:9543-9553 (2005). In general, PD-1-mediated inhibitory signal plays an important role in immune tolerance. Bour-Jordan et al., *Immunol. Rev.*, 241:180-205 (2011).

Increased PD-1 expression is found in tumor-infiltrating lymphocytes (TILs), and expression of PD-1 ligands in tumor cells has been reported in a variety of cancers of different tissues including lung, liver, stomach, kidney, breast, ovary, pancreas, melanocytes, and esophagus. In general, PD-1 ligand expression on tumor cells has been correlated to poor prognosis of cancer patients across multiple tumor types. Okazaki and Honjo, *Int Immunol.*, 19:813-824 (2007).

Blockade of the PD-1/PD-L1 interaction could lead to enhanced tumor-specific T cell immunity and therefore be helpful in clearance of tumor cells by the immune system. In a murine model of aggressive pancreatic cancer, T. Nomi et al. demonstrated the therapeutic efficacy of PD-1/PD-L1 blockade, showing administration of either anti-PD-1 or anti-PD-L antibody significantly inhibited tumor growth. Nomi et al., *Clin. Cancer Res.*, 13:2151-2157 (2007). Antibody blockade effectively promoted tumor-reactive CD8+ T cell infiltration into the tumor, resulting in the upregulation of anti-tumor effectors including IFN-γ, granzyme B, and perforin. In another study, using a model of squamous cell carcinoma in mice, antibody blockade of PD-1 or PD-L1 significantly inhibited tumor growth. Tsushima et al., *Oral Oncol.*, 42:268-274 (2006).

Recently, it has been shown that PD-1 is highly expressed on T cells from HIV-infected individuals and that receptor expression correlates with impaired T cell function and disease progression. Day et al., *Nature*, 443:350-354 (2006); Trautmann et al., *Nat. Med.*, 12:198-1202 (2006). In both studies, blockade of the ligand PD-L significantly increased the expansion of HIV-specific, IFN-γ-producing cells in vitro.

Accordingly, therapeutic modulation of PD-1 signaling by antagonist molecules may revert immune cells from tolerance and reactivate them to eradicate cancer and chronic viral infections.

Lymphocyte Activation Gene 3 (LAG-3)

Lymphocyte Activation Gene 3 protein (LAG-3, CD223) is a negative co-stimulatory receptor that modulates T cell homeostasis, proliferation, and activation. Sierro et al., *Expert Opin. Ther Targets*, 15: 91-101 (2010). An immunoglobulin superfamily member, LAG-3 is a CD4-like protein which, like CD4, binds to MHC class II molecules, but with two-fold higher affinity and at a distinct site from CD4. Huard et al., *Proc. Natl Acad. Sc. USA*, 94:5744-9 (1997). LAG-3 is expressed on activated CD8+ T cells, γδ T cells, natural killer, B-cells, plasmacytoid dendritic cells, and regulatory T cells (Tregs). The role of LAG-3 as a negative regulator of T cell responses is based on studies with LAG-3 knockout mice and use of blocking anti-LAG-3 antibodies in model in vitro and in vivo systems. Sierro et al. (2010), op. ci.; Hannier et al., *J. Immunol*, 161:4058-65 (1998); Macon-Lemaitre et al., *Immunology*, 115:170-8 (2005); Workman et al., *Eur J. Immunol.*, 33:970-9 (2003). Both natural and induced Tregs express increased LAG-3, which is required for their maximal suppressive function. Camisaschi et al., *J. Immunol.*, 184:6545-6551 (2010); Huang, et al., *Immunity*, 21:503-513 (2004). Furthermore, ectopic expression of LAG-3 on CD4+ effector T cells reduces their proliferative capacity and confers on them regulatory potential against third party T cells. Huang, ibid. Recent studies have also shown that high LAG-3 expression on exhausted lymphocytic choriomeningitis virus (LCMV)-specific CD8+ T cells contributes to their unresponsive state and limits CD8+ T cell antitumor responses. Blackburn et al., *Nat Immunol.*, 10:29-37 (2009) and Grosso et al., *J. Clin. Invest.*, 117:3383-3392 (2007).

The important role LAG-3 plays in antitumor immune response and immune response to infection makes it a target of interest for immunotherapy. Blocking LAG-3 with antagonists, including monoclonal antibodies, has been proposed for treatment of certain cancers and chronic viral infections. Turnis et al., *Eur J. Immunol.*, 45:1892-1905 (2015).

As the importance of PD-1- and LAG-3-mediated signaling becomes better understood, there is an ongoing need for discovery of new inhibitory anti-PD-1 and anti-LAG-3 antibodies that can effectively alter T cell functionality or increase the reactivity of tumor cells to immune effector cells. Moreover, the design of bispecific molecules that could combine the effects of PD-1 and LAG-3 inhibition would also be a desirable improvement in therapeutic approaches to cancer treatment.

SUMMARY OF THE INVENTION

The present invention provides new antibodies that bind to PD-1 with high affinity and new antibodies that bind to LAG-3 with high affinity. The invention also provides PD-1/LAG-3 bispecific Fabs-in-Tandem immunoglobulins (FIT-Igs) that are reactive with both PD-1 and LAG-3. Antibodies and bispecific binding proteins of the present invention can block LAG-3 on TILs to reduce the Tumor-infiltrated Treg cells population or to recover TILs to a cytotoxic phenotype. Additionally, antibodies and bispecific binding proteins of the invention can be used for inhibiting PD-1/PD-L1 signaling, in order to reactivate tumor infiltrated cytotoxic T cells. The bispecific, multivalent binding proteins described herein will be useful as PD-1/LAG-3 bispecific inhibitors to provide a synergistic combination effect to overcome antitumor immune suppression and thereby improve outcomes even for patients that do not respond or have stopped responding to anti-PD-1 or anti-LAG-3 therapies alone.

The invention also provides methods of making and using the anti-PD-1 and anti-LAG-3 antibodies and PD-1/LAG-3 bispecific binding proteins described herein as well as various compositions that may be used in methods of detecting PD-1 and/or LAG-3 in a sample or in methods of treating or preventing a disorder in an individual that is associated with PD-1 and/or LAG-3 activity.

In a further embodiment, the invention provides a bispecific Fabs-in-Tandem immunoglobulin (FIT-Ig) binding protein comprising first, second, and third polypeptide chains, wherein said first polypeptide chain comprises, from amino to carboxyl terminus, (i) $VL_A$-CL-$VH_B$-CH1-Fc wherein CL is directly fused to $VH_B$, or (ii) $VH_B$-CH1-$VL_A$-CL-Fc wherein CH1 is directly fused to $VL_A$;

wherein said second polypeptide chain comprises, from amino to carboxyl terminus, $VH_A$-CH1; and wherein said third polypeptide chain comprises, from amino to carboxyl terminus, $VL_B$-CL;

wherein VL is a light chain variable domain, CL is a light chain constant domain, VH is a heavy chain variable domain, CH1 is a heavy chain constant domain, Fc is an immunoglobulin Fc region, A is an epitope of PD-1 or LAG-3 and B is an epitope of PD-1 or LAG-3, with the proviso that A and B are different. In accordance with the present invention, such FIT-Ig binding proteins bind to both PD-1 and LAG-3.

In preferred embodiments, the Fab fragments of such FIT-Ig binding proteins incorporate $VL_A$-CL and $VH_A$-CH1 domains from a parental antibody binding to one of the antigen targets PD-1 or LAG-3, and incorporate $VL_B$-CL and $VH_B$-CH1 domains from a different parental antibody binding to the other of the antigen targets PD-1 and LAG-3. Thus, VH-CH1/VL-CL pairing will result in tandem Fab moieties recognizing PD-1 and LAG-3.

In accordance with the present invention, a PD-1/LAG-3 FIT-Ig binding protein may advantageously comprise first, second, and third polypeptide chains, wherein said first polypeptide chain comprises, from amino to carboxyl terminus, $VL_{PD-1}$-CL-$VH_{LAG-3}$-CH1-Fc wherein CL is directly fused to $VH_{LAG-3}$, wherein said second polypeptide chain comprises, from amino to carboxyl terminus, $VH_{PD-1}$-CH1; and wherein said third polypeptide chain comprises, from amino to carboxyl terminus, $VL_{LAG-3}$-CL; wherein $VL_{PD-1}$ is a light chain variable domain of an anti-PD-1 antibody, CL is a light chain constant domain, $VH_{PD-1}$ is a heavy chain variable domain of an anti-PD-1 antibody, CH1 is a heavy chain constant domain, $VL_{LAG-3}$ is a light chain variable domain of an anti-LAG-3 antibody, $VH_{LAG-3}$ is a heavy chain variable domain of an anti-LAG-3 antibody, and Fc is an immunoglobulin Fc region. Advantageously, in the first polypeptide chain, the domains $VL_{PD-1}$-CL are the same as the light chain of an anti-PD-1 parental antibody, the domains $VH_{PD-1}$-CH1 are the same as the heavy chain variable and heavy chain constant domains of an anti-PD-1 parental antibody, the domains $VL_{LAG-3}$-CL are the same as the light chain of an anti-LAG-3 parental antibody, and the domains $VH_{LAG-3}$-CH1 are the same as the heavy chain variable and heavy chain constant domains of an anti-LAG-3 parental antibody.

In alternative embodiments, a PD-1/LAG-3 FIT-Ig binding protein may advantageously comprise first, second, and third polypeptide chains, wherein said first polypeptide chain comprises, from amino to carboxyl terminus, $VL_{LAG-3}$-CL-$VH_{PD-1}$-CH1-Fc wherein CL is directly fused to $VH_{PD-1}$, wherein said second polypeptide chain comprises, from amino to carboxyl terminus, $VH_{LAG-3}$-CH1; and wherein said third polypeptide chain comprises, from amino to carboxyl terminus, $VL_{PD-1}$-CL; wherein $VL_{PD-1}$ is a light chain variable domain of an anti-PD-1 antibody, CL is a light chain constant domain, $VH_{PD-1}$ is a heavy chain variable domain of an anti-PD-1 antibody, CH1 is a heavy chain constant domain, $VL_{LAG-3}$ is a light chain variable domain of an anti-LAG-3 antibody, $VH_{LAG-3}$ is a heavy chain variable domain of an anti-LAG-3 antibody, and Fc is an immunoglobulin Fc region. Advantageously, in the first polypeptide chain, the domains $VL_{LAG-3}$-CL are the same as the light chain of an anti-LAG-3 parental antibody, the domains $VH_{LAG-3}$-CH1 are the same as the heavy chain variable and heavy chain constant domains of an anti-LAG-3 parental antibody, the domains $VL_{PD-1}$-CL are the same as the light chain of an anti-PD-1 parental antibody, and the domains $VH_{PD-1}$-CH1 are the same as the heavy chain variable and heavy chain constant domains of an anti-PD-1 parental antibody.

In alternative embodiments, a PD-1/LAG-3 FIT-Ig binding protein may advantageously comprise first, second, and third polypeptide chains, wherein said first polypeptide chain comprises, from amino to carboxyl terminus, $VH_{LAG-3}$-CH1-$VL_{PD-1}$-CL-Fc wherein CH1 is directly fused to $VL_{PD-1}$, wherein said second polypeptide chain comprises, from amino to carboxyl terminus, $VL_{LAG-3}$-CL; and wherein said third polypeptide chain comprises, from amino to carboxyl terminus, $VH_{PD-1}$-CH1; wherein $VL_{PD-1}$ is a light chain variable domain of an anti-PD-1 antibody, CL is a light chain constant domain, $VH_{PD-1}$ is a heavy chain variable domain of an anti-PD-1 antibody, CH1 is a heavy chain constant domain, $VL_{LAG-3}$ is a light chain variable domain of an anti-LAG-3 antibody, $VH_{LAG-3}$ is a heavy chain variable domain of an anti-LAG-3 antibody, and Fc is an immunoglobulin Fc region. Advantageously, in the first polypeptide chain, the domains $VL_{LAG-3}$-CL are the same as the light chain of an anti-LAG-3 parental antibody, the domains $VH_{LAG-3}$-CH1 are the same as the heavy chain variable and heavy chain constant domains of an anti-LAG-3 parental antibody, the domains $VL_{PD-1}$-CL are the same as the light chain of an anti-PD-1 parental antibody, and the domains $VH_{PD-1}$-CH1 are the same as the heavy chain variable and heavy chain constant domains of an anti-PD-1 parental antibody.

In alternative embodiments, a PD-1/LAG-3 FIT-Ig binding protein may advantageously comprise first, second, and third polypeptide chains, wherein said first polypeptide chain comprises, from amino to carboxyl terminus, $VH_{PD-1}$-CH1-$VL_{LAG-3}$-CL-Fc wherein CH1 is directly fused to $VL_{LAG-3}$, wherein said second polypeptide chain comprises, from amino to carboxyl terminus, $VL_{PD-1}$-CL; and wherein said third polypeptide chain comprises, from amino to carboxyl terminus, $VH_{LAG-3}$-CH1; wherein $VL_{PD-1}$ is a light chain variable domain of an anti-PD-1 antibody, CL is a light chain constant domain, $VH_{PD-1}$ is a heavy chain variable domain of an anti-PD-1 antibody, CH1 is a heavy chain constant domain, $VL_{LAG-3}$ is a light chain variable domain of an anti-LAG-3 antibody, $VH_{LAG-3}$ is a heavy chain variable domain of an anti-LAG-3 antibody, and Fc is an immunoglobulin Fc region. Advantageously, in the first polypeptide chain, the domains $VL_{LAG-3}$-CL are the same as the light chain of an anti-LAG-3 parental antibody, the domains $VH_{LAG-3}$-CH are the same as the heavy chain variable and heavy chain constant domains of an anti-LAG-3 parental antibody, the domains $VL_{PD-1}$-CL are the same as the light chain of an anti-PD-1 parental antibody, and the domains $VH_{PD-1}$-CH1 are the same as the heavy chain variable and heavy chain constant domains of an anti-PD-1 parental antibody.

In the foregoing formulas for the first polypeptide chain of a FIT-Ig binding protein, an Fc region may be a native or a variant Fc region. In particular embodiments, the Fc region is a human Fc region from IgG1, IgG2, IgG3, IgG4, IgA, IgM, IgE, or IgD. In particular embodiments, the Fc is a human Fc from IgG1, or a modified human Fc such as set forth in Table 6, infra (SEQ ID NO:28).

In an embodiment of the invention, FIT-Ig binding proteins of the present invention retain one or more properties of parental antibodies from which the sequences of their Fab fragments are utilized and incorporated into the FIT-Ig structure. In preferred embodiments, the FIT-Ig will retain binding affinity for the target antigens (i.e., LAG-3 and PD-1) comparable to that of the parental antibodies, meaning that the binding affinity of the FIT-Ig binding protein for the PD-1 and LAG-3 antigen targets does not vary by greater than 10-fold in comparison to the binding affinity of the parental antibodies for their respective target antigens, as measured by surface plasmon resonance or biolayer interferometry.

In one embodiment, a FIT-Ig binding protein of the present invention binds PD-1 and LAG-3 and is comprised of a first polypeptide chain comprising, consisting essentially of, or consisting of the sequence of amino acids 23-679 of SEQ ID NO:78; a second polypeptide chain comprising, consisting essentially of, or consisting of the sequence of amino acids 20-240 of SEQ ID NO:83; and a third polypeptide chain comprising, consisting essentially of, or consisting of the sequence of amino acids 23-236 of SEQ ID NO:86. (See Table 27.)

In a further embodiment, a FIT-Ig binding protein of the present invention binds PD-1 and LAG-3 and is comprised of a first polypeptide chain comprising, consisting essentially of, or consisting of the sequence of amino acids 23-684 of SEQ ID NO:88; a second polypeptide chain comprising, consisting essentially of, or consisting of the sequence of amino acids 20-235 of SEQ ID NO:91; and a third polypeptide chain comprising, consisting essentially of, or consisting of the sequence of amino acids 23-236 of SEQ ID NO:93. (See Table 28.)

In a further embodiment, a FIT-Ig binding protein of the present invention binds PD-1 and LAG-3 and is comprised of a first polypeptide chain comprising, consisting essentially of, or consisting of the sequence of amino acids 23-679 of SEQ ID NO:95; a second polypeptide chain comprising, consisting essentially of, or consisting of the sequence of amino acids 20-242 of SEQ ID NO:98; and a third polypeptide chain comprising, consisting essentially of, or consisting of the sequence of amino acids 23-236 of SEQ ID NO:100. (See Table 29.)

In a further embodiment, a FIT-Ig binding protein of the present invention binds PD-1 and LAG-3 and is comprised of a first polypeptide chain comprising, consisting essentially of, or consisting of the sequence of amino acids 23-684 of SEQ ID NO:102; a second polypeptide chain comprising, consisting essentially of, or consisting of the sequence of amino acids 20-235 of SEQ ID NO:105; and a third polypeptide chain comprising, consisting essentially of, or consisting of the sequence of amino acids 23-236 of SEQ ID NO:107. (See Table 30.)

In a further embodiment, a FIT-Ig binding protein of the present invention binds PD-1 and LAG-3 and is comprised of a first polypeptide chain comprising, consisting essentially of, or consisting of the sequence of amino acids 23-679 of SEQ ID NO:140; a second polypeptide chain comprising, consisting essentially of, or consisting of the sequence of amino acids of SEQ ID NO:144; and a third polypeptide chain comprising, consisting essentially of, or consisting of the sequence of amino acids of SEQ ID NO:146. (See FIT107-1-6a-1; Table 41.)

In a further embodiment, a FIT-Ig binding protein of the present invention binds PD-1 and LAG-3 and is comprised of a first polypeptide chain comprising, consisting essentially of, or consisting of the sequence of amino acids 23-684 of SEQ ID NO:147; a second polypeptide chain comprising, consisting essentially of, or consisting of the sequence of amino acids of SEQ ID NO:151; and a third polypeptide chain comprising, consisting essentially of, or consisting of the sequence of amino acids of SEQ ID NO:153. (See FIT-107-1-6b-1; Table 42.)

In a further embodiment, a FIT-Ig binding protein of the present invention binds PD-1 and LAG-3 and is comprised of a first polypeptide chain comprising, consisting essentially of, or consisting of the sequence of amino acids 23-679 of SEQ ID NO:154; a second polypeptide chain comprising, consisting essentially of, or consisting of the sequence of amino acids of SEQ ID NO:158; and a third polypeptide chain comprising, consisting essentially of, or consisting of the sequence of amino acids of SEQ ID NO:160. (See FIT-107-1-6a-2; Table 43.)

In a further embodiment, a FIT-Ig binding protein of the present invention binds PD-1 and LAG-3 and is comprised of a first polypeptide chain comprising, consisting essentially of, or consisting of the sequence of amino acids 23-684 of SEQ ID NO:161; a second polypeptide chain comprising, consisting essentially of, or consisting of the sequence of amino acids of SEQ ID NO:165; and a third polypeptide chain comprising, consisting essentially of, or consisting of the sequence of amino acids of SEQ ID NO:167. (See FIT-107-1-6b-2; Table 44.)

In a further embodiment, a FIT-Ig binding protein of the present invention binds PD-1 and LAG-3 and is comprised of a first polypeptide chain comprising, consisting essentially of, or consisting of the sequence of amino acids 23-679 of SEQ ID NO:168; a second polypeptide chain comprising, consisting essentially of, or consisting of the sequence of amino acids of SEQ ID NO:172; and a third polypeptide chain comprising, consisting essentially of, or consisting of the sequence of amino acids of SEQ ID NO:174. (See FIT-107-1-6a-3; Table 45.)

In a further embodiment, a FIT-Ig binding protein of the present invention binds PD-1 and LAG-3 and is comprised of a first polypeptide chain comprising, consisting essentially of, or consisting of the sequence of amino acids 23-684 of SEQ ID NO:175; a second polypeptide chain comprising, consisting essentially of, or consisting of the sequence of amino acids of SEQ ID NO:179; and a third polypeptide chain comprising, consisting essentially of, or consisting of the sequence of amino acids of SEQ ID NO:181. (See FIT-107-1-6b-3; Table 46.)

In a further embodiment, a FIT-Ig binding protein of the present invention binds PD-1 and LAG-3 and is comprised of a first polypeptide chain comprising, consisting essentially of, or consisting of the sequence of amino acids 23-679 of SEQ ID NO:182; a second polypeptide chain comprising, consisting essentially of, or consisting of the sequence of amino acids of SEQ ID NO:186; and a third polypeptide chain comprising, consisting essentially of, or consisting of the sequence of amino acids of SEQ ID NO:188. (See FIT-107-1-7a-1; Table 47.)

In a further embodiment, a FIT-Ig binding protein of the present invention binds PD-1 and LAG-3 and is comprised of a first polypeptide chain comprising, consisting essentially of, or consisting of the sequence of amino acids 23-687 of SEQ ID NO:189; a second polypeptide chain comprising, consisting essentially of, or consisting of the sequence of amino acids of SEQ ID NO:193; and a third polypeptide chain comprising, consisting essentially of, or consisting of the sequence of amino acids of SEQ ID NO:195. (See FIT-107-1-7b-1; Table 48.)

In a further embodiment, a FIT-Ig binding protein of the present invention binds PD-1 and LAG-3 and is comprised of a first polypeptide chain comprising, consisting essentially of, or consisting of the sequence of amino acids 23-679 of SEQ ID NO:196; a second polypeptide chain comprising, consisting essentially of, or consisting of the sequence of amino acids of SEQ ID N0:200; and a third polypeptide chain comprising, consisting essentially of, or consisting of the sequence of amino acids of SEQ ID NO:202. (See FIT-107-1-7a-2; Table 49.)

In a further embodiment, a FIT-Ig binding protein of the present invention binds PD-1 and LAG-3 and is comprised of a first polypeptide chain comprising, consisting essentially of, or consisting of the sequence of amino acids 23-687 of SEQ ID NO:203; a second polypeptide chain comprising, consisting essentially of, or consisting of the sequence of amino acids of SEQ ID NO:207; and a third polypeptide chain comprising, consisting essentially of, or consisting of the sequence of amino acids of SEQ ID NO:209. (See FIT-107-1-7b-2; Table 50.)

In a further embodiment, a FIT-Ig binding protein of the present invention binds PD-1 and LAG-3 and is comprised of a first polypeptide chain comprising, consisting essentially of, or consisting of the sequence of amino acids 23-679 of SEQ ID NO: 10; second polypeptide chain comprising, consisting essentially of, or consisting of the sequence of amino acids of SEQ ID NO:214; and third polypeptide chain comprising, consisting essentially of or consisting of the sequence of amino acids of SEQ ID NO:216. (See FIT107-1-7a-3; Table 51.)

In a further embodiment, a FT-Ig binding protein of the present invention binds PD-1 and LAG-3 and is comprised of a first poly peptide chain comprising, consisting essentially of, or consisting of the sequence of amino acids 23-687 of SEQ ID NO: 217; second polypeptide chain comprising consisting essentially of or consisting of the sequence of amino acids of SEQ ID NO:221; and a third polypeptide chain comprising, consisting essentially of, or consisting of the sequence of amino acids of SEQ ID NO:223. (See FIT107-1-7b-3; Table 52.)

The invention also provides novel antibodies capable of binding human PD-1, wherein the antigen-binding domain of the antibody comprises a set of six CDRs, i.e., CDR-H1, CDR-H2, CDR-H3, CDR-L1, CDR-L2, and CDR-L3, selected from the group of CDR sets defined below:

| CDR Set No. | CDR | CDR Amino Acid Sequence | SEQ ID NO: |
|---|---|---|---|
| 1 | CDR-H1 | SYMMS | residues 31-35 of SEQ ID NO: 4 |
|  | CDR-H2 | SMSGGGRDTYYPDSVKG | residues 50-66 of SEQ ID NO: 4 |
|  | CDR-H3 | RGTYAMDY | residues 99-106 of SEQ ID NO: 4 |
|  | CDR-L1 | LASQTIGTWLT | residues 24-34 of SEQ ID NO: 5 |
|  | CDR-L2 | AATSLAD | residues 50-56 of SEQ ID NO: 5 |
|  | CDR-L3 | QQLYSTPWT | residues 89-97 of SEQ ID NO: 5 |

-continued

| CDR Set No. | CDR | Amino Acid Sequence | SEQ ID NO: |
|---|---|---|---|
| 2 | CDR-H1 | TGYYWN | residues 31-36 of SEQ ID NO: 6 |
|   | CDR-H2 | YMSYDGNNNYNPSLKN | residues 51-66 of SEQ ID NO: 6 |
|   | CDR-H3 | DRGTTILGGTMDY | residues 99-111 of SEQ ID NO: 6 |
|   | CDR-L1 | KASQSVSNDVA | residues 24-34 of SEQ ID NO: 7 |
|   | CDR-L2 | YAFYRYT | residues 50-56 of SEQ ID NO: 7 |
|   | CDR-L3 | QQDYSSPWT | residues 89-97 of SEQ ID NO: 7 |
| 3 | CDR-H1 | FYTMS | residues 31-35 of SEQ ID NO: 8 |
|   | CDR-H2 | TISGGGRDTYYPDSVKG | residues 50-66 of SEQ ID NO: 8 |
|   | CDR-H3 | QGGNYLFAY | residues 99-107 of SEQ ID NO: 8 |
|   | CDR-L1 | KASQDVNTVVA | residues 24-34 of SEQ ID NO: 9 |
|   | CDR-L2 | WASTRHT | residues 50-56 of SEQ ID NO: 9 |
|   | CDR-L3 | QQHYTTPYT | residues 89-97 of SEQ ID NO: 9 |
| 4 | CDR-H1 | DYGMH | residues 31-35 of SEQ ID NO: 10 |
|   | CDR-H2 | YISSGSYTIYYADTVKG | residues 50-66 of SEQ ID NO: 10 |
|   | CDR-H3 | RGGSSHVNVMDY | residues 99-110 of SEQ ID NO: 10 |
|   | CDR-L1 | KASDHINNWLA | residues 24-34 of SEQ ID NO: 11 |
|   | CDR-L2 | GATSLET | residues 50-56 of SEQ ID NO: 11 |
|   | CDR-L3 | QQYWSPPYT | residues 89-97 of SEQ ID NO: 11 |
| 5 | CDR-H1 | DNNVE | residues 31-35 of SEQ ID NO: 12 |
|   | CDR-H2 | DINPNNGDTLYSQYFKD | residues 50-66 of SEQ ID NO: 12 |
|   | CDR-H3 | GKSDQFDY | residues 99-106 of SEQ ID NO: 12 |
|   | CDR-L1 | LASQTIGTWLA | residues 24-34 of SEQ ID NO: 13 |
|   | CDR-L2 | AATSLAD | residues 50-56 of SEQ ID NO: 13 |
|   | CDR-L3 | QQLYSSPWT | residues 89-97 of SEQ ID NO: 13 |
| 6 | CDR-H1 | SYAMS | residues 31-35 of SEQ ID NO: 14 |
|   | CDR-H2 | TISGGGRDTYYPDSVKG | residues 50-66 of SEQ ID NO: 14 |
|   | CDR-H3 | QGGTYLFAS | residues 99-107 of SEQ 1D NO: 14 |
|   | CDR-L1 | KASQDVNTAVA | residues 24-34 of SEQ ID NO: 15 |
|   | CDR-L2 | WASTRHT | residues 50-56 of SEQ ID NO: 15 |
|   | CDR-L3 | QQHYTTPYT | residues 89-97 of SEQ ID NO: 15 |
| 7 | CDR-H1 | DYEMH | residues 31-35 of SEQ ID NO: 16 |
|   | CDR-H2 | VIEPESGGTVYNQKFKG | residues 51-66 of SEQ ID NO: 16 |
|   | CDR-H3 | EGFNSDHYFDY | residues 99-109 of SEQ ID NO: 16 |
|   | CDR-L1 | RSSQNIVHSNGNTYLE | residues 24-39 of SEQ ID NO: 17 |
|   | CDR-L2 | KVFNRFS | residues 55-61 of SEQ ID NO: 17 |
|   | CDR-L3 | FQGSHVPYT | residues 94-102 of SEQ ID NO: 17 |
| 8 | CDR-H1 | SHLMS | residues 31-35 of SEQ ID NO: 18 |
|   | CDR-H7 | AISGGGADTYYPDSVKG | residues 50-66 of SEQ ID NO: 18 |
|   | CDR-H3 | QILAFDS | residues 99-105 of SEQ ID NO: 18 |
|   | CDR-L1 | HASQNIYVWLN | residues 24-34 of SEQ ID NO: 19 |
|   | CDR-L2 | KASNLHT | residues 50-56 of SEQ ID NO: 19 |
|   | CDR-L3 | QQGQSYPWT | residues 89-97 of SEQ ID NO: 19 |
| 9 | CDR-H1 | SHLMS | residues 31-35 of SEQ ID NO: 53 |
|   | CDR-H2 | AISGGGADTYYPASVKG | residues 50-66 of SEQ ID NO: 53 |
|   | CDR-H3 | QILAFDA | residues 99-105 of SEQ ID NO: 53 |
|   | CDR-L1 | HASQNIYVWLN | residues 24-34 of SEQ ID NO: 19 |
|   | CDR-L2 | KASNLHT | residues 50-56 of SEQ ID NO: 19 |
|   | CDR-L3 | QQGQSYPWT | residues 89-97 of SEQ ID NO: 19 |

The invention also provides novel antibodies capable of binding human LAG-3, wherein the antigen-binding domain of the antibody comprises a set of six CDRs, i.e., CDR-H1, CDR-H2, CDR-H3, CDR-L1, CDR-L2, and CDR-L3, selected from the group of CDR sets defined below:

| CDR Set No. | CDR | Amino Acid Sequence | SEQ ID NO: |
|---|---|---|---|
| 10 | CDR-H1 | DDYMH | residues 31-35 of SEQ ID NO: 60 |
|    | CDR-H2 | WIVPENGNTEYASKFQG | residues 50-66 of SEQ ID NO: 60 |
|    | CDR-H3 | YGDY | residues 99-102 of SEQ ID NO: 60 |
|    | CDR-L1 | RASQEISGYLS | residues 24-34 of SEQ ID NO: 61 |
|    | CDR-L2 | AASTLDS | residues 50-56 of SEQ ID NO: 61 |
|    | CDR-L3 | LQYASYPLT | residues 89-97 of SEQ ID NO: 61 |

-continued

| CDR Set No. | CDR | Amino Acid Sequence | SEQ ID NO: |
|---|---|---|---|
| 11 | CDR-H1 | DDYMH | residues 31-35 of SEQ ID NO: 60 |
| | CDR-H2 | WIVPENGNTEYASKFQG | residues 50-66 of SEQ ID NO: 60 |
| | CDR-H3 | YGDY | residues 99-102 of SEQ ID NO: 60 |
| | CDR-L1 | RASQEISGYLS | residues 24-34 of SEQ ID NO: 62 |
| | CDR-L2 | AASTLDS | residues 50-56 of SEQ ID NO: 62 |
| | CDR-L3 | LQYASYPLT | residues 89-97 of SEQ ID NO: 62 |
| 12 | CDR-H1 | DYEMH | residues 31-35 of SEQ ID NO: 63 |
| | CDR-H2 | AIDPETGGTAYNQKFKG | residues 50-66 of SEQ ID NO: 63 |
| | CDR-H3 | WGSTVFPY | residues 101-108 of SEQ ID NO: 63 |
| | CDR-L1 | KSTKSLLNSDGFTYLD | residues 24-39 of SEQ ID NO: 64 |
| | CDR-L2 | LVSNRFS | residues 55-61 of SEQ ID NO: 64 |
| | CDR-L3 | FQSNYLPWT | residues 94-102 of SEQ ID NO: 64 |
| 13 | CDR-H1 | DYEMH | residues 31-35 of SEQ ID NO: 65 |
| | CDR-H2 | AIHDPATGGTAYNQKFKG | residues 50-66 of SEQ ID NO: 65 |
| | CDR-H3 | WGTTVFPY | residues 99-106 of SEQ ID NO: 65 |
| | CDR-L1 | KSTKSLLNSDGFTYLD | residues 24-39 of SEQ ID NO: 66 |
| | CDR-L2 | LVSNRFS | residues 55-61 of SEQ ID NO: 66 |
| | CDR-L3 | FQSNYLPWT | residues 94-102 of SEQ ID NO: 66 |
| 14 | CDR-H1 | DDYMH | residues 31-35 of SEQ ID NO: 67 |
| | CDR-H2 | WIDPENGDTEYASKFQG | residues 50-66 of SEQ ID NO: 67 |
| | CDR-H3 | FDY | residues 99-101 of SEQ ID NO: 67 |
| | CDR-L1 | KSSQSLLDSDGKTYLN | residues 24-39 of SEQ ID NO: 68 |
| | CDR-L2 | LVSKLDS | residues 55-61 of SEQ ID NO: 68 |
| | CDR-L3 | WQGSHFPQT | residues 94-102 of SEQ ID NO: 68 |
| 15 | CDR-H1 | DDYVH | residue 31-35 of SEQ ID NO: 69 |
| | CDR-H2 | WIDPENGDTEYASKFQG | residues 50-66 of SEQ ID NO: 69 |
| | CDR-H3 | WDAEENY | residues 99-105 of SEQ ID NO: 69 |
| | CDR-L1 | RSSKSLLHSNGNTYLY | residues 24-39 of SEQ ID NO: 70 |
| | CDR-L2 | RMSNLAS | residues 55-61 of SEQ ID NO: 70 |
| | CDR-L3 | MQHLEYPFT | residues 94-102 of SEQ ID NO: 70 |
| 16 | CDR-H1 | DDYIH | residues 31-35 of SEQ ID NO: 71 |
| | CDR-H2 | WIDPENGDTEYASKFQG | residues 50-66 of SEQ ID NO: 71 |
| | CDR-H3 | DYRNWY | residues 100-105 of SEQ ID NO: 71 |
| | CDR-L1 | KSSQSLLDSDGKTYLN | residues 24-39 of SEQ ID NO: 68 |
| | CDR-L2 | LVSKLDS | residues 55-61 of SEQ ID NO: 68 |
| | CDR-L3 | WQGSHFPQT | residues 94-102 of SEQ ID NO :68 |
| 17 | CDR-H1 | DFNIKDDYMH | residues 26-35 of SEQ ID NO: 114 |
| | CDR-H2 | WIVPENGNTEYASKFQG | residues 50-66 of SEQ ID NO: 114 |
| | CDR-H3 | YGDY | residues 99-102 of SEQ ID NO: 114 |
| | CDR-L1 | RASQEISGYLS | residues 24-34 of SEQ ID NO: 117 |
| | CDR-L2 | AASTLDS | residues 50-56 of SEQ ID NO: 117 |
| | CDR-L3 | LQYASYPLT | residues 89-97 of SEQ ID NO: 117 |
| 18 | CDR-H1 | DDYMH | residues 31-35 of SEQ ID NO: 72 |
| | CDR-H2 | WIVPENGNTEYASKFQG | residues 50-66 of SEQ ID NO: 72 |
| | CDR-H3 | YGDY | residues 99-102 of SEQ ID NO: 72 |
| | CDR-L1 | RASQEISGYLS | residues 24-34 of SEQ ID NO: 77 |
| | CDR-L2 | AASTLDS | residues 50-56 of SEQ ID NO: 77 |
| | CDR-L3 | LQYASYPLT | residues 89-97 of SEQ ID NO: 77 |
| 19 | CDR-H1 | DDYMH | residues 30-34 of SEQ ID NO: 119 |
| | CDR-H2 | WIVPENGNTVYASKFQG | residues 48-64 of SEQ ID NO: 119 |
| | CDR-H3 | YGDY | residues 95-98 of SEQ ID NO: 119 |
| | CDR-LI | RASQEISGYLS | residues 24-34 of SEQ ID NO: 120 |
| | CDR-L2 | AASALDS | residues 50-56 of SEQ ID NO: 120 |
| | CDR-L3 | LQYASYPLT | residues 89-97 of SEQ ID NO: 120 |
| 20 | CDR-H1 | DDYMH | residues 31-35 of SEQ ID NO: 121 |
| | CDR-H2 | WIVPENGNTEYASKFQG | residues 50-66 of SEQ ID NO: 121 |
| | CDR-H3 | YGDY | residues 99-102 of SEQ ID NO: 121 |
| | CDR-L1 | RAMQEISGYLS | residues 24-34 of SEQ ID NO: 122 |
| | CDR-L2 | AASTLDS | residues 50-56 of SEQ ID NO: 122 |
| | CDR-L3 | LQYAYYPLT | residues 89-97 of SEQ ID NO: 122 |

| CDR Set No. | CDR | Amino Acid Sequence | SEQ ID NO: |
|---|---|---|---|
| 21 | CDR-H1 | DDYMH | residues 31-35 of SEQ ID NO: 123 |
|    | CDR-H2 | WIVPENGNTEYASKFQG | residues 50-66 of SEQ ID NO: 123 |
|    | CDR-H3 | YGDY | residues 99-102 of SEQ ID NO: 123 |
|    | CDR-L1 | RASQEISGYLS | residues 24-34 of SEQ ID NO: 124 |
|    | CDR-L2 | AASHLDS | residues 50-56 of SEQ ID NO: 124 |
|    | CDR-L3 | LQYASYPLT | residues 89-97 of SEQ ID NO: 124 |
| 22 | CDR-H1 | DDYMH | residues 31-35 of SEQ ID NO: 125 |
|    | CDR-H2 | WIVPENGLTEYASKFQG | residues 50-66 of SEQ ID NO: 125 |
|    | CDR-H3 | YGDY | residues 99-102 of SEQ ID NO: 125 |
|    | CDR-L1 | RASQEISGYLS | residues 24-34 of SEQ ID NO: 126 |
|    | CDR-L2 | ATSTLDS | residues 50-56 of SEQ ID NO: 126 |
|    | CDR-L3 | LQYASYPLT | residues 89-97 of SEQ ID NO: 126 |
| 23 | CDR-H1 | DDYMH | residues 31-35 of SEQ ID NO: 127 |
|    | CDR-H2 | WIVPENGKTEYASKFQG | residues 50-66 of SEQ ID NO: 127 |
|    | CDR-H3 | YGDY | residues 99-102 of SEQ ID NO: 127 |
|    | CDR-L1 | RASQEISGYLS | residues 24-34 of SEQ ID NO: 128 |
|    | CDR-L2 | AAMTLDS | residues 50-56 of SEQ ID NO: 128 |
|    | CDR-L3 | LQYASYPLT | residues 89-97 of SEQ ID NO: 128 |
| 24 | CDR-H1 | DDYMH | residues 31-35 of SEQ ID NO: 129 |
|    | CDR-H2 | WIVPENGNTHYASKFQG | residues 50-66 of SEQ ID NO: 129 |
|    | CDR-H3 | YGDY | residues 99-102 of SEQ ID NO: 129 |
|    | CDR-L1 | RASQEISGYLS | residues 24-34 of SEQ ID NO: 130 |
|    | CDR-L2 | EASTLDS | residues 50-56 of SEQ ID NO: 130 |
|    | CDR-L3 | LQYASVPLT | residues 89-97 of SEQ ID NO: 130 |
| 25 | CDR-H1 | DDYMH | residues 31-35 of SEQ ID NO: 131 |
|    | CDR-H2 | WIVPRNGNTMYASKFQG | residues 50-66 of SEQ ID NO: 131 |
|    | CDR-H3 | YGDY | residues 99-102 of SEQ ID NO: 131 |
|    | CDR-L1 | RASQEISGYLS | residues 24-34 of SEQ ID NO: 132 |
|    | CDR-L2 | AASTLDL | residues 50-56 of SEQ ID NO: 132 |
|    | CDR-L3 | LQYASYPLT | residues 89-97 of SEQ ID NO: 132 |
| 26 | CDR-H1 | DDYMH | residues 31-35 of SEQ ID NO: 135 |
|    | CDR-H2 | WIVPENANTVYASKFQG | SEQ ID NO: 224 |
|    | CDR-H3 | YGDY | residues 99-102 of SEQ ID NO: 135 |
|    | CDR-L1 | RASQEISGYLS | residues 24-34 of SEQ ID NO: 138 |
|    | CDR-L2 | AASALDS | residues 50-56 of SEQ ID NO: 138 |
|    | CDR-L3 | LQYASYPLT | residues 89-97 of SEQ ID NO: 138 |
| 27 | CDR-H1 | DDYMH | residues 31-35 of SEQ ID NO: 136 |
|    | CDR-H2 | WIVPRNANTVYASKFQG | SEQ 1D NO: 225 |
|    | CDR-H3 | YGDY | residues 99-102 of SEQ ID NO: 136 |
|    | CDR-L1 | RASQEISGYLS | residues 24-34 of SEQ ID NO: 139 |
|    | CDR-L2 | AASALDL | residues 50-56 of SEQ ID NO: 139 |
|    | CDR-L3 | LQYASYPLT | residues 89-97 of SEQ ID NO: 139 |
| 28 | CDR-H1 | DDYMH | residues 31-35 of SEQ ID NO: 136 |
|    | CDR-H2 | WIVPRNANTVYASTFQG | SEQ ID NO: 225 |
|    | CDR-H3 | YGDY | residues 99-102 of SEQ ID NO: 136 |
|    | CDR-L1 | RASQEISGYLS | residues 24-34 of SEQ ID NO: 117 |
|    | CDR-L2 | AASTLDS | residues 50-56 of SEQ ID NO: 117 |
|    | CDR-L3 | LQYASYPLT | residues 89-97 of SEQ ID NO: 117 |

In one embodiment, binding protein according to the invention is a bispecific, multivalent immunoglobulin binding protein comprising two or more antigen binding sites, wherein at least one antigen binding site comprises a CDR set selected from CDR Sets 1, 2, 3, and above and at least one antigen binding site comprises CDR Set above.

In an embodiment, an anti-PD-1 antibody according to the invention comprises VH and VL domains, wherein the two variable domains comprise amino acid sequences selected from the group consisting of:

SEQ ID NO: 4 and SEQ ID NO: 5   SEQ ID NO: 6 and SEQ ID NO: 7
SEQ ID NO: 8 and SEQ ID NO: 9   SEQ ID NO: 10 and SEQ ID NO: 11
SEQ ID NO: 12 and SEQ ID NO: 13 SEQ ID NO: 14 and SEQ ID NO: 15

-continued

SEQ ID NO: 16 and SEQ ID NO: 17 SEQ ID NO: 18 and SEQ ID NO: 19
SEQ ID NO: 20 and SEQ ID NO: 23 SEQ ID NO: 21 and SEQ ID NO: 23
SEQ ID NO: 22 and SEQ ID NO: 23 SEQ ID NO: 20 and SEQ ID NO: 24
SEQ ID NO: 21 and SEQ ID NO: 24 SEQ ID NO: 22 and SEQ ID NO: 24
SEQ ID NO: 20 and SEQ ID NO: 25 SEQ ID NO: 21 and SEQ ID NO: 25
SEQ ID NO: 22 and SEQ ID NO: 25 SEQ ID NO: 20 and SEQ ID NO: 26
SEQ ID NO: 21 and SEQ ID NO: 26 SEQ ID NO: 22 and SEQ ID NO: 26
SEQ ID NO: 20 and SEQ ID NO: 27 SEQ ID NO: 21 and SEQ ID NO: 27
SEQ ID NO: 22 and SEQ ID NO: 27 SEQ ID NO: 20 and SEQ ID NO: 34
SEQ ID NO: 31 and SEQ ID NO: 34 SEQ ID NO: 32 and SEQ ID NO: 34
SEQ ID NO: 33 and SEQ ID NO: 34 SEQ ID NO: 30 and SEQ ID NO: 35
SEQ ID NO: 31 and SEQ ID NO: 35 SEQ ID NO: 32 and SEQ ID NO: 35
SEQ ID NO: 33 and SEQ ID NO: 35 SEQ ID NO: 30 and SEQ ID NO: 36
SEQ ID NO: 31 and SEQ ID NO: 36 SEQ ID NO: 32 and SEQ ID NO: 36
SEQ ID NO: 33 and SEQ ID NO: 36 SEQ ID NO: 30 and SEQ ID NO: 37

-continued

SEQ ID NO: 31 and SEQ ID NO: 37 SEQ ID NO: 32 and SEQ ID NO: 37
SEQ ID NO: 33 and SEQ ID NO: 37 SEQ ID NO: 38 and SEQ ID NO: 43
SEQ ID NO: 39 and SEQ ID NO: 43 SEQ ID NO: 40 and SEQ ID NO: 43
SEQ ID NO: 41 and SEQ ID NO: 43 SEQ ID NO: 42 and SEQ ID NO: 43
SEQ ID NO: 38 and SEQ ID NO: 44 SEQ ID NO: 39 and SEQ ID NO: 44
SEQ ID NO: 40 and SEQ ID NO: 44 SEQ ID NO: 41 and SEQ ID NO: 44
SEQ ID NO: 42 and SEQ ID NO: 44 SEQ ID NO: 38 and SEQ ID NO: 45
SEQ ID NO: 39 and SEQ ID NO: 45 SEQ ID NO: 40 and SEQ ID NO: 45
SEQ ID NO: 41 and SEQ ID NO: 45 SEQ ID NO: 42 and SEQ ID NO: 45
SEQ ID NO: 38 and SEQ ID NO: 46 SEQ ID NO: 39 and SEQ ID NO: 46
SEQ ID NO: 40 and SEQ ID NO: 46 SEQ ID NO: 41 and SEQ ID NO: 46
SEQ ID NO: 42 and SEQ ID NO: 46 SEQ ID NO: 38 and SEQ ID NO: 47
SEQ ID NO: 39 and SEQ ID NO: 47 SEQ ID NO: 40 and SEQ ID NO: 47
SEQ ID NO: 41 and SEQ ID NO: 47 SEQ ID NO: 42 and SEQ ID NO: 47
SEQ ID NO: 48 and SEQ ID NO: 55 SEQ ID NO: 49 and SEQ ID NO: 55
SEQ ID NO: 50 and SEQ ID NO: 55 SEQ ID NO: 51 and SEQ ID NO: 55
SEQ ID NO: 52 and SEQ ID NO: 55 SEQ ID NO: 53 and SEQ ID NO: 55
SEQ ID NO: 54 and SEQ ID NO: 55 SEQ ID NO: 48 and SEQ ID NO: 56
SEQ ID NO: 49 and SEQ ID NO: 56 SEQ ID NO: 50 and SEQ ID NO: 56
SEQ ID NO: 51 and SEQ ID NO: 56 SEQ ID NO: 52 and SEQ ID NO: 56
SEQ ID NO: 53 and SEQ ID NO: 56 SEQ ID NO: 54 and SEQ ID NO: 56
SEQ ID NO: 48 and SEQ ID NO: 57 SEQ ID NO: 49 and SEQ ID NO: 57
SEQ ID NO: 50 and SEQ ID NO: 57 SEQ ID NO: 51 and SEQ ID NO: 57
SEQ ID NO: 52 and SEQ ID NO: 57 SEQ ID NO: 53 and SEQ ID NO: 57
SEQ ID NO: 54 and SEQ ID NO: 57.

In a further embodiment, an anti-LAG-3 antibody according to the invention comprises VH and VL domains, wherein the two variable domains comprise amino acid sequences selected from the group consisting of:

| | |
|---|---|
| SEQ ID NO: 60 and SEQ ID NO: 61 | SEQ ID NO: 60 and SEQ ID NO: 62 |
| SEQ ID NO: 63 and SEQ ID NO: 64 | SEQ ID NO: 65 and SEQ ID NO: 66 |
| SEQ ID NO: 67 and SEQ ID NO: 68 | SEQ ID NO: 69 and SEQ ID NO: 70 |
| SEQ ID NO: 71 and SEQ ID NO: 68 | SEQ ID NO: 74 and SEQ ID NO: 75 |
| SEQ ID NO: 74 and SEQ ID NO: 76 | SEQ ID NO: 74 and SEQ ID NO: 77 |
| SEQ ID NO: 72 and SEQ ID NO: 75 | SEQ ID NO: 72 and SEQ ID NO: 76 |
| SEQ ID NO: 72 and SEQ ID NO: 77 | SEQ ID NO: 73 and SEQ ID NO: 75 |
| SEQ ID NO: 73 and SEQ ID NO: 76 | SEQ ID NO: 73 and SEQ ID NO: 77 |
| SEQ ID NO: 121 and SEQ ID NO: 122 | SEQ ID NO: 123 and SEQ ID NO: 124 |
| SEQ ID NO: 125 and SEQ ID NO: 126 | SEQ ID NO: 127 and SEQ ID NO: 128 |
| SEQ ID NO: 129 and SEQ ID NO: 130 | SEQ ID NO: 131 and SEQ ID NO: 132 |
| SEQ ID NO: 135 and SEQ ID NO: 138 | SEQ ID NO: 136 and SEQ ID NO: 139 |
| SEQ ID NO: 136 and SEQ ID NO: 117 | SEQ ID NO: 226* and SEQ ID NO: 138 |
| SEQ ID NO: 227* and SEQ ID NO: 139 | SEQ ID NO: 227* and SEQ ID NO: 117 |

* wherein SEQ ID NO: 226 is the same as SEQ ID NO: 135 except with an Ala (A) instead of Gly (G) at amino acid 56 (G55A substitution by Kabat numbering); and SEQ ID NO: 227 is the same as SEQ ID NO: 136 except with an Ala (A) instead of Gly (G) at amino acid 56 (G55A substitution by Kabat numbering).

In another embodiment, an anti-PD-1 antibody or an anti-LAG-3 antibody may be used to make derivative binding proteins recognizing the same target antigen by techniques well established in the field. Such a derivative may be, e.g., a single-chain antibody (scFv), a Fab fragment (Fab), an Fab' fragment, an F(ab')$_2$, an Fv, and a disulfide linked Fv.

In another aspect of the invention, an antibody or bispecific binding protein described herein is capable of modulating a biological function of PD-1, LAG-3, or both. In another aspect, an anti-PD-1 antibody described herein is capable of inhibiting PD-1/PD-L1 signaling. Signal inhibition can be measured in a mixed lymphocyte reaction assay, such as performed in the working examples, infra. In another aspect, an anti-LAG-3 antibody described herein is capable of inhibiting MHC Class II/LAG-3 interaction. Such inhibition can be measured in a PBMC SEB activation assay, such as performed in the working examples, infra. In another aspect, bispecific PD-1/LAG-3 FIT-Ig binding protein described herein is capable of inhibiting both PD-1/PD-L1 signaling and MHC Class II/LAG-3 interaction.

In an embodiment, an anti-PD-1 antibody described herein or an antigen-binding fragment thereof has an on rate constant ($k_{on}$) to human PD-1 of at least $1 \times 10^4$ M$^{-1}$ s$^{-1}$, at least $3 \times 10^4$ M$^{-1}$ s$^{-1}$, at least $5 \times 10^4$ M$^{-1}$ s$^{-1}$, at least $7 \times 10^4$ M$^{-1}$ s$^{-1}$, at least $9 \times 10^4$ M$^{-1}$ s$^{-1}$, at least $1 \times 10^5$ M$^{-1}$ s$^{-1}$, at least $1.1 \times 10^5$ M$^{-1}$ s$^{-1}$, at least $1 \times 10^5$ M$^{-1}$ s$^{-1}$, at least $1.25 \times 10^5$ M$^{-1}$ s$^{-1}$, at least $1.4 \times 10^5$ M$^{-1}$ s$^{-1}$, at least $1.5 \times 10^5$ M$^{-1}$ s$^{-1}$, at least $3 \times 10^5$ M$^{-1}$ s$^{-1}$ or more, as measured by surface plasmon resonance or biolayer interferometry.

In another embodiment, an anti-PD-1 antibody described herein or antigen-binding fragment thereof has an off rate constant ($k_{off}$) to human PD-1 of less than $1 \times 10^{-5}$ s$^{-1}$, less than $5 \times 10^4$ s$^{-1}$, less than $3 \times 10^{-4}$ s$^{-1}$, less than $1 \times 10^{-4}$ s$^{-1}$, less than $8 \times 10^{-5}$ s$^{-1}$, less than $6 \times 10^{-5}$ s$^{-1}$, less than $4 \times 10^{-5}$ s$^{-1}$, less than $3 \times 10^{-5}$ s, or less than $1 \times 10^{-5}$ s$^{-1}$, as measured by surface plasmon resonance or biolayer interferometry.

In another embodiment, an anti-PD-1 antibody described herein or antigen-binding fragment thereof has a dissociation constant ($K_D$) to PD-1 of less than $1 \times 10^{-8}$ M, less than $5 \times 10^{-9}$ M, less than $3 \times 10^{-9}$ M, less than $1 \times 10^{-9}$ M, less than $8 \times 10^{-10}$ M, less than $6 \times 10^{-10}$ M, less than $4 \times 10^{-10}$ M, less than $2 \times 10^{-10}$ M, or less than $1 \times 10^{-10}$ M.

In an embodiment, an anti-LAG-3 antibody described herein or an antigen-binding fragment thereof has an on rate constant ($k_{on}$) to human LAG-3 of at least $5 \times 10$ M$^{-1}$ s$^{-1}$, at least $7 \times 10^3$ M$^{-1}$ s$^{-1}$, at least $1 \times 10^4$ M$^{-1}$ s$^{-1}$, at least $3 \times 10^4$ M$^{-1}$ s$^{-1}$, at least $5 \times 10^4$ M$^{-1}$ s$^{-1}$, at least $7 \times 10^4$ M$^{-1}$ s$^{-1}$, at least $1 \times 10^5$ M$^{-1}$ s$^{-1}$, or at least $2 \times 10^1$ M$^{-1}$ s$^{-1}$ or more, as measured by surface plasmon resonance or biolayer interferometry.

In another embodiment, an anti-LAG-3 antibody described herein or antigen-binding fragment thereof has an off rate constant ($k_{off}$) to human LAG-3 of less than $1.5 \times 10^3$ s$^{-1}$, less than $1 \times 10^{-3}$ s$^{-1}$, less than $8 \times 10^{-4}$ s$^{-1}$, less than $6 \times 10^{-4}$ s$^{-1}$, less than $4 \times 10^4$ s$^{-1}$, less than $2 \times 10^{-4}$ s$^{-1}$, less than $1 \times 10^4$ s$^{-1}$, less than $9 \times 10^{-5}$ s$^{-1}$, less than $8 \times 10^{-5}$ s$^{-1}$, less than $7 \times 10^{-5}$ s$^{-1}$, less than $5 \times 10^{-5}$ s$^{-1}$, less than $4 \times 10^{-5}$ s$^{-1}$, less than $2 \times 10^{-5}$ s$^{-1}$, or less than $1 \times 10^{-5}$ s$^{-1}$, as measured by surface plasmon resonance or biolayer interferometry.

In another embodiment, an anti-LAG-3 antibody described herein or antigen-binding fragment thereof has a dissociation constant ($K_D$) to LAG-3 of less than $5 \times 10^{-7}$ M, less than $2 \times 10^{-7}$ M, less than $1 \times 10^{-7}$ M, less than $8 \times 10^{-8}$ M, less than $6 \times 10^{-8}$ M, less than $4 \times 10^{-8}$ M; less than $2 \times 10^{-9}$ M; less than $1 \times 10^{-8}$ M; less than $8 \times 10^{-9}$ M; less than $6 \times 10^{-9}$ M, less than $4 \times 10^{-9}$ M; less than $2 \times 10^{-9}$ M; or less than $1 \times 10^{-9}$ M.

In an embodiment, a bispecific FIT-Ig binding protein capable of binding PD-1 and LAG-3 according to this invention has an on rate constant ($k_{on}$) to human PD-1 of at least $5 \times 10^3$ M$^{-1}$ s$^{-1}$, at least $1 \times 10^4$ M$^{-1}$ s$^{-1}$, at least $5 \times 10^4$ $M^{-1}$ $s^{-1}$, at least $1\times10^5$ $M^{-1}$ $s^{-1}$, at least $3\times10^5$ $M^{-1}$ $s^{-1}$, or at least $5\times10^5$ $M^1$ $s^{-1}$, or more, and the same binding protein has an on rate constant ($k_{on}$) to human LAG-3 of at least $5\times10^3$ $M^{-1}$ $s^{-1}$, at least $1\times10^4$ $M^{-1}$ $s^{-1}$, at least $5\times10^4$ $M^{-1}$ $s^{-1}$, at least $1\times10^5$ $M^{-1}$ $s^{-1}$, at least $3\times10^5$ $M^{-1}$ $s^{-1}$, or at least $5\times10^5$ $M^{-1}$ $s^{-1}$, or more, as measured by surface plasmon resonance or biolayer interferometry. In further embodiments, a bispecific FIT-Ig binding protein capable of binding PD-1 and LAG-3 as described herein will have an on rate constant ($k_{on}$) to human PD-1 that is no more than a 10-fold decrease from the $k_{on}$ for PD-1 of the parental anti-PD-1 antibody, and is no more than a 10-fold decrease from the $k_{on}$ for LAG-3 of the parental anti-LAG-3 antibody from which the anti-PD-1 and anti-LAG-3 specificities, respectively, of the FIT-Ig binding protein were derived. In other words, the FIT-Ig binding protein will retain an on rate constant for each antigen (PD-1 or LAG-3) that is higher than, the same as, or no more than one order of magnitude less than the on rate constant ($k_{on}$) exhibited by the parental antibodies reactive with the respective PD-1 or LAG-3 antigens. As disclosed herein, a PD-1/LAG-3 FIT-Ig binding protein for antigen may show improvement in $k_{on}$ for one or both antigens in comparison to the $k_{on}$ for the respective antigens exhibited by the parental antibodies, or the $k_{on}$ for one or both antigens may be essentially the same as exhibited by the parental antibodies, respectively, or, if there is a decrease in $k_{on}$ for one or both antigens shown by the FIT-Ig binding protein in comparison to a parental antibody, then that decrease is no more than a 10-fold decrease. Preferably a decrease in $k_{on}$ for a particular antigen in the FIT-Ig in comparison to the $k_{on}$ for that antigen of a parental antibody is less than 50%, more preferably less than a 25% decrease. Such high retained $k_{on}$ values in the bispecific FIT-Ig in comparison to the $k_{on}$s of the parental antibodies is a surprising achievement in the field.

In an embodiment, a bispecific FIT-Ig binding protein capable of binding PD-1 and LAG-3 according to this invention has an off rate constant ($k_{off}$) to human PD-1 of less than $2\times10^{-4}$ $s^{-1}$, less than $1\times10^{-4}$ $s^{-1}$, less than $5\times10^{-5}$ $s^{-1}$, less than $3\times10^{-5}$ $s^{-1}$, less than $2\times10^{-5}$ $s^{-1}$, less than $1\times10^{-5}$ $s^{-1}$, or less than $8\times10^{-6}$ $s^{-1}$, and the same binding protein has an off rate constant ($k_{off}$) to human LAG-3 of less than $2\times10^{-4}$ $s^{-1}$, less than $1\times10^{-4}$ $s^{-1}$, less than $5\times10^{-5}$ $s^{-1}$, less than $3\times10^{-5}$ $s^{-1}$, less than $2\times10^{-5}$ $s^{-1}$, less than $1\times10^{-5}$ $s^1$, or less than $8\times10^{-6}$ $s^{-1}$, as measured by surface plasmon resonance or biolayer interferometry.

In another embodiment, a bispecific FIT-Ig binding protein capable of binding PD-1 and LAG-3 according to this invention has a dissociation constant ($K_D$) to PD-1 of less than $2\times10^{-8}$ M, less than $1\times10^{-8}$ M, less than $5\times10^{-9}$ M, less than $1\times10^{-9}$ M, less than $6\times10^{10}$ M, less than $5\times10^{-10}$ M, less than $3\times10^{-10}$ M, less than $2\times10^{-10}$ M, less than $1\times10^{-1}$ M, less than $8\times10^{-11}$ M, less than $6\times10^{-11}$ M, less than $4\times10^{-11}$ M, or less than $1\times10^{-11}$ M, and the same binding protein has a dissociation constant ($K_D$) for human LAG-3 of less than $2\times10^{-8}$ M, less than $1\times10^{-8}$ M, less than $5\times10^{-9}$ M, less than $1\times10^{-9}$ M, less than $6\times10^{-1}$ M, less than $5\times10^{-10}$ M, less than $3\times10^{-10}$ M, less than $2\times10^{-10}$ M, less than $1\times10^{-10}$ M, less than $8\times10^{-11}$ M, less than $6\times10^{-11}$ M, less than $4\times10^{-11}$ M, or less than $1\times10^{-11}$ M. In further embodiments, a bispecific FIT-Ig binding protein capable of binding PD-1 and LAG-3 as described herein will have a dissociation constant ($K_D$) to human PD-1 that is no more than 10-fold different from the $K_D$ for PD-1 of the parental anti-PD-1 antibody, and is no more than 10-fold different from the $K_D$ for LAG-3 of the parental anti-LAG-3 antibody from which the anti-PD-1 and anti-LAG-3 specificities, respectively, of the FIT-Ig binding protein were derived. In other words, the FIT-Ig binding protein will retain the binding affinity of the parental antibodies for each antigen (PD-1 or LAG-3) as indicated by a dissociation constant ($K_D$) that is within one order of magnitude of the $K_D$ exhibited by the parental antibodies reactive with the PD-1 or LAG-3 antigens, respectively. As disclosed herein, a PD-1/LAG-3 FIT-Ig binding protein may show improvement in $K_D$ (i.e., has a lower $K_D$ value; more tightly binds) for one or both antigens in comparison to the $K_D$ for the respective antigens exhibited by the parental antibodies, or the $K_D$ for one or both antigens may be essentially the same as exhibited by the parental antibodies, respectively, or the $K_D$ for one or both antigens shown by the FIT-Ig binding protein may show a decrease (i.e., have a greater $K_D$ value, binds less tightly) in comparison to the $K_D$ of a parental antibody, but if there is a difference in $K_D$ between FIT-Ig binding protein and parental antibody, then that difference is no more than a 10-fold difference. Preferably, a PD-1/LAG-3 FIT-Ig binding protein shows a lower $K_D$ (binds more tightly) for one or both antigens in comparison to the $K_D$ for the respective antigens exhibited by the one or both parental antibodies. Retention of the binding affinity of the parental anti-PD-1 and anti-LAG-3 antibodies±10-fold change in $K_D$ is a surprising achievement in the field.

The invention also provides pharmaceutical compositions comprising at least one anti-PD-1 antibody or antigen-binding fragment thereof as described herein and a pharmaceutically acceptable carrier. The invention also provides pharmaceutical compositions comprising at least one anti-LAG-3 antibody or antigen-binding fragments thereof and a pharmaceutically acceptable carrier. The invention also provides pharmaceutical compositions comprising a combination of anti-PD-1 and anti-LAG-3 antibodies as described herein, or antigen-binding fragment(s) thereof, and a pharmaceutically acceptable carrier. The invention also provides bispecific, multivalent immunoglobulin binding proteins reactive with both PD-1 and LAG-3, which binding proteins incorporate VH/VL binding sites from anti-PD-1 and anti-LAG-3 antibodies described herein. In particular, the invention provides pharmaceutical compositions comprising at least one FIT-Ig binding protein capable of binding PD-1 and LAG-3 and a pharmaceutically acceptable carrier. Pharmaceutical compositions of the invention may further comprise at least one additional active ingredient. In an embodiment, such an additional ingredient includes, but is not limited to, a therapeutic agent, an imaging agent, a cytotoxic agent, an angiogenesis inhibitor, a kinase inhibitor, a co-stimulation molecule blocker, an adhesion molecule blocker, an antibody of different specificity or functional fragment thereof, a detectable label or reporter an agonist or antagonist for particular cytokine(s), a narcotic, a non-steroid anti-inflammatory drug (NSAID), an analgesic, an anesthetic, a sedative, a local anesthetic, a neuromuscular blocker, an antimicrobial agent, a corticosteroid, an anabolic steroid, an erythropoietin, an immunogen, an immunosuppressive agent, a growth hormone, a hormone replacement drug, a radiopharmaceutical, an antidepressant, an antipsychotic, a stimulant (e.g., an amphetamine, caffeine, etc.), a beta agonist, an inhaled steroid, an epinephrine or analog, a cytokine.

In another embodiment, a pharmaceutical composition further comprises at least one additional therapeutic agent for treating a disorder in which PD-1-mediated and/or LAG-3-mediated signaling activity is detrimental.

In a further embodiment, the invention provides isolated nucleic acids encoding one or more amino acid sequences of an anti-PD-1 antibody of the invention or an antigen-binding fragment thereof; isolated nucleic acids encoding one or more amino acid sequences of an anti-LAG-3 antibody of the invention or an antigen-binding fragment thereof; and isolated nucleic acids encoding one or more amino acid sequences of a bispecific Fabs-in-Tandem immunoglobulin (FIT-g) binding protein capable of binding both PD-1 and LAG-3. Such nucleic acids may be inserted into a vector for carrying out various genetic analyses or for expressing, characterizing, or improving one or more properties of an antibody or binding protein described herein. A vector may comprise a one or more nucleic acid molecules encoding one or more amino acid sequences of an antibody or binding protein described herein in which the one or more nucleic acid molecules is operably linked to appropriate transcriptional and/or translational sequences that permit expression of the antibody or binding protein in a particular host cell carrying the vector. Examples of vectors for cloning or expressing nucleic acids encoding amino acid sequences of binding proteins described herein include, but are not limited to, pcDNA, pTT, pTD, pEFBOS, pBV, pJV, and pBJ, and derivatives thereof.

The invention also provides a host cell comprising a vector comprising a nucleic acid encoding one or more amino acid sequences of an antibody or binding protein described herein. Host cells useful in the invention may be prokaryotic or eukaryotic. An exemplary prokaryotic host cell is *Escherichia coli*. Eukaryotic cells useful as host cells in the invention include protist cells, animal cells, plant cells, and fungal cells. An exemplary fungal cell is a yeast cell, including *Saccharomyces cerevisiae*. An exemplary animal cell useful as a host cell according to the invention includes, but is not limited to, a mammalian cell, an avian cell, and an insect cell. Preferred mammalian cells include, but are not limited to, CHO cells. HEK cells, and COS cells. An insect cell useful as a host cell according to the invention is an insect Sf9 cell.

In another aspect, the invention provides a method of producing anti-PD-1 antibody or a functional fragment thereof comprising culturing a host cell comprising an expression vector encoding the antibody or functional fragment in culture medium under conditions sufficient to cause expression by the host cell of the antibody or fragment capable of binding PD-1. In another aspect, the invention provides a method of producing anti-LAG-3 antibody or a functional fragment thereof comprising culturing a host cell comprising an expression vector encoding the antibody or functional fragment in culture medium under conditions sufficient to cause expression by the host cell of the antibody or fragment capable of binding LAG-3. In another aspect, the invention provides a method of producing a bispecific, multivalent binding protein capable of binding PD-1 and LAG-3, specifically a FIT-Ig binding protein binding PD-1 and LAG-3, comprising culturing a host cell comprising an expression vector encoding the FIT-Ig binding protein in culture medium under conditions sufficient to cause expression by the host cell of the binding protein capable of binding PD-1 and LAG-3. The proteins so produced can be isolated and used in various compositions and methods described herein.

In one embodiment, the present invention provides methods for treating cancer in a subject in need thereof, the method comprising administering to the subject an anti-PD-1 antibody or PD-1-binding fragment thereof as described herein, wherein the antibody or binding fragment is capable of binding PD-1 and inhibiting PD-1/PD-L1- or PD-1/PD-L2-mediated signaling in a cell expressing PD-1. In another embodiment, the present invention provides methods for treating cancer in a subject in need thereof, the method comprising administering to the subject an anti-LAG-3 antibody or LAG-3-binding fragment thereof as described herein, wherein the antibody or binding fragment is capable of binding LAG-3 and inhibiting MHC Class II/LAG-3-mediated signaling in a cell expressing LAG-3. In another embodiment, the present invention provides methods for treating cancer in a subject in need thereof, the method comprising administering to the subject a bispecific FIT-Ig binding protein capable of binding LAG-3 and PD-1 as described herein, wherein the binding protein is capable of binding LAG-3 and PD-1 and of inhibiting MHC Class II/LAG-3-mediated signaling in a cell expressing LAG-3 and of inhibiting PD-1/PD-L1 or PD-1/PD-L2 signaling in a cell expressing PD-1. In a further embodiment, a FIT-Ig binding protein of the present invention binds PD-1 and LAG-3 and is comprised of a first polypeptide chain comprising, consisting essentially of, or consisting of the sequence of amino acids 23-684 of SEQ ID NO:102; a second polypeptide chain comprising, consisting essentially of, or consisting of the sequence of amino acids 20-235 of SEQ ID NO:105; and a third polypeptide chain comprising, consisting essentially of, or consisting of the sequence of amino acids 23-236 of SEQ ID NO:107. (See Table 30.) In a further embodiment, a FIT-Ig binding protein of the present invention binds PD-1 and LAG-3 and is comprised of a first polypeptide chain comprising, consisting essentially of, or consisting of the sequence of amino acids 23-687 of SEQ ID NO:189; a second polypeptide chain comprising, consisting essentially of, or consisting of the sequence of amino acids 20-235 of SEQ ID NO:192; and a third polypeptide chain comprising, consisting essentially of, or consisting of the sequence of amino acids 23-236 of SEQ ID NO:194. (See Table 48.)

In another embodiment, the present invention provides methods for treating an autoimmune disease or a cancer in a subject in need thereof, wherein the binding protein is capable of binding LAG-3 and PD-1, and wherein the autoimmune disease or cancer is an autoimmune disease or cancer typically responsive to immunotherapy. In another embodiment, the cancer is a cancer that has not been associated with immunotherapy. In another embodiment, the cancer is a cancer that is a refractory or a recurring malignancy. In another embodiment, the binding protein inhibits the growth or survival of tumor cells. In another embodiment, the cancer is selected from the group consisting of melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies.

Methods of treatment described herein may further comprise administering to a subject in need thereof, of an immunostimulatory adjuvant, such as a CpG oligodeoxynucleotide (CpG ODN) comprising a full or partial phosphodiester or phosphorothioate backbone. For example, in a method of treatment of the invention, an immunostimulatory adjuvant may be incorporated into a composition comprising an antibody or FIT-Ig binding protein of the invention, and the composition administered to a subject in need of treatment. In another embodiment, a method of treatment of the invention may comprise a step of administering to a subject in need of treatment an antibody or FIT-Ig binding protein described herein and a separate step of administering an immunostimulatory adjuvant to the subject before, concurrently, or after the step of administering to the subject an antibody or FIT-Ig binding protein of the invention.

BRIEF DESCRIPTION OF THE DRAWINGS

FIGS. 1A and 1B show separate MLR tests, using responder lymphocytes from different donors.

FIGS. 2A and 28 show separate MLR tests, using responder lymphocytes from different donors.

FIGS. 3, 4, and 5 show separate MLR tests, using responder lymphocytes from different donors.

DETAILED DESCRIPTION OF THE INVENTION

Figure 1:
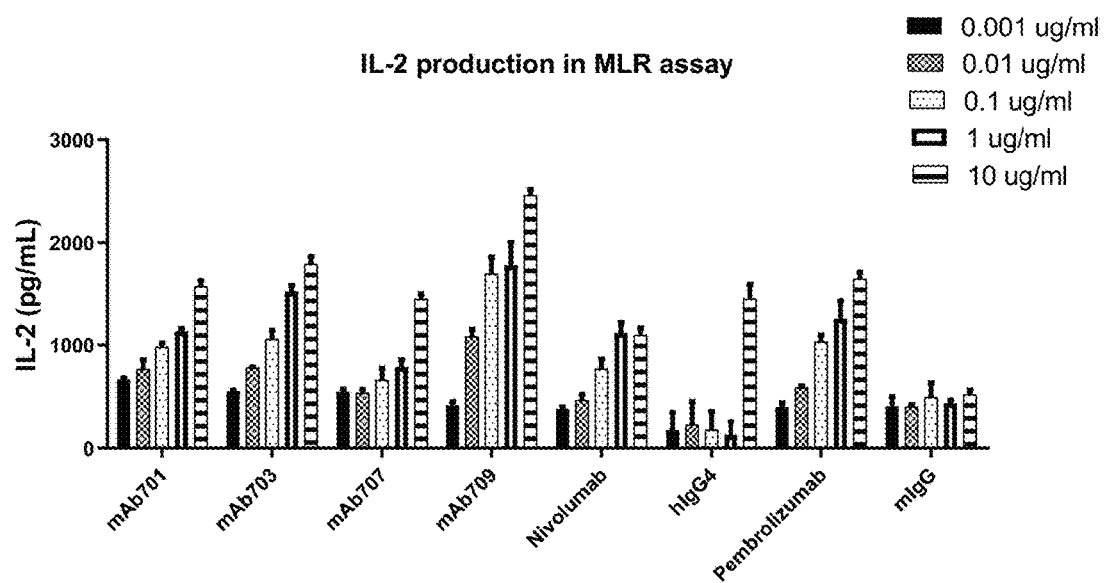
FIGS. 1A and 1B are bar graphs showing IL-2 production levels in a mixed lymphocyte reaction testing the effect of various anti-PD-1 antibodies disclosed herein, in comparison to two recombinant anti-PD-1 antibodies produced from published sequences (nivolumab and pembrolizumab) and control human and murine antibodies directed against irrelevant antigens ("hIgG4" and "mIgG").
Figure 1:
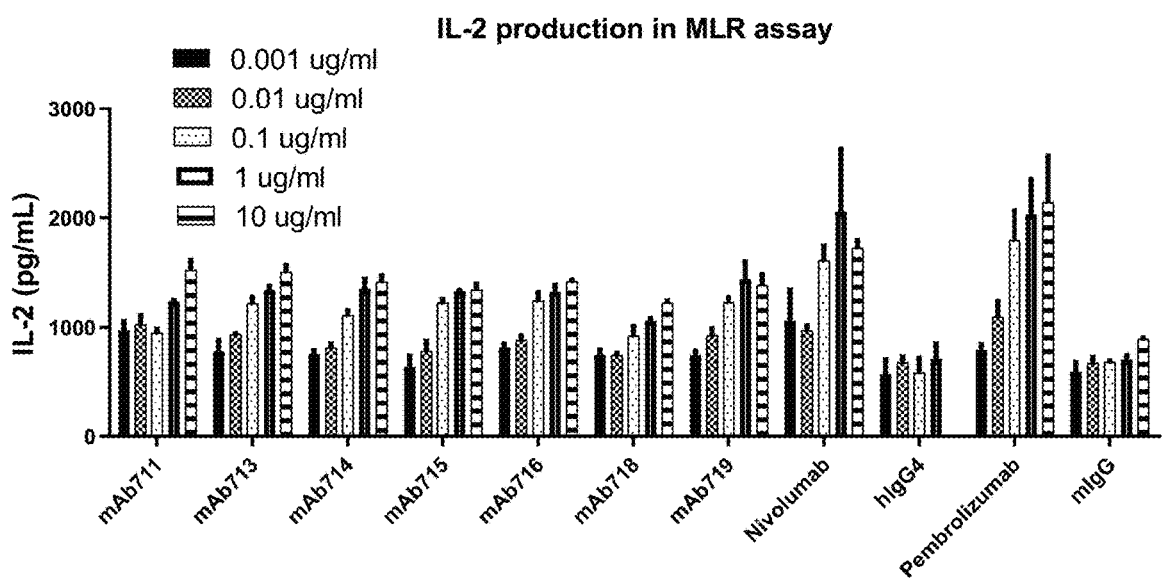

This invention pertains to novel anti-PD-1 antibodies, novel anti-LAG-3 antibodies, antigen-binding portions thereof, and multivalent, bispecific binding proteins such as Fabs-in-Tandem immunoglobulins (FIT-Igs) that bind both to PD-1 and LAG-3 targets. Various aspects of the invention relate to anti-PD-1 and anti-LAG-3 antibodies and antibody fragments, FIT-Ig binding proteins binding to human PD-1 and human LAG-3, and pharmaceutical compositions thereof, as well as nucleic acids, recombinant expression vectors and host cells for making such antibodies, functional antibody fragments, and binding proteins. Methods of using the antibodies, functional antibody fragments, and bispecific binding proteins of the invention to detect human PD-1, human LAG-3, or both; to inhibit human PD-1 and/or human LAG-3 activity, either in vitro or in vivo; and to treat diseases, especially cancer, that are mediated by PD-1 and/or LAG-3 binding to their respective ligands, i.e., PD-1 and MHC Class II, are also encompassed by the invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein amino acid sequence. The term "polypeptide" encompasses fragments and variants (including fragments of variants) thereof, unless otherwise contradicted by context. For an antigenic polypeptide, a fragment of polypeptide optionally contains at least one contiguous or nonlinear epitope of polypeptide. The precise boundaries of the at least one epitope fragment can be confirmed using ordinary skill in the art. The fragment comprises at least about 5 contiguous amino acids, such as at least about 10 contiguous amino acids, at least about 15 contiguous amino acids, or at least about 20 contiguous amino acids. A variant of a polypeptide is as described herein.

The term "isolated protein" or "isolated polypeptide" is a protein or polypeptide that by virtue of its origin or source of derivation is not associated with naturally associated components that accompany it in its native state, is substantially free of other proteins from the same species, is expressed by a cell from a different species, or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" refers to the process of rendering a chemical species such as a polypeptide substantially free of naturally associated components by isolation, e.g., using protein purification techniques well known in the art.

The term "biological activity" refers to all inherent biological properties of the anti-PD-1 or anti-LAG-3 antibodies described herein. Biological properties of anti-PD-1 antibodies include, but am not limited to, binding to PD-1 protein; biological properties of anti-LAG-3 antibodies include, but are not limited to, binding to MHC Class II proteins.

The term "specific binding" or "specifically binding" in reference to the interaction of an antibody, a binding protein, or a peptide with a second chemical species, means that the interaction is dependent upon the presence of a particular structure (e.g., an antigenic determinant or epitope) on the second chemical species. For example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody" broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as VH) and a heavy chain constant region. The heavy chain constant region is comprised of three domains: CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FRs). Each VH and VL is comprised of three CDRs and four FRs, arranged from amino-terminus to carboxy-terminus in the following order: FR1, CDR1, FR2, CDR2, FR3, CDR3, FR4. First, second and third CDRs of a VH domain are commonly enumerated as CDR-H1, CDR-H2, and CDR-H3; likewise, first, second and third CDRs of a VL domain are commonly enumerated as CDR-L1, CDR-L2, and CDR-L3. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, i.e., a CH2 domain and a CH3 domain, and optionally comprises a CH4 domain, for example, as in the case of the Fc regions of IgM and IgE antibodies. The Fc region of IgG, IgA, and IgD antibodies comprises a hinge region, a CH2 domain, and a CH3 domain. In contrast, the Fc region of IgM and IgE antibodies lacks a hinge region but comprises a CH2 domain, a CH3 domain and a CH4 domain. Variant Fc regions having replacements of amino acid residues in the Fc portion to alter antibody effector function are known in the art (see, e.g., Winter et al., U.S. Pat. Nos. 5,648,260 and 5,624,821). The Fc portion of an antibody mediates several important effector functions, for example, cytokine induction, ADCC, phagocytosis, complement dependent cytotoxicity (CDC), and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. In still another embodiment at least one amino acid residue is replaced in the constant region of the antibody, for example the Fc region of the antibody, such that effector functions of the antibody are altered. The dimerization of two identical heavy chains of an immunoglobulin is mediated by the dimerization of CH3 domains and is stabilized by the disulfide bonds within the hinge region that connects CH1 constant domains to the Fc constant domains (e.g., CH2 and CH3). The anti-inflammatory activity of IgG is completely dependent on sialylation of the N-linked glycan of the IgG Fc fragment. The precise glycan requirements for anti-inflammatory activity have been determined, such that an appropriate IgG1 Fc fragment can be created, thereby generating a fully recombinant, sialylated IgG1 Fc with greatly enhanced potency (see, Anthony et al., Science, 320:373-376 (2008)).

The terms "antigen-binding portion" and "antigen-binding fragment" or "functional fragment" of an antibody are used interchangeably and refer to one or more fragments of an antibody that retain the ability to specifically bind to an antigen, i.e., the same antigen (e.g., PD-1, LAG-3) as the full-length antibody from which the portion or fragment is derived. It has been shown that the antigen-binding function of an antibody can be performed by fragments of a full-length antibody. Such antibody embodiments may also be bispecific, dual specific, or multi-specific formats; specifically binding to two or more different antigens (e.g., PD-1 and a different antigen, such as LAG-3). Examples of binding fragments encompassed within the term "antigen-binding portion" of an antibody include (i) a Fab fragment, a monovalent fragment consisting of the VL, VH, CL, and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature, 341: 544-546 (1989); PCT Publication No. WO 90/05144), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, for example, Bird et al., Science, 242: 423-426 (1988); and Huston et al., Proc. Natl. Acad. Sci. USA, 85: 5879-5883 (1988)). Such single chain antibodies are also intended to be encompassed within the term "antigen-binding portion" of an antibody and equivalent terms given above. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci. USA, 90: 6444-6448 (1993). Such antibody binding portions are known in the art (Kontermann and Dübel eds., Antibody Engineering (Springer-Verlag, New York, 2001), p. 790 (ISBN 3-540-41354-5)). In addition, single chain antibodies also include "linear antibodies" comprising a pair of tandem Fv segments (VH-CH1-VH-CH1) which, together with complementary light chain polypeptides, form a pair of antigen binding regions (Zapata et al., Protein Eng., 8(10): 1057-1062 (1995); and U.S. Pat. No. 5,641,870)).

An immunoglobulin constant (C) domain refers to a heavy (CH) or light (CL) chain constant domain. Murine and human IgG heavy chain and light chain constant domain amino acid sequences are known in the art.

The term "monoclonal antibody" or "mAb" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic determinant (epitope). Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "human antibody" includes antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell, antibodies isolated from a recombinant, combinatorial human antibody library (Hoogenboom, H. R., Trends Biolechnol., 15: 62-70 (1997); Azzazy and Highsmith, Clin. Biochem., 35: 425-445 (2002); Gavilondo and Larrick, BioTechniques, 29: 128-145 (2000); Hoogenboom and Chames, Immunol. Today, 21: 371-378 (2000)), antibodies isolated from an animal (e.g., a mouse) that is transgenic for human immunoglobulin genes (see, e.g., Taylor et al., Nucl. Acids Res., 20: 6287-6295 (1992);

Kellermann and Green, *Curr Opin. Biotechnol.*, 13: 593-597 (2002); Little et al., *Immunol. Today,* 21: 364-370 (2000)); or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies that comprise heavy and light chain variable region sequences from one species and constant region sequences from another species, such as antibodies having murine heavy and light chain variable regions linked to human constant regions.

The term "CDR-grafted antibody" refers to antibodies that comprise heavy and light chain variable region sequences from one species but in which the sequences of one or more of the CDR regions of VH and/or VL are replaced with CDR sequences of another species, such as antibodies having human heavy and light chain variable regions in which one or more of the human CDRs has been replaced with murine CDR sequences.

The term "humanized antibody" refers to antibodies that comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which CDR sequences from a non-human species (e.g., mouse) are introduced into human VH and VL framework sequences. A humanized antibody is an antibody or a variant, derivative, analog or fragment thereof which immunospecifically binds to an antigen of interest and which comprises framework regions and constant regions having substantially the amino acid sequence of a human antibody but complementarity determining regions (CDRs) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody may be selected from any class of immunoglobulins, including IgM, IgG, IgD, IgA and IgE, and any isotype, including without limitation IgG1, IgG2, IgG3, and IgG4. The humanized antibody may comprise sequences from more than one class or isotype, and particular constant domains may be selected to optimize desired effector functions using techniques well known in the art.

The framework and CDR regions of a humanized antibody need not correspond precisely to the parental sequences, e.g., the donor antibody CDR or the acceptor framework may be mutagenized by substitution, insertion and/or deletion of at least one amino acid residue so that the CDR or framework residue at that site does not correspond to either the donor antibody or the consensus framework. In an exemplary embodiment, such mutations, however, will not be extensive. Usually, at least 80%, preferably at least 85%, more preferably at least 90%, and most preferably at least 95% of the humanized antibody residues will correspond to those of the parental FR and CDR sequences. Back mutation at a particular framework position to restore the same amino acid that appears at that position in the donor antibody is often utilized to preserve a particular loop structure or to correctly orient the CDR sequences for contact with target antigen.

The term "CDR" refers to the complementarity determining regions within antibody variable domain sequences. There are three CDRs in each of the variable regions of the heavy chain and the light chain, which are designated CDR-H1, CDR-H2, CDR-H3, CDR-L1, CDR-L2, and CDR-L3. The term "CDR set" as used herein refers to a group of three CDRs that occur in a single variable region capable of binding the antigen. The exact boundaries of these CDRs have been defined differently according to different systems. The system described by Kabat (Kabat et al., *Sequences of Proteins of Immunological Interest* (National Institutes of Health, Bethesda, Maryland (1987) and (1991)) not only provides an unambiguous residue numbering system applicable to any variable region of an antibody, but also provides precise residue boundaries defining the three CDRs.

The term "Kabat numbering", which is recognized in the art, refers to a system of numbering amino acid residues which are more variable (i.e., hypervariable) than other amino acid residues in the heavy and light chain variable regions of an antibody or an antigen-binding portion thereof. See, Kabat et al., *Ann. NY Acad. Sci.,* 190: 382-391 (1971); and Kabat et al., *Sequences of Proteins of Immunological Interest, Fifth Edition*, U.S. Department of Health and Human Services, NIH Publication No. 91-3242 (1991).

The growth and analysis of extensive public databases of amino acid sequences of variable heavy and light regions over the past twenty years have led to the understanding of the typical boundaries between framework regions (FRs) and CDR sequences within variable region sequences and have enabled persons skilled in the art to accurately determine the CDRs according to Kabat numbering, Chothia numbering, or other systems. See, e.g., Martin, "Protein Sequence and Structure Analysis of Antibody Variable Domains," In Kontermann and Dübel, eds., *Antibody Engineering* (Springer-Verlag, Berlin, 2001), chapter 31, pages 432-433.

The term "multivalent binding protein" denotes a binding protein comprising two or more antigen binding sites. A multivalent binding protein is preferably engineered to have three or more antigen binding sites, and is generally not a naturally occurring antibody. The term "bispecific binding protein" refers to a binding protein capable of binding two targets of different specificity. "Fabs-in-Tandem immunoglobulin" (FIT-Ig) binding proteins of the invention comprise two or more antigen binding sites and are typically tetravalent binding proteins. A FIT-Ig may be monospecific, i.e., capable of binding one antigen, or multispecific, i.e., capable of binding two or more antigens. A preferred FIT-Ig according to this invention binds both PD-1 and LAG-3 and, therefore, is bispecific. A FIT-Ig binding protein comprising two long (heavy) V-C-V-C-Fc chain polypeptides and four short (light) V-C chain polypeptides forms a hexamer exhibiting four Fab antigen binding sites (VH-CH1 paired with VL-CL, sometimes notated VH-CH1::VL-CL). Each half of a FIT-Ig comprises a heavy chain polypeptide and two light chain polypeptides, and complementary immunoglobulin pairing of the VH-CH1 and VL-CL elements of the three chains results in two Fab-structured antigen binding sites, arranged in tandem. In the present invention, it is preferred that the immunoglobulin domains comprising the Fab elements are directly fused in the heavy chain polypeptide, without the use of interdomain linkers. That is, the N-terminal V-C element of the long (heavy) polypeptide chains is directly fused at its C-terminus to the N-terminus of another V-C element, which in turn is linked to a C-terminal Fc region. In bispecific FIT-Ig binding proteins, the tandem Fab elements will be reactive with different antigens. Each Fab antigen binding site comprises a heavy chain variable domain and a light chain variable domain with a total of six CDRs per antigen binding site.

A description of the design, expression, and characterization of FIT-Ig molecules is provided in PCT Publication WO2015/103072. A preferred example of such FIT-Ig molecules comprises a heavy chain and two different light chains. The heavy chain comprises the structural formula $VL_A$-CL-$VH_B$-CH1-Fc where CL is directly fused to $VH_B$ or $VH_B$-CH1-$VL_A$-CL-Fc where CH1 is directly fused to $VL_A$, wherein $VL_A$ is a variable light domain from a parental antibody that binds antigen A, $VH_B$ is a variable heavy domain from a parental antibody that binds antigen B, CL is a light chain constant domain, CH1 is a heavy chain constant domain, and Fc is an immunoglobulin Fc region (e.g., the C-terminal hinge-CH2-CH3 portion of a heavy chain of an IgG1 antibody). The two light polypeptide chains of the FIT-Ig have the formulas $VH_A$-CH1 and $VL_B$-CL, respectively. In bispecific FIT-Ig embodiments, antigen A and antigen B are different antigens, or different epitopes of the same antigen. In the present invention, one of A and B is PD-1 and the other is LAG-3.

The term "activity" includes properties such as the ability to bind a target antigen with specificity, the affinity of an antibody for an antigen, the ability to neutralize the biological activity of a target antigen, the ability to inhibit interaction of a target antigen with its natural receptor(s), and the like. Preferred antibodies and binding proteins of the present invention have the ability to inhibit PD-1 binding to its ligand PD-L1, the ability to inhibit LAG-3 binding to its ligand MHC Class 11, or both in the case of bispecific binding proteins described herein.

The term "$k_{on}$" (also "Kon", "kon"), as used herein, is intended to refer to the on rate constant for association of a binding protein (e.g., an antibody) to an antigen to form an association complex, e.g., antibody/antigen complex, as is known in the art. The "$k_{on}$" also is known by the terms "association rate constant", or "ka", as used interchangeably herein. This value indicates the binding rate of an antibody to its target antigen or the rate of complex formation between an antibody and antigen as is shown by the equation below:

Antibody ("Ab")+Antigen ("Ag")→Ab–Ag.

The term "$k_{off}$" (also "Koff", "koff"), as used herein, is intended to refer to the off rate constant for dissociation, or "dissociation rate constant", of a binding protein (e.g., an antibody) from an association complex (e.g., an antibody/antigen complex) as is known in the art. This value indicates the dissociation rate of an antibody from its target antigen or separation of Ab-Ag complex over time into free antibody and antigen as shown by the equation below:

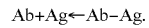

Ab+Ag←Ab–Ag.

The term "$K_D$" (also "$K_d$"), as used herein, is intended to refer to the "equilibrium dissociation constant" and refers to the value obtained in a titration measurement at equilibrium, or by dividing the dissociation rate constant ($k_{off}$) by the association rate constant ($k_{on}$). The association rate constant ($k_{on}$), the dissociation rate constant ($k_{off}$), and the equilibrium dissociation constant ($K_D$) are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Biolayer interferometry (BLI) using, e.g., the Octet® RED96 system (Pall ForteBio LLC), is another affinity assay technique. Additionally, a KinExA® (Kinetic Exclusion Assay) assay, available from Sapidyne Instruments (Boise, Idaho) can also be used.

The term "isolated nucleic acid" shall mean a polynucleotide (e.g., of genomic, cDNA, or synthetic origin, or some combination thereof) that, by human intervention, is not associated with all or a portion of the polynucleotides with which it is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably inked" to a coding sequence is ligated in such a way that expression of the coding sequence is achieved under conditions compatible with the control sequence. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader or signal sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, transfection, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), is intended to refer to a cell into which exogenous DNA has been introduced. In an embodiment, the host cell comprises two or more (e.g., multiple) nucleic acids encoding antibodies, such as the host cells described in U.S. Pat. No. 7,262,028, for example. Such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells selected from any of the Kingdoms of life. In another embodiment, eukaryotic cells include protist, fungal, plant and animal cells. In another embodiment, host cells include but are not limited to the prokaryotic cell line *Escherichia* col; mammalian cell lines CHO, HEK 293, COS, NS0, SP2 and PER.C6; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual,* 2nd ed. (Cold Spring Harbor Laboratory Press, Cold Spring Harbor, N.Y., 1989).

The term "agonist", as used herein, refers to a modulator that, when contacted with a molecule of interest, causes an increase in the magnitude of a certain activity or function of the molecule compared to the magnitude of the activity or function observed in the absence of the agonist. The terms "antagonist" and "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or reduce the biological or immunological activity of human PD-1 and human LAG-3.

As used herein, the term "effective amount" refers to the amount of a therapy that is sufficient to reduce or ameliorate the severity and/or duration of a disorder or one or more symptoms thereof; prevent the advancement of a disorder; cause regression of a disorder; prevent the recurrence, development, or progression of one or more symptoms associated with a disorder; detect a disorder, or enhance or improve the prophylactic or therapeutic effect(s) of another therapy (e.g., prophylactic or therapeutic agent).

Production of Anti-PD-1 and Anti-LAG-3 Antibodies

Anti-PD-1 and anti-LAG-3 antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr CHO cells, described in Urlaub and Chasin, *Proc. Natl. Acad. Sci. USA,* 77:4216-4220 (1980), used with a DHFR selectable marker, e.g., as described in Kaufman and Sharp, *J. Mol. Biol.,* 159: 601-621 (1982)), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In an exemplary system for recombinant expression of an antibody, or antigen-binding portion thereof, of the invention, a recombinant expression vector encoding both the antibody heavy chain and the antibody light chain is introduced into dhfr CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transfected host cells are cultured to allow for expression of the antibody heavy and light chains and intact antibody is recovered from the culture medium. Standard molecular biology techniques are used to prepare the recombinant expression vector, transfect the host cells, select for transfectants, culture the host cells and recover the antibody from the culture medium. Still further the invention provides a method of making a recombinant anti-PD-1 or anti-LAG-3 antibody of the invention by culturing a transfected host cell of the invention in a suitable culture medium until a recombinant antibody of the invention is produced. The method can further comprise isolating the recombinant antibody from the culture medium.

Production of Bispecific FIT-Igs Binding PD-1 and LAG-3

Clinical studies using immune checkpoint inhibitors such as antibodies targeting PD-1, PD-L1, and CTLA-4 have led to promising results, however it has been observed that only a subset of patients initially respond to these inhibitors, and increasing clinical evidence indicates that a substantial proportion of initial responders ultimately relapse, with lethal, drug-resistant disease months or years later. Syn et al., *The Lancet Oncology*, 18(12):e731-e741 (2017). Both LAG-3 and PD-1 are co-expressed on tolerized tumor infiltrated lymphocytes (TILS), contributing to immune suppression in tumors; and dual blockade of LAG-3 and PD-1 has been proposed as a means to restore antitumor function in CD8+ T cells. Matsuzaki et al., *Proc. Natl. Acad. Sci. USA*, 107(17): 7875-7880 (2010). Accordingly, the design of LAG-3/PD-1 bispecific binding proteins that can block both targets on immune suppressed T cells simultaneously, may provide an advance in this therapeutic area.

This invention provides Fabs-in-Tandem immunoglobulin binding proteins (FIT-Igs) that bind to both PD-1 and LAG-3. An exemplary embodiment of such FIT-Ig molecules comprises (1) a heavy polypeptide chain that comprises either the structural formula (i) $VL_A$-CL-$VH_B$-CH1-Fc wherein CL is directly fused to $VH_B$, or the structural formula (ii) $VH_B$-CH1-$VL_A$-CL-Fc wherein CH1 is directly fused to $VL_A$; (2) a light polypeptide chain of the formula $VH_A$-CH1; and (3) another light polypeptide chain of the formula $VL_B$-CL, wherein VL is a light chain variable domain, CL is a light chain constant domain, VH is a heavy chain variable domain, CH1 is a heavy chain constant domain, Fc is an immunoglobulin Fc region, A is an epitope of PD-1 or LAG-3 and B is an epitope of PD-1 or LAG-3, with the proviso that A and B are different. In accordance with the present invention, such FIT-Ig binding proteins bind to both PD-1 and LAG-3.

A FIT-Ig may comprise two such heavy chains (1), two such light chains (2), and two such light chains (3), forming a six-chain binding protein monomer exhibiting four functional Fab antigen binding sites. Such a FIT-Ig binding protein comprises two identical subunits, wherein each subunit comprises one heavy chain (1), one light chain (2), and one light chain (3) that together forma pair of Fab binding sites arranged in tandem. Pairing of the Fc regions of two such subunits yields a six-chain, bispecific, FIT-Ig binding protein of the invention having a total of four functional Fab binding units.

It is possible to use a peptide linker on the heavy chain to separate the tandemly connected Fab moieties, however for bispecific FIT-Igs according to the invention the omission of such linker sequences is preferred. Whereas in multivalent engineered immunoglobulin formats having tandem binding sites, it was commonly understood in the field that the adjacent binding sites would interfere with each other unless a flexible linker was used to separate the binding sites spatially. It has been discovered for the PD-1/LAG-3 FIT-Igs of the present invention, however, that the arrangement of the immunoglobulin domains according to the chain formulas given above results in polypeptide chains that are well-expressed in transfected mammalian cells, assemble appropriately, and are secreted as bispecific, multivalent immunoglobulin-like binding proteins that bind the target antigens PD-1 and LAG-3. See, Example 10, infra. Despite the absence of any linker sequences between the Fab binding sites, the PD-1/LAG-3 FIT-Igs of the invention retain the binding affinities for the target antigens, exhibiting comparable binding affinities to the parental mAbs. Moreover, omission of synthetic linker sequences from the binding proteins can avoid the creation of antigenic sites recognizable by mammalian immune systems, and in this way the elimination of linkers decreases possible immunogenicity of the FIT-Igs and leads to a half-life in circulation that is like a natural antibody, that is, the FIT-Ig is not rapidly cleared through immune opsonization and capture in the liver.

Each variable domain (VH or VL) in a FIT-Ig may be obtained from one or more "parental" monoclonal antibodies that bind one of the target antigens, i.e., PD-1 or LAG-3. FIT-Ig binding proteins are advantageously produced using variable domain sequences of anti-PD-1 and anti-LAG-3 monoclonal antibodies as disclosed herein. Preferably, the parental antibodies are humanized antibodies.

An aspect of the present invention pertains to selecting parental antibodies with at least one or more properties desired in the FIT-Ig molecule. In an embodiment, the antibody properties are selected from the group consisting of antigen specificity, affinity to antigen, potency, biological function, epitope recognition, stability, solubility, production efficiency, lack of immunogenicity, pharmacokinetics, bioavailability, tissue cross-reactivity, and orthologous antigen binding. PD-1 and LAG-3 are both cell surface proteins, and interaction with their respective ligands PD-L1 (cell surface receptor) and MHC Class II (surface proteins on antigen presenting cells) lead to intracellular signaling involved with T cell suppression and immune response. Accordingly, the ability of anti-PD-1 antibodies, anti-LAG-3 antibodies, and PD-1/LAG-3 FIT-Ig binding proteins according to the invention to inhibit PD-1/PD-L1 and/or MHC Class II/LAG-3 interaction makes them potent regulators of immune cell activation and immune effector cell activity.

Antibodies, functional fragments thereof, and binding proteins according to the invention may be purified (for an intended use) by using one or more of a variety of methods and materials available in the art for purifying antibodies and binding proteins. Such methods and materials include, but are not limited to, affinity chromatography (e.g., using resins, particles, or membranes conjugated to Protein A, Protein G, Protein L, or a specific ligand of the antibody, functional fragment thereof, or binding protein), ion exchange chromatography (for example, using ion exchange particles or membranes), hydrophobic interaction chromatography ("HIC"; for example, using hydrophobic particles or membranes), ultrafiltration, nanofiltration, diafiltration, size exclusion chromatography ("SEC"), low pH treatment (to inactivate contaminating viruses), and combinations thereof, to obtain an acceptable purity for an intended use. A non-limiting example of a low pH treatment to inactivate contaminating viruses comprises reducing the pH of a solution or suspension comprising an antibody, functional fragment thereof, or binding protein of the invention to pH 3.5 with 0.5 M phosphoric acid, at 18° C.-25° C., for 60 to 70 minutes.

Uses of Antibodies and Binding Proteins of the Invention

Given their ability to bind to human PD-1 and/or LAG-3, the antibodies described herein, functional fragments thereof, and bispecific multivalent binding proteins described herein can be used to detect PD-1 or LAG-3, or both, e.g., in a biological sample containing cells that express one or both of those target antigens. The antibodies, functional fragments, and binding proteins of the invention can be used in a conventional immunoassay, such as an enzyme linked immunosorbent assay (ELISA), a radioimmunoassay (RIA), or tissue immunohistochemistry. The invention provides a method for detecting PD-1 or LAG-3 in a biological sample comprising contacting a biological sample with an antibody, antigen-binding portion thereof, or binding protein of the invention and detecting whether binding to a target antigen occurs, thereby detecting the presence or absence of the target in the biological sample. The antibody, functional fragment, or binding protein may be directly or indirectly labeled with a detectable substance to facilitate detection of the bound or unbound antibody/fragment/binding protein. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase. Examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm.

The antibodies, functional fragments thereof, and binding proteins of the invention preferably are capable of neutralizing human PD-1 and/or human LAG-3 activity both in vitro and in vivo. Accordingly, the antibodies, functional fragments thereof, and binding proteins of the invention can be used to inhibit human PD-1 and/or human LAG-3 activity, e.g., inhibit cell signaling mediated by PD-1/PD-L1 (or PD-1/PD-L2) interaction and/or MHC Class II/LAG-3 interaction in a cell culture containing PD-1-expressing and/or LAG-3-expressing cells, in human subjects, or in other mammalian subjects having PD-1 or LAG-3 with which an antibody, functional fragment thereof, or binding protein of the invention cross-reacts. In one embodiment, the invention provides a method for restoring the activity of activated T cells (reversing suppression) comprising contacting human PD-1-expressing cells with an anti-PD-1 antibody or PD-1 binding protein of the invention such that PD-1 activity is inhibited. In another embodiment, the invention provides a method for restoring the activity of activated T cells (reversing suppression) comprising contacting human LAG-3-expressing cells with an anti-LAG-3 antibody or LAG-3 binding protein of the invention such that LAG-3 activity is inhibited.

In another embodiment, the invention provides a method for treating a subject suffering from a disease or disorder in which PD-1 and/or LAG-3 activity is detrimental, such method comprising administering to the subject an antibody or binding protein of the invention in an effective amount, such that activity mediated by PD-1/PD-L1 or PD-1/PD-L2 binding and/or MH-C Class II/LAG-3 binding in the subject is reduced.

As used herein, the term "a disorder in which PD-1 and/or LAG-3 activity is detrimental" is intended to include diseases and other disorders in which the interaction of PD-1 with one or both of its ligands (PD-L1, PD-L2) or the interaction of LAG-3 with its ligand (MHC Class II) in a subject suffering from the disorder is either responsible for the pathophysiology of the disorder or is a factor that contributes to a worsening of the disorder. Accordingly, a disorder in which PD-1 and/or LAG-3 activity is detrimental is a disorder in which inhibition of PD-1 and/or LAG-3 activity is expected to alleviate the symptoms and/or progression of the disorder.

In another embodiment, the present invention provides methods for treating an autoimmune disease or a cancer in a subject in need thereof, comprising administering to the subject an antibody, functional fragment thereof, or a binding protein described herein that is capable of binding LAG-3, PD-1, or both LAG-3 and PD-1, and wherein the autoimmune disease or cancer is a disease that is responsive to immunotherapy. In another embodiment, a method of the invention is used for treating an autoimmune disease or cancer that has not been associated with immunotherapy. In another embodiment, a method of the invention is used for treating a cancer that is a refractory or a recurring malignancy. In another embodiment, a LAG-3 or PD-antibody, functional fragment thereof, or a LAG-3/PD-1 bispecific binding protein of the invention is used in a method that inhibits the growth or survival of tumor cells.

In another embodiment, the invention provides a method for treating cancer in a subject comprising the step of administering to the subject an antibody to PD-1 or LAG-3 described herein, a functional fragment thereof, or a LAG-3/PD-1 bispecific binding protein described herein, e.g., such as a Fabs-in-tandem immunoglobulin (FIT-Ig) binding protein, wherein the cancer is selected from any of a group consisting of: a melanoma (e.g., metastatic malignant melanoma), a renal cancer (e.g., clear cell carcinoma), a prostate cancer (e.g. hormone refractory prostate adenocarcinoma), a pancreatic adenocarcinoma, a breast cancer, a colon cancer, a lung cancer (e.g. non-small cell lung cancer), an esophageal cancer, a squamous cell carcinoma of the head and neck, a liver cancer, an ovarian cancer, a cervical cancer, a thyroid cancer, a glioblastoma, a glioma, a leukemia, a lymphoma, a primary bone cancer (e.g., osteosarcoma, Ewing sarcoma, malignant fibrous histiocytoma, and chondrosarcoma), a metastatic cancer, and other neoplastic malignancies.

The invention also provides pharmaceutical compositions comprising an antibody, or antigen-binding portion thereof, or a bispecific multivalent binding protein of the invention (i.e., the primary active ingredient) and a pharmaceutically acceptable carrier. The pharmaceutical compositions comprising proteins of the invention are for use in, but not limited to, diagnosing, detecting, or monitoring a disorder; treating, managing, or ameliorating a disorder or one or more symptoms thereof; and/or research. In a specific embodiment, a composition comprises one or more antibodies or binding proteins of the invention. In another embodiment, the pharmaceutical composition comprises one or more antibodies or binding proteins of the invention and one or more prophylactic or therapeutic agents other than antibodies or binding proteins of the invention for treating a disorder in which PD-1 and/or LAG-3 activity is detrimental. In an embodiment, the prophylactic or therapeutic agents are known to be useful for or have been or currently are being used in the prevention, treatment, management, or amelioration of a disorder or one or more symptoms thereof. In accordance with these embodiments, the composition may further comprise a carrier, diluent, or excipient. An excipient is generally any compound or combination of compounds that provides a desired feature to a composition other than that of the primary active ingredient (i.e., other than an antibody, functional portion thereof, or binding protein of the invention).

The antibodies (including functional fragments thereof) and binding proteins of the invention can be incorporated into pharmaceutical compositions suitable for administration to a subject. Typically, the pharmaceutical composition comprises an antibody or binding protein of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols (such as, mannitol or sorbitol), or sodium chloride in the composition. Pharmaceutically acceptable carriers may further comprise minor amounts of auxiliary substances such as wetting or emulsifying agents, preservatives, or buffers, which enhance the shelf life or effectiveness of the antibody or binding protein present in the composition.

A pharmaceutical composition of the invention is formulated to be compatible with its intended route of administration. Examples of routes of administration include, but are not limited to, parenteral (e.g., intravenous, intradermal, subcutaneous, intramuscular), oral, intranasal (e.g., inhalation), transdermal (e.g., topical), intratumoral, transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic, such as lidocaine (xylocaine, lignocaine), to ease pain at the site of the injection.

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the primary active ingredient may be in powder form for constitution with a suitable vehicle (e.g., sterile pyrogen-free water) before use.

The methods of the invention may additionally comprise administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

An antibody, functional fragment thereof, or binding protein of the invention also can be administered with one or more additional therapeutic agents useful in the treatment of various diseases. Antibodies, functional fragments thereof, and binding proteins described herein can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody or binding protein of the present invention. The additional agent also can be an agent that imparts a beneficial attribute to the therapeutic composition, e.g., an agent that affects the viscosity of the composition.

Having now described the present invention in detail, the same will be more clearly understood by reference to the following examples, which are included for purposes of illustration only and are not intended to be limiting of the invention.

EXAMPLES

Example 1: Generation of Anti-human PD-1 Monoclonal Antibodies

Anti-human PD-1 monoclonal antibodies were generated as follows:

Example 1.1: Immunization with Human PD-1 Antigen

50 µg of recombinant purified human PD-1 extracellular domain (ECD) polypeptide mixed with Complete Freund's adjuvant were injected intraperitoneally into five 6-8 week-old Balb/C and five SJL mice on Day 1. On days 16 and 26, 25 μg of recombinant purified human PD-1 ECD immunogen mixed with Incomplete Freund's adjuvant were injected intraperitoneally into the same mice. A final boost with 25 μg of the immunogen was given 3-4 days before fusion.

Example 1.2: Generation of Hybridomas

Splenocytes obtained from the immunized mice described in Example 1.1 were fused with SP2/0-Ag-14 cells at a ratio of 5:1 according to the established method described in Kohler and Milstein, *Nature*, 256: 495-497 (1975) to generate hybridomas. Fusion products were plated in selection media containing hypoxanthine-aminopterin-thymidine (HAT) in 96-well plates at a density of 1×10$^5$ spleen cells per well. Seven to ten days post-fusion, macroscopic hybridoma colonies were observed.

Example 1.3: Assessment of PD-1 Binding Activity by ELISA and FACS

The presence of PD-1 specific antibodies was assayed by Enzyme-Linked Immunosorbent Assay (ELISA), as follows:

First, synthetic targets for anti-human PD-1, anti-cynomolgus PD-1 and anti-murine PD-1 were made to order by Synbio Technologies (Suzhou, China). Each target consisted of a polypeptide segment of the extracellular domain (ECD) of human, cynomolgus, or murine PD-1 protein fused to a human IgG Fc region. Synthetic genes encoding each ECD-Fc fusion protein were subcloned into a pCP expression vector (Chempartner, Shanghai, China) and the expression plasmids were transiently transfected into HEK 293E cells in 1-3 liters of medium and cultured for seven days in a CO$_2$ shaker. The ECD sequences used for each fusion are set forth in Table 1, below. The PD-1 ECD portion of each fusion protein is underlined.

TABLE 1

Amino Acid Sequences for PD-1 ECD-Fc Fusion Protein Targets

| SEQ ID NO. | PD-1 Source | Amino acid sequences 12345678901234567890 12345678901234567890 |
|---|---|---|
| 1 | human | LDSPDRPWNPPTFSPALLVVTEGDNATFTCSFSNTS ESFVLNWYRMSPSNQTDKLAAFPEDRSQPGQDCRFR VTQLENGRDFHMSVVRARRNDSGTYLCGAISLAPKA QIKESLRAELRVTERRAEVPTAHPSPSPRPAGQFQI EGRMDPKSCDKTHTCPPCPAPELLGGPSVFLFPPKP KDTLMISRTPEVTCVVVDVSHEDPEVKFNWYVDGVE VHNAKTKPREEQYNSTYRVVSVLTVLHQDWLNGKEY KCKVSNKALPAPIEKTISKAKGQPREPQVYTLPPSR EEMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| 2 | cynomolgus monkey | LESPDRPWNAPTFSPALLLVTEGDNATFTCSFSNAS ESFVLNWYRMSPSNQTDKLAAFPEDRSQPGQDCRFR VTRLPNGRDFHMSVVRARRNDSGTYLCGAISLAFKA QIKESLRAELRVTERRAEVPTAHPSPSPRPAGQFQI EGRMDPKSCDKTHTCPPCPAPELLGGPSVFLFPPKP KDTLMISRTPEVTCVVVDVSHEDPEVKFNWYVDGVE VHNAKTKPREEQYNSTYRVVSVLTVLHQDWLNGKEY KCKVSNKALPAPIEKTISKAKGQPREPQVYTLPPSR EEMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| 3 | mouse | LEVPNGPWRSLTFYPAWLTVSEGANATFTCSLSNWS EDLMLNWNRLSPSNQTEKQAAFCNGLSQPVQDARFQ IIQLPNRHDFHMNILDTRRNDSGIYLCGAISLHPKA |

TABLE 1-continued

Amino Acid Sequences for PD-1 ECD-Fc Fusion Protein Targets

| SEQ ID NO. | PD-1 Source | Amino acid sequences 12345678901234567890 12345678901234567890 |
|---|---|---|
| | | KIEESPGAELVVTERILETSTRYPSPSPKPEGRFQI EGRMDPKSCDKTHTCPPCPAPELLGGPSVFLFPPKP KDTLMISRTPEVTCVVVDVSHEDPEVKFNWYVDGVE VHNAKTKPREEQYNSTYRVVSVLTVLHQDWLNGKEY KCKVSNKALPAPIEKTISKAKGQPREPQVYTLPPSR EEMTKNQVSLTCLVKGFYPSDIAVEWESNGQPENNY KTTPPVLDSDGSFFLYSKLTVDKSRWQQGNVFSCSV MHEALHNHYTQKSLSLSPGK |

The supernatants of HEK 293E transfectants containing recombinant ECD/Fc fusions were harvested by centrifugation at 4000×g for 30 minutes, followed by protein A purification using MabSelect SuRe™ affinity resin (GE Healthcare). The fusion products were dialyzed against phosphate buffered saline (PBS) pH 7.4 and stored at −80° C.

ELISA plates were incubated overnight at 4° C. with 50 μl of the synthetic human PD-1 ECD/Fc fusion protein targets described above diluted in PBS buffer, pH 7.4, at 1 μg/ml. Plates were washed four times in washing buffer (PBS containing 0.05% Tween 20), and blocked for 1 hour at 37° C. with 200 μl per well blocking buffer (1% BSA in PBS containing 0.05% Tween 20). After blocking buffer was removed, hybridoma supernatant (or later diluted purified mAbs) were added to the wells at 100 μl per well and incubated at 37° C. for 1 hour. The wells were washed four times with washing buffer, and anti-mouse HRP (Sigma) for mouse anti-human PD-1 antibody characterization were diluted 1:5000 and added to the wells at 100 μl per well. The plates were incubated for 1 hour at 37° C. and washed four times in washing buffer. 100 μl of tetramethylbenzidine (TMB) chromogenic solution were added per well. Following color development, the reaction was stopped with 1 Normal HCl and absorbance at 450 nm was measured on a SpectraMax M5e plate reader (Molecular Devices; San Jose, California, US).

Example 1.4: Preparation of PD-1-Expressing Cell Lines and FACS Analysis

Stable cell lines overexpressing human PD-1 or cynomolgus PD-1 were generated by transfection of CHO-K1 cells (obtained from ATCC) with pLvx lentiviral plasmid vectors (Clontech) having inserted genes encoding either human PD-1 or cynomolgus PD-1. Single clones were isolated by limiting dilution. Clones were screened for expression level by FACS analysis using anti-PD-1 antibodies produced recombinantly from known antibody sequences (Chempartner), and clones having highest expression of PD-1 were selected for use in a FACS binding assays and functional assays, as described below.

Binding Assay for Cell Surface Targets: The ability of the purified antibodies to bind to cell membrane human PD-1 or cynomolgus monkey PD-1 was determined by FACS analysis. CHO-K1 cells stably expressing human PD-1 (CHO-K1-hPD-1 cells) or cynomolgus PD-1 (CHO-K1-cynoPD-1) were resuspended in PBS containing 2% FBS (FACS buffer) and seeded at 2×10$^4$ cells/well into 96-well round-bottomed plates (Corning; Cat. No. 3799). Supernatants of hybridomas producing anti-PD-1 antibodies were added to the wells and detected with AlexaFluor® 488 Donkey Anti-Mouse IgG (H+L) Highly Cross-Adsorbed Secondary Antibody (Invitrogen; Cat. No. A-21202), and the assay plate was then read on a flow cytometer. Hybridomas producing supernatant signaling positive against human PD-1 expressing targets were further characterized using CHO-K i/cynoPD-1 cells to determine cross-reactivity of the antibodies with cynomolgus PD-1.

Example 1.5: Receptor Blocking Assay (RBA)

Supernatants displaying PD-1 specific activity were tested for the ability to block PD-1 binding to its ligands PD-L1 and PD-L2 using immobilized human PD-1 ECD/Fc as a target and PD-L1/Fc and PD-L2/Fc fusion proteins, prepared in the same manner as the PD-1 ECD/Fc binding proteins described in Example 1.3 above. To determine the relative potency of the antibody-containing supernatants, their ability to inhibit the binding of a human PD-1 ligand (PD-L1 or PD-L2) to human PD-1 protein was evaluated. ELISA plates were coated with 100 µl of 50 ng/m of huPD-1/Fc (i.e., the extracellular domain of PD-1 grafted onto the N-terminus of a human Fc region, recovered as a homodimer) in PBS and incubated overnight at 4° C. Plates were washed four times in washing buffer (PBS containing 0.05% Tween 20) and blocked for 1 hour at 37° C. with 200 µl per well of blocking buffer (1% BSA in PBS containing 0.05% Tween 20). After blocking buffer was removed, hybridoma supernatant (50 µl) was added to the wells, mixed with either 50 µl biotinylated human PD-L1/Fc (1.0 mg/ml final concentration) in blocking buffer or 50 µl biotinylated human PD-L2/Fc (final concentration 50 µg/ml) in blocking buffer, then incubated at 37° C. for 1 hour. Signal was developed by adding streptavidin-HRP (Sigma, Cat. No. S2468) (100 µl/well of streptavidin-HRP at 1:5000 dilution) and incubating for 40 minutes at 37° C. and washed four times in washing buffer. 100 µl of TMB solution were added per well. Following color development, the reaction was stopped with 1 Normal HCl and absorbance at 450 nm was measured.

Example 1.6: Expression and Purification of Anti-PD-1 Monoclonal Antibodies

Murine monoclonal antibody-producing hybridoma cells were cultured in FreeStyle™ 293 Expression Medium (Gibco/Life Technologies) in a $CO_2$ shaker at 37° C. for 5 to 7 days. The conditioned medium was collected through centrifugation at 4000×g for 30 minutes to remove all cells and cell debris, then filtered through a 0.22 µm membrane before purification. Murine antibodies were applied and bound to a MabSelect™ SuRe (GE Healthcare) protein A resin column according to the manufacturer's guidelines, washed with PBS, eluted with buffer containing 20 mM citrate, 150 mM NaCl, pH 3.5. The eluted materials were neutralized with 1 M Tris at pH 8.0 immediately and dialyzed against PBS. One-step purified antibodies usually have above 90% purity, as detected by SEC-HPLC. Protein concentrations were determined by measuring absorbance at 280 nm or by NanoDrop™ microvolume spectrophotometer (Thermo Scientific). The purified antibodies were stored in aliquots in a −80° C. freezer.

Example 2: Binding Activity of Purified Anti-PD-1 Antibodies

Examples 2.1: Characterization by ELISA

A binding ELISA was performed in the same way as described in Example 1.3 above. Each purified antibody was 10-fold serially diluted and duplicated. After blocking of the 96-well assay plate with wells containing immobilized PD-1 ECD/Fc fusion protein targets, the purified antibody samples with diluted concentrations were added to wells of assay plates. The HRP-linked anti-mouse IgG antibody (A0168, Sigma) and TMB reagent were used to detect and develop the ELISA signal, which were read on a SpectraMax® M5e plate reader at wavelength of 450 nm. Curves were fitted using GraphPad software, and EC50 were calculated. Similarly, a receptor blocking assay (RBA) was also performed as described in Example 1.5 with titrated, purified antibodies, and top blocking percentages and IC50 values were determined.

Example 2.2: Characterization by FACS

CHO-K1/huPD-1 or CHO-K1/cynoPD-1 cells, described above, were charged at $2 \times 10^4$ cell per well into 96-well assay round-bottomed assay plates (Cat. No. 3799; Corning) and stained with purified anti-PD-1 antibodies. PD-1 antibodies were detected with AlexaFluor® Donkey anti-Mouse IgG (H+L) Highly Cross-Adsorbed Secondary Antibody, (Cat. No. A21202; Invitrogen), and cell fluorescence was monitored using a flow cytometer. The data were processed by GraphPad software, and EC50 values were calculated.

The results of these binding characterization assays are shown in Table 2 below.

TABLE 2

Binding Activity of Purified Anti-PD-1 Antibodies

| | ELISA | FACS | | Receptor Blocking Assay (RBA) | | | |
| | Coating | CHO-K1/ | CHO-K1/ | Ligand 1 (huPD-L1) | | Ligand 2 (huPD-L2) | |
| mAb Identifier | huPD-1/Fc EC50 (nM) | huPD-1 EC50 (nM) | cynoPD-1 EC50 (nM) | TOP inhibition (%) | IC50 (nM) | TOP inhibition (%) | IC50 (nM) |
| mAb701 | 0.10 | 3.0 | 3.8 | 87.1 | 5.32 | 94.1 | 2.67 |
| mAb703 | 0.05 | 0.5 | 0.7 | 96.0 | 3.00 | 95.7 | 2.02 |
| mAb707 | 0.10 | 27.4 | 4.3 | 87.7 | 13.94 | 23.1 | 9.91 |
| mAb709 | 0.01 | 0.2 | 0.2 | 91.6 | 0.80 | 93.7 | 0.52 |
| mAb711 | 0.03 | 18.6 | 3.0 | 89.3 | 11.56 | 27.4 | 6.77 |
| mAb713 | 0.08 | 1.1 | 0.9 | 94.4 | 2.95 | 93.5 | 2.52 |
| mAb714 | 0.05 | 1.6 | 0.8 | 92.3 | 2.95 | 93.1 | 2.24 |
| mAb715 | 0.04 | 1.1 | 0.9 | 86.9 | 2.91 | 88.0 | 2.17 |

TABLE 2-continued

Binding Activity of Purified Anti-PD-1 Antibodies

| | ELISA | FACS | | Receptor Blocking Assay (RBA) | | | |
| | Coating | CHO-K1/ | CHO-K1/ | Ligand 1 (huPD-L1) | | Ligand 2 (huPD-L2) | |
| mAb Identifier | huPD-1/Fc EC50 (nM) | huPD-1 EC50 (nM) | cynoPD-1 EC50 (nM) | TOP inhibition (%) | IC50 (nM) | TOP inhibition (%) | IC50 (nM) |
|---|---|---|---|---|---|---|---|
| mAb716 | 0.02 | 0.7 | 0.7 | 95.8 | 1.56 | 96.9 | 1.05 |
| mAb718 | 0.02 | 3.2 | 4.2 | 96.6 | 4.19 | 96.6 | 1.91 |
| mAb719 | 0.02 | 1.7 | 2.1 | 96.5 | 3.39 | 95.2 | 1.85 |
| Human IgG1 (control) | 63.95 | | | 0.0 | NA | 9.9 | NA |

Example 2.3: Affinity Measurement by Surface Plasmon Resonance (SPR)

The binding kinetics of purified antibodies were measured by surface plasmon resonance using a Biacore T7200 instrument (GE Healthcare) using standard procedures. Briefly, goat anti-mouse IgG Fc polyclonal antibody (Genway) was directly immobilized across a biosensor chip, and antibodies samples were injected over reaction matrices at a flow rate of 5 μl/min. The association and dissociation rate constants, $k_{on}$ ($M^{-1}$ $s^{-1}$) and $k_{off}$ ($s^{-1}$) respectively, were determined with a continuous flow rate of 30 μl/min. Rate constants were derived by making kinetic binding measurements at five different concentrations of human PD-1/Fc protein. The equilibrium dissociation constant $K_D$ (M) of the reaction between antibodies and related target proteins was then calculated from the kinetic rate constants using the formula $K_D = k_{off}/k_{on}$. Affinities for eleven murine anti-PD-1 antibodies were measured, as set forth in Table 3, below.

TABLE 3:

Affinity Measurements for 11 Anti-PD-1 Monoclonal Antibodies

| mAb Identifier | $k_{on}$ (1/Ms) | $k_{off}$ (1/s) | $K_D$ (M) |
|---|---|---|---|
| mAb701 | $7.52 \times 10^4$ | $5.12 \times 10^{-4}$ | $6.81 \times 10^{-9}$ |
| mAb703 | $3.47 \times 10^5$ | $8.50 \times 10^{-4}$ | $2.45 \times 10^{-9}$ |
| mAb707 | $5.26 \times 10^4$ | $3.10 \times 10^{-4}$ | $5.89 \times 10^{-9}$ |
| mAb709 | $1.11 \times 10^5$ | $1.04 \times 10^{-4}$ | $9.39 \times 10^{-9}$ |
| mAb711 | $4.80 \times 10^4$ | $2.52 \times 10^{-4}$ | $5.24 \times 10^{-9}$ |
| mAb713 | $1.45 \times 10^5$ | $2.85 \times 10^{-4}$ | $1.96 \times 10^{-9}$ |
| mAb714 | $9.94 \times 10^4$ | $2.10 \times 10^{-4}$ | $2.11 \times 10^{-9}$ |
| mAb715 | $1.58 \times 10^5$ | $2.37 \times 10^{-4}$ | $1.50 \times 10^{-9}$ |
| mAb716 | $1.26 \times 10^5$ | $1.40 \times 10^{-4}$ | $1.11 \times 10^{-9}$ |
| mAb718 | $5.84 \times 10^4$ | $2.83 \times 10^{-4}$ | $4.84 \times 10^{-9}$ |
| mAb719 | $7.15 \times 10^4$ | $2.15 \times 10^{-4}$ | $3.00 \times 10^{-9}$ |

Example 3: Functional Activity of Anti-PD-1 Antibodies

A mixed lymphocyte reaction (MLR) assay was performed using monocyte-derived dendritic cells from one donor and allogeneic CD4+ T cells from another donor. Whole blood samples were collected from healthy donors, and PBMC were isolated from whole blood using Ficoll-Pague gradient centrifugation. On day 1, PBMC from one donor were isolated and diluted with serum-free RPMI 1640 at $1 \times 10^6$ cells/m. The diluted PBMC were seeded into a 6-well tissue culture plate at 3 m/well and incubated for 3 hours. Supernatant was removed and unattached cells were washed off. The attached monocytes were polarized into dendritic cells with 250 U/ml of IL-4 and 500 U/ml of GM-CSF in RPMI 1640 with 10% FBS. The medium was replaced with fresh medium containing IL-4 and GM-CSF on day 4. At day 7, immature dendritic cells were collected and treated with 1 μg/ml bacterial lipopolysaccharide (LPS) (Sigma) in RPMI 1640 with 10% FBS for an additional 24 hrs. for maturation. At Day 8, CD4+ T cells were isolated from PBMC from another donor by negative selection and adjusted to final concentration at $2 \times 10^6$ cells/ml. Mature dendritic cells were treated with mitomycin C at 37° C. for 1.5 hr., then dendritic cells were washed with PBS and adjusted to a final concentration at $1 \times 10^6$ cells/ml. CD4+ T cells (responder cells) were added into 96-well plates at 100 i/well and pre-treated with test antibody at diluted concentration for 30 minutes. Mature dendritic cells (stimulator cells) were added into the wells at 100 μl/well. The final volume of each well is 200 μl. The mixed lymphocytes were incubated at 37° C. IL-2 production was measured after 72 hours (see FIGS. 1A and 1B); IFN-γ was measured at 120 hours (see FIGS. 2A and 2B).

Example 4: Cloning and Sequence Analysis of Anti-PD-1 mAbs

Total RNA of each hybridoma clone was isolated from $>5 \times 10^6$ cells with TRIzol reagent (Cat. No. 15596; Invitrogen). cDNA was synthesized by SuperScript™ III First-Strand Synthesis SuperMix (Cat. No. 18080; Invitrogen) and applied as a PCR template of Mouse Ig-Primer Set (Cat. No. 69831-3; Novagen). PCR products were analyzed by electrophoresis on a 1.2% agarose gel with SYBR™ Safe DNA gel stain (Invitrogen). DNA fragments with correct size were purified with NucleoSpin® Gel and PCR Clean-up (Cat No. 740609; Macherey-Nagel GmbH) according to manufacturer's instructions and subcloned to pMD18-T vector (Sino Biological Inc.) individually. Fifteen colonies from each transformation were selected and sequences of insert fragments were analyzed by DNA sequencing. Sequences were confirmed if at least 8 match consensus sequences for VH and VL. The protein sequences of murine anti-PD-1 mAbs variable regions were analyzed by sequence homology alignment and listed in Table 4. Complementarity determining regions (CDRs) were identified based on Kabat numbering and appear underlined in Table 4 below.

TABLE 4

Amino Acid Sequences of 8 Anti-PD-1 Murine Monoclonal Antibodies

| antibody | domain | SEQ ID NO. | amino acid squenees<br>12345678901234567890123456789012345678901234567890 |
|---|---|---|---|
| mAb701 | VH | 4 | EVLLVESGGGLVKPGGSLKLSCAASGFTFS<u>SYMMS</u>WIRQT<br>PERRLEWVA<u>SMSGGGRDTYYPDSVKG</u>RFTISRDNAKNTLY<br>LQMSSLRSEDTALYYCAR<u>RGTYAMDY</u>WGQGTSVTVSS |
|  | VL | 5 | DIQMTQSPASQSASLGESVTITC<u>LASQTIGTWL</u>TWYQQKP<br>GKSPQLLIY<u>AATSLAD</u>GVPSRFSGSGSGTKFSFKISSLQA<br>EDFVSYYC<u>QQLYSTPWT</u>FGGGTKLEIK |
| mAb703 | VH | 6 | DVQLQESGPGLVKPSQSLSLTCSVTGYSI<u>TTGYYWN</u>WIRQ<br>FPGNKLEWMG<u>YMSYDGNNNYNPSLKN</u>RISITRDTSKNQFL<br>LRLNSVTTEDTATYFCAR<u>DRGTTILGGTMDY</u>WGQGTSVTV<br>S |
|  | VL | 7 | SIVMTQTPKFLFVSAGDRVTIAC<u>KASQSVSNDVA</u>WYQQKP<br>GQSPKLLIYY<u>AFYRYT</u>GVPDRFTGSGYGTDFTFTISTVQA<br>EDLAVYFC<u>QQDYSSPWT</u>FGGGTKLEIK |
| mAb709 | VH | 8 | EVKLVESGGGLVKPGGSLKLSCAASGFTFS<u>FYTMS</u>WVRQT<br>PEKRLEWVA<u>TISGGGRDTYYPDSVKG</u>RFTISRDNAKNTLY<br>LHMSSLRSEDTALYYCAG<u>QGGNYLFAY</u>WGQGTLVTVSA |
|  | VL | 9 | DIVMTQSHKFMSTSVGDSVTITC<u>KASQDVNTVVA</u>WYQQKP<br>GQSLKVLIS<u>WASTRHT</u>GVPARFTGSGSGTDYTLTISSVQA<br>EDLALYYC<u>QQHYTTPYT</u>FGGGTQLEIK |
| mAb713 | VH | 10 | EVKLVESGGGLVKPGGSLELSCAASGFTSS<u>DYGMH</u>WVRQA<br>PEKGLEWVA<u>YISSGSYTIYYADTVKG</u>RFTISRDNAKNTLF<br>LQMTSLRSEDTAMYYCAK<u>RGGSSHVNVMDY</u>WGQGTSVTVS<br>S |
|  | VL | 11 | DIQMTQSSSYLSVSLGGRVTITC<u>KASDHINNWLA</u>WYQQKP<br>GNAPRLLIS<u>GATSLET</u>GVPSRFSGSGSGKDYTLSITSLQT<br>EDVATYYC<u>QQYWSPPYT</u>FGGGTKLEIK |
| mAb714 | VH | 12 | EVHLQQSGPELVKPGASVKIFCKASGYTFT<u>DNNVE</u>WVKQS<br>HGKSLEWIG<u>DINPNNGDTLYSQYFKD</u>KATLTVDKSSTTAY<br>MELRSLTSEDTGLYYCAR<u>GKSDQFDY</u>WGQGTTLTVSS |
|  | VL | 13 | DIQMTQSPASQSASLGESVTITC<u>LASQTIGTWLA</u>WYQQKP<br>GKSPQLLIY<u>AATSLAD</u>GVPSRFSGSGSGTKFSFKISSLQG<br>EDFVSYYC<u>QQLYSSPWT</u>FGGGTKLEIK |
| mAb715 | VH | 14 | EVMLVESGGGLLKPGGSLKLSCAASGFTFS<u>SYAMS</u>WVRQT<br>PEKRLEWVA<u>TISGGGRDTYYPDSVKG</u>RFTISRDNAKNTLY<br>LQMTSLRSEDTAFYYCAG<u>QGGTYLFAS</u>WGQGTLVTVSA |
|  | VL | 15 | DIVMTQSHKFMSTSVGDSVTITC<u>KASQDVNTAVA</u>WYQQKP<br>GQPPKVLIY<u>WASTRHT</u>GVPDRFTGSGSGTDYTLTISSVQA<br>EDLALYYC<u>QQHYTTPYT</u>FGGGTKLEIK |
| mAb718 | VH | 16 | QVQLQQSGAELVRPGASVTLSCKASGYTFT<u>DYEMH</u>WAKQT<br>PVHGLEWIG<u>VIEPESGGTVYNQKFKG</u>KAKLTADKSSRTAY<br>MELRSLTSEDSAVYYCTR<u>EGFNSDHYFDY</u>WGQGTTLTVSS |
|  | VL | 17 | DVLMTQTPLSLPVSLGDQASISC<u>RSSQNIVHSNGNTYLE</u>W<br>YLQKPGQSPKLLIY<u>KVFNRFS</u>GVPDRFSGSGSGTDFTLKI<br>SRVEAEDLGVYYC<u>FQGSHVPYT</u>FGGGTKLEIK |
| mAb719 | VH | 18 | EVKLVESGGGLVKPGGSLKLSCTASGFSFS<u>SHLMS</u>WVRQT<br>PEKRLEWVA<u>AISGGGADTYYPDSVKG</u>RFTISRDNAKNTLY<br>LQMRSLRSEDTALYYCTR<u>QILAFDS</u>WGQGTTLTVSS |
|  | VL | 19 | DIQMNQSPSSLSVSLGDTITITC<u>HASQNIYVWLN</u>WYQQKP<br>GNIPKLLIY<u>KASNLHT</u>GVPSRFSGGGSGTGFTLTISSLQP<br>EDIATYYC<u>QQGQSYPWT</u>EGGGTKLEIK |

Example 5: Humanization of Murine Anti-PD-1 Antibodies

Based on the human PD-1 binding activity, cynomolgus PD-1 cross-reactivity similarly to human, almost 100% blocking activity in the RBA assay, functional activity in MLR and at least nanomole affinity as measured by Biacore, four anti-PD-1 antibodies, mAb709, mAb713, mAb703, and mAb719, were selected for humanization.

Example 5.1: Humanization of Murine Antibody mAb709

The mAb709 variable region genes were employed to create a humanized antibody. In the first step of this process, the amino acid sequences of the VH and VL of mAb709 were compared against the available database of human Ig V-gene sequences in order to find the overall best-matching human germline Ig V-gene sequences. Additionally, the framework 4 segment of VH or VL was compared against the J-region database to find the human framework having the highest homology to the murine VH and VL regions, respectively. For the light chain, the closest human V-gene match was the O12 gene; and for the heavy chain, the closest human match was the VH3-7 gene. Humanized variable domain sequences were then designed where the CDR-L1, CDR-L2, and CDR-L3 of the mAb709 light chain were grafted onto framework sequences of the O12 gene with JK4 framework 4 sequence after CDR-L3; and the CDR-H1, CDR-H2, and CDR-H3 of the mAb709 heavy chain were grafted onto framework sequences of the VH3-7 with JH1 framework 4 sequence after CDR-H3. A 3-dimensional Fv model of mAb709 was then generated to determine if there were any framework positions where mouse amino acids were critical to support loop structures or the VH/VL interface. These residues in humanized sequences should be back-mutated to mouse residues at the same position to retain affinity/activity. In the case of the light chain, a Phe to Tyr back mutation at position 71 (F71Y, Kabat numbering), a Tyr to Ser back mutation at position 49 (Y49S, Kabat numbering), a Gln to Val back mutation at position 3 (Q3V, Kabat numbering), a Leu to Val back mutation at position 46 (L46V, Kabat numbering), a Ser to Thr at position 63 (S63T, Kabat numbering), an Ala to Ser back mutation at position 43 (A43S, Kabat numbering), and a Pro to Leu back mutation at position 44 (P44L, Kabat numbering) were identified as desirable back mutations. In the case of the heavy chain, an Arg to Gly mutation at position 98 (R94G, by Kabat numbering), and a Gly to Arg mutation at position 44 (G44R, by Kabat numbering), were identified as desirable back mutations. Mutated variable domains containing one or more of these back mutations were constructed. See Table 5 below. (Back mutated framework amino acid residues are indicated with double underscore original parental antibody are underlined.)

TABLE 5

Humanization VH/VL Design for mAb709 w/ Back Mutations to Murine Residues

| Humanized mAb709 VH or VL Identifier | SEQ ID NO. | Amino acid sequences 1234567890123456789012345678901234567890 |
|---|---|---|
| mAb709 VH.1 | 20 | EVQLVESGGGLVQPGGSLRLSCAASGFTFSFYTMSWVRQA PGKGLEWVATISGGGRDTYYPDSVKGRFTISRDNAKNSLY LQMNSLRAEDTAVYYCARQGGNYLFAYWGQGTLVTVSS |
| mAb709 VH.1A | 21 | EVQLVESGGGLVQPGGSLRLSCAASGFTFSFYTMSWVRQA PGKGLEWVATISGGGRDTYYPDSVKGRFTISRDNAKNSLY LQMNSLRAEDTAVYYCAGQGGNYLFAYWGQGTLVTVSS |
| mAb709 VH.1B | 22 | EVQLVESGGGLVQPGGSLRLSCAASGFTFSFYTMSWVRQA PGKRLEWVATISGGGRDTYYPDSVKGRFTISRDNAKNSLY LQMNSLRAEDTAVYYCAGQGGNYLFAYWGQGTLVTVSS |
| mAb009 VK.1A | 23 | DIQMTQSPSSLSASVGDRVTITCKASQDVNTVVAWYQQKP GKAPKLLIYWASTRHTGVPSRFSGSGSGTDYTLTISSLQP EDFATYYCQQHYTTPYTFGGGTKVEIK |
| mAb709 VK.1B | 24 | DIQMTQSPSSLSASVGDRVTITCKASQDVNTVVAWYQQKP GKAPKLLISWASTRHTGVPSRFSGSGSGTDYTLTISSLQP EDFATYYCQQHYTTPYTFGGGTKVEIK |
| mAb709 VK.1C | 25 | DIVMTQSPSSLSASVGDRVTITCKASQDVNTVVAWYQQKP GKAPKVLISWASTRHTGVPSRFSGSGSGTDYTLTISSLQP EDFATYYCQQHYTTPYTFGGGTKVEIK |
| mAb709 VK.1D | 26 | DIVMTQSPSSLSASVGDRVTITCKASQDVNTVVAWYQQKP GKAPKVLISWASTRHTGVPSRFTGSGSGTDYTLTISSLQP EDFATYYCQQHYTTPYTFGGGTKVEIK |
| mAb709 VK.1E | 27 | DIVMTQSPSSLSASVGDRVTITCKASQDVNTVVAWYQQKP GKSLKVLISWASTRHTGVPSRFTGSGSGTDYTLTISSLQP EDFATYYCQQHYTTPYTFGGGTKVEIK |

The humanized VH and VK genes were produced synthetically and then respectively cloned into vectors containing the human IgG1 and human kappa constant domains. (See Table 6, below.)

TABLE 6

Human Constant Region Sequence Used in Antibody Humanization

| Constant Region | SEQ ID NO: | Amino Acid Sequences 12345678901236567890 12345678901234567890 |
|---|---|---|
| human constant Ig gamma 1 mutant | 28 | ASTKGPSVFPLAPSSKSTSGGTAALGCLVKDYFP EPVTVSWNSGALTSGVHTFPAVLQSSGLYSLSSV VTVPSSSGTQTYICNVNHKPSNTKVDKKVEPKSC DKTHTCPPCPAPEAAGGPSVFLFPPKPKDTLMIS RTPEVTCVVVDVSHEDPEVKFNWYVDGVEVHNAK TKPREEQYNSTYRVVSVLTVLHQDWLNGKEYKCK VSNKALPAPIEKTISKAKGQPREPQVYTLPPSRE EMTKNQVSLTCLVKGFYPSDIAVEWESNGQPENN YKTTPTVLDSDGSFFLYSKLTVDKSRWQQGNVFS CSVMHEALHNHYTQKSLSLSPGK |
| human constant kappa | 29 | RTVAAPSVFIFPPSDEQLKSGTASVVCLLNNFYP REAKVQWKVDNALQSGNSQESVTEQDSKDSTYSL SSTLTLSKADYEKHKVYACEVTHQGLSSPVTKSF NRGEC |

The pairing of the humanized VH and the humanized VK chains created 15 humanized antibodies, named HumAb709-1 to HumAb709-15 (Table 7). A chimeric antibody with parental mouse VH/VL and human constant region sequences (mAb709c) was also produced as a positive control, for affinity comparison. All recombinant mAbs were expressed and purified.

TABLE 7

Production List of anti-PD-1 Humanized mAb709 Antibodies

| Antibody Identifier | VH Region in Heavy Chain | VL Region in Light K Chain |
|---|---|---|
| HumAb709-1 | mAb709 VH.1 | mAb709 VK.1A |
| HumAb709-2 | mAb709 VH.1A | mAb709 VK.1A |
| HumAb709-3 | mAb709 VH.1B | mAb709 VK.1A |
| HumAb709-4 | mAb709 VH.1 | mAb709 VK.1B |
| HumAb709-5 | mAb709 VH.1A | mAb709 VK.1B |
| HumAb709-6 | mAb709 VH.1B | mAb709 VK.1B |
| HumAb709-7 | mAb709 VH.1 | mAb709 VK.1C |

TABLE 7-continued

Production List of anti-PD-1 Humanized mAb709 Antibodies

| Antibody Identifier | VH Region in Heavy Chain | VL Region in Light K Chain |
|---|---|---|
| HumAb709-8 | mAb709 VH.1A | mAb709 VK.1C |
| HumAb709-9 | mAb709 VH.1B | mAb709 VK.1C |
| HumAb709-10 | mAb709 VH.1 | mAb709 VK.1D |
| HumAb709-11 | mAb709 VH.1A | mAb709 VK.1D |
| HumAb709-12 | mAb709 VH.1B | mAb709 VK.1D |
| HumAb709-13 | mAb709 VH.1 | mAb709 VK.1E |
| HumAb709-14 | mAb709 VH.1A | mAb709 VK.1E |
| HumAb709-15 | mAb709 VH.1B | mAb709 VK.1E |
| HumAb709c | SEQ ID NO: 8 | SEQ ID NO: 9 |

All 15 humanized antibodies and the chimeric antibody (mAb709c) were characterized by binding ELISA and cell-based RBA. For cell-based RBA, $2\times10^5$ cells/well of CHO-K1-huPD1 cells were added to a pre-blocked 96-well round-bottomed plate and after washing, 50 µl antibodies with diluted concentration ranging from 0.064 nM to 200 nM were added to each well. Next, 50 µl of 60 µg/ml biotinylated PD-L1/Fc or biotinylated PD-L2/Fc protein were added. After gentle mixing and incubation at 4° C., the cells were washed and stained by Alexa Fluor™ 488 streptavidin solution (1:1000, ThermoFisher Scientific; Cat. No. S32354). Signals were readout by FACS and curves were fitted by GraphPad software. Calculated IC50 values are shown in Table 8 below. Antibodies having positive (low) IC50 values (i.e., below about 1.0 nM for at least one PD-1 ligand) were further analyzed for binding affinity by surface plasmon resonance measurements using a Biacore T200 instrument Briefly, goat anti-human IgG Fc polyclonal antibody was directly immobilized across a biosensor chip, and anti-PD-1 humanized antibody or chimeric antibody samples were injected over reaction matrices at a flow rate of 5 µl/mm. The association and dissociation rate constants, k ($M^{-1}$ $s^{-1}$) and $k_{off}(s^{-1})$, respectively, were determined by making kinetic binding measurements at five different concentrations of human PD-1-His protein at a continuous flow rate of 30 µl/min. The equilibrium dissociation constant $K_D$ (M) of the reaction between antibodies and related target proteins was calculated from the kinetic rate constants using the formula $K_D=k_{off}/k_{on}$. Affinities for five of the mAb709 humanized anti-PD-1 derivatives are shown in Table 8. HumAb709-8 had minimal back-mutation(s) while maintaining to the greatest extent the affinity of the parental variable domains on chimeric mAb709c.

TABLE 8

RBA Values and Binding Affinities for Humanized mAb709 anti-PD-1 Antibodies

| Humanized Antibody ID | PD-L1 RBA IC50 (nM) | PD-L2 RBA IC50 (nM) | $k_{on}$ (1/Ms) | $k_{off}$ (1/s) | $K_D$ (M) |
|---|---|---|---|---|---|
| HumAb709-1 | 1.02 | 1.64 | $1.95 \times 10^5$ | $2.145 \times 10^{-3}$ | $1.10 \times 10^{-8}$ |
| HumAb709-2 | 0.47 | 0.99 | $8.03 \times 10^4$ | $5.5 \times 10^{-5}$ | $6.84 \times 10^{-10}$ |
| HumAb709-3 | 1.25 | 1.64 | | | |
| HumAb709-4 | 0.78 | 1.68 | | | |
| HumAb709-5 | 0.67 | 0.97 | | | |
| HumAb709-6 | 1.23 | 1.26 | | | |
| HumAb709-7 | 0.40 | 0.84 | $1.41 \times 10^5$ | $3.36 \times 10^{-4}$ | $2.36 \times 10^{-9}$ |
| HumAb709-8 | 0.44 | 1.00 | $1.27 \times 10^5$ | $4.69 \times 10^{-5}$ | $3.68 \times 10^{-1}$ |
| HumAb709-9 | 1.04 | 1.76 | | | |
| HumAb709-10 | 0.29 | 0.80 | $1.46 \times 10^5$ | $2.97 \times 10^{-4}$ | $2.04 \times 10^{-9}$ |
| HumAb709-11 | 0.55 | 0.92 | | | |
| HumtAb709-12 | 0.45 | 1.35 | | | |
| HumAb709-13 | 0.50 | 0.78 | | | |
| HumAb709-14 | 0.51 | 0.92 | | | |

TABLE 8-continued

RBA Values and Binding Affinities for Humanized mAb709 anti-PD-1 Antibodies

| Humanized Antibody ID | PD-L1 RBA IC50 (nM) | PD-L2 RBA IC50 (nM) | $k_{on}$ (1/Ms) | $k_{off}$ (1/s) | $K_D$ (M) |
|---|---|---|---|---|---|
| HumAb709-15 | 0.90 | 1.21 | | | |
| mAb709c | 0.62 | 0.56 | $1.21 \times 10^5$ | $6.88 \times 10^{-5}$ | $5.67 \times 10^{-1}$ |

Example 5.2: Humanization of Murine Antibody mAb713

The variable region genes for anti-PD-1 mAb713 were employed to create a humanized antibody. The amino acid sequences of the VH and VK of mAb713 were compared against the available database of human Ig V-gene sequences in order to find the overall best-matching human germline Ig V-gene sequences. Additionally, the framework 4 segment of VH or VL was compared against the J-region database to find the framework having the highest homology to the murine VH and VL regions, respectively. For the light chain, the closest human V-gene match was the O18 gene; and for the heavy chain, the closest human match was the VH3-48 gene. Humanized variable domain sequences were then designed where the CDR-L1, CDR-L2, and CDR-L3 of the mAb713 light chain were grafted onto framework sequences of the O18 gene with JK4 framework 4 sequence after CDR-L3; and the CDR-H1, CDR-H2, and CDR-H3 of the mAb713 heavy chain were grafted onto framework sequences of the VH3-48 with JH6 framework 4 sequence after CDR-H3. A 3-dimensional Fv model of mAb709 was then generated to determine if there were any framework positions where mouse amino acids were critical to support loop structures or the VH/VL interface. These residues in humanized sequences should be back-mutated to mouse residues at the same position to retain affinity/activity. In the case of the light chain, a Phe to Tyr back mutation at position 71 (F71Y, Kabat numbering), a Tyr to Ser back mutation at position 49 (Y49S, Kabat numbering), and a Thr to Lys back mutation at position 69 (T69K, Kabat numbering) were identified as desirable back mutations. In the case of the heavy chain, an Arg to Lys mutation at position 98 (R94K, by Kabat numbering), a Phe to Ser back mutation at position 29 (F29S, Kabat numbering), and a Ser to Ala back mutation at position 49 (S49A, by Kabat numbering), were identified as desirable back mutations. Mutated variable domains containing one or more of these back mutations were constructed. See Table 9 below. (Back mutated framework amino acid residues are indicated with double underscore: murine CDRs from the original parental antibody are underlined.)

TABLE 9

Variable Domain Sequence Variants for mAb713 VH and VL

| mAb713 VH/VL variants | SEQ ID NO. | Amino acid sequence 12345678901234567890 12345678901234567890 |
|---|---|---|
| mAb713 VH.1 | 30 | EVQLVESGGGLVQPGGSLRLSCAASGFTFSDYGMH WVRQAPGKGLEWVSYISSGSYTIYYADTVKGRFTI SRDNAKNSLYLQMNSLRDEDTAVYYCARRGGSSHV NVMDYWGQGTTVTVSS |
| mAb713 VH.1A | 31 | EVQLVESGGGLVQPGGSLRLSCAASGFTFSDYGMH WVRQAPGKGLEWVSYISSGSYTIYYADTVKGRFTI SRDNAKNSLYLQMNSLRDEDTAVYYCAKRGGSSHV NVMDYWGQGTTVTVSS |
| mAb713 VH.1B | 32 | EVQLVESGGGLVQPGGSLRLSCAASGFTSSDYGMH WVRQAPGKGLEWVSYISSGSYTIYYADTVKGRFTI SRDNAKNSLYLQMNSLRDEDTAVYYCAKRGGSSHV NVMDYWGQGTTVTVSS |
| mAb713 VH.1C | 33 | EVQLVESGGGLVQPGGSLRLSCAASGFTSSDYGMH WVRQAPGKGLEWVAYISSGSYTIYYADTVKGRFTI SRDNAKNSLYLQMNSLRDEDTAVYYCAKRGGSSHV NVMDYWGQGTTVTVSS |
| mAb713 VK.1 | 34 | DIQMTQSPSSLSASVGDRVTITCKASDHINNWLAW YQQKPGKAPKLLIYGATSLETGVPSRFSGSGSGTD FTFTISSLQPEDIATTYCQQYWSPPYTFGGGTKVE IK |
| mAb713 VK.1A | 35 | DIQMTQSPSSLSASVGDRVTITCKASDHINNWLAW YQQKPGKAPKLLIYGATSLETGVPSRFSGSGSGTD YTFTISSLQPEDIATYYCQQYWSPPYTFGGGTKVE IK |
| mAb713 VK.1B | 36 | DIQMTQSPSSLSASVGDRVTITCKASDHINNWLAW YQQKPGKAPKLLISGATSLETGVPSRFSGSGSGTD YTFTISSLQPEDIATYYCQQYWSPPYTFGGGTKVE IK |
| mAb713 VK.1C | 37 | DIQMTQSPSSLSASVGDRVTITCKASDHINNWLAW YQQKPGKAPKLLISGATSLETGVPSRFSGSGSGKD YTFTISSLQPEDIATYYCQQYWSPPYTFGGGTKVE IK |

The humanized VH and VK genes were produced synthetically and then individually cloned into vectors containing the human IgG1 and human kappa constant domains (see Table 6, supra). The pairing of the human VH variants and the human VK variants created 16 humanized antibodies, named HumAb713-1 to HumAb713-16 (Table 10). A chimeric antibody (mAb73c) with parental mouse VH/VL and human constant sequences was also produced as a positive control, for affinity comparison.

TABLE 10

Production List for Humanized mAb713 An-PD-1 Antibodies

| Antibody identifier | VH Region in Heavy Chain | VL Region in Light κChain |
|---|---|---|
| HumAb713-1 | mAb713 VH.1 | mAb713 VK.1 |
| HumAb713-2 | mAb713 VH.1A | mAb713 VK.1 |
| HumAb713-3 | mAb713 VH.1B | mAb713 VK.1 |
| HumAb713-4 | mAb713 VH.1C | mAb713 VK.1 |
| HumAb713-5 | mAb713 VH.1 | mAb713 VK.1A |
| HumAb713-6 | mAb713 VH.1A | mAb713 VK.1A |

TABLE 10-continued

Production List for Humanized mAb713 An-PD-1 Antibodies

| Antibody identifier | VH Region in Heavy Chain | VL Region in Light κChain |
|---|---|---|
| HumAb713-7 | mAb713 VH.1B | mAb713 VK.1A |
| HumAb713-8 | mAb713 VH.1C | mAb713 VK.1A |
| HumAb713-9 | mAb713 VH.1 | mAb713 VK.1B |
| HumAb713-10 | mAb713 VH.1A | mAb713 VK.1B |
| HumAb713-11 | mAb713 VH.1B | mAb713 VK.1B |
| HumAb713-12 | mAb713 VH.1C | mAb713 VK.1B |
| HumAb713-13 | mAb713 VH.1 | mAb713 VK.1C |
| HumAb713-14 | mAb713 VH.1A | mAb713 VK.1C |
| HumAb713-15 | mAb713 VH.1B | mAb713 VK.1C |
| HumAb713-16 | mAb713 VH.1C | mAb713 VK.1C |
| mAb713c | SEQ ID NO: 10 | SEQ ID NO: 11 |

All 16 humanized antibodies and the chimeric antibody (mAb713c) were characterized by binding ELISA, cell-based RBA, and Biacore affinity testing. The results are summarized in Table 11.

TABLE 11

RBA Values and Binding Affinities for Humanized mAb713 anti-PD-1 Antibodies

| Humanized Antibody ID | PD-L1 RBA IC50 (nM) | PD-L2 RBA IC50 (nM) | $k_{on}$ (1/Ms) | $k_{off}$ (1/s) | $K_D$ (M) |
|---|---|---|---|---|---|
| HumAb713-1 | 0.50 | 1.20 | $9.010 \times 10^4$ | $1.003 \times 10^4$ | $1.113 \times 10^{-8}$ |
| HumAb713-2 | 1.71 | 3.13 | | | |
| HumAb713-3 | 0.77 | 1.24 | $8.447 \times 10^4$ | $2.082 \times 10^4$ | $2.465 \times 10^{-9}$ |
| HumAb713-4 | 1.06 | 2.24 | | | |
| HumAb713-5 | 0.91 | 2.95 | | | |
| HumAb713-6 | 1.04 | 1.46 | | | |
| HumAb713-7 | 0.76 | 1.40 | $1.237 \times 10^5$ | $3.500 \times 10^{-4}$ | $2.829 \times 10^{-9}$ |
| HumAb713-8 | 1.05 | 1.91 | | | |
| HumAb713-9 | 1.20 | 2.00 | | | |
| HumAb713-10 | 0.80 | 1.23 | | | |
| HumAb713-11 | 0.51 | 0.97 | $1.591 \times 10^5$ | $3.776 \times 10^4$ | $2.373 \times 10^{-9}$ |
| HumAb713-12 | 0.94 | 1.59 | | | |
| HumAb713-13 | 0.70 | 2.13 | | | |
| HumAb713-14 | 0.91 | 1.45 | | | |
| HumAb713-15 | 0.88 | 1.65 | | | |
| HumAb713-16 | 0.65 | 1.63 | | | |
| mAb713c | 0.91 | 2.20 | $2.182 \times 10^5$ | $2.839 \times 10^4$ | $1.301 \times 10^{-9}$ |

Figure 5:
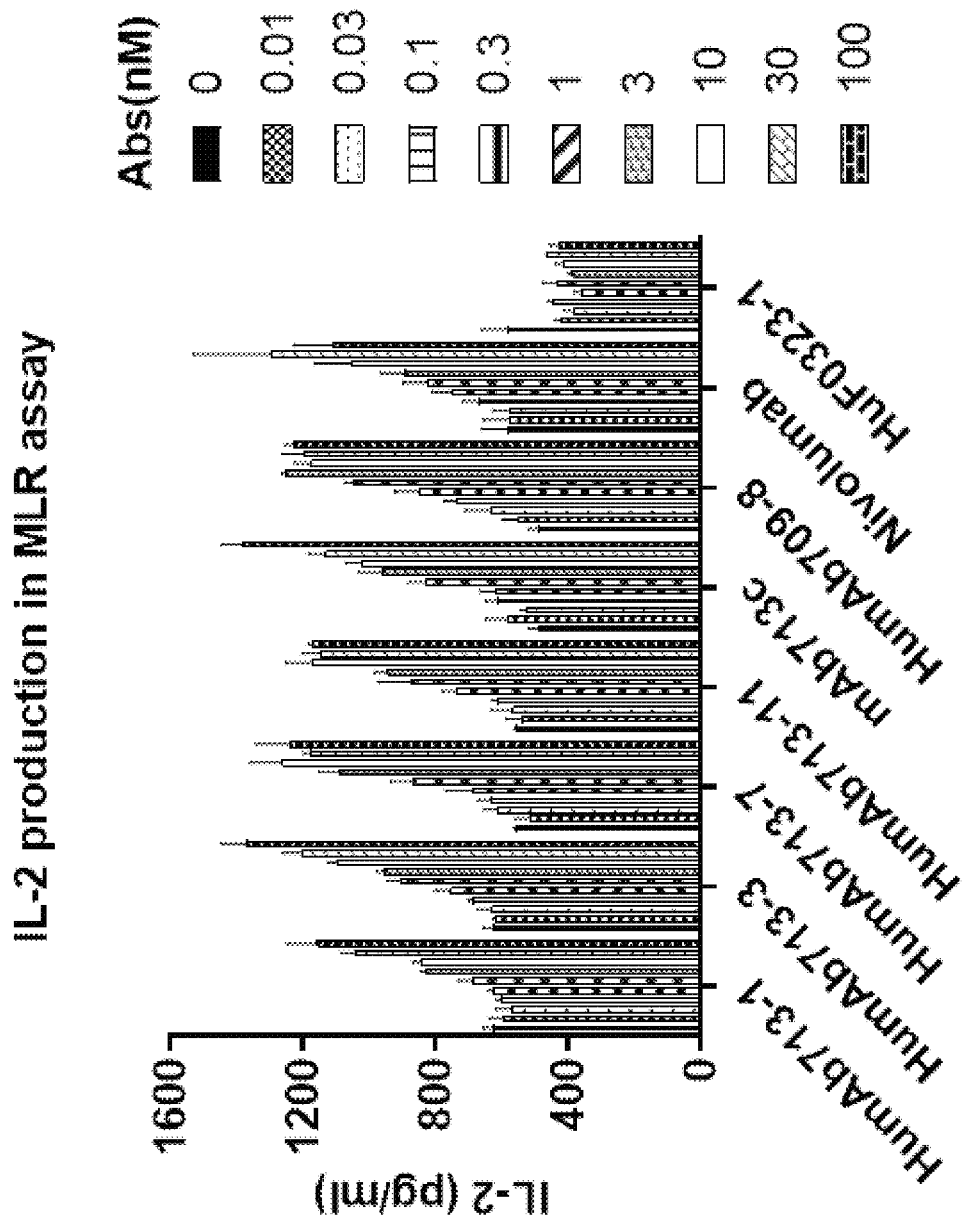
FIG. 5 shows bar graphs of IL-2 production levels in a mixed lymphocyte reaction testing the effect of various humanized anti-PD-1 antibodies disclosed herein, in comparison to a chimera with the parental murine mAb713 variable domains (mAb713c), a recombinant therapeutic anti-PD-1 antibody produced from published sequences (nivolumab), and a control human antibody directed against irrelevant antigen ("HuF0323-1").

HumAb713-7 had minimal back-mutation(s) while maintaining the affinity characteristics of the parental variable domains of the chimeric antibody, mAb713c. Functional activity of mAb713 humanized antibodies were validated in an MLR assay as described in Example 3. As seen in FIG. 5, HumAb713-7 exhibited comparable activity with the chimeric antibody mAb713c in MLR, in line with its retained binding properties.

Example 5.3: Humanization of Murine Antibody mAb703

Following the same procedure as in Example 5.1 and 5.2, murine anti-PD-1 antibody mAb703 was selected and humanized. Humanized variable domains, some containing one or more back mutations, were constructed, and the amino acid sequences are set forth in Table 12 below. (Back mutated framework amino acid residues are indicated with double underscore murine CDRs from the original parental antibody are underlined.)

TABLE 12

Variable Domain Sequence Variants for mAb703 VH and VL

| mAb703 VH/VL variants | SEQ ID NO. | Amino acid sequence 12345678901234567890 12343678901234567890 |
|---|---|---|
| mAb703 VH.1A | 38 | EVQLQESGPGLVKPSETLSLTCAVSGYSISTG YYWNWIRQPPGKGLEWIGYMSYDGNNNYNPSL KNRVTISRDTSKNQFSLKLSSVTAADTAVYYC ARDRGTTILGGTMDYWGQGTTVTVSS |
| mAb703 VH.1B | 39 | EVQLQESGPGLVKPSETLSLTCAVSGYSISTG YYWNWIRQPPGKGLEWIGYMSYDGNNNYNPSL KNRITISRDTSKNQFSLKLSSVTAADTAVYYC ARDRGTTILGGTMDYWGQGTTVTVSS |
| mAb703 VH.1C | 40 | EVQLQESGPGLVKPSETLSLTCAVSGYSISTG YYWNWIRQPPGKGLEWMGYMSYDGNNNYNPSL KNRITISRDTSKNQFSLKLSSVTAADTAVYYC ARDRGTTILGGTMDYWGQGTTVTVSS |
| mAb703 VH.1D | 41 | EVQLQESGPGLVKPSETLSLTCAVSGYSITTG YYWNWIRQPPGKGLEWMGYMSYDGNNNYNPSL KNRITISRDTSKNQFSLKLSSVTAADTAVYYC ARDRGTTILGGTMDYWGQGTTVTVSS |
| mAb703 VH.1E | 42 | EVQLQESGPGLVKPSETLSLTCAVSGYSITTG YYWNWIRQPPGKKLEWMGYMSYDGNNNYNPSL KNRITISRDTSKNQFSLKLSSVTAADTAVYFC ARDRGTTILGGTMDYWGQGTTVTVSS |
| mAb703 VK.1 | 43 | DIQMTQSPSSLSASVGDRVTITCKASQSVSND VAWYQQKPGKAPKLLIYYAFYRYTGVPSRFSG SGSGTDFTLTISSLQPEDFATYYCQQDYSSPW TFGGGTKVEIK |
| mAb703 VK.1A | 44 | DIQMTQSPSSLSASVGDRVTITCKASQSVSND VAWYQQKPGKAPKLLIYYAFYRYTGVPSRFSG SGYGTDFTLTISSLQPEDFATYYCQQDYSSPW TFGGGTKVEIK |

TABLE 12-continued

Variable Domain Sequence Variants for mAb703 VH and VL

| mAb703 VH/VL variants | SEQ ID NO. | Amino acid sequence 12345678901234567890 12343678901234567890 |
|---|---|---|
| mAb703 VK.1B | 45 | DIQMTQSPSSLSASVGDRVTITCKASQSVSND VAWYQQKPGKAPKLLIYYAFYRYTGVPDRFSG SGYGTDFTLTISSLQPEDFATYYCQQDYSSPW TFGGGTKVEIK |
| mAb703 VK.1C | 46 | DIQMTQSPSSLSASVGDRVTITCKASQSVSND VAWYQQKPGKSPKLLIYYAFYRYTGVPDRFSG SGYGTDFTLTISSLQPEDFATYFCQQDYSSPW TFGGGTKVEIK |
| mAb703 VK.1D | 47 | SIVMTQSPSSLSASVGDRVTITCKASQSVSND VAWYQQKPGKSPKLLIYYAFYRYTGVPDRFTG SGYGTDFTLTISSLQPEDFATYFCQQDYSSPW TFGGGTKVEIK |

The humanized VH and VK genes were produced synthetically and then individually cloned into vectors containing the human IgG1 and human kappa constant domains (see Table 6, supra). The pairing of the human VH variants and the human VK variants created 25 humanized antibodies, named HumAb703-1 to HumAb73-25 (Table 713). A chimeric antibody with parental mouse VH/VL and human constant sequences was also produced as a positive control, for affinity comparison.

TABLE 13

Production List for Humanized mAb703 Anti-PD-1 Antibodies

| Antibody Identifier | VH Region in Heavy Chain | VL Region in Light K Chain |
|---|---|---|
| HumAb703-1 | mAb703 VH.1A | mAb703 VK.1 |
| HumAb703-2 | mAb703 VH.1B | mAb703 VK.1 |
| HumAb703-3 | mAb703 VH.1C | mAb703 VK.1 |
| HumAb703-4 | mAb703 VH.1D | mAb703 VK.1 |
| HumAb703-5 | mAb703 VH.1E | mAb703 VK.1 |
| HumAb703-6 | mAb703 VH.1A | mAb703 VK.1A |
| HumAb703-7 | mAb703 VH.1B | mAb703 VK.1A |
| HumAb703-8 | mAb703 VH.1C | mAb703 VK.1A |
| HumAb703-9 | mAb703 VH.1D | mAb703 VK.1A |
| HumAb703-10 | mAb703 VH.1E | mAb703 VK.1A |
| HumAb703-11 | mAb703 VH.1A | mAb703 VK.1B |
| HumAb703-12 | mAb703 VH.1B | mAb703 VK.1B |
| HumAb703-13 | mAb703 VH.1C | mAb703 VK.1B |
| HumAb703-14 | mAb703 VH.1D | mAb703 VK.1B |
| HumAb703-15 | mAb703 VH.1E | mAb703 VK.1B |
| HumAb703-16 | mAb703 VH.1A | mAb703 VK.1C |
| HumAb703-17 | mAb703 VH.1B | mAb703 VK.1C |
| HumAb703-18 | mAb703 VH.1C | mAb703 VK.1C |
| HumAb703-19 | mAb703 VH.1D | mAb703 VK.1C |
| HumAb703-20 | mAb703 VH.1E | mAb703 VK.1C |
| HumAb703-21 | mAb703 VH.1A | mAb703 VK.1D |
| HumAb703-22 | mAb703 VH.1B | mAb703 VK.1D |
| HumAb703-23 | mAb703 VH.1C | mAb703 VK.1D |
| HumAb703-24 | mAb703 VH.1D | mAb703 VK.1D |
| HumAb703-25 | mAb703 VH.1E | mAb703 VK.1D |
| mAb703c | SEQ ID NO: 6 | SEQ ID NO: 7 |

All 25 humanized antibodies and the chimeric antibody (mAb703c) were characterized by binding ELISA and Biacore affinity testing. Affinity results for the positive binders are summarized in Table 14.

TABLE 14

Binding Affinities for Selected Humanized mAb703 anti-PD-1 Antibodies

| Humanized Antibody in | $k_{on}$ (1/Ms) | $k_{off}$ (1 is) | $K_D$ (M) |
|---|---|---|---|
| HumAb703-11 | $1.874 \times 10^5$ | $1.757 \times 10^{-3}$ | $9.374 \times 10^{-9}$ |
| HumAb703-12 | $1.770 \times 10^5$ | $1.594 \times 10^{-3}$ | $9.003 \times 10^{-9}$ |
| HumAb703-13 | $1.454 \times 10^5$ | $1.537 \times 10^{-3}$ | $1.057 \times 10^{-8}$ |
| HumAb703-18 | $6.572 \times 10^4$ | $1.242 \times 10^{-3}$ | $1.890 \times 10^{-8}$ |
| HumAb703-22 | $2.294 \times 10^5$ | $1.593 \times 10^{-3}$ | $694.2 \times 10^{-9}$ |
| mAb703c | $3.594 \times 10^5$ | $9.664 \times 10^{-4}$ | $2.684 \times 10^{-9}$ |

Figure 2:
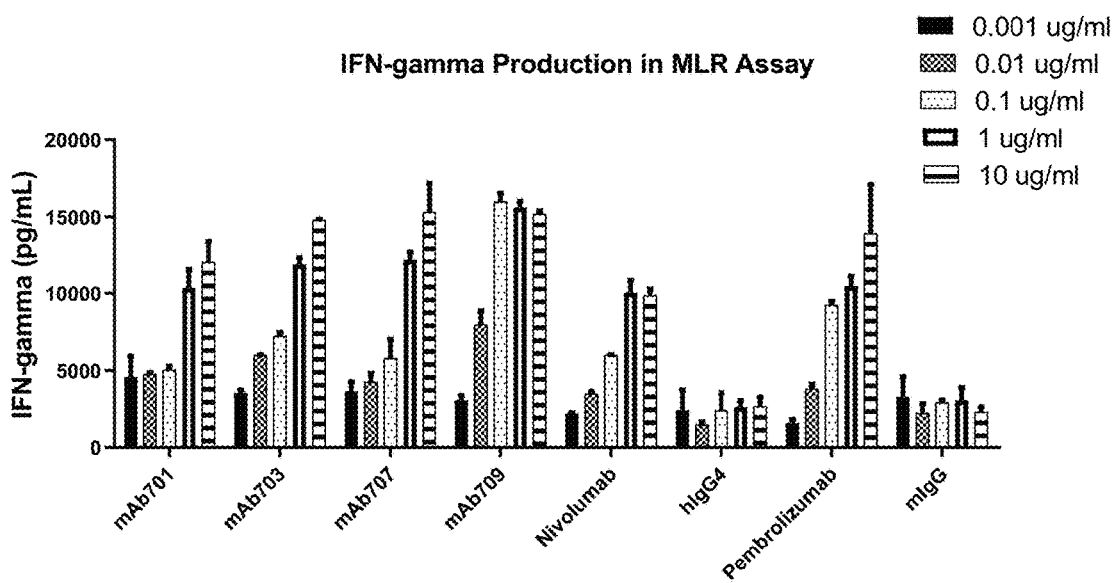
FIGS. 2A and 2B are bar graphs showing gamma interferon (IFN-gamma) production levels in a mixed lymphocyte reaction testing the effect of various anti-PD-1 antibodies disclosed herein, in comparison to two recombinant anti-PD-1 antibodies produced from published sequences (nivolumab and pembrolizumab) and control human and murine antibodies directed against irrelevant antigens ("hIgG4" and "mIgG").
Figure 2:
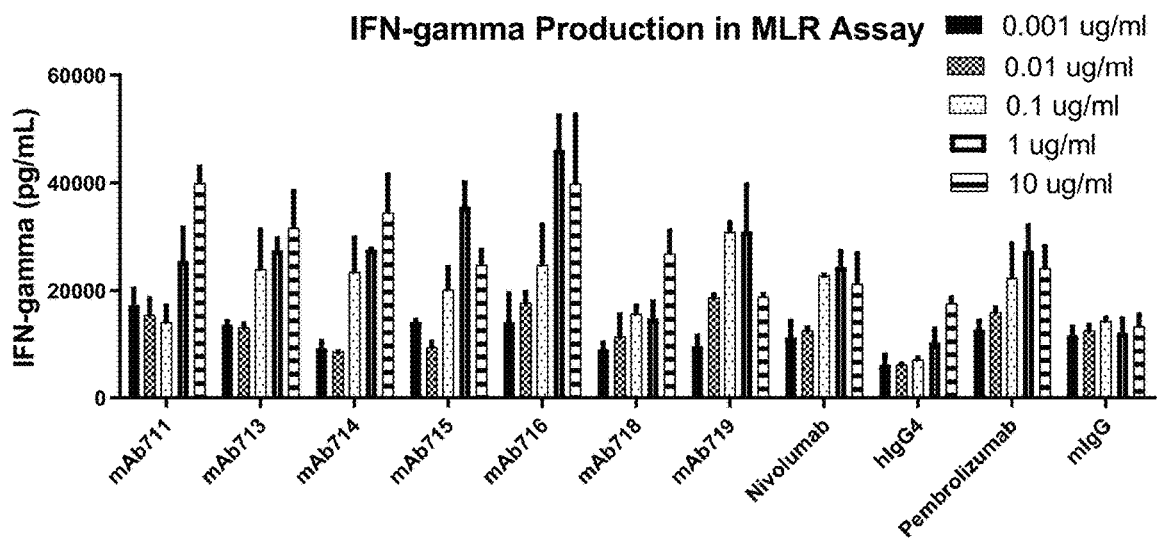
Figure 3:
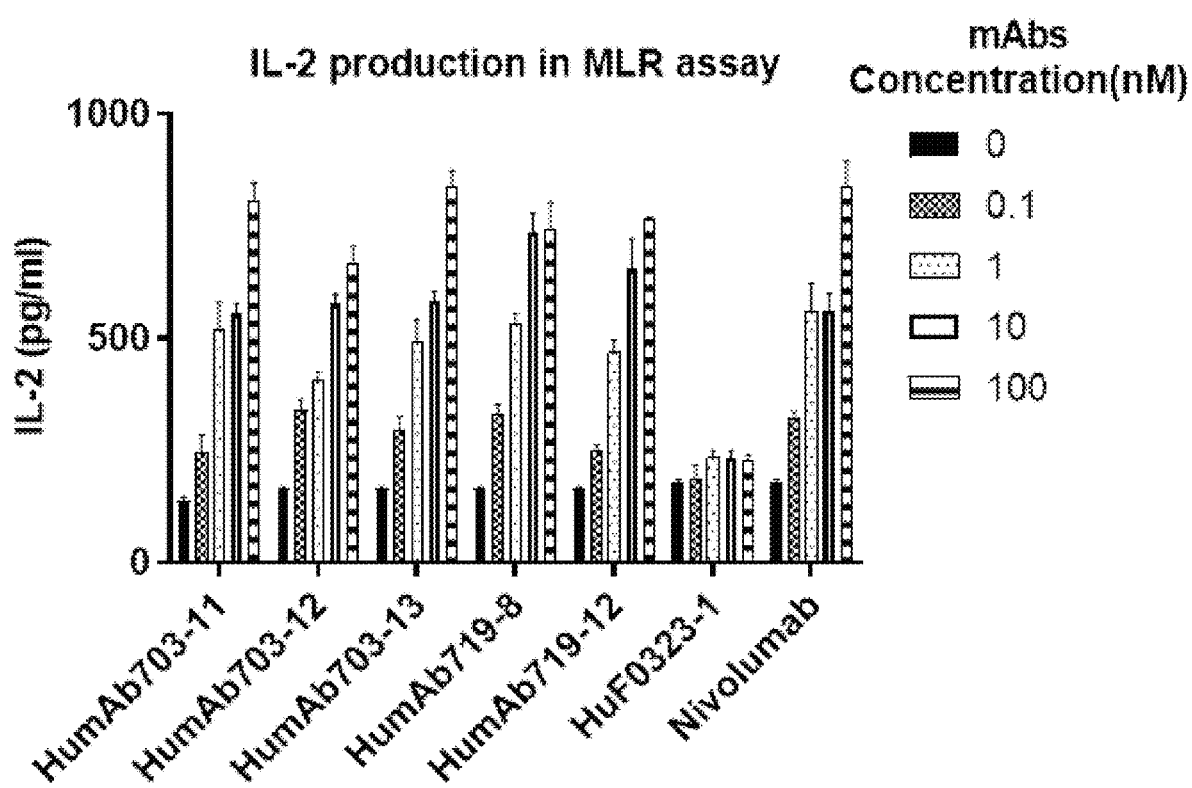
FIG. 3 shows bar graphs of IL-2 production levels in a mixed lymphocyte reaction testing the effect of various humanized anti-PD-1 antibodies disclosed herein, in comparison to a recombinant therapeutic anti-PD-1 antibody produced from published sequences (nivolumab), and a control human antibody directed against irrelevant antigen ("HuF0323-1").
Figure 4:
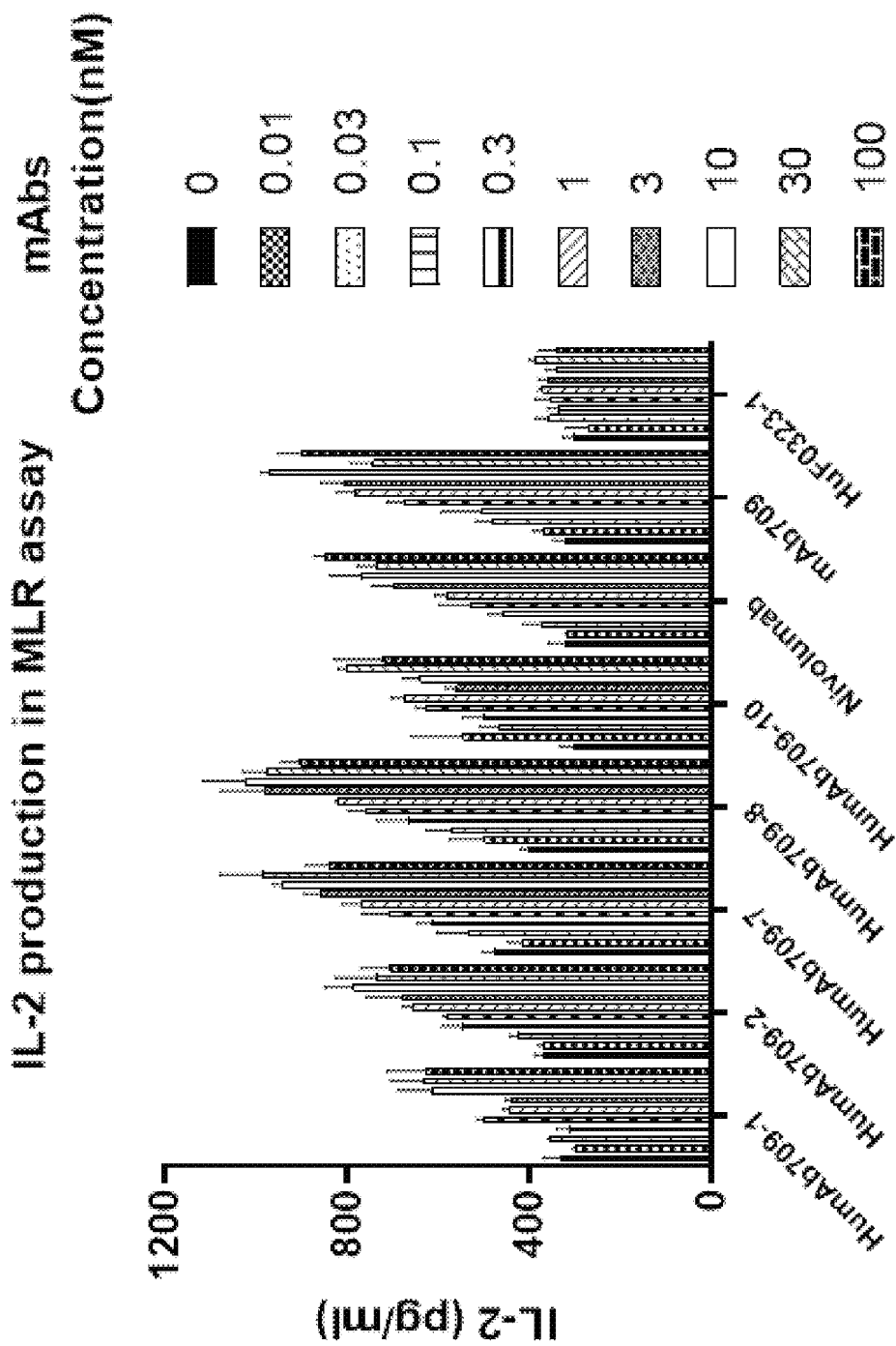
FIG. 4 shows bar graphs of IL-2 production levels in a mixed lymphocyte reaction testing the effect of various humanized anti-PD-1 antibodies disclosed herein, in comparison to the parental murine mAb709, a recombinant therapeutic anti-PD-1 antibody produced from published sequences (nivolumab), and a control human antibody directed against irrelevant antigen ("HuF0323-1").

The functional activity of humanized mAb703 antibodies was validated in MLR assays conducted as described in Example 3, as shown in FIGS. 2A and 3.

Example 5.4: Humanization of Murine Antibody mAb719

Following the same procedure as in Example 5.1 and 5.2, murine anti-PD-1 antibody mAb719 was selected and humanized. Humanized variable domains, some containing one or more back mutations, were constructed, and the amino acid sequences are set forth in Table 15 below. (Back mutated framework amino acid residues are indicated with double underscore murine CDRs from the original parental antibody are underlined.) In addition, an Asp→Ala substitution in CDR-H2 and a Ser→Ala substitution in CDR-13 were made to avoid possible isomerization of Asp often seen recombinant antibodies. (See, mAb719 VH.1E and mAb719 VH.1F sequences in Table 15.)

TABLE 15

Variable Domain Sequence Variants for mAb719 VH and VL

| mAb719 VH/VL variants | SEQ ID NO. | Amino acid sequence 12345678901231567890 12345678901234567890 |
|---|---|---|
| mAb719 VH.1 | 48 | EVQLLESGGGLVQPGGSLRLSCAASGFTFSSHL MSVNRQAPGKGLEWVSAISGGGADTYYPDSVKG RFTISRDNSKNTLYLQMNSLRAEDTAVYYCAKQ ILAFDS-WGQGTTVTVSS |
| mAb719 VH.1A | 49 | EVQLLESGGGLVQPGGSLRLSCAASGFTFSSHL MSWVRQAPGKGLEWVSAISGGGADTYYPDSVKG RFTISRDNSKNTLYLQMNSLRAEDTAVYYCTRQ ILAFDS-WGQGTTVTVSS |
| mAb719 VH.1B | 50 | EVQLLESGGGLVQPGGSLRLSCAASGFSFSSHL MSWVRQAPGKGLEWVSAISGGGADTYYPDSVKG RFTISRDNSKNTLYLQMNSLRAEDTAVYYCTRQ ILAFDS-WGQGTTVTVSS |
| mAb719 VH.1C | 51 | EVQLLESGGGLVQPGGSLRLSCAASGFSFSSHL MSWVRQAPGKGLEWVAAISGGGADTYYPDSVKG RFTISRDNSKNTLYLQMNSLRAEDTAVYYCTRQ ILAFDS-WGQGTTVTVSS |
| mAb719 VH.1D | 52 | EVQLLESGGGLVQPGGSLRLSCAASGFSFSSHL MSWVRQAPGKRLEWVAAISGGGADTYYPDSVKG RFTISRDNSKNTLYLQMNSLRAEDTAVYYCTRQ ILAFDS-WGQGTTVTVSS |
| mAb719 VH.1E | 53 | EVQLLESGGGLVQPGGSLRLSCAASGFSFSSHL MSWVRQAPGKGLEWVAAISGGGADTYYPASVKG RFTISRDNSKNTLYLQMNSLRAEDTAVYYCTRQ ILAFDA-WGQGTTVTVSS |

TABLE 15-continued

Variable Domain Sequence Variants for mAb719 VH and VL

| mAb719 VH/VL variants | SEQ ID NO. | Amino acid sequence 12345678901231567890 12345678901234567890 |
|---|---|---|
| mAb719 VH.1F | 54 | EVQLLESGGGLVQPGGSLRLSCAASGF<u>S</u>FSSHL MSWVRQAPGK<u>R</u>LEWV<u>AA</u>ISGGGADTYYP<u>AS</u>VKG RFTISRDNSKNTLYLQMNSLRAEDTAVYYC<u>TRQ</u> ILAFD<u>A</u>-WGQGTTVTVSS |
| mAb719 VK.1 | 55 | DIQMTQSPSSLSASVGDRVTITC<u>HASQNIYVWL</u> <u>N</u>WYQQKPGKAPKLLIYK<u>ASNLHTG</u>VPSRFSGSG <u>S</u>GTDFTFTISSLQPEDIATYYC<u>QQGQSYPWT</u>FG GGTKVEIK |
| mAb719 VK.1A | 56 | DIQM<u>N</u>QSPSSLSASVGDRVTITC<u>HASQNIYVWL</u> <u>N</u>WYQQKPGKAPKLLIYK<u>ASNLHTG</u>VPSRFSGSG <u>S</u>GTDFTFTISSLQPEDIATYYC<u>QQGQSYPWT</u>FG GGTKVEIK |
| mAb719 VK.1B | 57 | DIQM<u>N</u>QSPSSLSASVGDRVTITC<u>HASQNIYVWL</u> <u>N</u>WYQQKPGK<u>I</u>PKLLIYK<u>ASNLHTG</u>VPSRFSGSG <u>S</u>GTDFTFTISSLQPEDIATYWC<u>QQGQSYPWT</u>FG GGTKVEIK |

The humanized VH and VK genes were produced synthetically and then individually cloned into vectors containing the human IgG and human kappa constant domains (see Table 6, supra). The pairing of the human VH variants and the human VK variants created 21 humanized antibodies, named HumAb719-1 to HumAb719-21 (Table 16). A chimeric antibody with parental mouse VH/VL and human constant sequences was also produced as a positive control, for affinity comparison. All recombinant mAbs were expressed and purified.

TABLE 16

Production List for Humanized mAb719 Anti-PD-1 Antibodies

| Antibody Identifier | VH Region in Heavy Chain | VL Region in Light K Chain |
|---|---|---|
| HumAb719-1 | mAb719 VH.1 | mAb719 VK.1 |
| HumAb719-2 | mAb719 VH.1A | mAb719 VK.1 |
| HumAb719-3 | mAb719 VH.1B | mAb719 VK.1 |
| HumAb719-4 | mAb719 VH.1C | mAb719 VK.1 |
| HumAb719-5 | mAb719 VH.1D | mAb719 VK.1 |
| HumAb719-6 | mAb719 VH.1E | mAb719 VK.1 |
| HumAb719-7 | mAb719 VH.1F | mAb719 VK.1 |
| HumAb719-8 | mAb719 VH.1 | mAb719 VK.1A |
| HumAb719-9 | mAb719 VH.1A | mAb719 VK.1A |
| HumAb719-10 | mAb719 VH.1B | mAb719 VK.1A |
| HumAb719-11 | mAb719 VH.1C | mAb719 VK.1A |
| HumAb719-12 | mAb719 VH.1D | mAb719 VK.1A |
| HumAb719-13 | mAb719 VH.1E | mAb719 VK.1A |
| HumAb719-14 | mAb719 VH.1F | mAb719 VK.1A |
| HumAb719-15 | mAb719 VH.1 | mAb719 VK.1B |
| HumAb719-16 | mAb719 VH.1A | mAb719 VK.1B |
| HumAb719-17 | mAb719 VH.1B | mAb719 VK.1B |
| HumAb719-18 | mAb719 VH.1C | mAb719 VK.1B |
| HumAb719-19 | mAb719 VH.1D | mAb719 VK.1B |
| HumAb719-20 | mAb719 VH.1E | mAb719 VK.1B |
| HumAb719-21 | mAb719 VH.1F | mAb719 VK.1B |
| mAb719c | SEQ ID NO: 18 | SEQ ID NO: 19 |

All 21 humanized antibodies and the chimeric antibody (mAb719c) were characterized by binding ELISA and affinity determination using Octet® RED96 biolayer interferometry system (Pall FortéBio LLG), using a biosensor having immobilized human PD-Fc as the antibody target. Rate constants were derived by making kinetic binding measurements at five different concentrations of antibody. The affinities showed higher than previous Biacore testing due to the bivalent binding target Affinity results for the positive binders are summarized in Table 17.

TABLE 17

Binding Affinities for Selected Humanized mAb719 anti-PD-1 Antibodies

| Humanized Antibody ID | $k_{on}$ (1/Ms) | $k_{off}$ (1/s) | $K_D$ (M) |
|---|---|---|---|
| HumAb719-8 | $1.066 \times 10^5$ | $4.905 \times 10^{-5}$ | $4.602 \times 10^{-10}$ |
| HumAb719-11 | $5.944 \times 10^4$ | $2.270 \times 10^{-4}$ | $3.819 \times 10^{-9}$ |
| HumAb719-12 | $6.882 \times 10^4$ | $5.805 \times 10^{-5}$ | $8.435 \times 10^{-10}$ |
| HuniAb719-21 | $1.042 \times 10^5$ | $6.256 \times 10^{-5}$ | $6.005 \times 10^{-10}$ |
| mAb719c | $9.735 \times 10^4$ | $<1.00 \times 10^{-5}$ | $<1.027 \times 10^{-10}$ |

The functional activity of humanized mAb719 antibodies was validated in MLR assays, as shown in FIGS. 2B and 3.

Example 6: Pharmacokinetic Properties of Lead Anti-PD-1 Antibodies

Pharmacokinetic properties of HumAb709-8 and HumAb713-7 were assessed in male Sprague-Dawley (SD) rats. Antibodies were administered to male SD rats at a single intravenous dose of 5 mg/kg. Serum samples were collected at different time points over a period of 28 days with sampling at 0, 5, 15, and 30 minutes; 1, 2, 4, 8, and 24 hours; and 2, 4, 7, 10, 14, 21, and 28 days serial bleeding via tail vein, and analyzed by general ELISAs. Briefly, ELISA plates were coated with 125 ng/well of goat anti-human IgG Fc antibody (Rockland, Cat #: 609-101-017) at 4° C. overnight, blocked with LX PBS/1% BSA/0.05% Tween-20/ 0.05% ProClin™ 300. All serum samples were diluted 20-fold in blocking buffer first. Additional dilution was made in 5% pooled rat serum and incubated on the plate for 60 minutes at 37° C. Detection was carried out with Anti-human IgG (Fab fragment) peroxidase conjugated (Sigma; Cat. No. A0293) and concentrations were determined with the help of standard curves using the four-parameter logistic fit. Values for the pharmacokinetic parameters were determined by non-compartmental model using WinNonlin software (Pharsight Corporation, Mountain View, Calif.). As demonstrated by these results (Table 18), the properties of HumAb09-8 and HumAb13-7 are stable.

TABLE 18

Pharmacokinetic properties of HumAb719-8 and HumAb713-7

| PK parameters Antibody | CL mL/day/kg | Vss mL/kg | Beta $t_{1/2}$ day | AUC day*µg/mL | MRT day |
|---|---|---|---|---|---|
| HumAb709-8 | 8.6 | 129.6 | 10.9 | 594.2 | 15.4 |
| HumAb713-7 | 6.4 | 114.4 | 12.7 | 789.3 | 18.1 |

Example 7: Generation of Anti-LAG-3 Monoclonal Antibodies

Anti-LAG-3 monoclonal antibodies (mAbs) were generated by hybridoma fusion.

Example 7.1: Immunization, Hybridoma Fusion and Cloning

Immunization of Balb/C mice was performed in the same manner as described above for anti-PD-1 antibody generation (Example 1), except using human LAG-3 D1-D2/murine Fc homodimer as the immunogen. Immunized animals were boosted 2-4 times at 2-3-week intervals. Three days after final boosting, the splenocytes from immunized mice were isolated and fused with the murine myeloma cell line, SP2/0, using standard techniques.

Example 7.2: Identification and Characterization of Anti-LAG-3 Antibodies

Synthetic targets for anti-human LAG-3 and anti-cynomolgus LAG-3 were made to order by Synbio Technologies (Suzhou, China). Each target consisted of a polypeptide segment of the extracellular domain of human or cynomolgus LAG-3 protein fused to a human IgG Fc region. Synthetic genes encoding each LAG-3 ECD/Fc fusion protein were subcloned into a pCP expression vector (Chempartner, Shanghai, CN) and the expression plasmids were transiently transfected into HEK 293E cells in 1-3 liters of medium and cultured for seven days in a $CO_2$ shaker. The ECD sequences used for each fusion are set forth in Table 19, below. The LAG-3 ECD portion of each fusion protein is underlined.

TABLE 19

Amino Acid Sequences for LAG-3 ECD/Fc Fusion Protein Targets

| SEQ ID NO. | LAG-3 Source | amino acid sequences 12345678901234567890 12345678901234567890 |
|---|---|---|
| 58 | human | LQPGAEVPVVWAQEGAPAQLPCSPTIPLQDLSLLRR AGVTWQHQPDSGPPAAAPGHPLAPGPHPAAPSSWGP RPRRYTVLSVGPGGLRSGRLPLQPRVQLDERGRQRG DFSLWLRPARRADAGEYRAAVHLRDRALSCRLRLRL GQASMTASPPGSLRASDWVILNCSFSRPDRPASVHW FRNRGQGRVPVRESPHHHLAESFLFLPQVSPMDSGP WGCILTYRDGFNVSIMYNLTVLGLEPPTPLTVYAGA GSRVGLPCRLPAGVGTRSFLTAKWTPPGGGPDLLVT GDNGDFTLRLEDVSQAQAGTYTCHIHLQEQQLNATV TLAIITVTPKSFGPSGSLGKLLCEVTPVSGQERFVW SSLDTPSQRSFSGPWLEAQEAQLLSQPWQCQLYQGE RLLGAAVYFTELSSPGAQRSGRAPGALPAGHLIEGR MDPKSCDKTHTCPPCPAPELLGGPSVFLFPPKPKDT LMISRTPEVTCVVVDVSHEDPEVKFNWYVDGVEVHN AKTKPREEQYNSTYRVVSVLTVLHQDWLNGKEYKCK VSNKALPAPIEKTISKAKGQPREPQVYTLPPSREEM TKNQVSLTCLVKGFYPSDIAVEWESNGQPENNYKTT PPVLDSDGSFFLYSKLTVDKSRWQQGNVFSCSVMHE ALHNHYTQKSLSLSPGK |
| 59 | cynomolgus monkey | PQPGAEISVVWAQEGAPAQLPCSPTIPLQDLSLLRR AGVTWQHQPDSGPPAXAPGHPPVPGHRPAAPYSWGP RPRRYTVLSVGPGGLRSGRLPLQPRVQLDERGRQRG DFSLWLRPARRADAGEYRATVHLRDRALSCRLRLRV GQASMTASPPGSLRTSDWVILNCSFSRPDRPASVHW FRSRGQGRVPVQGSPHHHLAESFLFLPHVGPMDSGL WGCILTYRDGFNVSIMYNLTVLGLEPATPLTVYAGA GSRVELPCRLPPAVGTQSFLTAKWAPPGGGPDLLVA GDNGDFTLRLEDVSQAQAGTYICHIRLQGQQLNATV TLAIITVTPKSFGPSGSLGKLLCEVTPASGQEHFVW SPLNTPSQRSFSGPWLEAQEAQLLSQPWQCQLHQGE RLLGAAVYFTELSSPGAQRSGRAPGALRAGHLIEGR MDPKSCDKTHTCPPCPAPELLGGPSVFLFPPKPKDT LMISRTPEVTCVVVDVSHEDPEVKFNWYVDGVEVHN AKTKPREEQYNSTYRVVSVLTVLHQDWLNGKEYKCK VSNKALPAPIEKTISKAKGQPREPQVYTLPPSREEM TKNQVSLTCLVKGFYPSDIAVEWESNGQPENNYKTT PPVLDSDGSFFLYSKLTVDKSRWQQGNVFSCSVMHE ALHNHYTQKSLSLSPGK |

The supernatants of hybridoma clones were primarily screened by ELISA. Briefly, 50 µl/well of 1 µg/l human LAG-3 ECD/Fc in $NaHCO_3$ were directly coated in each well of 96-well plate overnight. Plates were washed 3 times with 1×PBST, 300 µl per well. After blocking with 1% BSA in PBST at 250 µl per well and incubating at room temperature for 1 hour, the hybridoma supernatants were added at 50 µl per well and incubated at 37° C. for 1 hour. After washing, an HRP-linked goat anti-mouse IgG Fc secondary antibody (Cat. No. A0168, Sigma) was added at 100 µl/well and the plates were incubated at room temperature for 1 hour. TMB reagent (InnoReagents) was used to detect and develop the ELISA signal at 100 µl/well for 15 minutes, the reaction was stopped with 1 Normal HCL. The plates were read with a plate reader (SpectraMax® M5e, Molecular Devices, USA) at a wavelength of 450 nm. The ELISA-positive antibody producer clones were further verified by FACS analysis using methods similar to Example 1.4, above, except that stable HEK 293F cell lines expressing either human LAG-3 or cynomolgus LAG-3 were used. Hybridomas producing LAG-3 binding activity were selected and further characterized in a receptor blocking assay (RBA).

Example 7.3: Receptor Blocking Assay (RBA)

Supernatants displaying LAG-3 specific activity were tested for the ability to block LAG-3 receptor binding to MHC Class II. Raji human B cell lymphoblasts express high levels of MCH Class II and were used as binding targets for LAG-3 ECD/Fc proteins described above. Briefly, Raji cells were harvested and resuspend in FACS buffer and plated in 96-well plates ($2\times10^5$ cells/well). Anti-LAG-3 hybridoma supernatants were mixed with soluble LAG-3 ECD/Fc and the mixture was added to wells at a final volume of 100 µl/well. After adding the mixture to cells, the plates were incubated at room temperature for 30 minutes. After washing twice with PBS, the cells were incubated with anti-human IgG Alexa Fluor® 488 secondary antibody at 4° C. for 1 hour, washed twice with PBS, then fluorescence was measured on a flow cytometer.

Example 7.4: Expression and Purification of Anti-LAG-3 Monoclonal Antibodies

Murine monoclonal antibody-producing hybridoma cells were cultured in FreeStyle™ 293 Expression Medium (Gibco/Life Technologies) in a $CO_2$ shaker at 37° C. for 5 to 7 days. The conditioned medium was collected through centrifugation at 4000×g for 30 minutes to remove all cells and cell debris, then filtered through a 0.22 µm membrane before purification. Murine antibodies were applied and bound to a MabSelect™ SuRe (GE Healthcare) protein A resin column according to the manufacturer's guidelines, washed with PBS, eluted with buffer containing 20 mM citrate, 150 mM NaCl, pH3.5. The eluted materials were neutralized with 1 M Tris at pH 8.0 immediately and dialyzed against PBS. One-step purified antibodies usually have above 90% purity, as detected by SEC-HPLC. Protein concentrations were determined by measuring absorbance at 280 nm or by NanoDrop™ microvolume spectrophotometer (Thermo Scientific). The purified antibodies were stored in aliquots in a −80° C. freezer.

Example 7.5: Binding Activity of Purified Anti-LAG-3 Antibodies

Characterization by ELISA

A binding ELISA was performed in the same way as described in Example 7.2 above. Each purified antibody was 10-fold serially diluted. After blocking of a 96-well assay plate with wells containing immobilized LAG-3 ECD/Fc fusion protein targets, the purified antibody samples with diluted concentrations were added to wells of the assay plate. The HRP-linked anti-mouse IgG antibody (A0168, Sigma) and TMB reagent were used to detect and develop the ELISA signal, which were read on a SpectraMax M5e plate reader at wavelength of 450 nm. Curves were fitted using GraphPad software, and EC50 values were calculated. Similarly, a RBA was also performed as described in Example 7.3 with titrated, purified antibodies, and maximum inhibition percentages and IC50 values were determined.

Characterization by FACS

FACS analysis was performed using methods similar to Example 1.4, above, except that stable HEK 293F cell lines expressing either human LAG-3 cynomolgus LAG-3 were used. LAG-3 expressing cells were charged at $2\times10^4$ cell per well into 96-well assay round-bottomed assay plates (Cat. No. 3799; Corning) and stained with purified anti-LAG-3 antibodies. LAG-3 antibodies were detected with AlexaFluor® Donkey anti-Mouse Ig (H+L) Highly Cross-Adsorbed Secondary Antibody (Cat. No. A21202; Invitrogen), and cell fluorescence was monitored using a flow cytometer. The data were processed by GraphPad software, and EC50 values were calculated.

The results of these binding characterization assays are shown in Table 20 below.

TABLE 20

Binding Activity of Purified Murine Anti-LAG-3 Antibodies

| | Binding to Human LAG-3 | | | Binding to Cynomolgus LAG-3 | | |
|---|---|---|---|---|---|---|
| | ELISA | FACS | | ELISA | FACS | |
| mAb Identifier | EC50 (nM) | EC50 (nM) | Max-MFI | EC50 (nM) | EC50 (nM) | Max-MFI |
| mAb742 | 0.22 | 2.8 | 102.9 | 0.32 | 56.4 | 48.5 |
| mAb743 | 0.26 | 30.4 | 115.7 | 0.26 | 111.5 | 36.9 |
| mAb744 | 0.19 | 9.5 | 135.0 | 0.21 | 67.0 | 37.8 |
| mAb745 | 0.27 | 32.2 | 54.8 | 0.30 | 224.3 | 26.0 |
| mAb746 | 0.31 | 13 | 120.8 | 0.21 | 4.1 | 66.2 |
| mAb747 | 0.25 | 1.1 | 104.4 | 0.34 | 3.1 | 65.2 |
| mAb748 | 0.24 | 13.4 | 73.1 | 0.25 | 79.6 | 31.9 |
| mAb749 | 0.55 | 3.3 | 123.6 | 0.33 | 14.3 | 67.4 |
| mAb750 | 0.25 | 24.1 | 88.7 | 0.32 | 113.6 | 36.7 |
| mAb751 | 0.22 | 26.2 | 88.9 | 0.27 | 79.3 | 33.1 |
| mAb757 | 0.23 | 25.3 | 91.8 | 0.30 | 77.2 | 35.1 |
| mAb758 | 0.87 | 9.8 | 64.8 | 3.18 | 15.0 | 17.3 |
| mAb759 | 0.43 | 3.0 | 60.2 | 0.53 | 6.3 | 18.6 |
| mAb760 | N/A | N/A | 12.3 | N/A | N/A | 4.9 |
| mAb761 | 0.1.18 | 17.8 | 105.2 | 1.24 | 34.6 | 39.5 |
| Human IgG1 (control) | 0.13 | 0.9 | 190.6 | 78.23 | 63.7 | 28.1 |

In this table, "N/A" denotes no binding activity measured.

Example 7.6: Characterization by RBA and Antigen-Dependent Activation Assay

Purified anti-LAG-3 antibodies also were tested in a RBA in the same manner as described in Example 7.3. Antibodies were also tested in an antigen-specific T cell activation assay, as follows: A huLAG-3 expressing murine T hybridoma cell line was generated to order by ChemPartner (Shanghai, CN). Mouse splenocytes from the same strain of mice were used as effector cells. The hybridoma expressing the huLAG-3 receptor protein is capable of binding to MHC Class II-positive mouse splenocytes, with inhibitory effect via engagement of Class II. The assay tests for anti-LAG-3 antibody-mediated reversal of the inhibitory effect, as measured by increased production of IL-2. Mouse spleenocytes were harvested from 6-8 week-old female C57BL/6 mice, red blood cells were lysed using Red Blood Cell Lysis Buffer (Sigma-Aldrich; R7757) according to the maker's instructions. Next, 50 µl T hybridoma-huLAG-3 cells ($2\times10^6$ cells/ml) were seeded in each well of a 96-well culture plate, and then a series of anti-LAG-3 monoclonal antibodies in solution at 50 µl/well were added and incubated at 37° C. for 30 min. Mouse splenocytes ($4\times10^6$ cells/ml) and the antigen (20 µg/ml) were mixed and incubated at 37° C. for 30 min. The mixture (100 µl/well) was added into each well that was already seeded with T hybridoma-huLAG-3 cells and anti-LAG-3 mAbs. The mixture of antibodies, T hybridoma-huLAG-3 cells, mouse splenocytes, and the antigen was cultured for 3 days. After 72 hours, 100 µl of cell culture supernatant were aspirated and diluted into appropriate concentrations for performing a mouse IL-2 quantitative ELISA using an R&D Systems ELISA kit according to the manufacturer's protocol. The ELISA plate was read on a SpectraMax M5 plate reader (Molecular Devices) using the ELISA-Endpoint-TMB & HRP protocol. RBA and Antigen-dependent Activation assay results are shown in Table 21.

TABLE 21

Characterization of Murine Anti-LAG-3 Antibodies

| | FACS RBA Raji 1 µg/ml HuLAG-3 ECD/Fc | | Antigen-dependent Activation Mouse IL-2 | |
|---|---|---|---|---|
| mAb Identifier | IC50 (nM) | Max. Inhib. (%) | EC50 (nM) | Max IL-2 (pg/ml) |
| mAb742 | 3.84 | 96.5 | ++ | 732.8 |
| mAb743 | 11.66 | 96.6 | ++ | 583.2 |
| mAb744 | 10.77 | 96.5 | ++ | 612.3 |
| mAb745 | 12.38 | 95.0 | + | 357.1 |
| mAb746 | 2.92 | 96.2 | 1.28 | 653.5 |
| mAb747 | 2.84 | 96.3 | 1.27 | 729.2 |
| mAb748 | 4.80 | 96.1 | ++ | 539.2 |
| mAb749 | 4.73 | 93.9 | +++ | 513.0 |
| mAb750 | 7.15 | 96.6 | +++ | 552.5 |
| mAb751 | 6.59 | 96.0 | ++ | 447.0 |
| mAb757 | 1.80 | 96.8 | ++ | 570.9 |
| mAb758 | N/A | 7.9 | − | 182.9 |
| mAb759 | 86.46 | 34.2 | | |
| mAb760 | N/A | 3.4 | | |
| mAb761 | 17.98 | 96.0 | | |
| Human IgG1 (control) | 2.30 | 94.7 | 0.71 | 785.7 |

Example 7.7: Binding Affinity Determination by Biacore

For antibodies with high binding affinity in ELISA and FACS assays, as well as potent functional activity, binding affinities were determined based on measurement of binding kinetic constants in real time binding reactions using Biacore surface plasmon resonance. Briefly, the binding assay of antibody to antigen was performed using a Biacore T200 system through an antibody capture approach. Anti-mouse IgG Fc antibody was immobilized on a CM5 sensor chip according to the manufacturer's instructions. The test anti-LAG-3 murine monoclonal antibody was injected and captured by the immobilized anti-mouse IgG Fc. Then serial concentrations of LAG-3 antigen were individually injected, and the binding profile was recorded for each concentration of antigen analyte. The assay temperature was 25° C., and the association and dissociation times were 180 and 1200 seconds, respectively. The Biacore data were fitted using Biacore T200 evaluation software 1.0 according to a 1:1 binding model to calculate the association ($k_{on}$) and dissociation ($k_{off}$) rate constants and from these calculations the equilibrium dissociation constant ($K_D$) was determined. The affinities ($K_D$) for four selected anti-LAG-3 antibodies are shown in Table 22, below.

TABLE 22

Binding Affinity for Selected Anti-LAG-3 Antibodies

| Antibody Identifier | Affinity for LAG-3 Antigen ($K_D$) |
|---|---|
| mAb746 | $3.774 \times 10^{-8}$ M |
| mAb747 | $5.201 \times 10^{-8}$ M |
| mAb749 | $1.893 \times 10^{-7}$ M |
| mAb750 | $7.506 \times 10^{-8}$ M |

Example 7.8: Comparison of Anti-LAG-3 Antibody Function in PBMC Assay

Figure 6:
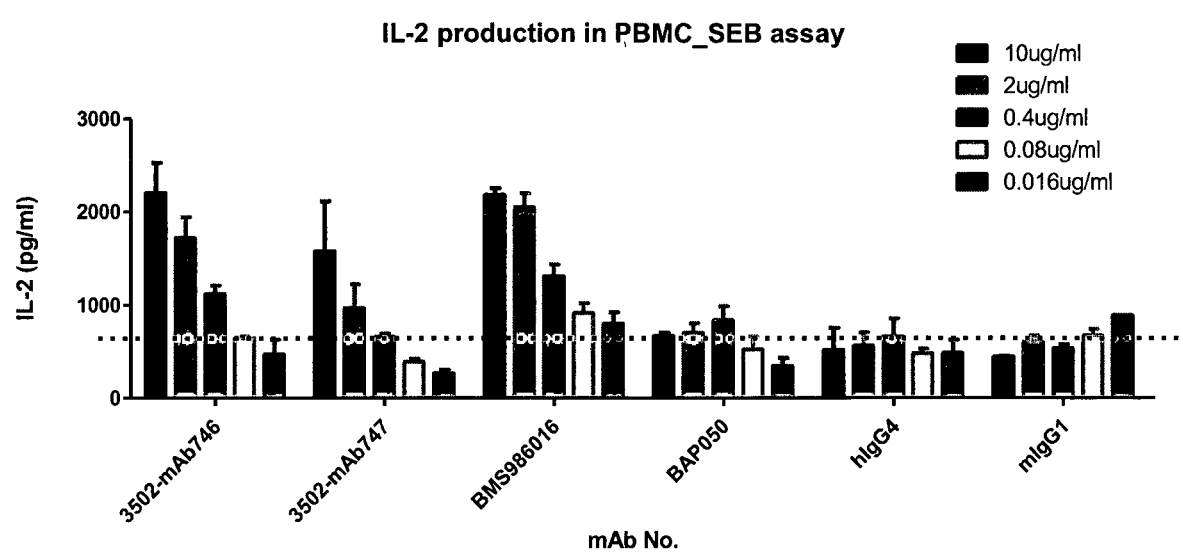
FIG. 6 is a bar graph showing IL-2 production in a SEB T cell activation assay comparing the reversal of T cell suppression effect at various concentrations of two murine anti-LAG-3 antibodies described herein. The functionality of anti-LAG-3 antibodies of the invention ("3502-mAb746" and 3502-mAb747") is compared against a recombinant anti-LAG-3 mAb produced from a published sequence ("BMS-986016"), a recombinant murine anti-LAG-3 antibody produced from a published sequence ("BAP050"), and control human and murine antibodies directed against irrelevant antigens ("hIgG4" and "mIgG").

To further verify the anti-LAG-3 antibodies function in human PBMC, a bacterial toxin stimulation assay using superantigen *Staphylococcus aureus* enterotoxin B (SEB) was conducted. SEB is a known superantigen for activating the immune system by stimulation of human T cells, which in turn causes an over-production of several cytokines. PBMC were isolated from a blood sample from a healthy human donor. PBMC were seeded into a 96-well assay plate with at $2 \times 10^5$ cells/well, then various anti-LAG-3 test antibodies were added into the plates and incubated with the PBMC at 37° C. for 30 min. An SEB solution was added, to a final concentration of 10 ng/ml. The plates were then incubated for 96 hours. At the end of this incubation, 100 µl of cell culture supernatant were collected and IL-2 production was measured using an ELISA IL-2 detection kit (R&D Systems; Cat. No. DY202). Results are shown in FIG. 6.

Example 8: Sequencing of Murine Anti-LAG-3 Antibody Variable Regions

To amplify heavy and light chain variable regions, total RNA of selected hybridoma clones was isolated from $>5 \times 10^6$ cells with TRIzol® RNA isolation reagent (Invitrogen; Cat. No. 15596). cDNA was synthesized by SuperScript™ III First-Strand Synthesis SuperMix (Invitrogen; Cat. No. 18080) and applied as a PCR template of Mouse Ig-Primer Set (Novagen; Cat. No. 69831-3). PCR products were analyzed by electrophoresis on a 1.2% agarose gel with SYBR™ Safe DNA gel stain (Invitrogen). DNA fragments of correct size were purified with NucleoSpin® Gel and PCR Clean-up (Macherey-Nagel GmbH; Cat. No. 740609) according to manufacturer's instructions and subcloned into pMD18-T cloning vectors individually. Fifteen colonies from each transformation were selected and sequences of insert fragments were analyzed by DNA sequencing. Sequences were confirmed if at least 8 matches for consensus sequences for VH and VL were found. The variable region sequences of seven murine mAbs analyzed by sequence homology alignment are listed in Table 23. Complementarity determining regions (CDRs) were identified based on Kabat numbering.

TABLE 23

VH/VL Amino Acid Sequences of 7 Murine Anti-LAG-3 Antibodies

| α-LAG-3 mAb ID | Domain | SEQ ID NO. | amino acid sequences 1234567890123456789012345678901234567890 |
|---|---|---|---|
| mAb746 | VH | 60 | EVQLQQSGAELVRPGASVKLSCTASDFNIKDDYMHWVKQR PEQGLDWIGWIVPENGNTEYASKFQGKATITADTSSNTAY LQLSSLTSEDTAVYYCTVYGDYWGQGTTLTVSS |
| | VL | 61 | DIQMTQSPSSLSASLGERVSLNCRASQEISGYLSWLQQKS DGTIKRLIYAASTLDSGVPKRFSGSRSGSDYSLTISSLES EDFADYYCLQYASYPLTFGAGTKLELK |
| mAb747 | VH | 60 | EVQLQQSGAELVRPGASVKLSCTASDFNIKDDYMHWVKQR PEQGLDWIGWIVPENGNTEYASKFQGKATITADTSSNTAY LQLSSLTSEDTAVYYCTVYGDYWGQGTTLTVSS |
| | VL | 62 | DIQMTQSPSSLSASLGERVSLNCRASQEISGYLSWLQQKP DGTIKRLIYAASTLDSGVPKRFSGSRSGSDYSLTISSLES EDFAAYYCLQYASYPLTFGAGTKLELK |
| mAb742 | VH | 63 | QGQLQQSGAELVRPGASVTLSCKASGYTFNDYEMHWVKQT PVHGLEWIGAIDPETGGTAYNQKFKGKAILTADKSSSTAY MELRSLTSEDSAVYYCIRWGSTVFPYWGQGTLVTVS |
| | VL | 64 | DGVLTQTPLSLPVNIGDQASISCKSTKSLLNSDGFTYLDW YLQKPGQSPQLLIYLVSNRFSGVPDRFSGSGSGTDFTLKI SRVEAEDLGVYYCFQSNYLPWTFGGGTKLEIK |
| mAb744 | VH | 65 | QVQLQQSGAELVRPGTSVTLSCKASGYTFTDYEMHWMKQT PVHGLEWIGAIDPATGGTAYNQKFKGKAILTADKSSSTAY MDFRSLTSEDSAVYYCIRWGTTVFPYWGQGTLVTVS |
| | VL | 66 | DVVLTQTPLSLPVNIGDQASISCKSTKSLLNSDGFTYLDW YLQKPGQSPQLLIYLVSNRFSGVPDRFSGSGSGTDFTLKI SRVEAEDLGVYYCFQSNYLPWTFGGGTKLEIK |
| mAb748 | VH | 67 | EVQMQQSGAELVRPGASVKLSCTVSGFNIKDDYMHWVKQR PEQGLEWIGWIDPENGDTEYASKFQGKATITADTSSNTAY LQLNSLTSEDTAVYYCTYFDYWGQGTTLTVSS |
| | VL | 68 | DVVMTQTPLTLSVTIGQPASISCKSSQSLLDSDGKTYLNW LLQRPGQSPKRLIYLVSKLDSGVPDRFTGSGSGTDFTLKI SRVEAEDLGVYYCWQGSHFPQTFGGGTKLEIK |

TABLE 23-continued

VH/VL Amino Acid Sequences of 7 Murine Anti-LAG-3 Antibodies

| α-LAG-3 mAb ID | Domain | SEQ ID NO. | amino acid sequences |
|---|---|---|---|
| mAb749 | VH | 69 | EVQLQQSGAELVRPGASVKVSCTASDFNIKDDYVHWVKQR PEQGLEWIGWIDPENGDTEYASKFQGKATITADTSSNTAY LQLSSLTSEDTAVYFCSTWDAEENYWGQGTTLSVSS |
|  | VL | 70 | DIVLTQAAPSVPVTPGESVSISCRSSKSLLHSNGNTYLYW FLQRPGQSPQVLIYRMSNLASGVPVRFSGSGSGTAFTLRI SRVEAEDVGVYYCMQHLEYPFTFGSGTKLEIK |
| mAb750 | VH | 71 | EVQLQQSGAELVRPGASVKLSCTPSGLNIKDDYIHWVKQR PEQGLEWIGWIDPENGDTEYASKFQGKATITADTSSNTAY LQLSSLTSEDSAVYYCCTADYRNWYWGQGTTLTVSS |
|  | VL | 68 | DVVMTQTPLTLSVTIGQPASISCKSSQSLLDSDGKTYLNW LLQRPGQSPKRLIYLVSKLDSGVPDRFTGSGSGTDFTLKI SRVEAEDLGVYYCWQGSHFPQTFGGGTKLEIK |

Example 9: Humanization of Murine Anti-LAG-3 Antibody mAb747

Based on the antigen binding activity, cynomolgus LAG-3 protein cross-reactivity, functional activity, and affinity, mAb747 was selected for humanization.

Example 9.1: Humanization of mAb747

The anti-LAG-3 mAb747 variable region genes were employed to create a humanized mAb. In the first step of this process, the amino acid sequences of the VH and VK of mAb747 (SEQ ID NO:60 and SEQ ID NO:62) were compared against the available database of human Ig V-gene sequences in order to find the overall best-matching human germline Ig V-gene sequences. Additionally, the framework 4 sequence of VH or VL was compared against the J-region database to find the human framework having the highest homology to the murine VH and VL regions, respectively. For the light chain, the closest human V-gene match was the A 1 gene, and for the heavy chain the closest human match was the VH1-f gene. Humanized variable domain sequences were then designed where the CDR-L1, CDR-L2, and CDR-L3 of the mAb747 light chain were grafted onto framework sequences of the A1 gene with JK4 framework 4 sequence after CDR-L3; and the CDR-H1, CDR-H2, and CDR-H3 sequences of the mAb747 heavy chain were grafted onto framework sequences of the VH1-f with JH1 framework 4 sequence after CDR-H3. A 3-dimensional Fv model of mAb747 was then generated to determine if there were any framework positions where mouse amino acids were critical to support loop structures or the VH/VL interface. Such residues in humanized sequences should be back-mutated to mouse residues at the same position to retain affinity/activity. Several desirable back-mutations were indicated for mAb747 VH and VL, and three alternative VH and VL designs were constructed, as shown in Table 24, below. (Back mutated framework amino acid residues are indicated with double underscore; murine CDRs from the original parental antibody are underlined.)

TABLE 24

| Humanization VH/VL Design for mAb747-Back Mutations to Muriue Residues | | |
|---|---|---|
| Humanized VH/VL Identifier | SEQ ID NO. | amino acid sequences |
| mAb747 VH.2A | 72 | EVQLVQSGAEVKKPGASVKVSCKASDFNIKDDYMHWVRQA PGQGLSWIGWIVPENGNTEYASKFQGRVTITADTSINTAY MELSRLRSDDTAVYYCTVYGDY----WGQGTTVTVSS |
| mAb747 VH.2B | 73 | EVQLVQSGAEVKKPGASVKVSCKASDFNIKDDYMHWVRQA PGQGLEWIGWIVPENGNTEYASKFQGKATITADTSINTAY MELSRLRSDDTAVYYCTVYGDY----WGQGTTVTVSS |
| mAb747 VH.1G | 74 | EVQLVQSGAEVKKPGATVKISCKASDFNIKDDYMHWVQQA PGKGLEWIGWIVPENGNTEYASKFQGRVTITADTSTNTAY MELSSLRSEDTAVYYCTVYGDY----WGQGTTVTVSS |
| mAb747 VK.1E | 75 | DIQMTQSPSSLSASVGDRVTINCRASQEISGYLSWLQQKP GKTIKRLIYAASTLDSGVPSRFSGSRSGSDYTLTISSLQP EDFATYYCLQYASYPLTFGGGTKVEIK |
| mAb747 VK.2A | 76 | DIQMTQSPSSLSASVGDRVTINCRASQEISGYLSWLQQKP EKTIKRLIYAASTLDSGVPSRFSGSRSGSDYTLTISSLQP EDFATYYCLQYASYPLTFGGGTKVEIK |
| mAb747 VK.2B | 77 | DIQMTQSPSSLSASVGDRVTINCRASQEISGYLSWLQQKP EGTIKRLIYAASTLDSGVPSRFSGSRSGSDYTLTISSLQP EDFATYYCLQYASYPLTFGGGTKVEIK |

The humanized VH and VK genes were produced synthetically and then cloned into vectors containing the human IgG1 and human kappa constant domains, respectively. The pairing of the human VH and the human VK created 9 humanized anti-LAG-3 antibodies, named HumAb747-34 to -42 (Table 25). A chimeric antibody with parental mouse VH/VL and human constant sequences was also produced (mAb747c) as a positive control, for affinity comparison.

TABLE 25

Production List Humanized mAb747 Anti-LAG-3 Antibodies

| Antibody Identifier | VH Region in Heavy Chain | VL Region in Light κ Chain |
|---|---|---|
| HumAb747-34 | mAb747 VH.1G | mAb747 VK.1E |
| HumAb747-35 | mAb747 VH.1G | mAb747 VK.2A |
| HumAb747-36 | mAb747 VH.1G | mAb747 VK.2B |
| HumAb747-37 | mAb747 VH.2A | mAb747 VK.1E |
| HumAb747-38 | mAb747 VH.2A | mAb747 VK.2A |
| HumAb747-39 | mAb747 VH.2A | mAb747 VK.2B |
| HumAb747-40 | mAb747 VH.2B | mAb747 VK.1E |
| HumAb747-41 | mAb747 VH.2B | mAb747 VK.2A |
| HumAb747-42 | mAb747 VH.2B | mAb747 VK.2B |

All 9 humanized antibodies (Table 25) and a chimeric antibody having the parental murine VH and VL domains (mAb747c) were ranked by dissociation rate constant ($k_{off}$). Briefly, antibodies were characterized for affinities and binding kinetics by Octet RED96 biolayer interferometry (Pall FortéBio LLC). Antibodies were captured by Anti-HIgG Fc Capture (AHC) Biosensors (Pall) at a concentration of 100 nM for 30 seconds. Sensors were then dipped into running buffer (1× pH7.2 PBS, 0.05% Tween 20, 0.1% BSA) for 60 seconds to check baseline. Binding was measured by dipping sensors into a single concentration of recombinant human LAG-3-his protein (Novoprotein). Dissociation was followed by dipping sensors into running buffer for 1200 seconds. The association and dissociation curves were fitted to a 1:1 Langmuir binding model using FortéBio Data Analysis software (Pall). Results are shown in Table 26.

TABLE 26 off-rate ranking of humanized anti-LAG-3 antibodies

| Antibody | Off-rate ($k_{off}$) (1/s) |
|---|---|
| mAb747c | $3.77 \times 10^{-4}$ |
| HumAb747-42 | $8.30 \times 10^{-4}$ |
| HumAb747-39 | $1.14 \times 10^{-3}$ |

HumAb747-42 showed an off-rate constant only 2.2-fold greater than that of the chimeric control having the parental variable domains.

Example 10: Production of PD-1/LAG-3 Fabs-in-Tandem Immunoglobulins (FIT-Igs)

Bispecific Fabs-in-Tandem Immunoglobulin binding proteins recognizing both human PD-1 and human LAG-3 were constructed.

For each of the FIT-Ig constructs described in the following tables, the signal sequence used in the expression vector for each of the three component polypeptide chains is shown. Either MDMRVPAQLLGLLLLWFPGSRC (SEQ ID NO:79) or MEFGLSWLFLVAILKGVQC (SEQ ID NO:84) was used in the production of the FIT-Ig proteins described below, although many alternative signal peptides will be known to those skilled in the art and may be used as well. It will be understood that such signal sequences are cleaved during secretion of the polypeptides by the expressing host cell, and thus the signal sequences are not part of the final FIT-Ig binding proteins.

Example 10.1: FIT07-1-2a

A PD-1/LAG-3 FIT-Ig designated FIT107-1-2a was constructed utilizing coding sequences for immunoglobulin domains from the parental antibodies mAb709 (murine anti-PD-1, see Table 4 supra) and mAb746 (murine anti-LAG-3, see Table 23 supra). FIT-Ig FIT107-1-2a is a hexamer comprised of three component polypeptide chains:
Polypeptide chain #1 has the domain formula: VL-CL of mAb709 fused directly to VH-CH1 of mAb746 fused directly to hinge-CH2-CH3 of a mutant human constant IgG1 (see Table 6, supra);
Polypeptide chain #2 has the domain formula: VH-CH1 of mAb709; and
Polypeptide chain #3 has the domain formula: light chain (VL-CL) of mAb746.
The amino acid sequences for the three expressed FIT107-1-2a polypeptide chains are shown in Table 27 below.

TABLE 27

Amino Acid Sequences of FIT107-1-2a Component Chains

| Polypeptide | SEQ ID NO: | Amino Acid Sequence<br>12345678901234567890123456789012345678 90 |
|---|---|---|
| FIT107-1-2a GIT-Ig Polypeptide Chain #1 | 78 | MDMRVPAQLLGLLLLWFPGSRCDIVMTQSHKFMSTSVGDS<br>VTITCKASQDVNTVVAWYQQKPGQSLKVLISWASTRHTGV<br>PARFTGSGSGTDYTLTISSVQAEDLALYYCQQHYTTPYTF<br>GGGTQLEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>QQSGAELVRPGASVKLSCTASDFNIKDDYMHWVKQRPEQG<br>LDWIGWIVPENGNTEYASKFQGKATITADTSSNTAYLQLS<br>SLTSEDTAVYYCTVYGDYWGQTTLTVSSASTKGPSVFPL<br>APSSKSTSGGTAALGCLVKDYFPEPVTVSWNSGALTSGVH<br>TFPAVLQSSGLYSLSSVVTVPSSSLGTQTYICNVNHKPSN<br>TKVDKKVEPKSCDKTHTCPPCPAPEAAGGPSVFLFPPKPK |

TABLE 27-continued

Amino Acid Sequences of FIT107-1-2a Component Chains

| Polypeptide | SEQ ID NO: | Amino Acid Sequence<br>123456789012345678901234567890 |
|---|---|---|
| | | DTLMISRTPEVTCVVVDVSHEDPEVKFNWYVDGVEVHNAK<br>TKPREEQYNSTYRVVSVLTVLHQDWLNGKEYKCKVSNKAL<br>PAPIEKTISKAKGQPREPQVYTLPPSREEMTKNQVSLTCL<br>VKGFYPSDIAVEWESNGQPENNYKTTPPVLDSDGSFFLYS<br>KLTVDKSRWQQGNVFSCSVMHEALHNHYTQKSLSLSPGK |
| signal sequence | 79 | HDMRVPAQLLGLLLLWFPGSRC |
| VL-CL of mAb murine mAb709 (VL underlined) | 80 | <u>DIVMTQSHKFMSTSVGDSVTITCKASQDVNTVVAWYQQKP<br>GQSLKVLISWASTRHTGVPARFTGSGSGTDYTLTISSVQA<br>EDLALYYCQQHYTTPYTFGGGTQLEIK</u>RTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of mAb murine mAb746 (VH underlined) | 81 | <u>EVQLQQSGAELVRPGASVKLSCTASDFNIKDDYMHWVKQR<br>PEQGLDWIGWIVPENGNTEYASKFQGKATITADTSSNTAY<br>LQLSSLTSEDTAVYYCTVYGDYWGQGTTLTVSS</u>ASTKGPS<br>VFPLAPSSKSTSGGTAALGCLVKDYFPEPVTVSWNSGALT<br>SGVHTFPAVLQSSGLYSLSSWTVPSSSLGTQTYICNVNH<br>KPSNTKVDKKVEPKSC |
| hinge-CH2-CH3 of human IgG1 | 82 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |
| FIT107-1-2a FIT-Ig Polypeptide Chain #2 | 83 | MEFGLSWLFLVAILKGVQCEVKLVESGGGLVKPGGSLKLS<br>CAASGFTFSFYTMSWVRQTPEKRLEWVATISGGGRDTYYP<br>DSVKGRFTISRDNAKNTLYLHMSSLRSEDTALYYCAGQGG<br>NYLFAYWGQGTLVTVSAASTKGPSVFPLAPSSKSTSGGTA<br>ALGCLVKDYFPEPVTVSWNSGALTSGVHTFPAVLQSSGLY<br>SLSSVVTVPSSSLGTQTYICNVNHKPSNTKVDKKVEPKSC |
| signal sequence | 84 | MEFGLSWLFLVAILKGVQC |
| VH-CH1 of murine mAb709 (VH underlined) | 85 | <u>EVKLVESGGGLVKPGGSLKLSCAASGFTFSFYTMSWVRQT<br>PEKRLEWVATISGGGRDTYYPDSVKGRFTISRDNAKNTLY<br>LHMSSLRSEDTALYYCAGQGGNYLFAYWGQGTLVTVSS</u>AS<br>TKGPSVFPLAPSSKSTSGGTAALGCLVKDYFPEPVTVSWN<br>SGALTSGVHTFPAVLQSSGLYSLSSVVTVPSSSLGTQTYI<br>CNVNHKPSNTKVDKKVEPKSC |
| FIT107-1-2a FIT-Ig Polypeptide Chain #3 | 86 | <u>MDMRVPAQLLGLLLLWFPGSRC</u>DIQMTQSPSSLSASLGER<br>VSLNCRASQEISGYLSWLQQKSDGTIKRLIYAASTLDSGV<br>PKRFSGSRSGSDYSLTISSLESEDFADYYCLQYASYPLTF<br>GAGTKLELKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of murine mAb746 (VL underlined) | 87 | <u>DIQMTQSPSSLSASLGERVSLNCRASQEISGYLSWLQQKS<br>DGTIKRLIYAASTLDSGVPKRFSGSRSGSDYSLTISSLES<br>EDFADYYCLQYASYPLTFGAGTKLELK</u>RTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 10.2: FIT107-1-2b

Another bispecific Fabs-in-Tandem Immunoglobulin recognizing both human PD-1 and human LAG-3 was constructed. This PD-1/LAG-3 FIT-Ig was designated FIT107-1-2b. Construction of FIT107-1-2b binding protein utilized coding sequences for immunoglobulin domains from the parental murine antibodies mAb709 and mAb746, but in this FIT-Ig construct, the LAG-3-binding domain was in the N-terminal (outer) position, and the PD-1-binding domain was in the inner position, fused C-terminal to the VL-CL domains of the LAG-3 binding region. FIT-Ig FIT107-1-2b is a hexamer comprised of three component polypeptide chains:

Polypeptide chain #1 has the domain formula: VL-CL of mAb746 fused directly to VH-CH1 of mAb709 fused directly to hinge-CH2-CH3 of a mutant human constant IgG1 (see Table 6, supra);

Polypeptide chain #2 has the domain formula: VH-CH1 of mAb746; and

Polypeptide chain #3 has the domain formula: light chain (VL-CL) of mAb709.

The amino acid sequences for the three expressed FIT107-1-2b polypeptide chains are shown in Table 28 below:

TABLE 28

Amino Acid Sequences of FIT107-1-2b Component Chains

| Polypeptide | SEQ ID NO: | Amino Acid Sequence 12345678901234567890123456789012345678 90 |
|---|---|---|
| FIT107-1-2b FIT-Ig Polypeptide Chain #1 | 88 | MDMRVPAQLLGLLLLWFPGSRCDIQMTQSPSSLSASLGER VSLNCRASQEISGYLSWLQQKSDGTIKRLIYAASTLDSGV PKRFSGSRSGSDYSLTISSLESEDFADYYCLQYASYPLTF GAGTKLELKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGECEVKL VESGGGLVKPGGSLKLSCAASGFTFSFYTMSWVRQTPEKR LEWVATISGGGRDTYYPDSVKGRFTISRDNAKNTLYLHMS SLRSEDTALYYCAGQGGNYLFAYWGQGTLVTVSAASTKGP SVFPLAPSSKSTSGGTAALGCLVKDYFPEPVTVSWNSGAL TSGVHTFPAVLQSSGLYSLSSVVTVPSSSLGTQTYICNVN HKPSNTKVDKKVEPKSCDKTHTCPPCPAPEAAGGPSVFLF PPKPKDTLMISRTPEVTCVVVDVSHEDPEVKFNWYVDGVE VHNAKTKPREEQYNSTYRVVSVLTVLHQDWLNGKEYKCKV SNKALPAPIEKTISKAKGQPREPQVYTLPPSREEMTKNQV SLTCLVKGFYPSDIAVEWESNGQPENNYKTTPPVLDSDGS FFLYSKLTVDKSRWQQGNVFSCSVMHEALHNHYTQKSLSL SPGK |
| signal sequence | 79 | MDMRVPAQLLGLLLLWFPGSRC |
| VL-CL of murine mAb746 (VL underlined) | 89 | DIQMTQSPSSLSASLGERVSLNCRASQEISGYLSWLQQKS DGTIKRLIYAASTLDSGVPKRFSGSRSGSDYSLTISSLES EDFADYYCLQYASYPLTFGAGTKLELKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| VH-CH1 of murine mAb709 (VH underlined) | 90 | EVKLVESGGGLVKPGGSLKLSCAASGFTFSFYTMSWVRQT PEKRLEWVATISGGGRDTYYPDSVKGRFTISRDNAKNTLY LHMSSLRSEDTALYYCAGQGGNYLFAYWGQGTLVTVSAAS TKGPSVFPLAPSSKSTSGGTAALGCLVKDYFPEPVTVSWN SGALTSGVHTFPAVLQSSGLYSLSSVVTVPSSSLGTQTYI CNVNHKPSNTKVDKKVEPKSC |
| hinge-CH2-CH3 of human IgG1 | 82 | DKTHTCPPCPAPEAAGGPSVFLFPPKPKDTLMISRTPEVT CVVVDVSHEDPEVKFNWYVDGVEVHNAKTKPREEQYNSTY RVVSVLTVLHQDWLNGKEYKCKVSNKALPAPIEKTISKAK GQPREPQVYTLPPSREEMTKNQVSLTCLVKGFYPSDIAVE WESNGQPENNYKTTPPVLDSDGSFFLYSKLTVDKSRWQQG NVFSCSVMHEALHNHYTQKSLSLSPGK |
| FIT107-1-2b FIT-Ig Polypeptide Chain #2 | 91 | MEFGLSWLFLVAILKGVQCEVQLQQSGAELVRPGASVKLS CTASDFNIKDDYMHWVKQRPEQGLDWIGWIVPENGNTEYA SKFQGKATITADTSSNTAYLQLSSLTSEDTAVYYCTVYGD YWGQGTTLTVSSASTKGPSVFPLAPSSKSTSGGTAALGCL VKDYFPEPVTVSWNSGALTSGVHTFPAVLQSSGLYSLSSV VTVPSSSLGTQTYICNVNHKPSNTKVDKKVEPKSC |
| signal sequence | 84 | MEFGLSWLFLVAILKGVQC |
| VH-CH1 of murine mAb746 (VH underlined) | 92 | EVQLQQSGAELVRPGASVKLSCTASDFNIKDDYMHWVKQR PEQGLDWIGWIVPENGNTEYASKFQGKATITADTSSNTAY LQLSSLTSEDTAVYYCTVYGDYWGQGTTLTVSSASTKGPS VFPLAPSSKSTSGGTAALGCLVKDYFPEPVTVSWNSGALT SGVHTFPAVLQSSGLYSLSSVVTVPSSSLGTQTYICNVNH KPSNTKVDKKVEPKSC |

TABLE 28-continued

Amino Acid Sequences of FIT107-1-2b Component Chains

| Polypeptide | SEQ ID NO: | Amino Acid Sequence<br>12345678901234567890123456789012345678890 |
|---|---|---|
| FIT107-1-2b<br>FIT-Ig Polypeptide<br>Chain #3 | 93 | MDMRVPAQLLGLLLLWFPGSRCDIVMTQSHKFMSTSVGDS<br>VTITCKASQDVNTVVAWYQQKPGQSLKVLISWASTRHTGV<br>PARFTGSGSGTDYTLTISSVQAEDLALYYCQQHYTTPYTF<br>GGGTQLEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of<br>murine mAb709<br>(VL underlined) | 94 | DIVMTQSHKFMSTSVGDSVTITCKASQDVNTVVAWYQQKP<br>GQSLKVLISWASTRHTGVPARFTGSGSGTDYTLTISSVQA<br>EDLALYYCQQHYTTPYTFGGGTQLEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 10.3: FIT107-1-5a

A PD-1/LAG-3 FIT-Ig designated FIT107-1-5a was constructed utilizing coding sequences for immunoglobulin domains from the parental humanized antibodies HumAb709-8 (anti-PD-1, SEQ ID NO:21 and SEQ ID NO:25) and HumAb747-42 (SEQ ID NO:73 and SEQ ID NO:77). FIT-Ig FIT107-1-5a is hexamer comprised of three component polypeptide chains:

Polypeptide chain #1 has the domain formula: VL-CL of HumAb709-8 fused directly to V-CH1 of HumAb747-42 fused directly to hinge-CH2-CH3 of a mutant human constant IgG1 (see Table 6, supra),
Polypeptide chain #2 has the domain formula: VH-CH1 of HumAb79-8; and
Polypeptide chain #3 has the domain formula: light chain (VL-CL) of HumAb747-42.
The amino acid sequences for the three expressed FIT107-1-5a polypeptide chains are shown in Table 29 below:

TABLE 29

Amino Acid Sequences of FIT107-1-5a Component Chains

| Polypeptide | SEQ ID NO: | Amino Acid Sequence<br>12345678901234567890123456789012345678890 |
|---|---|---|
| FIT107-1-5a<br>FIT-Ig Polypeptide<br>Chain #1 | 95 | MDMRVPAQLLGLLLLWFPGSRCDIVMTQSPSSLSASVGDR<br>VTITCKASQDVNTVVAWYQQKPGKAPKVLISWASTRHTGV<br>PSRFSGSGSGTDYTLTISSLQPEDFATYYCQQHYTTPYTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VQSGAEVKKPGASVKVSCKASDFNIKDDYMHWVRQAPGQG<br>LEWIGWIVPENGNTEYASKFQGKATITADTSINTAYMELS<br>RLRSDDTAVYYCTVYGDYWGQGTTVTVSSASTKGPSVFPL<br>APSSKSTSGGTAALGCLVKDYFPEPVTVSWNSGALTSGVH<br>TFPAVLQSSGLYSLSSVVTVPSSSLGTQTYICNVNHKPSN<br>TKVDKKVEPKSCDKTHTCPPCPAPEAAGGPSVFLFPPKPK<br>DTLMISRTPEVTCVVVDVSHEDPEVKFNWYVDGVEVHNAK<br>TKPREEQYNSTYRVVSVLTVLHQDWLNGKEYKCKVSNKAL<br>PAPIEKTISKAKGQPREPQVYTLPPSREEMTKNQVSLTCL<br>VKGFYPSDIAVEWESNGQPENNYKTTPPVLDSDGSFFLYS<br>KLTVDKSRWQQGNVFSCSVMHEALHNHYTQKSLSLSPGK |
| signal sequence | 79 | MDMRVPAQLLGLLLLWFPGSRC |
| VL-CL of mAb<br>HumAb709-8<br>(VL underlined) | 96 | DIVMTQSPSSLSASVGDRVTITCKASQDVNTVVAWYQQKP<br>GKAPKVLISWASTRHTGVPSRFSGSGSGTDYTLTISSLQP<br>EDFATYYCQQHYTTPYTFGGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CL of mAb<br>HumAb747-42<br>(VH underlined) | 97 | EVQLVQSGAEVKKPGASVKVSCKASDFNIKDDYMHWVRQA<br>PGQGLEWIGWIVPENGNTEYASKFQGKATITADTSINTAY<br>MELSRLRSDDTAVYYCTVYGDYWGQGTTVTVSSASTKGPS<br>VFPLAPSSKSTSGGTAALGCLVKDYFPEPVTVSWNSGALT<br>SGVHTFPAVLQSSGLYSLSSVVTVPSSSLGTQTYICNVNH<br>KPSNTKVDKKVEPKSC |

TABLE 29-continued

Amino Acid Sequences of FIT107-1-5a Component Chains

| Polypeptide | SEQ ID NO: | Amino Acid Sequence<br>12345678901234567890123456789012345678 90 |
|---|---|---|
| hinge-CH2-CH3 of human IgG1 | 82 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |
| FIT107-1-5a FIT-Ig Polypeptide Chain #2 | 98 | MEFGLSWLFLVAILKGVQCEVQLVESGGGLVQPGGSLRLS<br>CAASGFTFSFYTMSWVRQAPGKGLEWVATISGGGRDTYYP<br>DSVKGRFTISRDNAKNSLYLQMNSLRAEDTAVYYCAGQGG<br>NYLFAYWGQGTLVTVSSASTKGPSVFPLAPSSKSTSGGTA<br>ALGCLVKDYFPEPVTVSWNSGALTSGVHTFPAVLQSSGLY<br>SLSSVVTVPSSSLGTQTYICNVNHKPSNTKVDKKVEPKSC |
| signal sequence | 84 | MEFGLSWLFLVAILKGVQC |
| VH-CH1 of HumAb709-8 (VH underlined) | 99 | EVQLVESGGGLVQPGGSLRLSCAASGFTFSFYTMSWVRQA<br>PGKGLEWVATISGGGRDTYYPDSVKGRFTISRDNAKNSLY<br>LQMNSLRAEDTAVYYCAGQGGNYLFAYWGQGTLVTVSSAS<br>TKGPSVFPLAPSSKSTSGGTAALGCLVKDYFPEPVTVSWN<br>SGALTSGVHTFPAVLQSSGLYSLSSVVTVPSSSLGTQTYI<br>CNVNHKPSNTKVDKKVEPKSC |
| FIT107-1-5a FIT-Ig Polypeptide Chain #3 | 100 | MDMRVPAQLLGLLLLWFPGSRCDIQMTQSPSSLSASVGDR<br>VTINCRASQEISGYLSWLQQKPEGTIKRLIYAASTLDSGV<br>PSRFSGSRSGSDYTLTISSLQPEDFATYYCLQYASYPLTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of HumAb747-42 (VL underlined) | 101 | DIQMTQSPSSLSASVGDRVTINCRASQEISGYLSWLQQKP<br>EGTIKRLIYAASTLDSGVPSRFSGSRSGSDYTLTISSLQP<br>EDFATYYCLQYASYPLTFGGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 10.4: FIT107-1-5b

Another bispecific Fabs-in-Tandem Immunoglobulin recognizing both human PD-1 and human LAG-3 was constructed. This PD-1/LAG-3 FIT-Ig was designated FIT107-1-5b. Construction of FIT107-1-5b binding protein utilized coding sequences for immunoglobulin domains from the parental humanized antibodies HumAb709-8 and HumAb747-42, but in this FIT-Ig construct, the LAG-3-binding domain was in the N-terminal (outer) position, and the PD-1-binding domain was in the inner position, fused C-terminal to the VL-CL domains of the N-terminal LAG-3 binding region. FIT-Ig FIT107-1-5b is hexamer comprised of three component polypeptide chains:

Polypeptide chain #1 has the domain formula: VL-CL of HumAb747-42 fused directly to VH-CH1 of HumAb709-8 fused directly to hinge-CH2-CH3 of a mutant human constant IgG1 (see Table 6, supra);

Polypeptide chain #2 has the domain formula: VH-CH1 of mAb747-42; and

Polypeptide chain #3 has the domain formula: light chain (VL-CL) of HumAb709-8.

The amino acid sequences for the three expressed FIT107-1-5b polypeptide chains are shown in Table 30 below:

TABLE 30

Amino Acid Sequences of FIT107-1-5b Component Chains

| Polypeptide | SEQ ID NO: | Amino Acid Sequence<br>12345678901234567890123456789012345678 90 |
|---|---|---|
| FIT-1-5b FIT-Ig Polypeptide Chain #1 | 102 | MDMRVPAQLLGLLLLWFPGSRCDIQMTQSPSSLSASVGDR<br>VTINCRASQEISGYLSWLQQKPEGTIKRLIYAASTLDSGV<br>PSRFSGSRSGSDYTLTISSLQPEDFATYYCLQYASYPLTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VESGGGLVQPGGSLRLSCAASGFTFSFYTMSWVRQAPGKG<br>LEWVATISGGGRDTYYPDSVKGRFTISRDNAKNSLYLQMN<br>SLRAEDTAVYYCAGQGGNYLFAYWGQGTLVTVSSASTKGP<br>SVFPLAPSSKSTSGGTAALGCLVKDYFPEPVTVSWNSGAL<br>TSGVHTFPAVLQSSGLYSLSSVVTVPSSSLGTQTYICNVN |

TABLE 30-continued

Amino Acid Sequences of FIT107-1-5b Component Chains

| Polypeptide | SEQ ID NO: | Amino Acid Sequence |
|---|---|---|
| | | HKPSNTKVDKKVEPKSCDKTHTCPPCPAPEAAGGPSVFLF<br>PPKPKDTLMISRTPEVTCVVVDVSHEDPEVKFNWYVDGVE<br>VHNAKTKPREEQYNSTYRVVSVLTVLHQDWLNGKEYKCKV<br>SNKALPAPIEKTISKAKGQPREPQVYTLPPSREEMTKNQV<br>SLTCLVKGFYPSDIAVEWESNGQPENNYKTTPPVLDSDGS<br>FFLYSKLTVDKSRWQQGNVFSCSVMHEALHNHYTQKSLSL<br>SPGK |
| signal sequence | 79 | MDMRVPAQLLGLLLLWFPGSRC |
| VL-CL of HumAb747-42 (VL underlined) | 103 | DIQMTQSPSSLSASVGDRVTINCRASQEISGYLSWLQQKP<br>EGTIKRLIYAASTLDSGVPSRFSGSRSGSDYTLTISSLQP<br>EDFATYYCLQYASYPLTFGGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of HumAb709-8 (VH underlined) | 104 | EVQLVESGGGLVQPGGSLRLSCAASGFTFSFYTMSWVRQA<br>PGKGLEWVATISGGGRDTYYPDSVKGRFTISRDNAKNSLY<br>LQMNSLRAEDTAVYYCAGQGGNYLFAYWGQGTLVTVSSAS<br>TKGPSVFPLAPSSKSTSGGTAALGCLVKDYFPEPVTVSWN<br>SGALTSGVHTFPAVLQSSGLYSLSSVVTVPSSSLGTQTYI<br>CNVNHKPSNTKVDKKVEPKSC |
| hinge-CH2-CH3 of human IgG1 | 82 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |
| FIT107-1-5b FIT-Ig Polypeptide Chain #2 | 105 | MEFGLSWLFLVAILKGVQCEVQLVQSGAEVKKPGASVKVS<br>CKASDFNIKDDYMHWVRQAPGQGLEWIGWIVPENGNTEYA<br>SKFQGKATITADTSINTAYMELSRLRSDDTAVYYCTVYGD<br>YWGQGTTVTVSSASTKGPSVFPLAPSSKSTSGGTAALGCL<br>VKDYFPEPVTVSWNSGALTSGVHTFPAVLQSSGLYSLSSV<br>VTVPSSSLGTQTYICNVNHKPSNTKVDKKVEPKSC |
| signal sequence | 84 | MEFGLSWLFLVAILKGVQC |
| VH-CH1 of HumAb747-42 (VH underlined) | 106 | EVQLVQSGAEVKKPGASVKVSCKASDFNIKDDYMHWVRQA<br>PGQGLEWIGWIVPENGNTEYASKFQGKATITADTSINTAY<br>MELSRLRSDDTAVYYCTVYGDYWGQGTTVTVSSASTKGPS<br>VFPLAPSSKSTSGGTAALGCLVKDYFPEPVTVSWNSGALT<br>SGVHTFPAVLQSSGLYSLSSVVTVPSSSLGTQTYICNVNH<br>KPSNTKVDKKVEPKSC |
| FIT107-1-5b FIT-Ig Polypeptide Chain #3 | 107 | MDMRVPAQLLGLLLLWFPGSRCDIVMTQSPSSLSASVGDR<br>VTITCKASQDVNTVVAWYQQKPGKAPKVLISWASTRHTGV<br>PSRFSGSGSGTDYTLTISSLQPEDFATYYCQQHYTTPYTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of mAb HuMAb709-8 (VL underlined) | 108 | DIVMTQSPSSLSASVGDRVTITCKASQDVNTVVAWYQQKP<br>GKAPKVLISWASTRHTGVPSRFSGSGSGTDYTLTISSLQP<br>EDFATYYCQQHYTTPYTFGGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 10.5: Expression and Purification of FIT-Igs

The four PD-1/LAG-3 FIT-Ig constructs FIT107-1-2a, FIT107-1-2b, FIT07-1-5a and FIT107-1-5b are a type of bispecific, multivalent binding protein known as a Fabs-in-Tandem Immunoglobulin (or FIT-Ig) described generally in WO 2015/103072 and WO 2017/136820. The binding proteins were produced by co-expression of three component polypeptide chains in a mammalian host cell transfected with expression vectors for all three chains. The design of the binding protein calls for the long polypeptide chain (Chain #1) to pair with both the short polypeptide chains (Chains #2 and #3) to form functional tandem Fab moieties, and also the long chain is designed to dimerize via the Fc region (hinge-CH2-CH3), such that a six-chain binding protein exhibiting four intact Fab binding sites is formed. In the binding proteins FIT107-1-2a and FIT107-1-5a, the N-terminal or "outer" Fab binding sites bind PD-1 and the adjacent "inner" Fab binding sites bind LAG-3. The outer Fab fragment (anti-PD-1) of FIT107-1-2a and FIT107-1-5a is joined to the inner Fab fragment (anti-LAG-3) only through the long chain (Chain #1) by direct fusion of VL-CL$_{mAb709}$ or VL-CL$_{HumAb709-8}$ as the case may be at its C-terminus to the N-terminus of VH-CH1mAb746 or VH-CH1$_{HumAb747-42}$, respectively, without the use of linkers connecting the immunoglobulin domains. Similarly, the outer Fab fragment (anti-LAG-3) of FIT107-1-2b and FIT107-1-5b is joined to the inner Fab fragment (anti-PD-1) only through the long chain (Chain #1) by direct fusion of VL-CL$_{mAb746}$ or VL-CL$_{mAb747-42}$ as the case may be at its C-terminus to the N-terminus of VH-CH1$_{mAb709}$ or VH-CH1$_{mAb709-8}$, respectively, without the use of linkers connecting the immunoglobulin domains.

Expression vectors coding for polypeptide Chains #1, #2, and #3 of each FIT-Ig (FIT107-1-2a, FIT107-1-2b, FIT107-1-5a and FIT107-1-5b) were transiently co-expressed using polyethyleneimine (PEI) as a transfection agent in human embryonic kidney 293E cells. Briefly, DNA in FreeStyle™ 293 Expression Medium was mixed with the PEI with the final concentration of DNA to PEI ratio of 1:2, incubated for 15-20 minutes at room temperature, and then added to the HEK293E cells (0.0-1.2×10$^6$/ml, cell viability >95%) at 60 μg DNA/120 ml culture. After 6-24 hours culture in shaker, peptone was added to the transfected cells at a final concentration of 5%, with shaking at 125 rpm/min., at 37° C., 8% CO$_2$. On the 6th-7th day, supernatant was harvested by centrifugation and filtration, and FIT-Ig protein was purified using Protein A chromatography (Pierce, Rockford, IL) according to the manufacturer's instructions.

For the expression FIT107-1-2a, FIT107-1-2b, FIT107-1-5a and FIT07-1-5b, the DNA coding for expression of Chains #1, #2, and #3 were transfected using a molar ratio for Chain #1: Chain #2: Chain #3 of 1:3:3. This was designed to cause proportionally more of the short chains #2 and #3 to be expressed relative to the long chain (Chain #1), which in turn would decrease the occurrence of VL-CL and VH-CH1 segments on the long chain (Chain #1) that were not paired with corresponding light chains and thus would fail to form a functional Fab fragment. FIT-Ig protein expression products were purified by Protein A chromatography. The composition and purity of the purified FIT-Igs were analyzed by size exclusion chromatography (SEC). Purified FIT-Ig, in PBS, was applied on a TSKgel SuperSW3000, 300×4.6 mm column (TOSOH). An HPLC instrument, Model U3000 (DIONEX) was used for SEC using UV detection at 280 nm and 214 nm. See Table 31, below.

TABLE 31

Expression and SEC analysis of PD-1/LAG-3 FIT-Ig binding proteins

| FIT-Ig protein | DNA molar ratio: Chain #1: #2: #3 | Expression level (mg/L) | % Peak Monomeric Fraction by SEC |
|---|---|---|---|
| FIT107-1-2a | 1:3:3 | 5.40 | >90% |
| FIT107-1-2b | 1:3:3 | 5.04 | >80% |
| FIT107-1-5a | 1:3:3 | 7.95 | >80% |
| FIT107-1-5b | 1:3:3 | 8.52 | >80% |

The lower monomeric fraction contents for FIT107-1-2b, -5a, and -5b indicate some possible aggregation.

Example 11: Binding Affinities of FIT-Igs for Target Antigens

The kinetics of FIT-Ig binding to PD-1 and LAG-3 targets was determined by Biacore SPR measurements. Binding affinities of FIT107-1-2a and FIT107-1-2b for both target antigens PDL-1 and LAG-3 are shown in Table 32, below.

TABLE 32

Binding Affinities for FIT107-1-2a and FIT107-1-2b

| Target immobilized on sensor chip | Analyte | Analyte Specificity | $k_{on}$ (1/Ms) | $k_{off}$ (1/s) | $K_D$ (M) |
|---|---|---|---|---|---|
| HuPD-1 ECD/Fc and HuLAG-3 ECD/Fc | FIT107-1-2a | outer: PD-1 inner: LAG-3 | $6.97 \times 10^4$ | $1.17 \times 10^{-5}$ | $1.68 \times 10^{-10}$ |
|  | FIT107-1-2b | outer: LAG-3 inner: PD-1 | $1.68 \times 10^5$ | $8.76 \times 10^{-5}$ | $5.23 \times 10^{-10}$ |
|  | mAb709c | PD-1 | $2.88 \times 10^5$ | $9.72 \times 10^{-6}$ | $3.37 \times 10^{-11}$ |
|  | mAb746c | LAG-3 | $9.51 \times 10^3$ | $1.54 \times 10^{-4}$ | $1.62 \times 10^{-8}$ |
|  | mAb709c + mAb746c | PD-1 and LAG-3 | $2.82 \times 10^5$ | $2.08 \times 10^{-5}$ | $7.35 \times 10^{-11}$ |
| HuPD-1 ECD/Fc | mAb709c | PD-1 | $2.52 \times 10^5$ | $8.82 \times 10^{-6}$ | $3.50 \times 10^{-11}$ |
| HuLAG-3 ECD/Fc | mAb746c | LAG-3 | $5.58 \times 10^3$ | $1.81 \times 10^{-4}$ | $3.25 \times 10^{-8}$ |

Example 12: FIT-Ig Specificity and Function Determinations

Figure 7:
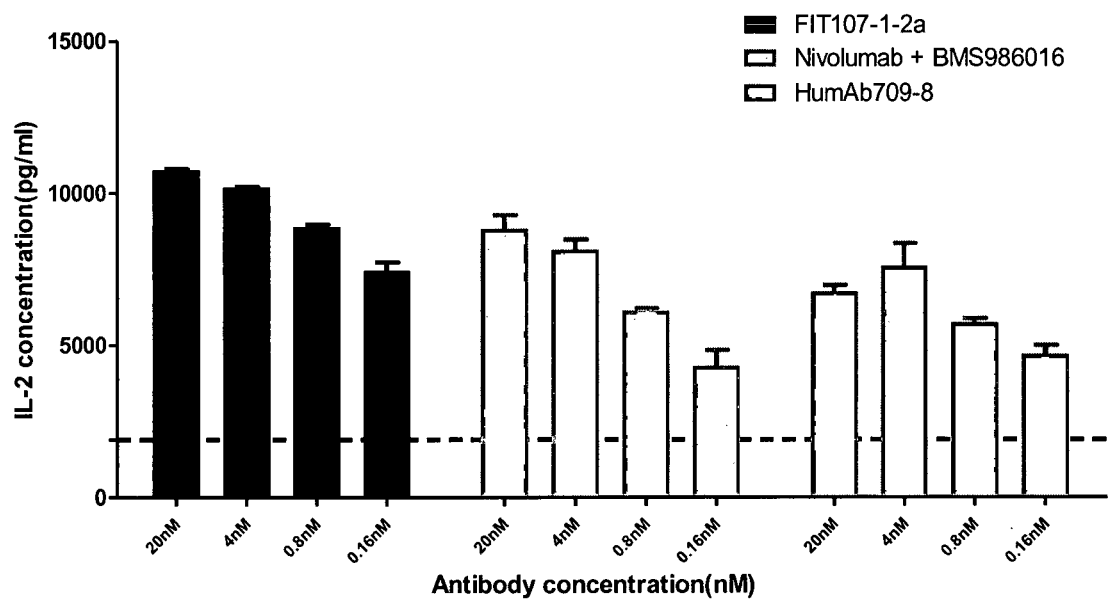
FIG. 7 is a bar graph showing IL-2 production in a SEB T cell activation assay comparing the reversal of T cell suppression effect at various concentrations of several a FIT-Ig bispecific binding protein, FIT107-1-2a, described herein. The functionality of FIT107-1-2a is compared against a combination of a recombinant anti-LAG-3 mAb of known sequence (BMS-986016) and a recombinant anti-PD-1 mAb of known sequence (nivolumab), and against an anti-PD-1 antibody alone ("PD-1", mAb709 disclosed herein).

The anti-PD 1 and anti-LAG-3 bispecificity and biological activity of the FIT107-1-2a binding protein was tested in a PBMC activation assay using Staphylococcal enterotoxin B (SEB) as a superantigen (see, Example 7.8). Briefly, PBMC were isolated from a healthy donor, then seeded into a 96-well plate with 50 μl/well at 2×10$^5$ cells/well. Test binding proteins (i.e., FIT107-1-2a, a combination of commercially available anti-PD-1 and anti-LAG-3 monoclonal antibodies, or a monoclonal anti-PD-1 antibody) were added into the plates and incubated with PBMC at 37° C. for 30 min. SEB solution was added to a final concentration of 10 ng/ml. The plates were incubated for 96 hours, then 100 μl cell culture supernatant were collected and IL-2 production was measured using an ELISA IL-2 detection kit (R&D Systems; Cat. No. DY202). The results are shown in FIG. 7. The FIT107-1-2a bispecific FIT-Ig protein was able to enhance T cell activation, as indicated by IL-2 production, in comparison to an anti-PD-1 antibody alone or a mixture of anti-LAG-3 and anti-PD-1 antibodies.

Figure 8:
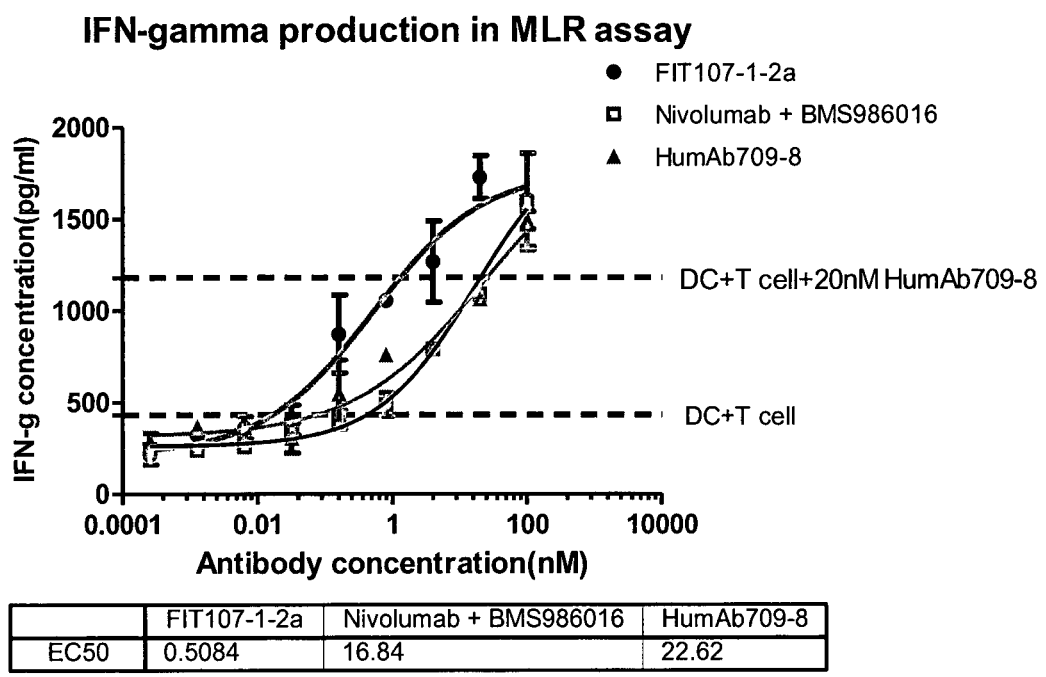
FIG. 8 presents curves showing relative gamma interferon (IFN-g) production levels in a mixed lymphocyte reaction testing the effect of FIT107-1-2a bispecific FIT-Ig binding protein at various concentrations, in comparison to a combination of a recombinant anti-LAG-3 mAb of known sequence (BMS-986016) and a recombinant anti-PD-1 mAb of known sequence (nivolumab), and against humanized anti-PD-1 antibody HumAb709-8 disclosed herein).

In addition, a mixed lymphocyte reaction (MLR) assay was performed in a similar manner as described in Example 3, to further verify anti-PD-1 and anti-LAG-3 function for FIT107-1-2a. The mixed lymphocyte reaction is an ex vivo cellular immune response that occurs between two allogeneic lymphocyte populations when mixed together. Allogeneic lymphocytes undergo blast transformation, DNA synthesis and cellular proliferation in response to the major histocompatibility antigen (MHC Class I and II) differences between the two cell populations, which designated as Responder and Stimulator cells. In the MLR for testing FIT107-1-2a, at day 1, PBMC were purified from healthy donors and CD14+ monocytes were isolated. Monocytes were seeded into 6-well plates and treated with 35 ng/ml IL-4 (R&D Systems) and 50 ng/ml GM-CSF (R&D Systems) in RPMI 1640 medium plus 10% FBS. The medium was exchanged after day 4. At Day 7, monocytes differentiated into immature dendritic cells were collected and further processed for two days in maturation medium with 20 ng/ml TNF-α (R&D Systems), 50 μg/ml Poly I:C (Sigma), 35 ng/ml IL-4 and 50 ng/ml GM-CSF. For MLR co-culture assays, X-VIVO™ 15 serum free medium was used to avoid serum interference in antibody efficacy. 96-well U-bottom plates were seeded with allogeneic CD4+ T cells (responder cells) at $1\times10^5$ cells/well and pre-treated with test binding protein (i.e., FIT107-1-2a, a combination of commercially available anti-PD-1 and anti-LAG-3 monoclonal antibodies, or a monoclonal anti-PD-1 antibody) for 30 min. Then mature dendritic cells (stimulator cells) were seeded into the wells at $1\times10^4$ cells/well, and co-cultured with the responder cells for five days, at which time 100 μl of supernatant was collected and IFN-γ production was measured by ELISA. The results are shown in FIG. 8. The FIT-Ig bispecific binding protein showed an EC50 of 0.5084 nM, as compared with EC50 values of 16.84 nM for a combination of anti-PD-1 and anti-LAG-3 antibodies or an anti-PD-1 antibody alone. Thus, the FIT-Ig binding protein enhanced IFN-γ (gamma interferon) production in the MLR at a concentration over 30-fold lower than the single antibody or antibody combination.

Example 13: New Batch Humanization of mAb747

The anti-LAG-3 mAb747 variable region genes were employed to create a further anti-LAG-3 humanized mAb. In the first step of this process, the amino acid sequences of the VH and VK of mAb747 (SEQ ID NO:60 and SEQ ID NO:62) were compared against the available database of human Ig V-gene sequences in order to find best-matching human germline Ig V-gene sequences. Additionally, the framework 4 (FW4) sequence of VH or VL was compared against the J-region database to find the human framework having the highest homology to the murine VH and VL regions, respectively. For the light chain, the best human V-gene match was the A30 gene, and for the heavy chain the best human match was the VH1-69-2 gene. Humanized variable domain sequences were then designed where the CDR-L1, CDR-L2, and CDR-L3 of the mAb747 light chain were grafted onto framework sequences of the A30 gene with JK4 framework 4 sequence after CDR-L3; and the CDR-H1, CDR-H2, and CDR-H3 sequences of the mAb747 heavy chain were grafted onto framework sequences of the VH1-69-2 with JH6 framework 4 sequence after CDR-H3. A 3-dimensional Fv model of mAb747 was then generated to determine if there were any framework positions where mouse amino acids were critical to support loop structures or the VH/VL interface. Such residues in humanized sequences should be back-mutated to mouse residues at the same position to retain affinity/activity. Several desirable back-mutations were indicated for mAb747 VH and VL, and three alternative VH and VL designs were constructed, as shown in Table 33, below. (Back mutated framework amino acid residues are indicated with double underscore: CDRs are underlined according to Kabat numbering system except VH CDR1 defined with ABM numbering system.)

TABLE 33

Humanization VH/VL Design for mAb747-Back Mutations to Murine Residues

| Humanized VH/VL Identifier | SEQ ID NO. | Amino acid sequences 1234567890123456789012345678901234567890 |
|---|---|---|
| huEpi001-VHv1 | 109 | EVQLVQSGAEVKKPGATVKISCKVSDFNIKDDYMHWVQQA PGKGLEWIGWIVPENGNTEYASKFQGRVTITADTSTDTAY LELSSLRSEDTAVYYCTVYGDYWGQGTTVTVSS |
| huEpi001-VHv2 | 110 | EVQLVQSGAEVKKPGATVKLSCKASDFNIKDDYMHWVQQA PGKGLEWIGWIVPEMGMTEYASKFQGRVTITAPTSTDTAY LELSSLRSEDTAVYYCTVYGDYWGQGTTVTVSS |
| huEpi001-VHv3 | 111 | EVQLVQSGAEVKKPGATVKLSCTASDFNIKDDYMHWVQQA PGKGLEWIGWIVPENGNTEYASKFQGRVTITADTSTDTAY LELSSLRSEDTAVYYCTVYGDYWGQGTTVTVSS |
| huEpi001-VHv4 | 112 | EVQLVQSGAEVKKPGATVKLSCTASDFNIKDDYMHWVKQA PGKGLEWIGWIVPENGNTEYASKFQGRATITADTSTNTAY LELSSLRSEDTAVYYCTVYGDYWGQGTTVTVSS |
| huEpi001-VHv5 | 113 | EVQLVQSGAEVKKPGATVKLSCTASDFNIKDDYMHWVKQR PEQGLEWIGWIVPENGNTEYASKFQGRATITADTSTNTAY LELSSLRSEDTAVYYCTVYGDYWGQGTTVTVSS |
| huEpi001-VHv6 | 114 | EVQLVQSGAEVKKPGATVKLSCTASDFNIKDDYMHWVKQR PEQGLDWIGWIVPENGNTEYASKFQGKATITADTSTNTAY LELSSLRSEDTAVYYCTVYGDYWGQGTTVTVSS |
| huEpi001-VLv1 | 115 | DIQMTQSPSSLSASVGDRVTITCRASQEISGYLSWLQQKP GKAIKSLIYAASTLDSGVPSRFSGSRSGTDFTLTISSLQP EDFATYYCLQYASYPLTFGQGTKLEIK |

TABLE 33-continued

Humanization VH/VL Design for mAb747-Back Mutations to Murine Residues

| Humanized VH/VL Identifier | SEQ ID NO. | Amino acid sequences 12345678901234567890123456789012345678 90 |
|---|---|---|
| huEpi001-VLv2 | 116 | DIQMTQSPSSLSASVGDRVTITCRASQEISGYLSWLQQKP GKAIKRLIYAASTLDSGVPSRFSGSRSGTDFTLTISSLQP EDFATYYCLQYASYPLTFGQGTKLEIK |
| huEpi001-VLv3 | 117 | DIQMTQSPSSLSASVGDRVTITCRASQEISGYLSWLQQKP GGAIKRLIYAASTLDSGVPSRFSGSRSGSDYTLTISSLQP EDFADYYCLQYASYPLTFGQGTKLELK |
| huEpi001-VLv4 | 118 | DIQMTQSPSSLSASVGDRVTITCRASQEISGYLSWLQQKP GGAIKRLIYAASTLDSGVPSRFSGSRSGSDYTLTISSLEP EDFADYYCLQYASYPLTFGQGTKLELK |

The humanized V Hand VK genes were produced synthetically and then cloned into vectors containing the human IgG1 and human kappa constant domains, respectively. The pairing of the human VH and the human VK created 9 humanized anti-LAG-3 antibodies, named HumAb747-43 to HumAb747-60 (Table 34). The chimeric antibody with parental mouse VH/VL and human constant sequences described above was also used (mAb747c) as a positive control, for affinity comparison.

TABLE 34

Production List Humanized mAb747 Anti-LAG-3 Antibodies

| Antibody Identifier | VH Region in Heavy Chain | VL Region in Light κ Chain |
|---|---|---|
| HumAb747-43 | huEpi001-VHv1 | huEpi001 VLv1 |
| HumAb747-44 | huEpi001-VHv2 | huEpi001 VLv1 |
| HumAb747-45 | huEpi001-VHv3 | huEpi001 VLv1 |
| HumAb747-46 | huEpi001-VHv4 | huEpi001 VLv1 |
| HumAb747-47 | huEpi001-VHv1 | huEpi001 VLv2 |
| HumAb747-48 | huEpi001-VHv2 | huEpi001 VLv2 |
| HumAb747-49 | huEpi001-VHv3 | huEpi001 VLv2 |
| HumAb747-50 | huEpi001-VHv4 | huEpi001 VLv2 |
| HumAb747-51 | huEpi001-VHv1 | huEpi001 VLv3 |
| HumAb747-52 | huEpi001-VHv2 | huEpi001 VLv3 |
| HumAb747-53 | huEpi001-VHv3 | huEpi001 VLv3 |
| HumAb747-54 | huEpi001-VHv4 | huEpi001 VLv3 |
| HumAb747-55 | huEpi001-VHv1 | huEpi001 VLv4 |
| HumAb747-56 | huEpi001-VHv2 | huEpi001 VLv4 |
| HumAb747-57 | huEpi001-VHv3 | huEpi001 VLv4 |
| HumAb747-58 | huEpi001-VHv4 | huEpi001 VLv4 |
| HumAb747-59 | huEpi001-VHv5 | huEpi001 VLv3 |
| HumAb747-60 | huEpi001-VHv6 | huEpi001 VLv3 |

All 18 humanized antibodies (Table 34) and a chimeric antibody having the parental murine VH and VL domains (mAb747c) were ranked by dissociation rate constant ($k_{off}$). Briefly, antibodies were characterized for affinities and binding kinetics by Octet®RED96 biolayer interferometry (Pall ForteBio LLC). Antibodies were captured by Anti-hIgG Fc Capture (AHC) Biosensors (Pall) at a concentration of 100 nM for 30 seconds. Sensors were then dipped into running buffer (1× pH7.2 PBS, 0.05% Tween 20, 0.1% BSA) for 60 seconds to check baseline. Binding was measured by dipping sensors into a single concentration of recombinant human LAG-3-his protein (Novoprotein). Dissociation was followed by dipping sensors into running buffer for 1200 seconds. The association and dissociation curves were fitted to a 1:1 Langmuir binding model using ForteBio Data Analysis software (Pall). Results are shown in Table 35. In each test group, the off-rates of antibodies were able to be compared with that of mAb747c. The off-rate ratios were calculated by the off-rate of antibody to that of mAb747c of its group and were compared all together. The lower the ratio was, the higher was the affinity of the antibody.

TABLE 35

Off-rate Ranking of Humanized Anti-LAG-3 Antibodies

| Test group | Antibody | Off-rate ($k_{off}$) (1/s) | off-rate ratio to that of mAb747c |
|---|---|---|---|
| 1 | HumAb747-43 | $9.25 \times 10^{-3}$ | 682% |
|   | HumAb747-44 | $1.10 \times 10^{-2}$ | 809% |
|   | HumAb747-45 | $1.08 \times 10^{-2}$ | 797% |
|   | HumAb747-46 | $1.09 \times 10^{-2}$ | 801% |
|   | HumAb747-47 | $1.44 \times 10^{-2}$ | 1062% |
|   | HumAb747-48 | $8.03 \times 10^{-3}$ | 592% |
|   | mAb747c | $1.36 \times 10^{-3}$ | 100% |
| 2 | HumAb747-49 | $7.73 \times 10^{-3}$ | 575% |
|   | HumAb747-50 | $7.19 \times 10^{-3}$ | 534% |
|   | HumAb747-51 | $1.19 \times 10^{-2}$ | 888% |
|   | HumAb747-52 | $4.36 \times 10^{-3}$ | 324% |
|   | HumAb747-53 | $4.30 \times 10^{-3}$ | 319% |
|   | HumAb747-54 | $4.23 \times 10^{-3}$ | 314% |
|   | mAb717c | $1.35 \times 10^{-3}$ | 100% |
| 3 | HumAb747-55 | $1.19 \times 10^{-2}$ | 972% |
|   | HumAb747-56 | $4.31 \times 10^{-3}$ | 352% |
|   | HumAb747-57 | $4.11 \times 10^{-3}$ | 335% |
|   | HumAb747-58 | $4.05 \times 10^{-3}$ | 331% |
|   | mAb747c | $1.23 \times 10^{-3}$ | 100% |
| 4 | HumAb747-59 | $1.20 \times 10^{-3}$ | 226% |
|   | HumAb747-60 | $8.10 \times 10^{-4}$ | 153% |
|   | mAb747c | $5.30 \times 10^{-4}$ | 100% |

HumAb747-60 showed an off-rate constant only 1.5-fold greater than that of the chimeric control having the parental variable domains.

Figure 9:
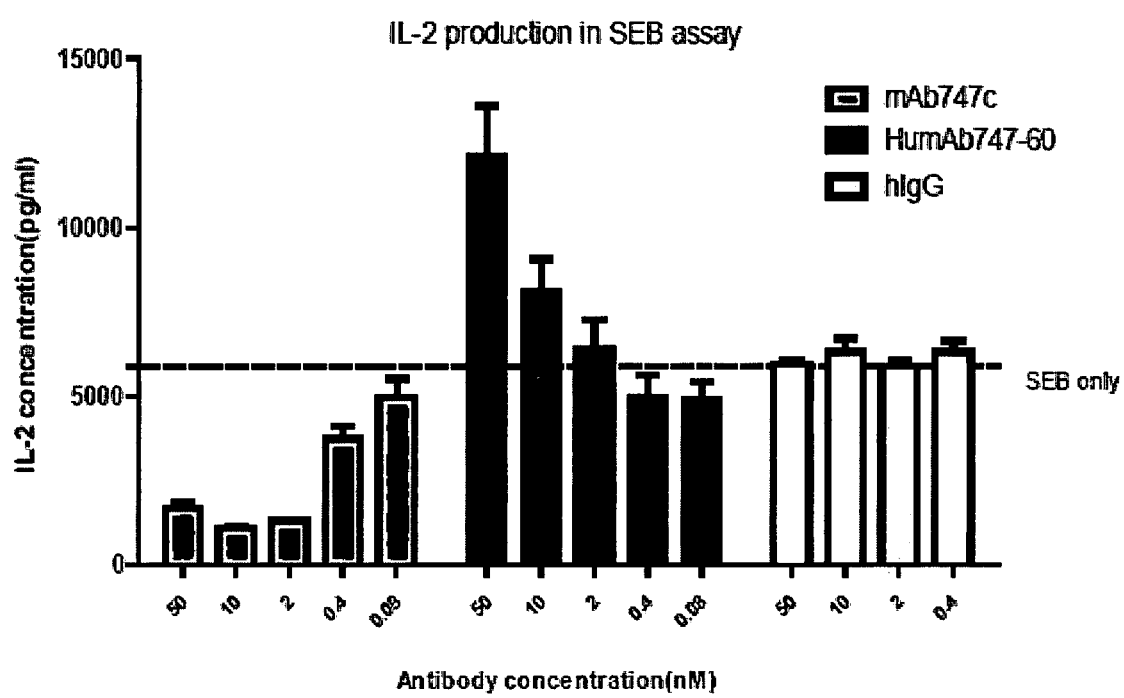
FIG. 9 is a bar graph showing IL-2 production in a SEB T cell activation assay comparing the reversal of T cell suppression effect at various concentrations of a chimeric anti-LAG-3 antibody mAb747c and a humanized anti-LAG-3 antibody HumAb747-60. See, Example 13. The functionality of humanized anti-LAG-3 antibody of the invention (HumAb747-60) is compared against a chimeric anti-LAG-3 mAb produced using murine variable domains described herein and a human antibody directed against an irrelevant antigen ("hIgG4", control).

To further verify the anti-LAG-3 antibodies function in human PBMC, a bacterial toxin stimulation assay using superantigen *Staphylococcus aureus* enterotoxin B (SEB) was conducted, in the manner described in Example 7.8 supra. IL-2 production was measured using a PerkinElmer IL-2 detection kit (PerkinElmer; Cat. No. TRF1221M). HumAb747-60 was able to enhance IL-2 secretion of SEB-stimulated PBMC by blocking LAG-3 signal pathway. Results are shown in FIG. 9. HumAb747-60 was thus proven functional and was selected for further engineering.

Example 14: Affinity Maturation of HumAb747-60

Example 14.1: Affinity Maturation Library Construction and Screening

Although HumAb747-60 showed an off-rate constant only 1.5-fold greater than that of the chimeric control mAb747c, the PBMC-SEB assay results indicated HumAb747-60 has a slightly weaker functional activity. To further improve the affinity, the CDR residues (in ABM numbering system) were optimized by affinity maturation based on HumAb747-39 (see Tables 24, 25). Two phage libraries were designed and constructed. One was designed to mutate CDR-L1, CDR-L3 and CDR-H3 (ABM numbering), each of which had one randomly mutated residue. The other was designed to mutate CDR-L2, CDR-H1 and CDR-H2(ABM numbering), each of which had one randomly mutated residue.

The phage display libraries were constructed using the method reported in *Journal of Immunological Methods*, 201:35-55 (1997). Briefly, VH-CH1 and VL-CL were amplified with degenerated primers that introduce mutations, and then cloned into two multiple cloning sites (MCS) of a phagemid vector sequentially. The phagemid vectors were then electro-transformed into TG1 (Cat. No. 60502-1, Lucigen), resulting in libraries of approximately $1.2 \times 10^8$ clones, respectively, showing high sequence diversity. The libraries were rescued with M13K07 helper phage (Cat. No. N0315S) at approximately a 1:20 ratio (cell to phage). Phage display library selections were performed with recombinant human LAG-3 protein, followed by washing steps. A Fab fragment of HumAb747-39 was also constructed in a phagemid vector as a positive control. Selected phage were used for infection of host cells. The binding ability of Fab supernatants from single clones were screened by ELISA. Briefly, the Fab supernatants of single clones were prepared by overnight culturing at 30° C. with 1 mM IPTG. 2 μg/ml of human LAG-3 protein in 100 μL of phosphate buffered saline (PBS) were directly coated in each well of 96-well plates. The HRP-linked anti-c-myc antibody (Cat. No. Ab1261, Abcam) and TMB reagent were used to detect and develop the ELISA signal, which was read out by a plate reader (SpectraMax® Plus 384 absorbance plate reader, Molecular Devices) at wavelength of 450 nm.

Positive clones in the screening ELISA were picked for sequencing. Considering sequence redundancy and signal strength in the screening ELISA, the following 7 clones were selected for further evaluation. The VH/VL sequences are shown in Table 36. (Mutated amino acid residues identified by affinity maturation are indicated with double underscore; CDRs are underlined according to Kabat numbering system.)

TABLE 36

VH/VL Amino Acid Sequences of 7 Antibodies with affinity matured mutations

| Affinity matured clones | Domain | SEQ ID NO. | protein sequences 12345678901234567890123456789012345678901234567890 |
|---|---|---|---|
| B2-53 | VH | 119 | EVQLVQSGAEVKKPGASVKVSCKASGFNIKDDYMHWVRQAPG QGLEWIGWIVPENGNTVYASKFQGRVTITADTSINTAYMELS RLRSDDTAVYYCTVYGDYWGQGTTVTVSS |
|  | VL | 120 | DIQMTQSPSSLSASVGDRVTINCRASQEISGYLSWLQQKPEG TIKRLIYAASALDSGVPSRFSGSRSGSDYTLTISSLQPEDFA TYYCLQYASYPLTFGGGTKVEIK |
| B3-21 | VH | 121 | EVQLVQSGAEVKKPGASVKVSCKASDFNIKDDYMHWVRQAPG QGLEWIGWIVPENGNTEYASKFQGRVTITADTSINTAYMELS RLRSDDTAVYYCTVYGDVWGQGTTVTVSS |
|  | VL | 122 | DIQMTQSPSSLSASVGDRVTINCRAMQEISGYLSWLQQKPEG TIKRLIYAASTLDSGVPSRFSGSRSGSDYTLTISSLQPEDFA TYYCLQYAYYPLTFGGGTKVEIK |
| B3-43 | VH | 123 | EVQLVQSGAEVKKPGASVKVSCKASGFNIKDDYMHWVCQAPG QGLEWIGWIVPENGNTEYASKFQGRVTITADTSINTAYMELS RLRSDDTAVYYCTVYGDYWGQGTTVTVSS |
|  | VL | 124 | DIQMTQSPSSLSASVGDRVTINCRASQEISGYLSWLQQKPEG TIKRLIYAASHLDSGVPSRFSGSRSGSDYTLTISSLQPEDFA TYYCLQYASYPLTFGGGTKVEIK |
| B3-46 | VH | 125 | EVQLVQSGAEVKKPGASVKVSCKASGFNIKDDYMHWVRQAPG QGLEWIGWIVPENGLTEYASKFQGRVTITADTSINTAYMELS RLRSDDTAVYYCTVYGDYWGQGTTVTVSS |
|  | VL | 126 | DIQMTQSPSSLSASVGDRVTINCRASQEISGYLSWLQQKPEG TIKRLIYATSTLDSGVPSRFSGSRSGSDYTLTISSLQPEDFA TYYCLQYASYPLTFGGGTKVEIK |
| B3-48 | VH | 127 | EVQLVQSGAEVKKPGASVKVSCKASDFSIKDDYMHWVRQAPG QGLEWIGWIVPENGKTEYASKFQGRVTITADTSINTAYMELS RLRSDDTAVYYCTVYGDYWGQGTTVTVSS |
|  | VL | 128 | DIQMTQSPSSLSASVGDRVTINCRASQEISGYLSWLQQKPEG TIKRLIYAAMTLDSGVPSRFSGSRSGSDYTLTISSLQPEDFA TYYCLQYASYPLTFGGGTKVEIK |
| B3-69 | VH | 129 | EVQLVQSGAEVKKPGASVKVSCKASGFNIKDDYMHWVRQAPG QGLEWIGWIVPENGNTHYASKFQGRVTITADTSINTAYMELS RLRSDDTAVYYCTVYGDYWGQGTTVTVSS |
|  | VL | 130 | DIQMTQSPSSLSASVGDRVTINCRASQEISGYLSWLQQKPEG TIKRLIYEASTLDSGVPSRFSGSRSGSDYTLTISSLQPEDFA TYYCLQYASYPLTFGGGTKVEIK |

TABLE 36-continued

VH/VL Amino Acid Sequences of 7 Antibodies with affinity matured mutations

| Affinity matured clones | Domain | SEQ ID NO. | protein sequences<br>12345678901234567890123456789012345678901234567890 |
|---|---|---|---|
| D1-70 | VH | 131 | EVQLVQSGAEVKKPGASVKVSCKAS<u>G</u>FNIKDDYMHWVRQAPG<br>QGLEWIGWIVP<u>R</u>NG<u>NTM</u>YASKF<u>Q</u>GRVTITADTSINTAYMELS<br>RLRSDDTAVYYCT<u>VYGDYW</u>GQGTTVTVSS |
|  | VL | 132 | DIQMTQSPSSLSAS<u>V</u>GDRVTINCRAS<u>Q</u>EISGYLSWLQQKPEG<br>TIKRLIY<u>AASTLDL</u>GVPSRFSGSRSGSDYTLTISSLQPEDFA<br>TYYC<u>LQYASYPLT</u>FGGGTKVEIK |

Example 14.2: IgG Conversion and Characterization of Positive Clones

The seven Fab clones were converted to full IgG proteins. Briefly, the VH and VL genes were produced synthetically and then cloned into vectors containing coding sequences for the human IgG1 and human kappa constant domains, respectively. The heavy chain and cognate light chain plasmids were co-transfected into HEK 293E cells, individually. After approximately six days of post-transfection cell culture, the supernatants were harvested and subjected to Protein A affinity chromatography. The affinity of purified antibodies was ranked by Octet® RED96 biolayer interferometry (see, Example 9.1, supra). Results are shown in Table 37.

TABLE 37

Off-Rate Ranking of Ant-LAG-3 Antibodies After Affinity Maturation

| Test group | Full-length Antibody | Off-rate ($k_{off}$) (1/s) | off-rate ratio to that of mAb747c |
|---|---|---|---|
| 1 | B3-21-IgG | $1.98 \times 10^{-3}$ | 132% |
|  | B3-43-IgG | $5.88 \times 10^{-3}$ | 392% |
|  | B3-46-IgG | $2.48 \times 10^{-3}$ | 165% |
|  | B3-48-IgG | $2.85 \times 10^{-3}$ | 190% |
|  | B3-69-IgG | $3.59 \times 10^{-3}$ | 239% |
|  | B2-53-IgG | $1.80 \times 10^{-3}$ | 120% |
|  | mAb747c | $1.50 \times 10^{-3}$ | 100% |
| 2 | D1-70-IgG | $2.60 \times 10^{-3}$ | 160% |
|  | HumAb747-42 | $4.28 \times 10^{-3}$ | 263% |
|  | HumAb747-39 | $3.91 \times 10^{-3}$ | 240% |
|  | mAb747c | $1.63 \times 10^{-3}$ | 100% |

D1-70-IgG and B2-53-IgG showed an off-rate constant with minimal increase compared to HumAb747-39 reflecting the most affinity increase after mutations. Therefore, the mutations in D1-70-IgG and B2-53-IgG were introduced to the sequence of HumAb747-60 that was the best candidate after humanization.

Example 14.3: Generation and Characterization of Further Engineered Antibodies The mutations in D1-70 identified by the affinity maturation process were D26G, E53R and E58M in the VH domain, and S56L in the VL domain (residue position as determined by Kabat numbering system). The mutations in B82-53 identified by the affinity maturation process were D26G and E58V in the VH domain, and T53A in the VL domain (residue position as determined by Kabat numbering). These mutations were incorporated into the VH/VL sequences of HumAb747-60, separately or in combination.

There was a NG pattern in CDR-H2 of HumAb747-60, which may have resulted in heterogeneity during manufacturing because of deamination reactions, therefore a mutation from NG to NA was also evaluated. The G55A mutation in they VH domain was calculated not to disturb the activity of HumAb747-60 while breaking the NG pattern. Amino acid sequences for the antibody variants including the mutations discussed above are shown in Table 38. (CDRs are underlined according to Kabat numbering.)

TABLE 38

Engineered VH/VL Design for HumAb747-60

| Engineered VH/VL Identifier | SEQ ID NO. | amino acid sequences<br>12345678901234567890123456789012345678901234567890 |
|---|---|---|
| huEpi001-VHv6 (G55A) | 133 | EVQLVQSGAEVKKPGATVKLSCTASDFNI<u>KDDYMH</u>WVKQR<br>PEQGLDWIGW<u>IVPENANTEYASKFQG</u>KATITADTSTNTAY<br>LELSSLRSEDTAVYYCT<u>VYGDYW</u>GQGTTVTVSS |
| huEpi001-VHv6.1 | 134 | EVQLVQSGAEVKKPGATVKLSCTASGFNI<u>KDDYMH</u>WVKQR<br>PEQGLDWIGW<u>IVPRNGNTMYASKFQG</u>KATITADTSTNTAY<br>LELSSLRSEDTAVYYCT<u>VYGDYW</u>GQGTTVTVSS |
| huEpi001-VHv6.2 | 135 | EVQLVQSGAEVKKPGATVKLSCTASGFNI<u>KDDYMH</u>WVKQR<br>PEQGLDWIGW<u>IVPENGNTVYASKFQG</u>KATITADTSTNTAY<br>LELSSLRSEDTAVYYCT<u>VYGDYW</u>GQGTTVTVSS |

TABLE 38-continued

Engineered VH/VL Design for HumAb747-60

| Engineered VH/VL Identifier | SEQ ID NO. | amino acid sequences<br>1234567890123456789012345678901234567890 |
|---|---|---|
| huEpi001-VHv6.3 | 136 | EVQLVQSGAEVKKPGATVKLSCTASGFNIKDDYMHWVKQR<br>PEQGLDWIGWIVPRNGNTVYASKFQGKATI<u>TADTSTNTAY</u><br>LELSSLRSEDTAVYYCTV<u>YGDYW</u>GQGTTVTVSS |
| huEpi001-VLv3.4 | 137 | DIQMTQSPSSLSASVGDRVTITCRASQEISGYLSWLQQKP<br>GGAIKRLIY<u>AASTLDLG</u>VPSRFSGSRSGSDYTLTISSLQP<br>EDFADYYC<u>LQYASYPLT</u>FGQGTKLELK |
| huEpi001-VLv3.5 | 138 | DIQMTQSPSSLSASVGDRVTITCRASQEISGYLSWLQQKP<br>GGAIKRLIY<u>AASALDSG</u>VPSRFSGSRSGSDYTLTISSLQP<br>EDFADYYC<u>LQYASYPLT</u>FGQGTKLELK |
| huEpi001-VLv3.6 | 139 | DIQMTQSPSSLSASVGDRVTITCRASQEISGYLSWLQQKP<br>GGAIKRLIY<u>AASALDLG</u>VPSRFSGSRSGSDYTLTISSLQP<br>EDFADYYC<u>LQYASYPLT</u>FGQGTKLELK |

The engineered VH and VK genes were produced synthetically and then cloned into vectors containing the human IgG1 and human kappa constant domains, respectively. The pairing of the human VH and the human VK created 13 engineered anti-LAG-3 antibodies, named HumAb747V-61 to HumAb747V-73 (Table 39). The chimeric antibody with parental mouse VH/VL and human constant sequences (mAb747c) was used as a positive control for affinity comparison.

TABLE 39

Production List Engineered Anti-LAG-3 Antibodies

| Antibody Identifier | VH Region in Heavy Chain | VL Region in Light κ Chain |
|---|---|---|
| HumAb747V-61 | huEpi001-VHv6 (G55A) | huEpi001 VLv3 |
| HumAb747V-62 | huEpi001-VHv6.1 | huEpi001 VLv3.4 |
| HumAb747V-63 | huEpi001-VHv6.1 | huEpi001 VLv3.5 |
| HumAb747V-64 | huEpi001-VHv6.1 | huEpi001 VLv3.6 |
| HumAb747V-65 | huEpi001-VHv6.1 | huEpi001 VLv3 |
| HumAb747V-66 | huEpi001-VHv6.2 | huEpi001 VLv3.4 |
| HumAb747V-67 | huEpi001-VHv6.2 | huEpi001 VLv3.5 |
| HumAb747V-68 | huEpi001-VHv6.2 | huEpi001 VLv3.6 |
| HumAb747V-69 | huEpi001-VHv6.2 | huEpi001 VLv3 |
| HumAb747V-70 | huEpi001-VHv6.3 | huEpi001 VLv3.4 |
| HumAb747V-71 | huEpi001-VHv6.3 | huEpi001 VLv3.5 |
| HumAb747V-72 | huEpi001-VHv6.3 | huEpi001 VLv3.6 |
| HumAb747V-73 | huEpi001-VHv6.3 | huEpi001 VLv3 |

All 13 humanized antibodies (Table 39) and chimeric anti-LAG-3 antibody mAb747c having the parental murine VH and VL domains were ranked by dissociation rate constant ($k_{off}$) in the same manner described in Example 9.1 supra. Results are shown in Table 40. In each test group, the off-rates of antibodies were able to be compared with that of mAb747c. The off-rate ratios were calculated by the off-rate of antibody to that of mAb747c of its group and were compared all together. The lower the ratio was, the higher was the affinity of the antibody.

TABLE 40

Off-Rate Ranking of Anti-LAG-3 Antibodies with Further Engineering

| Test group | Full-length Antibody | Off-rate ($k_{off}$) (1/s) | off-rate ratio to that of mAb747c |
|---|---|---|---|
| 1 | HumAb747V-61 | $6.86 \times 10^{-4}$ | 112% |
|   | HumAb747V-62 | $4.80 \times 10^{-4}$ | 78% |
|   | HumAb747V-63 | $5.22 \times 10^{-4}$ | 85% |
|   | HumAb747V-64 | $4.50 \times 10^{-4}$ | 73% |
|   | HumAb747V-65 | $2.92 \times 10^{-4}$ | 47% |
|   | HumAb747V-66 | $5.84 \times 10^{-4}$ | 95% |
|   | mAb747c | $6.15 \times 10^{-4}$ | 100% |
| 2 | HumAb747V-67 | $3.19 \times 10^{-4}$ | 47% |
|   | HumAb747V-68 | $2.95 \times 10^{-4}$ | 41% |
|   | HumAb747V-69 | $3.57 \times 10^{-4}$ | 53% |
|   | HumAb747V-70 | $2.73 \times 10^{-4}$ | 40% |
|   | HumAb747V-71 | $2.92 \times 10^{-4}$ | 43% |
|   | HumAb747V-72 | $2.47 \times 10^{-4}$ | 37% |
|   | mAb747c | $6.76 \times 10^{-4}$ | 100% |
| 3 | HumAb747V-73 | $3.21 \times 10^{-4}$ | 51% |
|   | mAb747c | $6.31 \times 10^{-1}$ | 100% |

On the basis of HumAb747-60, most antibodies with CDR mutations adopted after affinity maturation showed improved off-rate in comparison to the off-rate of mAb747c, predicting improved affinity. HumAb747V-61 had a similar off-rate to mAb747c, which indicated that the VH G55A amino acid substitution did not disturb the affinity. The antibodies that had off-rate ratios less than 60% that of mAb747c in their test group were further evaluated in a cell-based functional assay.

Figure 10:
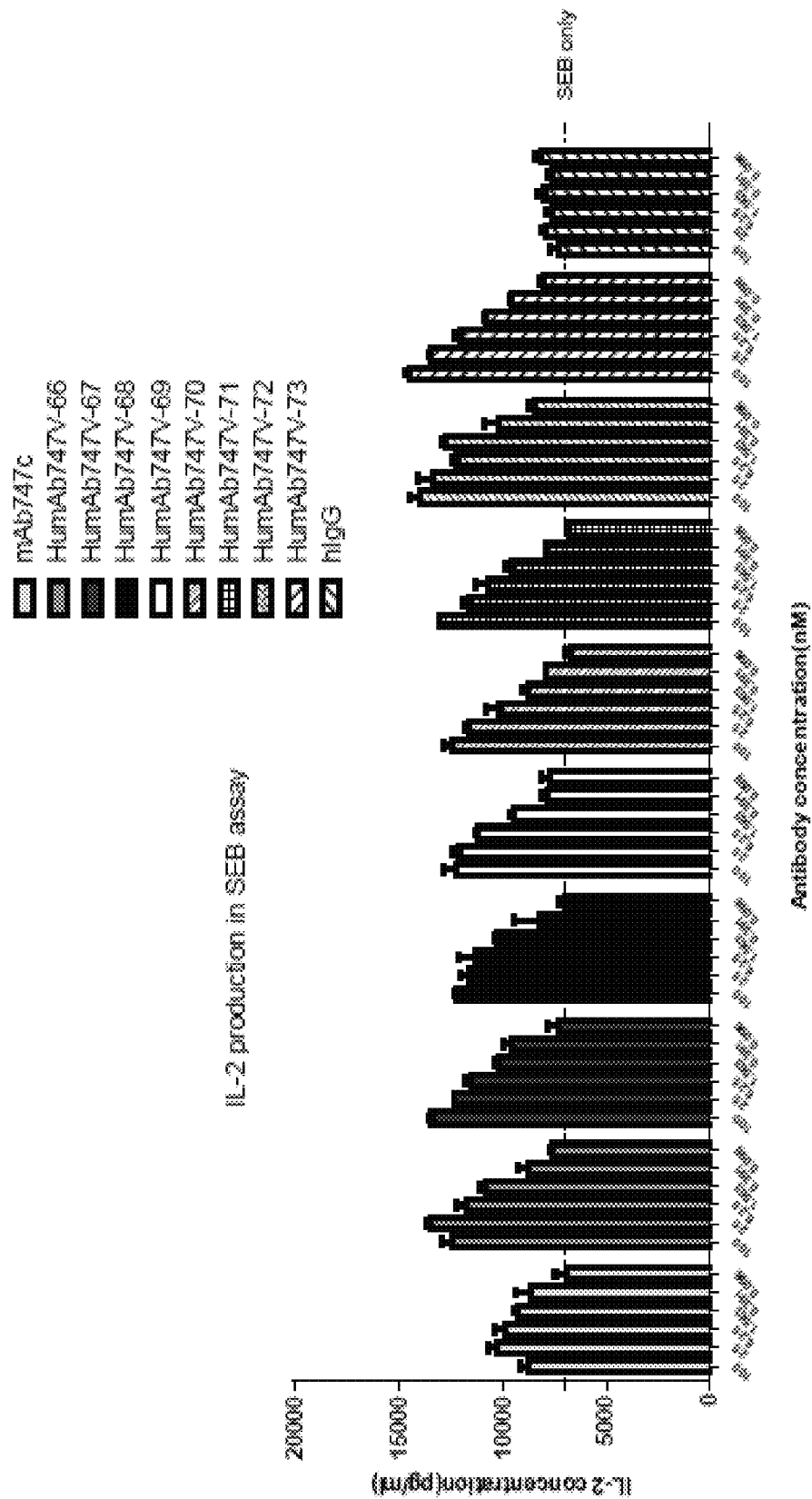
FIG. 10 is a bar graph showing IL-2 production in a SEB T cell activation assay comparing the reversal of T cell suppression effect at various concentrations of a chimeric anti-LAG-3 antibody mAb747c and a high-affinity variants of humanized anti-LAG-3 antibody HumAb747-60 incorporating mutations indicated after affinity maturation experiments. See, Example 14. The functionality of anti-LAG-3 variant antibodies of the invention (HumAb747V-66 to HumAb747V-73) is compared against a chimeric anti-LAG-3 mAb produced using murine variable domains described herein and a human antibody directed against an irrelevant antigen ("hIgG4", control).

The anti-LAG-3 activity was tested in a PBMC activation assay using Staphylococcal enterotoxin B (SEB) as a superantigen. Briefly, PBMC were seeded into a 96-well plate with $2 \times 10^5$ cells/well. Test proteins (anti-LAG-3 monoclonal antibodies) were added into the plates and incubated with PBMC at 37° C. for 30 min. SEB solution was added to a final concentration of 10 ng/ml. The plates were incubated for 96 hours, then 100 μl cell culture supernatant were collected and IL-2 production was measured using a PerkinElmer IL-2 detection kit (PerkinElmer, Cat. No. TRF1221M). Results are shown in FIG. 10. The results show that the engineered antibody variants can enhance IL-2 production from SEB-stimulated PBMC by blocking LAG-3-mediated signaling.

Based on the PBMC-SEB assay results, HumAb747V-67, HumAb747V-72, and HumAb747V-73 demonstrated superior LAG-3-blocking activity; therefore, these three antibodies were used for generating FIT-Ig binding proteins targeting LAG-3 and also PD-1.

Example 15: Generation of PD-1/LAG-3 FIT-Igs Using New Anti-LAG-3 Antibody Sequences The anti-LAG-3 antibodies HumAb747V-67, HumAb747V-72 and HumAb747V-73 generated as described above, and two anti-PD-1 antibodies, HumAb709-8 (see Tables 5 and 7, supra) and HumAb713-7 (see Tables 9 and 10, supra), were used to generate FIT-Ig binding proteins, following the procedures described in Example 10, supra. The G55A mutation was included in sequence design of all the VH domains of the anti-LAG-3 Fab moieties.

Example 15.1: Production of PD-1/LAG-3 FIT-Ig Binding Protein FIT107-1-6a-1

A PD-1/LAG-3 FIT-Ig designated FIT107-1-6a-1 was constructed utilizing coding sequences for immunoglobulin domains from the parental antibodies mAb709-8 (humanized anti-PD-1, see Tables 5 and 6, supra) and HumAb747V-67 (humanized anti-LAG-3, see Tables 38 and 39, supra). FIT-Ig FIT107-1-6a-1 is a hexamer comprised of three component polypeptide chains:
Polypeptide chain #1 has the domain formula: VL-CL of HumAb709-8 fused directly to VH-CH1 of HumAb747V-67 fused directly to hinge-CH2-CH3 of a mutant human constant IgG1 (see Table 6, supra);
Polypeptide chain #2 has the domain formula: VH-CH1 of HumAb709-8; and
Polypeptide chain #3 has the domain formula: light chain (VL-CL) of HumAb747V-676.
The amino acid sequences for the three expressed FIT107-1-6a-1 polypeptide chains are shown in Table 41 below.

TABLE 41

Amino Acid Sequences of FIT107-1-6a-1 Component Chains

| Polypeptide | SEQ ID NO: | Amino Acid Sequence<br>1234567890123456789012345678901234567890 |
|---|---|---|
| FIT107-1-6a-1 FIT-Ig Polypeptide Chain #1 | 140 | MDMRVPAQLLGLLLLWFPGSRCDIVMTQSPSSLSASVGDR<br>VTITCKASQDVNTVVAWYQQKPGKAPKVLISWASTRHTGV<br>PSRFSGSGSGTDYTLTISSLQPEDFATYYCQQHYTTPYTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VQSGAEVKKPGATVKLSCTASGFNIKDDYMHWVKQRPEQG<br>LDWIGWIVPENANTVYASKFQGKATITADTSTNTAYLELS<br>SLRSEDTAVYYCTVYGDYWGQGTTVTVSSASTKGPSVFPL<br>APSSKSTSGGTAALGCLVKDYFPEPVTVSWNSGALTSGVH<br>TFPAVLQSSGLYSLSSVVTVPSSSLGTQTYICNVNHKPSN<br>TKVDKKVEPKSCDKTHTCPPCPAPEAAGGPSVFLFPPKPK<br>DTLMISRTPEVTCVVVDVSHEDPEVKFNWYVDGVEVHNAK<br>TKPREEQYNSTYRVVSVLTVLHQDWLNGKEYKCKVSNKAL<br>PAPIEKTISKAKGQPREPQVYTLPPSREEMTKNQVSLTCL<br>VKGFYPSDIAVEWESNGQPENNYKTTPPVLDSDGSFFLYS<br>KLTVDKSRWQQGNVFSCSVMHEALHNHYTQKSLSLSPGK |
| signal sequence | 79 | MDMRVPAQLLGLLLLWFPGSRC |
| VL-CL of mAb HumAb709-8 (VL underlined) | 141 | <u>DIVMTQSPSSLSASVGDRVTITCKASQDVNTVVAWYQQKP<br>GKAPKVLISWASTRHTGVPSRFSGSGSGTDYTLTISSLQP<br>EDFATYYCQQHYTTPYTFGGGTKVEIK</u>RTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of mAb HumAb747V-67 (VH underlined) | 142 | <u>EVQLVQSGAEVKKPGATVKLSCTASGFNIKDDYMHWVKQR<br>PEQGLDWIGWIVPENAMTVYASKFQGKATITADTSTNTAY<br>LELSSLRSEDTAVYYCTVYGDYWGQGTTVTVSS</u>ASTKGPS<br>VFPLAPSSKSTSGGTAALGCLVKDYFPEPVTVSWNSGALT<br>SGVHTFPAVLQSSGLYSLSSVVTVPSSSLGTQTYICNVNH<br>KPSNTKVDKKVEPKSC |
| hinge-CH2-CH3 of human IgG1 | 143 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |
| FIT107-1-6a-1 FIT-Ig Polypeptide Chain #2 | 143 | MEFGLSWLFLVAILKGVQCEVQLVESGGGLVQPGGSLRLS<br>CAASGFTFSFYTMSVVVRQAPGKGLEWVATISGGGRDTYY<br>PDSVKGRFTISRDNAKNSLYLQMNSLRAEDTAVYYCAGQG<br>GNYLFAYWGQGTLVTVSSASTKGPSVFPLAPSSKSTSGGT<br>AALGCLVKDYFPEPVTVSWNSGALTSGVHTFPAVLQSSGL<br>YSLSSVVTVPSSSLGTQTYICNVNHKPSNTKVDKKVEPKS<br>C |

TABLE 41-continued

Amino Acid Sequences of FIT107-1-6a-1 Component Chains

| Polypeptide | SEQ ID NO: | Amino Acid Sequence<br>12345678901234567890123456789012345678 90 |
|---|---|---|
| signal sequence | 84 | MEFGLSWLFLVAILKGVQC |
| VH-CH1 of<br>HumAb709-8<br>(VH underlined) | 144 | EVQLVESGGGLVQPGGSLRLSCAASGFTFSFYTMSWVRQA<br>PGKGLEWVATISGGGRDTYYPDSVKGRFTISRDNAKNSLY<br>LQMNSLRAEDTAVYYCAGQGGNYLFAYWGQGTLVTVSSAS<br>TKGPSVFPLAPSSKSTSGGTAALGCLVKDYFPEPVTVSWN<br>SGALTSGVHTFPAVLQSSGLYSLSSVVTVPSSSLGTQTYI<br>CNVNHKPSNTKVDKKVEPKSC |
| FIT107-1-6a-1<br>FIT-Ig Polypeptide<br>Chain #3 | 145 | MDMRVPAQLLGLLLLWFPGSRCDIQMTQSPSSLSASVGDR<br>VTITCRASQEISGYLSWLQQKPGGAIKRLIYAASALDSGV<br>PSRFSGSRSGSDYTLTISSLQPEDFADYYCLQYASYPLTF<br>GQGTKLELKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of<br>HumAb747V-67<br>(VH underlined) | 146 | DIQMTQSPSSLSASVGDRVTITCRASQEISGYLSWLQQKP<br>GGAIKRLIYAASALDSGVPSRFSGSRSGSDYTLTISSLQP<br>EDFADYYCLQYASYPLTFGQGTKLELKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 15.2: Production of PD-1/LAG-3 FIT-Ig Binding Protein FIT17-1-6b-1

Another bispecific Fabs-in-Tandem Immunoglobulin recognizing both human PD-1 and human LAG-3 was constructed. This PD-1/LAG-3 FIT-Ig was designated FIT107-1-6b-1. Construction of FIT107-1-6b-1 binding protein utilized coding sequences for immunoglobulin domains from parental antibodies HumAb747V-67 (anti-LAG-3) and HumAb709-8 (anti-PD-1). This FIT-Ig construct exhibited a LAG-3-binding domain in the N-terminal (outer) position and a PD-1-binding domain in the inner position fused C-terminal to the VL-CL domains of the LAG-3 binding region. FIT-Ig FIT107-1-6b-1 is a hexamer comprised of three component polypeptide chains:

Polypeptide chain #1 has the domain formula: VL-CL of HumAb747V-67 fused directly to VH-CH1 of HumAb709-8 fused directly to hinge-CH2-CH3 of a mutant human constant IgG1 (see Table 6, supra);

Polypeptide chain #2 has the domain formula: VH-CH of HumAb747V-67; and

Polypeptide chain #3 has the domain formula: light chain (VL-CL) of HumAb709-8.

The amino acid sequences for the three expressed FIT107-1-6b-1 polypeptide chains are shown in Table 42 below:

TABLE 42

Amino Acid Sequences of FIT107-1-6b-1 Component Chains

| Polypeptide | SEQ ID NO: | Amino Acid Sequence<br>12345678901234567890123456789012345678 90 |
|---|---|---|
| FIT107-1-6b-1<br>FIT-Ig Polypeptide<br>Chain #1 | 147 | MDMRVPAQLLGLLLLWFPGSRCDIQMTQSPSSLSASVGDR<br>VTITCRASQEISGYLSWLQQKPGGAIKRLIYAASALDSGV<br>PSRFSGSRSGSDYTLTISSLQPEDFADYYCLQYASYPLTF<br>GQGTKLELKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VESGGGLVQPGGSLRLSCAASGFTFSFYTMSWVRQAPGKG<br>LEWVATISGGGRDTYYPDSVKGRFTISRDNAKNSLYLQMN<br>SLRAEDTAVYYCAGQGGNYLFAYWGQGTLVTVSSASTKGP<br>SVFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSCDKTHTCPPCPAPEAAGGPSVFLF<br>PPKPKDTLMISRTPEVTCVVVDVSHEDPEVKFNWYVDGVE<br>VHNAKTKPREEQYNSTYRVVSVLTVLHQDWLNGKEYKCKV<br>SNKALPAPIEKTISKAKGQPREPQVYTLPPSREEMTKNQV<br>SLTCLVKGFYPSDIAVEWESNGQPENNYKTTPPVLDSDGS<br>FFLYSKLTVDKSRWQQGNVFSCSVMHEALHNHYTQKSLSL<br>SPGK |

TABLE 42-continued

Amino Acid Sequences of FIT107-1-6b-1 Component Chains

| Polypeptide | SEQ ID NO: | Amino Acid Sequence<br>12345678901234567890123456789012345678 90 |
|---|---|---|
| signal sequence | 79 | MDMRVPAQLLGLLLLWFPGSRC |
| VL-CL of mAb HumAb747V-67 (VL underlined) | 148 | <u>DIQMTQSPSSLSASVGDRVTITCRASQEISGYLSWLQQKP</u><br><u>GGAIKRLIYAASALDSGVPSRFSGSRSGSDYTLTISSLQP</u><br><u>EDFADYYCLQYASYPLTFGQGTKLELK</u>RTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of mAb HumAb709-8 (VH underlined) | 149 | <u>EVQLVESGGGLVQPGGSLRLSCAASGFTFSFYTMSWVRQA</u><br><u>PGKGLEWVATISGGGRDTYYPDSVKGRFTISRDNAKNSLY</u><br><u>LQMNSLRAEDTAVYYCAGQGGNYLFAYWGQGTLVTVSS</u>AS<br>TKGPSVFPLAPSSKSTSGGTAALGCLVKDYFPEPVTVSWN<br>SGALTSGVHTFPAVLQSSGLYSLSSVVTVPSSSLGTQTYI<br>CNVNHKPSNTKVDKKVEPKSC |
| hinge-CH2-CH3 of human IgG1 | 82 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |
| FIT107-1-6b-1 FIT-Ig Polypeptide Chain #2 | 150 | <u>MEFGLSWLFLVAILKGVQC</u>EVQLVQSGAEVKKPGATVKLS<br>CTASGFNIKDDYMHWVKQRPEQGLDWIGWIVPENANTVY<br>ASKFQGKATITADTSTNTAYLELSSLRSEDTAVYYCTVYG<br>DYWGQGTTVTVSSASTKGPSVFPLAPSSKSTSGGTAALGC<br>LVKDYFPEPVTVSWNSGALTSGVHTFPAVLQSSGLYSLSS<br>WTVPSSSLGTQTYICNVNHKPSNTKVDKKVEPKSC |
| signal sequence | 84 | MEFGLSVfLFLVAILKGVQC |
| VH-CH1 of HumAb747V-67 (VH underlined) | 151 | <u>EVQLVQSGAEVKKPGATVKLSCTASGFNIKDDYMHWVKQR</u><br><u>PEQGLDWIGWIVPENANTVYASKFQGKATITADTSTNTAY</u><br><u>LELSSLRSEDTAVYYCTVYGDYWGQGTTVTVSS</u>ASTKGPS<br>VFPLAPSSKSTSGGTAALGCLVKDYFPEPVTVSWNSGALT<br>SGVHTFPAVLQSSGLYSLSSVVTVPSSSLGTQTYICNVNH<br>KPSNTKVDKFCVEPKSC |
| FIT107-1-6b-1 FIT-Ig Polypeptide Chain #3 | 152 | <u>MDMRVPAQLLGLLLLWFPGSRC</u>DIVMTQSPSSLSASVGDR<br>VTITCKASQDVNTVVAWYQQKPGKAPKVLISWASTRHTGV<br>PSRFSGSGSGTDYTLTISSLQPEDFATYYCQQHYTTPYTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of HumAb709-8 (VL underlined) | | <u>DIVMTQSPSSLSASVGDRVTITCKASQDVNTVVAWYQQKP</u><br><u>GKAPKVLISWASTRHTGVPSRFSGSGSGTDYTLTISSLQP</u><br><u>EDFATYYCQQHYTTPYTFGGGTKVEIK</u>RTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 15.3: Production of PD-1/LAG-3 FIT-Ig Binding Protein FIT107-1-6a-2

A PD-1/LAG-3 FIT-Ig designated FIT107-1-6a-2 was constructed utilizing coding sequences for immunoglobin domains from the parental antibodies HumAb709-8 (humanized anti-PD-1) and HumAb747V-72 (humanized anti-LAG-3). FIT-Ig FIT107-1-6-2 is a hexamer comprised of three component polypeptide chain:

Polypeptide chain #1 has the domain formula: VL-CL of HumAb709-8 fused directly to VH-CH1 of HumAb747V-72 fused directly to hinge-CH2-CH3 of a mutant human constant IgG1 (see Table 6, supra);
Polypeptide chain #2 has the domain formula: VH-CH1 of HumAb709-8; and
Polypeptide chain #3 has the domain formula: light chain (VL-CL) of HumAb747V-72.
The amino acid sequences for the three expressed FIT107-1-6a-2 polypeptide chains are shown in Table 43 below.

TABLE 43

Amino Acid Sequences of FIT107-1-6a-2 Component Chains

| Polypeptide | SEQ ID NO: | Amino Acid Sequence 1234567890123456789012345678901234567890 |
|---|---|---|
| FIT107-1-6a-2 FIT-Ig Polypeptie Chain #1 | 154 | MDMRVPAQLLGLLLLWFPGSRCDIVMTQSPSSLSASVGDR VTITCKASQDVNTVVAWYQQKPGKAPKVLISWASTRHTGV PSRFSGSGSGTDYTLTISSLQPEDFATYYCQQHYTTPYTF GGGTKVEIKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGECEVQL VQSGAEVKKPGATVKLSCTASGFNIKDDYMHWVKQRPEQG LDWIGWIVPRNANTVYASKFQGKATITADTSTNTAYLELS SLRSEDTAVYYCTVYGDYWGQGTTVTVSSASTKGPSVFPL APSSKSTSGGTAALGCLVKDYFPEPVTVSWNSGALTSGVH TFPAVLQSSGLYSLSSVVTVPSSSLGTQTYICNVNHKPSN TKVDKKVEPKSCDKTHTCPPCPAPEAAGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVYTLPPSREEMTKNQVSLTCL VKGFYPSDIAVEWESNGQPENNYKTTPPVLDSDGSFFLYS KLTVDKSRWQQGNVFSCSVMHEALHNHYTQKSLSLSPGK |
| signal sequence | 79 | MDMRVPAQLLGLLLLWFPGSRC |
| VL-CL of mAb HumAb709-8 (VL underlined) | 155 | DIVMTQSPSSLSASVGDRVTITCKASQDVNTVVAWYQQKP GKAPKVLISWASTRHTGVPSRFSGSGSGTDYTLTISSLQP EDFATYYCQQHYTTPYTFGGGTKVEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| VH-CH1 of mAb HumAb747V-72 (VH underlined) | 156 | EVQLVQSGAEVKKPGATVKLSCTASGFNIKDDYMHWVKQR PEQGLDWIGWIVPRNANTVYASKFQGKATITADTSTNTAY LELSSLRSEDTAVYYCTVYGDYWGQGTTVTVSSASTKGPS VFPLAPSSKSTSGGTAALGCLVKDYFPEPVTVSWNSGALT SGVHTFPAVLQSSGLYSLSSVVTVPSSSLGTQTYICNVNH KPSNTKVDKKVEPKSC |
| hinge-CH2-CH3 of human IgG1 | 82 | DKTHTCPPCPAPEAAGGPSVFLFPPKPKDTLMISRTPEVT CVVVDVSHEDPEVKFNWYVDGVEVHNAKTKPREEQYNSTY RVVSVLTVLHQDWLNGKEYKCKVSNKALPAPIEKTISKAK GQPREPQVYTLPPSREEMTKNQVSLTCLVKGFYPSDIAVE WESNGQPENNYKTTPPVLDSDGSFFLYSKLTVDKSRWQQG NVFSCSVMHEALHNHYTQKSLSLSPGK |
| FIT107-1-6a-2 FIT-Ig Polypeptide Chain #2 | 157 | MEFGLSWLFLVAILKGVQCEVQLVESGGGLVQPGGSLRLS CAASGFTFSFYTMSWVRQAPGKGLEWVATISGGGRDTYY PDSVKGRFTISRDNAKNSLYLQMNSLRAEDTAVYYCAGQG GNYLFAYWGQGTLVTVSSASTKGPSVFPLAPSSKSTSGGT AALGCLVKDYFPEPVTVSWNSGALTSGVHTFPAVLQSSGL YSLSSVVTVPSSSLGTQTYICNVNHKPSNTKVDKKVEPKS C |
| signal sequence | 84 | MEFGLSWLFLVAILKGVQC |
| VH-CH1 of HumAb709-8 (VH underlined) | 158 | EVQLVESGGGLVQPGGSLRLSCAASGFTFSFYTMSWVRQA PGKGLEWVATISGGGRDTYYPDSVKGRFTISRDNAKNSLY LQMNSLFAEDTAVYYCAGQGGNYLFAYWGQGTLVTVSSAS TKGPSVFPLAPSSKSTSGGTAALGCLVKDYFPEPVTVSWN SGALTSGVHTFPAVLQSSGLYSLSSVVTVPSSSLGTQTYI CNVNHKPSNTKVDKKVEPKSC |
| FIT107-1-6a-2 FIT-Ig Polypeptide Chain #3 | 159 | MDMRVPAQLLGLLLLWFPGSRCDIQMTQSPSSLSASVGDR VTITCRASQEISGYLSWLQQKPGGAIKRLIYAASALDLGV PSRFSGSRSGSDYTLTISSLQPEDFADYYCLQYASYPLTF GQGTKLELKRTVAAPSVFIFPPSDEQLKSGTASVVCLLNN |

TABLE 43-continued

Amino Acid Sequences of FIT107-1-6a-2 Component Chains

| Polypeptide | SEQ ID NO: | Amino Acid Sequence<br>12345678901234567890123456789012345678 90 |
|---|---|---|
| | | FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of<br>HumAb747V-72<br>(VL underlined) | 160 | DIQMTQSPSSLSASVGDRVTITCRASQEISGYLSWLQQKP<br>GGAIKRLIYAASALDLGVPSRFSGSRSGSDYTLTISSLQP<br>EDFADYYCLQYASYPLTFGQGTKLELKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 15.4: Production of PD-1/LAG-3 FIT-Ig Binding Protein FIT17-1-6b-2

A PD-1/LAG-3 FIT-Ig designated FIT107-1-6b-2 was constructed utilizing coding sequences for immunoglobulin domains from the parental antibodies Hun Ab79-8 (humanized anti-PD-1) and HumAb747V-72 (humanized anti-LAG-3). FIT-Ig FIT107-1-6b-2 is a hexamer comprised of three component polypeptide chain:

Polypeptide chain #1 has the domain formula: VL-CL of HumAb747V-72 fused directly to VH-CH1 of HumAb709-8 fused directly to hinge-CH2-CH3 of a mutant human constant IgG1;
Polypeptide chain #2 has the domain formula: VH-CH1 of HumAb747V-72; and
Polypeptide chain #3 has the domain formula: light chain (VL-CL) of HumAb709-8.
The amino acid sequences for the three expressed FIT107-1-6b-2 polypeptide chains are shown in Table 44 below.

TABLE 44

Amino Acid Sequences of FIT107-1-6b-2 Component Chains

| Polypeptide | SEQ ID NO: | Amino Acid Sequence<br>12345678901234567890123456789012345678 90 |
|---|---|---|
| FIT107-1-6b-2<br>FIT-Ig Polypeptide<br>Chain #1 | 161 | MDMRVPAQLLGLLLLWFPGSRCDIQMTQSPSSLSASVGDR<br>VTITCRASQEISGYLSWLQQKPGGAIKRLIYAASALDLGV<br>PSRFSGSRSGSDYTLTISSLQPEDFADYYCLQYASYPLTF<br>GQGTKLELKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VESGGGLVQPGGSLRLSCAASGFTFSFYTMSWVRQAPGKG<br>LEWVATISGGGRDTYYPDSVKGRFTISRDNAKNSLYLQMN<br>SLRAEDTAVYYCAGQGGNYLFAYWGQGTLVTVSSASTKGP<br>SVFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSCDKTHTCPPCPAPEAAGGPSVFLF<br>PPKPKDTLMISRTPEVTCVVVDVSHEDPEVKFNWYVDGVE<br>VHNAKTKPREEQYNSTYRVVSVLTVLHQDWLNGKEYKCKV<br>SNKALPAPIEKTISKAKGQPREPQVYTLPPSREEMTKNQV<br>SLTCLVKGFYPSDIAVEWESNGQPENNYKTTPPVLDSDGS<br>FFLYSKLTVDKSRWQQGNVFSCSVMHEALHNHYTQKSLSL<br>SPGK |
| signal sequence | 79 | MDMRVPAQLLGLLLLWFPGSRC |
| VL-CL of mAb<br>HumAb747V-72<br>(VL underlined) | 162 | DIQMTQSPSSLSASVGDRVTITCRASQEISGYLSWLQQKP<br>GGAIKRLIYAASALDLGVPSRFSGSRSGSDYTLTISSLQP<br>EDFADYYCLQYASYPLTFGQGTKLELKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of mAb<br>HumAb709-8<br>(VH underlined) | 163 | EVQLVESGGGLVQPGGSLRLSCAASGFTFSFYTMSWVRQA<br>PGKGLEWVATISGGGRDTYYPDSVKGRFTISRDNAKNSLY<br>LQMNSLRAEDTAVYYCAGQGGNYLFAYWGQGTLVTVSSAS<br>TKGPSVFPLAPSSKSTSGGTAALGCLVKDYFPEPVTVSWN<br>SGALTSGVHTFPAVLQSSGLYSLSSVVTVPSSSLGTQTYI<br>CNVNHKPSNTKVDKKVEPKSC |
| hinge-CH2-CH3<br>of human IgG1 | 82 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |

TABLE 44-continued

Amino Acid Sequences of FIT107-1-6b-2 Component Chains

| Polypeptide | SEQ ID NO: | Amino Acid Sequence<br>12345678901234567890123456789012345678 90 |
|---|---|---|
| FIT107-1-6b-2<br>FIT-Ig Polypeptide<br>Chain #2 | 164 | MEFGLSWLFLVAILKGVQCEVQLVQSGAEVKKPGATVKLS<br>CTASGFNIKDDYMHWVKQRPEQGLDWIGWIVPRNANTVY<br>ASKFQGKATITADTSTNTAYLELSSLRSEDTAVYYCTVYG<br>DYWGQGTTVTVSSASTKGPSVFPLAPSSKSTSGGTAALGC<br>LVKDYFPEPVTVSWNSGALTSGVHTFPAVLQSSGLYSLSS<br>VVTVPSSSLGTQTYICNVNHKPSNTKVDKKVEPKSC |
| signal sequence | 84 | MEFGLSWLFLVAILKGVQC |
| VH-CH1 of<br>HumAb747V-72<br>(VH underlined) | 165 | <u>EVQLVQSGAEVKKPGATVKLSCTASGFNIKDDYMHWVKQR</u><br><u>PEQGLDWIGWIVPRNANTVYASKFQGKATITADTSTNTAY</u><br><u>LELSSLRSEDTAVYYCTVYGDYWGQGTTVTVSS</u>ASTKGPS<br>VFPLAPSSKSTSGGTAALGCLVKDYFPEPVTVSWNSGALT<br>SGVHTFPAVLQSSGLYSLSSVVTVPSSSLGTQTYICNVNH<br>KPSNTKVDKKVEPKSC |
| FIT107-1-6b-2<br>FIT-Ig Polypeptide<br>Chain #3 | 166 | MDMRVPAQLLGLLLLWFPGSRCDIVMTQSPSSLSASVGDR<br>VTITCKASQDVNTVVAWYQQKPGKAPKVLISWASTRHTGV<br>PSRFSGSGSGTDYTLTISSLQPEDFATYYCQQHYTTPYTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of<br>HumAb709-8<br>(VL underlined) | 167 | <u>DIVMTQSPSSLSASVGDRVTITCKASQDVNTVVAWYQQKP</u><br><u>GKAPKVLISWASTRHTGVPSRFSGSGSGTDYTLTISSLQP</u><br><u>EDFATYYCQQHYTTPYTF</u>GGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 15.5; Production of PD-1/LAG-3 FIT-Ig Binding Protein FIT107-1-6a-3

A PD-1/LAG-3 FIT-Ig designated FIT107-1-6a-3 was constructed utilizing coding sequences for immunoglobulin domains from the parental antibodies HumAb709-8 (humanized anti-PD-1) and HumAb747V-73 (humanized anti-LAG-3). FIT-Ig FIT107-1-6a-3 is a hexamer comprised of three component polypeptide chains;

Polypeptide chain #1 has the domain formula; VL-CL of HumAb709-8 fused directly to VH-CH1 of HumAb747V-73 fused directly to hinge-CH2-CH3 of a mutant human constant IgG1;
Polypeptide chain #2 has the domain formula; VH-CH1 of HumAb709-8; and
Polypeptide chain #3 has the domain formula; light chain (VL-CL) of HumAb747V-73.
The amino acid sequences for the three expressed FIT107-1-6a-3 polypeptide chains are shown in Table 45 below.

TABLE 45

Amino Acid Sequences of FIT107-1-6a-3 Component Chains

| Polypeptide | SEQ ID NO: | Amino Acid Sequence<br>12345678901234567890123456789012345678 90 |
|---|---|---|
| FIT107-1-6a-3<br>FIT-Ig Polypeptide<br>Chain #1 | 168 | MDMRVPAQLLGLLLLWFPGSRCDIVMTQSPSSLSASVGDR<br>VTITCKASQDVNTVVAWYQQKPGKAPKVLISWASTRHTGV<br>PSRFSGSGSGTDYTLTISSLQPEDFATYYCQQHYTTPYTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VQSGAEVKKPGATVKLSCTASGFNIKDDYMHWVKQRPEQG<br>LDWIGWIVPRNANTVYASKFQGKATITADTSTNTAYLELS<br>SLRSEDTAVYYCTVYGDYWGQGTTVTVSSASTKGPSVFPL<br>APSSKSTSGGTAALGCLVKDYFPEPVTVSWNSGALTSGVH<br>TFPAVLQSSGLYSLSSVVTVPSSSLGTQTYICNVNHKPSN<br>TKVDKKVEPKSCDKTHTCPPCPAPEAAGGPSVFLPPKFK<br>DTLMISRTPEVTCVVVDVSHEDPEVKFNWYVDGVEVHNAK<br>TKPREEQYNSTYRVVSVLTVLHQDWLNGKEYKCKVSNKAL<br>PAPIEKTISKAKGQPREPQVYTLPPSREEMTKNQVSLTCL<br>VKGFYPSDIAVEWESNGQPENNYKTTPPVLDSDGSFFLYS<br>KLTVDKSRWQQGNVFSCSVMHEALHNHYTQKSLSLSPGK |

TABLE 45-continued

Amino Acid Sequences of FIT107-1-6a-3 Component Chains

| Polypeptide | SEQ ID NO: | Amino Acid Sequence |
|---|---|---|
| signal sequence | 79 | MDMRVPAQLLGLLLLWFPGSRC |
| VL-CL of mAb HumAb709-8 (VL underlined) | 169 | <u>DIVMTQSPSSLSASVGDRVTITCKASQDVNTVVAWYQQKP<br>GKAPKVLISWASTRHTGVPSRFSGSGSGTDYTLTISSLQP<br>EDFATYYCQQHYTTPYTFGGGTKVEIK</u>RTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of mAb HumAb747V-73 (VH underlined) | 170 | <u>EVQLVQSGAEVKKPGATVKLSCTASGFNIKDDYMHWVKQR<br>PEQGLDWIGWIVPRNANTVYASKFQGKATITADTSTNTAY<br>LELSSLRSEDTAVYYCTVYGDYWGQGTTVTVSS</u>ASTKGPS<br>VFPLAPSSKSTSGGTAALGCLVKDYFPEPVTVSWNSGALT<br>SGVHTFPAVLQSSGLYSLSSVVTVPSSSLGTQTYICNVNH<br>KPSNTKVDKKVEPKSC |
| hinge-CH2-CH3 of human IgG1 | 82 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |
| FIT107-1-6a-3 FIT-Ig Polypeptide Chain #2 | 171 | <u>MEFGLSWLFLVAILKGVQC</u>EVQLVESGGGLVQPGGSLRLS<br>CAASGFTFSFYTMSWVRQAPGKGLEWVATISGGGRDTYY<br>PDSVKGRFTISRDNAKNSLYLQMNSLRAEDTAVYYCAGQG<br>GNYLFAYWGQGTLVTVSSASTKGPSVFPLAPSSKSTSGGT<br>AALGCLVKDYFPEPVTVSWNSGALTSGVHTFPAVLQSSGL<br>YSLSSVVTVPSSSLGTQTYICNVNHKPSNTKVDKKVEPKS<br>C |
| signal sequence | 84 | MEFGLSWLFLVAILKGVQC |
| VH-CH1 of HumAb709-8 (VH underlined) | 172 | <u>EVQLVESGGGLVQPGGSLRLSCAASGFTFSFYTMSWVRQA<br>PGKGLEWVATISGGGRDTYYPDSVKGRFTISRDNAKNSLY<br>LQMNSLRAEDTAVYYCAGQGGNYLFAYWGQGTLVTVSS</u>AS<br>TKGPSVFPLAPSSKSTSGGTAALGCLVKDYFPEPVTVSWN<br>SGALTSGVHTFPAVLQSSGLYSLSSVVTVPSSSLGTQTYI<br>CNVNHKPSNTKVDKKVEPKSC |
| FIT107-1-6a-3 FIT-Ig Polypeptide Chain #3 | 173 | <u>MDMRVPAQLLGLLLLWFPGSRC</u>DIQMTQSPSSLSASVGDR<br>VTITCRASQEISGYLSWLQQKPGGAIKRLIYAASTLDSGV<br>PSRFSGSRSGSDYTLTISSLQPEDFADYYCLQYASYPLTF<br>GQGTKLELKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of HumAb747V-73 (VL underlined) | 174 | <u>DIQMTQSPSSLSASVGDRVTITCRASQEISGYLSWLQQKP<br>GGAIKRLIYAASTLDSGVPSRFSGSRSGSDYTLTISSLQP<br>EDFADYYCLQYASYPLTFGQGTKLELK</u>RTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 15.6: Production of PD-1/LAG-3 FIT-Ig Binding Protein FIT107-1-6b-3

A PD-1/LAG-3 FIT-Ig designated FIT107-1-6b-3 was constructed utilizing coding sequences for immunoglobulin domains from the parental antibodies HumAb709-8 (humanized anti-PD-1) and HumAb747V-73 (humanized anti-LAG-3). FIT-Ig FIT107-1-6b-3 is a hexamer comprised of three component polypeptide chains:

Polypeptide chain #1 has the domain formula: VL-CL of HumAb747V-73 fused directly to VH-CH1 of HumAb709-8 fused directly to hinge-CH2-CH3 of a mutant human constant IgG1;

Polypeptide chain #2 has the domain formula: VH-CH1 of HumAb747V-73; and

Polypeptide chain #3 has the domain formula: light chain (VL-CL) of HumAb709-8.

The amino acid sequences for the three expressed FIT107-1-6b-3 polypeptide chains are shown in Table 46 below.

TABLE 46

Amino Acid Sequences of FIT107-1-6b-3 Component Chains

| Polypeptide | SEQ ID NO: | Amino Acid Sequence<br>1234567890123456789012345678901234567890 |
|---|---|---|
| FIT107-1-6b-3 FIT-Ig Polypeptide Chain #1 | 175 | MDMRVPAQLLGLLLLWFPGSRCDIQMTQSPSSLSASVGDR<br>VTITCRASQEISGYLSWLQQKPGGAIKRLIYAASTLDSGV<br>PSRFSGSRSGSDYTLTISSLQPEDFADYYCLQYASYPLTF<br>GQGTKLELKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VESGGGLVQPGGSLRLSCAASGFTFSFYTMSWVRQAPGKG<br>LEWVATISGGGRDTYYPDSVKGRFTISRDNAKNSLYLQMN<br>SLRAEDTAVYYCAGQGGNYLFAYWGQGTLVTVSSASTKGP<br>SVFPLAPSSKSTSGGTAALGCLVKDYFPEPVTVSWNSGAL<br>TSGVHTFPAVLQSSGLYSLSSVVTVPSSSLGTQTYICNVN<br>HKPSNTKVDKKVEPKSCDKTHTCPPCPAPEAAGGPSVFLF<br>PPKPKDTLMISRTPEVTCVVVDVSHEDPEVKFNWYVDGVE<br>VHNAKTKPREEQYNSTYRVVSVLTVLHQDWLNGKEYKCKV<br>SNKALPAPIEKTISKAKGQPREPQVYTLPPSREEMTKNQV<br>SLTCLVKGFYPSDIAVEWESNGQPENNYKTTPPVLDSDGS<br>FFLYSKLTVDKSRWQQGNVFSCSVMHEALHNHYTQKSLSL<br>SPGK |
| signal sequence | 79 | MDMRVPAQLLGLLLLWFPGSRC |
| VL-CL of mAb HumAb747V-73 (VL underlined) | 176 | <u>DIQMTQSPSSLSASVGDRVTITCRASQEISGYLSWLQQKP</u><br><u>GGAIKRLIYAASTLDSGVPSRFSGSRSGSDYTLTISSLQP</u><br><u>EDFADYYCLQYASYPLTFGQGTKLELK</u>RTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of mAb HumAb709-8 (VH underlined) | 177 | <u>EVQLVESGGGLVQPGGSLRLSCAASGFTFSFYTMSWVRQA</u><br><u>PGKGLEWVATISGGGRDTYYPDSVKGRFTISRDNAKNSLY</u><br><u>LQMNSLRAEDTAVYYCAGQGGNYLFAYWGQGTLVTVSS</u>AS<br>TKGPSVFPLAPSSKSTSGGTAALGCLVKDYFPEPVTVSWN<br>SGALTSGVHTFPAVLQSSGLYSLSSVVTVPSSSLGTQTYI<br>CNVNHKPSNTKVDKKVEPKSC |
| hinge-CH2-CH3 of human IgG1 | 82 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |
| FIT107-1-6b-3 FIT-Ig Polypeptide Chain #2 | 178 | MEFGLSWLFLVAILKGVQCEVQLVQSGAEVKKPGATVKLS<br>CTASGFNIKDDYMHWVKQRPEQGLDWIGWIVPRNANTVY<br>ASKFQGKATITADTSTNTAYLELSSLRSEDTAVYYCTVYG<br>DYWGQGTTVTVSSASTKGPSVFPLAPSSKSTSGGTAALGC<br>LVKDYFPEPVTVSWNSGALTSGVHTFPAVLQSSGLYSLSS<br>VVTVPSSSLGTQTYICNVNHKPSNTKVDKKVEPKSC |
| signal sequence | 84 | MEFGLSWLFLVAILKGVQC |
| VH-CH1 of HumAb747V-73 (VH underlined) | 179 | <u>EVQLVQSGAEVKKPGATVKLSCTASGFNIKDDYMHWVKQR</u><br><u>PEQGLDWIGWIVPRNANTVYASKFQGKATITADTSTNTAY</u><br><u>LELSSLRSEDTAVYYCTVYGDYWGQGTTVTVSS</u>ASTKGPS<br>VFPLAPSSKSTSGGTAALGCLVKDYFPEPVTVSWNSGALT<br>SGVHTFPAVLQSSGLYSLSSVVTVPSSSLGTQTYICNVNH<br>KPSNTKVDKKVEPKSC |
| FIT107-1-6b-3 FIT-Ig Polypeptide Chain #3 | 180 | MDMRVPAQLLGLLLLWFPGSRCDIVMTQSPSSLSASVGDR<br>VTITCKASQDVNTVVAWYQQKPGKAPKVLISWASTRHTGV<br>PSRFSGSGSGTDYTLTISSLQPEDFATYYCQQHYTTPYTF<br>GGGTKVEIKRTVAAPSVFIFPPSDEQLKSGTASVVCLLNN |

TABLE 46-continued

Amino Acid Sequences of FIT107-1-6b-3 Component Chains

| Polypeptide | SEQ ID NO: | Amino Acid Sequence<br>123456789012345678901234567890 |
|---|---|---|
| | | FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of HumAb709-8 (VL underlined) | 181 | DIVMTQSPSSLSASVGDRVTITCKASQDVNTVVAWYQQKP<br>GKAPKVLISWASTRHTGVPSRFSGSGSGTDYTLTISSLQP<br>EDFATYYCQQHYTTPYTFGGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 15.7: Production of PD-1/LAG-3 FIT-Ig Binding Protein FIT107-1-7a 1

A PD-1/LAG-3 FIT-Ig designated FIT107-1-7a-1 was constructed utilizing coding sequences for immunoglobulin domains from the parental antibodies HumAb713-7 (humanized anti-PD-1; see Tables 9 and 10, supra) and HumAb747V-67 (humanized anti-LAG-3). FIT-Ig FIT107-1-7a-1 is a hexamer comprised of three component polypeptide chains:

Polypeptide chain #1 has the domain formula: VL-CL of HumAb713-7 fused directly to VH-CH1 of HumAb747V-67 fused directly to hinge-CH2-CH3 of a mutant human constant IgG1;
Polypeptide chain #2 has the domain formula: VH-CH1 of HumAb713-7; and
Polypeptide chain #3 has the domain formula: light chain (VL-CL) of HumAb747V-67.
The amino acid sequences for the three expressed FIT107-1-7a-1 polypeptide chains are shown in Table 47 below.

TABLE 47

Amino Acid Sequences of FIT107-1-7a-1 Component Chains

| Polypeptide | SEQ ID NO: | Amino Acid Sequence<br>123456789012345678901234567890 |
|---|---|---|
| FIT107-1-7a-1 FIT-Ig Polypeptide Chain #1 | 182 | MDMRVPAQLLGLLLLWFPGSRCDIQMTQSPSSLSASVGDR<br>VTITCKASDHINNWLAWYQQKPGKAPKLLIYGATSLETGV<br>PSRFSGSGSGTDYTFTISSLQPEDIATYYCQQYWSPPYTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VQSGAEVKKPGATVKLSCTASGFNIKDDYMHWVKQRPEQG<br>LDWIGWIVPENANTVYASKFQGKATITADTSTNTAYLELS<br>SLRSEDTAVYYCTVYGDYWGQGTTVTVSSASTKGPSVFPL<br>APSSKSTSGGTAALGCLVKDYFPEPVTVSWNSGALTSGVH<br>TFPAVLQSSGLYSLSSVVTVPSSSLGTQTYICNVNHKPSN<br>TKVDKKVEPKSCDKTHTCPPCPAPEAAGGPSVFLFPPKPK<br>DTLMISRTPEVTCVVVDVSHEDPEVKFNWYVDGVEVHNAK<br>TKPREEQYNSTYRVVSVLTVLHQDWLNGKEYKCKVSNKAL<br>PAPIEKTISKAKGQPREPQVYTLPPSREEMTKNQVSLTCL<br>VKGFYPSDIAVEWESNGQPENNYKTTPPVLDSDGSFFLYS<br>KLTVDKSRWQQGNVFSCSVMHEALHNHYTQKSLSLSPGK |
| signal sequence | 79 | MDMRVPAQLLGLLLLWFPGSRC |
| VL-CL of mAb HumAb713-7 (VL underlined) | 183 | DIQMTQSPSSLSASVGDRVTITCKASDHINNWLAWYQQKP<br>GKAPKLLIYGATSLETGVPSRFSGSGSGTDYTFTISSLQP<br>EDIATYYCQQYWSPPYTFGGGTKVEIKRTVAAPSVFIFPP<br>SDEQLKSGTASVVCLLNKFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of mAb HumAb747V-67 (VH underlined) | 184 | EVQLVQSGAEVKKPGATVKLSCTASGFNIKDDYMHWVKQR<br>PEQGLDWIGWIVPENANTVYASKFQGKATITADTSTNTAY<br>LELSSLRSEDTAVYYCTVYGDYWGQGTTVTVSSASTKGPS<br>VFPLAPSSKSTSGGTAALGCLVKDYFPEPVTVSWNSGALT<br>SGVHTFPAVLQSSGLYSLSSVVTVPSSSLGTQTYICNVNH<br>KPSNTKVDKKVEPKSC |
| hinge-CH2-CH3 of human IgG1 | 82 | DKTHTCPPCPAPEAAGGPSVFLFPPKFKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |

TABLE 47-continued

Amino Acid Sequences of FIT107-1-7a-1 Component Chains

| Polypeptide | SEQ ID NO: | Amino Acid Sequence<br>1234567890123456789012345678901234567890 |
|---|---|---|
| FIT107-1-7a-1<br>FIT-Ig Polypeptide<br>Chain #2 | 185 | MEFGLSWLFLVAILKGVQCEVQLVESGGGLVQPGGSLRLS<br>CAASGFTSSDYGMHWVRQAPGKGLEWVSYISSGSYTIYY<br>ADTVKGRFTISRDNAKNSLYLQMNSLRDEDTAVYYCAKRG<br>GSSHVNVMDYWGQGTTVTVSSASTKGPSVFPLAPSSKSTS<br>GGTAALGCLVKDYFPEPVTVSWNSGALTSGVHTFPAVLQS<br>SGLYSLSSVVTVPSSSLGTQTYICNVNHKPSNTKVDKKVE<br>PKSC |
| signal sequence | 84 | MEFGLSWLFLVAILKGVQC |
| VH-CH1 of<br>HumAb713-7<br>(VH underlined) | 186 | <u>EVQLVESGGGLVQPGGSLRLSCAASGFTSSDYGMHWVRQA</u><br><u>PGKGLEWVSYISSGSYTIYYADTVKGRFTISRDNAKNSLY</u><br><u>LQMNSLRDEDTAVYYCAKRGGSSHVNVMDYWGQGTTVTVS</u><br>SASTKGPSVFPLAPSSKSTSGGTAALGCLVKDYFPEPVTV<br>SWNSGALTSGVHTFPAVLQSSGLYSLSSVVTVPSSSLGTQ<br>TYICNVNHKPSNTKVDKKVEPKSC |
| FIT107-1-7a-1<br>FIT-Ig Polypeptide<br>Chain #3 | 187 | MDMRVPAQLLGLLLLWFPGSRCDIQMTQSPSSLSASVGDR<br>VTITCRASQEISGYLSWLQQKPGGAIKRLIYAASALDSGV<br>PSRFSGSRSGSDYTLTISSLQPEDFADYYCLQYASYPLTF<br>GQGTKLELKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL Of<br>HumAb747V-67<br>(VL underlined) | 188 | <u>DIQMTQSPSSLSASVGDRVTITCRASQEISGYLSWLQQKP</u><br><u>GGAIKRLIYAASALDSGVPSRFSGSRSGSDYTLTISSLQP</u><br><u>EDFADYYCLQYASYPLTF</u>GQGTKLELKRTVAAPSVFIFFP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 15.8: Production of PD-1/LAG-3 FIT-Ig Binding Protein FIT107-1-7b-1

A PD-1/LAG-3 FIT-Ig designated FIT107-1-7b-1 was constructed utilizing coding sequences for immunoglobulin domains from the parental antibodies HumAb713-7 (humanized anti-PD-1) and HumAb747V-67 (humanized anti-LAG-3). FIT-Ig FIT107-1-7b-1 is a hexamer comprised of three component polypeptide chains:

Polypeptide chain #1 has the domain formula: VL-CL of HumAb747V-67 fused directly to VH-CH1 of HumAb713-7 fused directly to hinge-CH2-CH3 of a mutant human constant IgG1;
Polypeptide chain #2 has the domain formula: VH-CH1 of HumAb747V-67; and
Polypeptide chain #3 has tire domain formula: light chain (VL-CL) of HumAb713-7.
The amino acid sequences for the three expressed FIT107-1-7b–1 polypeptide chains are shown in Table 48 below.

TABLE 48

Amino Acid Sequences of FIT107-1-7b-1 Component Chains

| Polypeptide | SEQ ID NO: | Amino Acid Sequence<br>1234567890123456789012345678901239567890 |
|---|---|---|
| FIT107-1-7b-1<br>FIT-Ig Polypeptide<br>Chain #1 | 189 | MDMRVPAQLLGLLLLWFPGSRCDIQMTQSPSSLSASVGDR<br>VTITCRASQEISGYLSWLQQKPGGAIKRLIYAASALDSGV<br>PSRFSGSRSGSDYTLTISSLQPEDFADYYCLQYASYPLTF<br>GQGTKLELKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VESGGGLVQPGGSLRLSCAASGFTSSDYGMHWVRQAPGKG<br>LEWVSYISSGSYTIYYADTVKGRFTISRDNAKNSLYLQMN<br>SLRDEDTAVYYCAKRGGSSHVNVMDYWGQGTTVTVSSAST<br>KGPSVFPLAPSSKSTSGGTAALGCLVKDYFPEPVTVSWNS<br>GALTSGVHTFPAVLQSSGLYSLSSVVTVPSSSLGTQTYIC<br>NVNHKPSNTKVDKKVEPKSCDKTHTCPPCPAPEAAGGPSV<br>FLFPPKPKDTLMISRTPEVTCVVVDVSHEDPEVKFNWYVD<br>GVEVHNAKTKPREEQYNSTYRVVSVLTVLHQDWLNGKEYK<br>CKVSNKALPAPIEKTISKAKGQPREPQVYTLPPSREEMTK<br>NQVSLTCLVKGFYPSDIAVEWESNGQPENNYKTTPPVLDS<br>DGSFFLYSKLTVDKSRWQQGNVFSCSVMHEALHNKYTQKS<br>LSLSPGK |

TABLE 48-continued

Amino Acid Sequences of FIT107-1-7b-1 Component Chains

| Polypeptide | SEQ ID NO: | Amino Acid Sequence<br>12345678901234567890123456789012395678 90 |
|---|---|---|
| signal sequence | 79 | MDMRVPAQLLGLLLLWFPGSRC |
| VL-CL of mAb HumAb747V-67 (VL underlined) | 190 | <u>DIQMTQSPSSLSASVGDRVTITCRASQEISGYLSWLQQKP GGAIKRLIYAASALDSGVPSRFSGSRSGSDYTLTISSLQP EDFADYYCLQYASYPLTFGQGTKLELK</u>RTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| VH-CH1 of mAb HumAb713-7 (VH underlined) | 191 | <u>EVQLVESGGGLVQPGGSLRLSCAASGFTSSDYGMHWVRQA PGKGLEWVSYISSGSYTIYYADTVKGRFTISRDNAKNSLY LQMNSLRDEDTAVYYCAKRGGSSHVNVMDYWGQGTTVTVS S</u>ASTKGPSVFPLAPSSKSTSGGTAALGCLVKDYFPEPVTV SWNSGALTSGVHTFPAVLQSSGLYSLSSVVTVPSSSLGTQ TYICNVNHKPSNTKVDKKVEPKSC |
| hinge-CH2-CH3 of human IgG1 | 82 | DKTHTCPPCPAPEAAGGPSVFLFPPKPKDTLMISRTPEVT CVVVDVSHEDPEVKFNWYVDGVEVHNAKTKPREEQYNSTY RVVSVLTVLHQDWLNGKEYKCKVSNKALPAPIEKTISKAK GQPREPQVYTLPPSREEMTKNQVSLTCLVKGFYPSDIAVE WESNGQPENNYKTTPPVLDSDGSFFLYSKLTVDKSRWQQG NVFSCSVMHEALHNHYTQKSLSLSPGK |
| FIT107-1-7b-1 FIT-Ig Polypeptide Chain #2 | 192 | <u>MEFGLSWLFLVAILKGVQC</u>EVQLVQSGAEVKKPGATVKLS CTASGFNIKDDYMHWVKQRPEQGLDWIGWIVPENANTVY ASKFQGKATITADTSTNTAYLELSSLRSEDTAVYYCTVYG DYWGQGTTVTVSSASTKGPSVFPLAPSSKSTSGGTAALGC LVKDYFPEPVTVSWNSGALTSGVHTFPAVLQSSGLYSLSS VVTVPSSSLGTQTYICNVNHKPSNTKVDKKVEPKSC |
| signal sequence | 84 | MEFGLSWLFLVAILKGVQC |
| VH-CH1 of HumAb747V-67 (VH underlined) | 193 | <u>EVQLVQSGAEVKKPGATVKLSCTASGFNIKDDYMHWVKQR PEQGLDWIGWIVPENANTVYASKFQGKATITADTSTNTAY LELSSLRSEDTAVYYCTVYGDYWGQGTTVTVSS</u>ASTKGPS VFPLAPSSKSTSGGTAALGCLVKDYFPEPVTVSWNSGALT SGVHTFPAVLQSSGLYSLSSVVTVPSSSLGTQTYICNVNH KPSNTKVDKKVEPKSC |
| FIT107-1-7b-1 FIT-Ig Polypeptide Chain #3 | 194 | <u>MDMRVPAQLLGLLLLWFPGSRC</u>DIQMTQSPSSLSASVGDR VTITCKASDHINNWLAWYQQKPGKAPKLLIYGATSLETGV PSRFSGSGSGTDYTFTISSLQPEDIATYYCQQYWSPPYTF GGGTKVEIKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGEC |
| signal sequence | 79 | MDMRVPAQLLGLLLLWFPGSRC |
| VL-CL of HumAb713-7 (VL underlined) | 195 | <u>DIQMTQSPSSLSASVGDRVTITCKASDHINNWLAWYQQKP GKAPKLLIYGATSLETGVPSRFSGSGSGTDYTFTISSLQP EDIATYYCQQYWSPPYTFGGGTKVEIK</u>RTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |

Example 15.9: Production of PD-1/LAG-3 FIT-Ig Binding Protein FIT107-1-7a-2

A PD-1/LAG-3 FIT-Ig designated FIT107-1-7a-2 was constructed utilizing coding sequences for immunoglobulin domains from the parental antibodies HumAb713-7 (humanized anti-PD-1) and HumAb747V-72 (humanized anti-LAG-3). FIT-Ig FIT107-1-7a-2 is a hexamer comprised of three component polypeptide chains:

Polypeptide chain #1 has the domain formula: VL-CL of HumAb713-7 fused directly to VH-CH1 of HumAb747V-72 fused directly to hinge-CH2-CH3 of a mutant human constant IgG1 (see Table 6, supra).
Polypeptide chain #2 has the domain formula: VH-CH1 of HumAb713-7; and
Polypeptide chain #3 has the domain formula: light chain (VL-CL) of HumAb747V-72.
The amino acid sequences for the three expressed FIT107-1-7a-2 polypeptide chains are shown in Table 49 below.

TABLE 49

| Amino Acid Sequences of FIT107-1-7a-2 Component Chains | | |
|---|---|---|
| Polypeptide | SEQ ID NO: | Amino Acid Sequence 1234567890123456789012345678901234567890 |
| FIT107-1-7a-2 FIT-Ig Polypeptide Chain #1 | 196 | MDMRVPAQLLGLLLLWFPGSRCDIQMTQSPSSLSASVGDR VTITCKASDHINNWLAWYQQKPGKAPKLLIYGATSLETGV PSRFSGSGSGTDYTFTISSLQPEDIATYYCQQYWSPPYTF GGGTKVEIKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGECEVQL VQSGAEVKKPGATVKLSCTASGFNIKDDYMHWVKQRPEQG LDWIGWIVPRNANTVYASKFQGKATITADTSTNTAYLELS SLRSEDTAVYYCTVYGDYWGQGTTVTVSSASTKGPSVFPL APSSKSTSGGTAALGCLVKDYFPEPVTVSWNSGALTSGVH TFPAVLQSSGLYSLSSVVTVPSSSLGTQTYICNVNHKPSN TKVDKKVEPKSCDKTHTCPPCPAFEAAGGPSVFLFPPKPK DTLMISRTPEVTCVVVDVSHEDPEVKFNWYVDGVEVKNAK TKPREEQYNSTYRVVSVLTVLHQDWLNGKEYKCKVSNKAL PAPIEKTISKAKGQPREPQVYTLPPSREEMTKNQVSLTCL VKGFYPSDIAVEWESNGQPENNYKTTPPVLDSDGSFFLYS KLTVDKSRWQQGNVFSCSVMHEALHNHYTQKSLSLSPGK |
| signal sequence | 79 | MDMRVPAQLLGLLLLWFPGSRC |
| VL-CL of mAb HumAb713-7 (VL underlined) | 197 | <u>DIQMTQSPSSLSASVGDRVTITCKASDHINNWLAWYQQKP GKAPKLLIYGATSLETGVPSRFSGSGSGTDYTFTISSLQP EDIATYYCQQYWSPPYTFGGGTKVEIKR</u>TVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| VH-CH1 of mAb HumAb747V-72 (VH underlined) | 198 | <u>EVQLVQSGAEVKKPGATVKLSCTASGFNIKDDYMHWVKQR PEQGLDWIGWIVPRNANTVYASKFQGKATITADTSTNTAY LELSSLRSEDTAVYYCTVYGDYWGQGTTVTVSS</u>ASTKGPS VFPLAPSSKSTSGGTAALGCLVKDYFPEPVTVSWNSGALT SGVHTFPAVLQSSGLYSLSSVVTVPSSSLGTQTYICNVNH KPSNTKVDKKVEPKSC |
| hinge-CH2-CH3 of human IgG1 | 82 | DKTHTCPPCPAPEAAGGPSVFLFPPKPKDTLMISRTPEVT CVVVDVSHEDPEVKFNWYVDGVEVHNAKTKPREEQYNSTY RVVSVLTVLHQDWLNGKEYKCKVSNKALPAPIEKTISKAK GQPREPQVYTLPPSREEMTKNQVSLTCLVKGFYPSDIAVE WESNGQPENNYKTTPPVLDSDGSFFLYSKLTVDKSRWQQG NVFSCSVMHEALHNHYTQKSLSLSPGK |
| FIT107-1-7a-2 FIT-Ig Polypeptide Chain #2 | 199 | MEFGLSWLFLVAILKGVQCEVQLVESGGGLVQPGGSLRLS CAASGFTSSDYGMHWVRQAPGKGLEWVSYISSGSYTIYYA DTVKGRFTISRDNAKNSLYLQMNSLRDEDTAVYYCAKRGG SSHVNVMDYWGQGTTVTVSSASTKGPSVFPLAPSSKSTSG GTAALGCLVKDYFPEPVTVSWNSGALTSGVHTFPAVLQSS GLYSLSSVVTVPSSSLGTQTYICNVNHKPSNTKVDKKVEP KSC |
| signal sequence | 84 | MEFGLSWLFLVAILKGVQC |
| VH-CH1 of HumAb713-7 (VH underlined) | 200 | <u>EVQLVESGGGLVQPGGSLRLSCAASGFTSSDYGMHWVRQA PGKGLEWVSYISSGSYTIYYADTVKGRFTISRDNAKNSLY LQMNSLRDEDTAVYYCAKRGGSSHVNVMDYWGQGTTVTVS</u> SASTKGPSVFPLAPSSKSTSGGTAALGCLVKDYFPEPVTV SWNSGALTSGVHTFPAVLQSSGLYSLSSVVTVPSSSLGTQ TYICNVNHKPSNTKVDKKVEPKSC |
| FIT107-1-7a-2 FIT-Ig Polypeptide Chain #3 | 201 | MDMRVPAQLLGLLLLWFPGSRCDIQMTQSPSSLSASVGDR VTITCRASQEISGYLSWLQQKPGGAIKRLIYAASALDLGV PSRFSGSRSGSDYTLTISSLQPEDFADYYCLQYASYPLTF GQGTKLELKRTVAAPSVFIFPPSDEQLKSGTASVVCLLNN |

TABLE 49-continued

Amino Acid Sequences of FIT107-1-7a-2 Component Chains

| Polypeptide | SEQ ID NO: | Amino Acid Sequence<br>12345678901234567890123456789012345 67890 |
|---|---|---|
| | | FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of<br>HumAb747V-72<br>(VL underlined) | 202 | DIQMTQSPSSLSASVGDRVTITCRASQEISGYLSWLQQKP<br>GGAIKRLIYAASALDLGVPSRFSGSRSGSDYTLTISSLQP<br>EDFADYYCLQYASYPLTFGQGTKLELKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 15.10: Production of PD-1/LAG-3 FIT-Ig Binding Protein FIT107-1-7b-2

A PD-1/LAG-3 FIT-Ig designated FIT107-1-7b-2 was constructed utilizing coding sequences for immunoglobulin domains from the parental antibodies HumAb713-7 (humanized anti-PB-1) and HumAb747V-72 (humanized anti-LAG-3). FIT-Ig FIT107-1-75-2 is a hexamer comprised of three component polypeptide chains:

Polypeptide chain #1 has the domain formula: VL-CL of HumAb747V-72 fused directly to VH-CH1 of HumAb713-7 fused directly to hinge-CH2-CH3 of a mutant human constant IgG1;
Polypeptide chain #2 has the domain formula: VH-CH1 of HumAb747V-72; and
Polypeptide chain #3 has the domain formula; light chain (VL-CL) of HumAb713-7.
The amino acid sequences for the three expressed FIT107-1-7b-2 polypeptide chains are shown in Table 50 below.

TABLE 50

Amino Acid Sequences of FIT107-1-7b-2 Component Chains

| Polypeptide | SEQ ID NO: | Amino Acid Sequence<br>12345678901234567890123456789012345 67890 |
|---|---|---|
| FIT107-1-7b-2<br>FIT-Ig Polypeptide<br>Chain #1 | 203 | MDMRVPAQLLGLLLLWFPGSRCDIQMTQSPSSLSASVGDR<br>VTITCRASQEISGYLSWLQQKPGGAIKRLIYAASALDLGV<br>PSRFSGSRSGSDYTLTISSLQPEDFADYYCLQYASYPLTF<br>GQGTKLELKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VESGGGLVQPGGSLRLSCAASGFTSSDYGMHWVRQAPGKG<br>LEWVSYISSGSYTIYYADTVKGRFTISRDNAKNSLYLQMN<br>SLRDEDTAVYYCAKRGGSSHVNVMDYWGQGTTVTVSSAST<br>KGPSVFPLAPSSKSTSGGTAALGCLVKDYFPEPVTVSWNS<br>GALTSGVHTFPAVLQSSGLYSLSSVVTVPSSSLGTQTYIC<br>NVNHKPSNTKVDKKVEPKSCDKTHTCPPCPAPEAAGGPSV<br>FLFPPKPKDTLMISRTPEVTCVVVDVSHEDPEVKFNWYVD<br>GVEVHNAKTKPREEQYNSTYRVVSVLTVLHQDWLNGKEYK<br>CKVSNKALPAPIEKTISKAKGQPREPQVYTLPPSREEMTK<br>NQVSLTCLVKGFYPSDIAVEWESNGQPENNYKTTPPVLDS<br>DGSFFLYSKLTVDKSRWQQGNVFSCSVMHEALHNHYTQKS<br>LSLSPGK |
| signal sequence | 79 | MDMRVPAQLLGLLLLWFPGSRC |
| VL-CL ofmAb<br>HumAb747V-72<br>(VL underlined) | 204 | DIQMTQSPSSLSASVGDRVTITCRASQEISGYLSWLQQKP<br>GGAIKRLIYAASALDLGVPSRFSGSRSGSDYTLTISSLQP<br>EDFADYYCLQYASYPLTFGQGTKLELKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of mAb<br>HumAb713-7<br>(VH underlined) | 205 | EVQLVESGGGLVQPGGSLRLSCAASGFTSSDYGMHWVRQA<br>PGKGLEWVSYISSGSYTIYYADTVKGRFTISRDNAKNSLY<br>LQMNSLRDEDTAVYYCAKRGGSSHVNVMDYWGQGTTVTVS<br>SASTKGPSVFPLAPSSKSTSGGTAALGCLVKDYFPEPVTV<br>SWNSGALTSGVHTFPAVLQSSGLYSLSSVVTVPSSSLGTQ<br>TYICNVNHKPSNTKVDKKVEPKSC |
| hinge-CH2-CH3<br>of human IgG1 | 82 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |

TABLE 50-continued

Amino Acid Sequences of FIT107-1-7b-2 Component Chains

| Polypeptide | SEQ ID NO: | Amino Acid Sequence<br>12345678901234567890123456789012345678 90 |
|---|---|---|
| FIT107-1-7b-2<br>FIT-Ig Polypeptide<br>Chain #2 | 206 | MEFGLSWLFLVAILKGVQCEVQLVQSGAEVKKPGATVKLS<br>CTASGFNIKDDYMHWVKQRPEQGLDWIGWIVPRNANTVY<br>ASKFQGKATITADTSTNTAYLELSSLRSEDTAVYYCTVYG<br>DYWGQGTTVTVSSASTKGPSVFPLAPSSKSTSGGTAALGC<br>LVKDYFPEPVTVSWNSGALTSGVHTFPAVLQSSGLYSLSS<br>VVTVPSSLGTQTYICNVNHKPSNTKVDKKVEPKSC |
| signal sequence | 84 | MEFGLSWLFLVAILKGVQC |
| VH-CH1 of<br>HumAb747V-72<br>(VH underlined) | 207 | <u>EVQLVQSGAEVKKPGATVKLSCTASGFNIKDDYMHWVKQR</u><br><u>PEQGLDWIGWIVPRNANTVYASKFQGKATITADTSTNTAY</u><br><u>LELSSLRSEDTAVYYCTVYGDYWGQGTTVTVSS</u>ASTKGPS<br>VFPLAPSSKSTSGGTAALGCLVKDYFPEPVTVSWNSGALT<br>SGVHTFPAVLQSSGLYSLSSVVTVPSSLGTQTYICNVNH<br>KPSNTKVDKKVEPKSC |
| FIT107-1-7b-2<br>FIT-Ig Polypeptide<br>Chain #3 | 208 | MDMRVPAQLLGLLLLWFPGSRCDIQMTQSPSSLSASVGDR<br>VTITCKASDHINNWLAWYQQKPGKAPKLLIYGATSLETGV<br>PSRFSGSGSGTDYTFTISSLQPEDIATYYCQQYWSPPYTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of<br>HumAb713-7<br>(VL underlined) | 209 | <u>DIQMTQSPSSLSASVGDRVTITCKASDHINNWLAWYQQKP</u><br><u>GKAPKLLIYGATSLETGVPSRFSGSGSGTDYTFTISSLQP</u><br><u>EDIATYYCQQYWSPPYT</u>FGGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 15.11: Production of PD-1/LAG-3 FIT-Ig Binding Protein FIT107-1-7a-3

A PD-1/LAG-3 FIT-Ig designated FIT107-1-7a-3 was constructed utilizing coding sequences for immunoglobulin domains from the parental antibodies HumAb713-7 (humanized anti-PD-1) and HumAb747V-73 (humanized anti-LAG-3). FIT-Ig FIT107-1-7a-3 is a hexamer comprised of three component polypeptide chains:

Polypeptide chain #1 has the domain formula: VL-CL of HumAb713-7 fused directly to VH-CH1 of HumAb747V-73 fused directly to hinge-CH2-CH3 of a mutant human constant IgG1;
Polypeptide chain #2 has the domain formula: VH-CH1 of HumAb713-7; and
Polypeptide chain #3 has the domain formula: light chain (VL-CL) of HumAb747V-73.

The amino acid sequences for the three expressed FIT107-1-7a-3 polypeptide chains are shown in Table 51 below.

TABLE 51

Amino Acid Sequences of FIT107-1-7a-3 Component Chains

| Polypeptide | SEQ ID NO: | Amino Acid Sequence<br>12345678901234567890123456789012395 67890 |
|---|---|---|
| FIT107-1-7a-3<br>FIT-Ig Polypeptide<br>Chain #1 | 210 | MDMRVPAQLLGLLLLWFPGSRCDIQMTQSPSSLSASVGDR<br>VTITCKASDHINNWLAWYQQKPGKAPKLLIYGATSLETGV<br>PSRFSGSGSGTDYTFTISSLQPEDIATYYCQQYWSPPYTF<br>GGGTKVEIKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VQSGAEVKKPGATVKLSCTASGFNIKDDYMHWVKQRPEQG<br>LDWIGWIVPRNANTVYASKFQGKATITADTSTNTAYLELS<br>SLRSEDTAVYYCTVYGDYWGQGTTVTVSSASTKGPSVFPL<br>APSSKSTSGGTAALGCLVKDYFPEPVTVSWNSGALTSGVH<br>TFPAVLQSSGLYSLSSVVTVPSSLGTQTYICNVNHKPSN<br>TKVDKKVEPKSCDKTHTCPPCPAPEAAGGPSVFLFPPKPK<br>DTLMISRTPEVTCVVVDVSHEDPEVKFNWYVDGVEVHNAK<br>TKPREEQYNSTYRVVSVLTVLHQDWLNGKEYKCKVSNKAL<br>PAPIEKTISKAKGQPREPQVYTLPPSREEMTKNQVSLTCL<br>VKGFYPSDIAVEWESNGQPENNYKTTPPVLDSDGSFFLYS<br>KLTVDKSRWQQGNVFSCSVMHEALHNHYTQKSLSLSPGK |

TABLE 51-continued

Amino Acid Sequences of FIT107-1-7a-3 Component Chains

| Polypeptide | SEQ ID NO: | Amino Acid Sequence<br>123456789012345678901234567890123 9567890 |
|---|---|---|
| signal sequence | 79 | MDMRVPAQLLGLLLLWFPGSRC |
| VL-CL of mAb HumAb713-7 (VL underlined) | 211 | <u>DIQMTQSPSSLSASVGDRVTITCKASDHINNWLAWYQQKP</u><br><u>GKAPKLLIYGATSLETGVPSRFSGSGSGTDYTFTISSLQP</u><br><u>EDIATYYCQQYWSPPYTFGGGTKVEIK</u>RTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of mAb HumAb747V-73 (VH underlined) | 212 | <u>EVQLVQSGAEVKKPGATVKLSCTASGFNIKDDYMHWVKQR</u><br><u>PEQGLDWIGWIVPRNANTVYASKFQGKATITADTSTNTAY</u><br><u>LELSSLRSEDTAVYYCTVYGDYWGQGTTVTVSS</u>ASTKGPS<br>VFPLAPSSKSTSGGTAALGCLVKDYFPEPVTVSWNSGALT<br>SGVHTFPAVLQSSGLYSLSSVVTVPSSSLGTQTYICNVNH<br>KPSNTKVDKKVEPKSC |
| hinge-CH2-CH3 of human IgG1 | 82 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVHEALHNHYTQKSLSLSPGK |
| FIT107-1-7a-3 FIT-Ig Polypeptide Chain #2 | 213 | <u>MEFGLSWLFLVAILKGVQC</u>EVQLVESGGGLVQPGGSLRLS<br>CAASGFTSSDYGMHWVRQAPGKGLEWVSYISSGSYTIYY<br>ADTVKGRFTISRDNAKNSLYLQMNSLRDEDTAVYYCAKRG<br>GSSHVNVMDYWGQGTTVTVSSASTKGPSVFPLAPSSKSTS<br>GGTAALGCLVKDYFPEPVTVSWNSGALTSGVHTFPAVLQS<br>SGLYSLSSVVTVPSSSLGTQTYICNVNHKPSNTKVDKKVE<br>PKSC |
| signal sequence | 84 | MEFGLSWLFLVAILKGVQC |
| VH-CH1 of HumAb713-7 (VH underlined) | 214 | <u>EVQLVESGGGLVQPGGSLRLSCAASGFTSSDYGMHWVRQA</u><br><u>PGKGLEWVSYISSGSYTIYYADTVKGRFTISRDNAKNSLY</u><br><u>LQMNSLRDEDTAVYYCAKRGGSSHVNVMDYWGQGTTVTVS</u><br><u>S</u>ASTKGPSVFPLAPSSKSTSGGTAALGCLVKDYFPEPVTV<br>SWNSGALTSGVHTFPAVLQSSGLYSLSSVVTVPSSSLGTQ<br>TYICNVNHKPSNTKVDKKVEPKSC |
| FIT107-1-7a-3 FIT-Ig Polypeptide Chain #3 | 215 | <u>MDMRVPAQLLGLLLLWFPGSRC</u>DIQMTQSPSSLSASVGDR<br>VTITCRASQEISGYLSWLQQKPGGAIKRLIYAASTLDSGV<br>PSRFSGSRSGSDYTLTISSLQPEDFADYYCLQYASYPLTF<br>GQGTKLELKRTVAAPSVFIFPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of HumAb747V-73 (VL underlined) | 216 | <u>DIQMTQSPSSLSASVGDRVTITCRASQEISGYLSWLQQKP</u><br><u>GGAIKRLIYAASTLDSGVPSRFSGSRSGSDYTLTISSLQP</u><br><u>EDFADYYCLQYASYPLTFGQGTKLELK</u>RTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 15.12: Production of PD-1/LAG-3 FIT-Ig Binding Protein FIT107-1-7b-3

A PD-1/LAG-3 FIT-Ig designated FIT107-1-7b-3 was constructed utilizing coding sequences for immunoglobulin domains from the parental antibodies HumAb713-7 (humanized anti-PD-1) and HumAb747V-73 (humanized anti-LAG-3). FIT-Ig FIT107-1-7b-3 is a hexamer comprised of three component polypeptide chains:

Polypeptide chain #1 has the domain formula: VL-CL of HumAb747V-73 fused directly to VH-CH 1 of HumAb713-7 fused directly to hinge-CH2-CH3 of a mutant human constant IgG1;
Polypeptide chain #2 has the domain formula: VH-CH1 of HumAb747V-73; and
Polypeptide chain #3 has the domain formula: light chain (VL-CL) of HumAb713-7.

The amino acid sequences for the three expressed FIT107-1-7b-3 polypeptide chains are shown in Table 52 below.

TABLE 52

| Amino Acid Sequences of FIT107-1-7b-3 Component Chains | | |
|---|---|---|
| Polypeptide | SEQ ID NO: | Amino Acid Sequence<br>1234567890123456789012345678901234567890 |
| FIT107-1-7b-3 FIT-Ig Polypeptide Chain #1 | 217 | MDMRVPAQLLGLLLLWFPGSRCDIQMTQSPSSLSASVGDR<br>VTITCRASQEISGYLSWLQQKPGGAIKRLIYAASTLDSGV<br>PSRFSGSRSGSDYTLTISSLQPEDFADYYCLQYASYPLTF<br>GQGTKLELKRTVAAPSVFIPPPSDEQLKSGTASVVCLLNN<br>FYPREAKVQWKVDNALQSGNSQESVTEQDSKDSTYSLSST<br>LTLSKADYEKHKVYACEVTHQGLSSPVTKSFNRGECEVQL<br>VESGGGLVQPGGSLRLSCAASGFTSSDYGMHWVRQAPGKG<br>LEWVSYISSGSYTIYYADTVKGRFTISRDNAKNSLYLQMN<br>SLKDEDTAVYYCAKRGGSSHVNVMDYWGQGTTVTVSSAST<br>KGPSVFPLAPSSKSTSGGTAALGCLVKDYFPEPVTVSWNS<br>GALTSGVHTFPAVLQSSGLYSLSSVVTVPSSSLGTQTYIC<br>NVNHKPSNTKVDKKVEPKSCDKTHTCPPCPAPEAAGGPSV<br>FLFPPKPKDTLMISRTPEVTCVVVDVSHEDPEVKFNWYVD<br>GVEVHNAKTKPREEQYNSTYRVVSVLTVLHQDKLNGKEYK<br>CKVSNKALPAPIEKTISKAKGQPREPQVYTLPPSREEMTK<br>NQVSLTCLVKGFYPSDIAVEWESNGQPENSYKTTPPVLDS<br>DGSFFLYSKLTVDKSRWQQGNVFSCSVMHEALHNKYTQKS<br>LSLSPGK |
| signal sequence | 79 | MDMRVPAQLLGLLLLWFPGSRC |
| VL-CL of mAb HumAb747V-73 (VL underlined) | 218 | <u>DIQMTQSPSSLSASVGDRVTITCRASQEISGYLSWLQQKP</u><br><u>GGAIKRLIYAASTLDSGVPSRFSGSRSGSDYTLTISSLQP</u><br><u>EDFADYYCLQYASYPLTFGQGTKLELK</u>RTVAAPSVFIPPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| VH-CH1 of mAb HumAb713-7 (VH underlined) | 219 | <u>EVQLVESGGGLVQPGGSLRLSCAASGFTSSDYGMHWVRQA</u><br><u>PGKGLEWVSYISSGSYTIYYADTVKGRFTISRDNAKNSLY</u><br><u>LQMNSLRDEDTAVYYCAKRGGSSHVNVMDYWGQGTTVTVS</u><br><u>S</u>ASTKGPSVFPLAPSSKSTSGGTAALGCLVKDYFPEPVTV<br>SWNSGALTSGVHTFPAVLQSSGLYSLSSVVTVPSSSLGTQ<br>TYICNVNHKPSNTKVDKKVEPKSC |
| hinge-CH2-CH3 of human IgG1 | 82 | DKTHTCPPCPAPEAAGGPSVFLFPPKPKDTLMISRTPEVT<br>CVVVDVSHEDPEVKFNWYVDGVEVHNAKTKPREEQYNSTY<br>RVVSVLTVLHQDWLNGKEYKCKVSNKALPAPIEKTISKAK<br>GQPREPQVYTLPPSREEMTKNQVSLTCLVKGFYPSDIAVE<br>WESNGQPENNYKTTPPVLDSDGSFFLYSKLTVDKSRWQQG<br>NVFSCSVMHEALHNHYTQKSLSLSPGK |
| FIT107-1-7b-3 FIT-Ig Polypeptide Chain #2 | 220 | MEFGLSWLFLVAILKGVQCEVQLVQSGAEVKKPGATVKLS<br>CTASGFNIKDDYMHWVKQRPEQGLDWIGWIVPRNANTVY<br>ASKFQGKATITADTSTNTAYLELSSLRSEDTAVYYCTVYG<br>DYWGQGTTVTVSSASTKGPSVFPLAPSSKSTSGGTAALGC<br>LVKDYFPEPVTVSWNSGALTSGVHTFPAVLQSSGLYSLSS<br>VVTVPSSSLGTQTYICNVNHKPSNTKVDKKVEPKSC |
| signal sequence | 84 | MEFGLSWLFLVAILKGVQC |
| VH-CH1 of HumAb747V-73 (VH underlined) | 221 | <u>EVQLVQSGAEVKKPGATVKLSCTASGFNIKDDYMHWVKQR</u><br><u>PEQGLDWIGWIVPRNANTVYASKFQGKATITADTSTNTAY</u><br><u>LELSSLRSEDTAVYYCTVYGDYWGQGTTVTVSS</u>ASTKGPS<br>VFPLAPSSKSTSGGTAALGCLVKDYFPEPVTVSWNSGALT<br>SGVHTFPAVLQSSGLYSLSSVVTVPSSSLGTQTYICNVNH<br>KPSNTKVDKKVEPKSC |
| FIT107-1-7b-3 FIT-Ig Polypeptide Chain #3 | 222 | MDMRVPAQLLGLLLLWFPGSRCDIQMTQSPSSLSASVGDR<br>VTITCKASDHINNWLAWYQQKPGKAPKLLIYGATSLETGV<br>PSRFSGSGSGTDYTFTISSLQPEDIATYYCQQYWSPPYTF<br>GGGTKVEIKRTVAAPSVFIPPPSDEQLKSGTASVVCLLNN |

TABLE 52-continued

Amino Acid Sequences of FIT107-1-7b-3 Component Chains

| Polypeptide | SEQ ID NO: | Amino Acid Sequence<br>12345678901234567890123456789012345677890 |
|---|---|---|
| | | FYPREAKVQWKVDNALQSGNSQESVTEQDSKDSTYSLSST<br>LTLSKADYEKHKVYACEVTHQGLSSPVTKSFNRGEC |
| signal sequence | 79 | MDMRVPAQLLGLLLLWFPGSRC |
| VL-CL of<br>HumAb713-7<br>(VL underlined) | 223 | DIQMTQSPSSLSASVGDRVTITCKASDHINNWLAWYQQKP<br>GKAPKLLIYGATSLETGVPSRFSGSGSGTDYTFTISSLQP<br>EDIATYYCQQYWSPPYTFGGGTKVEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |

Example 16: Characterization of New FIT-Ig Proteins

Example 16.1: Expression and SEC Analysis

The 12 FIT-Ig binding proteins described above (Tables 41-52) were expressed in the same manner as described in Example 10.5, supra, and purified by Protein A chromatography. The composition and purity of the purified FIT-Igs were analyzed by size exclusion chromatography (SEC). Purified FIT-Ig, in PBS, was applied on a TSKgel SuperSW3000, 300×4.6 mm column (TOSOH). A DIONEX™ UltiMate 3000 HPLC instrument (Thermo Scientific) was used for SEC using UV detection at 280 nm and 214 nm See Table 53, below.

TABLE 53

Expression and SEC Analysis of PD-1/LAG-3 FIT-Ig Binding Proteins

| FIT-Ig protein | DNA molar ratio: Chain #1: #2: #3 | Expression level (mg/L) | % Peak Monomeric Fraction by SEC |
|---|---|---|---|
| FIT107-1-6a-1 | 1:2:1.5 | 6.21 | 78.9% |
| FIT107-1-6b-1 | 1:2:1.5 | 8.58 | 55.4% |
| FIT107-1-6a-2 | 1:2:1.5 | 6.11 | 90.9% |
| FIT107-1-6b-2 | 1:2:1.5 | 15.86 | 43.2% |
| FIT107-1-6a-3 | 1:2:1.5 | 11.37 | 43.0% |
| FIT107-1-6b-3 | 1:2:1.5 | 17.22 | 11.0% |
| FIT107-1-7a-1 | 1:2:1.5 | 14.47 | 80.0% |
| FIT107-1-7b-1 | 1:2:1.5 | 17.96 | 94.8% |
| FIT107-1-7a-2 | 1:2:1.5 | 19.25 | 88.3% |
| FIT107-1-7b-2 | 1:2:1.5 | 22.12 | 98.5% |
| FIT107-1-7a-3 | 1:2:1.5 | 14.31 | 80.9% |
| FIT107-1-7b-3 | 1:2:1.5 | 29.20 | 98.7% |

The FIT-Ig proteins that had lower monomeric fraction contents (<80%) were excluded in further characterization.

Example 16.2: Functional Assays

Figure 11:
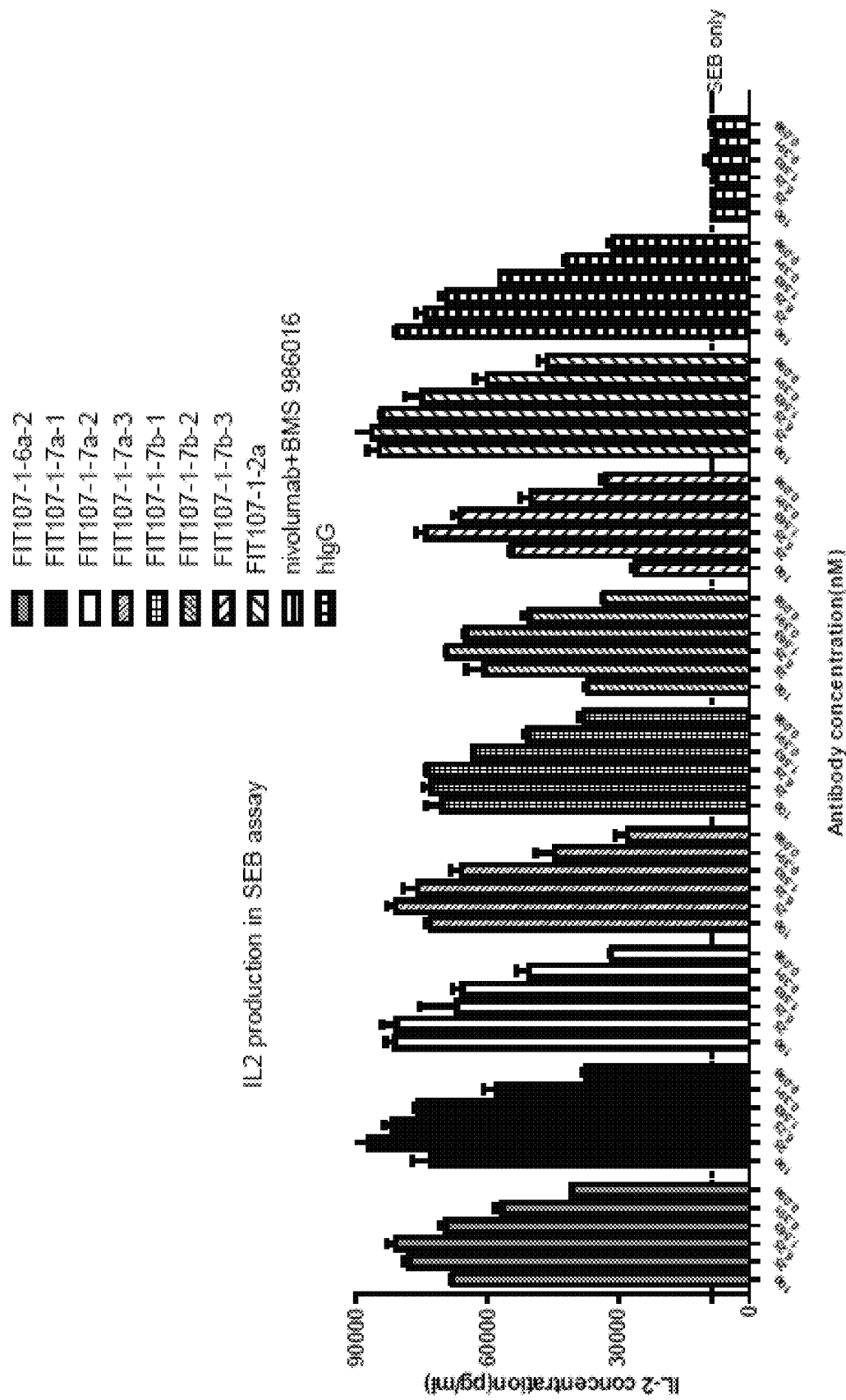
FIG. 11 is a bar graph showing IL-2 production in a SEB T cell activation assay comparing the reversal of T cell suppression effect at various concentrations of a FIT-Ig binding protein specific for both LAG-3 and PD-1 targets. See, Example 16.2. The functionality of PD-1/LAG-3 FIT-Ig bispecific antibodies of the invention is compared against a combination of recombinant anti-PD-1 and anti-LAG-3 monoclonal antibodies prepared from published sequences ("nivolumab+BMS 986016") and a human antibody directed against an irrelevant antigen ("hIgG", control).

The PD-1/LAG-3 FIT-Ig activity was tested in a PBMC activation assay using Staphylococcal enterotoxin B (SEB) as a superantigen as described in Example 12. Results are shown in FIG. 11. The results showed that all the tested FIT-Ig variants can enhance IL-2 secretion from SEB-stimulated PBMC. The enhancement was somehow reversed in the highest doses of FIT107-1-7b-2 and FIT107-1-7b-3, therefore these two FIT-Ig proteins were not prioritized as lead molecules.

Example 16.3: Binding Activity

The kinetics of FIT-Ig binding to PD-1 and LAG-3 targets was determined by biolayer interferometry using the Octet® RED96 system (Pall ForteBio LLC). Binding affinities for both target antigens PD-1 and LAG-3 are shown in Table 54, below. All FIT-Ig proteins retained affinity for both huPD-1 and huLAG-3, All the FIT-Ig proteins that were tested against cynomolgus antigens also showed cross-reactivity with cynomolgus antigens.

TABLE 54

Binding Affinities for PD-1/LAG-3 FIT-Ig Binding Proteins

| FIT-Ig captured on sensor chip | Analyte | $k_{on}$ (1/Ms) | $k_{off}$ (1/s) | $K_D$ (M) |
|---|---|---|---|---|
| FIT107-1-7b-1 | Human PD-1-His | $8.96 \times 10^4$ | $9.35 \times 10^{-4}$ | $1.04 \times 10^{-8}$ |
| | Cyno PD-1-his | $2.15 \times 10^5$ | $7.75 \times 10^{-4}$ | $3.61 \times 10^{-9}$ |
| | Human LAG-3-His | $2.00 \times 10^5$ | $2.43 \times 10^{-4}$ | $1.22 \times 10^{-9}$ |
| | Cyno LAG-3-His | $5.19 \times 10^5$ | $6.36 \times 10^{-5}$ | $1.23 \times 10^{-10}$ |
| FIT107-1-7b-3 | Human PD-1-His | $1.16 \times 10^5$ | $1.03 \times 10^{-3}$ | $8.86 \times 10^{-9}$ |
| | Cyno PD-1-His | $2.48 \times 10^5$ | $9.19 \times 10^{-4}$ | $3.71 \times 10^{-9}$ |
| | Human LAG-3-His | $1.44 \times 10^5$ | $3.28 \times 10^{-4}$ | $2.28 \times 10^{-9}$ |
| | Cyno LAG-3-His | $2.81 \times 10^5$ | $4.70 \times 10^{-5}$ | $1.67 \times 10^{-10}$ |
| FIT107-1-6a-2 | Human PD-1-His | $1.87 \times 10^5$ | $2.39 \times 10^{-4}$ | $1.28 \times 10^{-9}$ |
| | Cyno PD-1-His | $3.06 \times 10^5$ | $1.07 \times 10^{-3}$ | $3.49 \times 10^{-9}$ |
| | Human LAG-3-His | $1.15 \times 10^5$ | $1.17 \times 10^{-4}$ | $1.02 \times 10^{-9}$ |
| | Cyno LAG-3-His | $1.91 \times 10^5$ | $8.17 \times 10^{-5}$ | $4.28 \times 10^{-10}$ |
| FIT107-1-7a-1 | Human PD-1-His | $1.77 \times 10^5$ | $5.38 \times 10^{-4}$ | $3.04 \times 10^{-9}$ |
| | Human LAG-3-His | $1.69 \times 10^5$ | $1.24 \times 10^{-4}$ | $7.32 \times 10^{-10}$ |
| FIT107-1-7a-2 | Human PD-1-His | $1.66 \times 10^5$ | $5.26 \times 10^{-4}$ | $3.17 \times 10^{-9}$ |
| | Human LAG-3-His | $1.05 \times 10^5$ | $1.28 \times 10^{-4}$ | $1.22 \times 10^{-9}$ |
| FIT107-1-7a-3 | Human PD-1-His | $2.08 \times 10^5$ | $6.28 \times 10^{-4}$ | $3.01 \times 10^{-9}$ |
| | Human LAG-3-His | $9.10 \times 10^4$ | $1.34 \times 10^{-4}$ | $1.47 \times 10^{-9}$ |
| FIT107-1-7b-2 | Human PD-1-His | $1.05 \times 10^5$ | $8.27 \times 10^{-4}$ | $7.90 \times 10^{-9}$ |
| | Human LAG-3-His | $1.74 \times 10^5$ | $2.46 \times 10^{-4}$ | $1.41 \times 10^{-9}$ |

Example 16.4: Rat Pharmacokinetic Data

Based on the purity after one-step purification, expression titer in transient transfection, the binding affinity retained, as well as the functional activity in the PBMC-SEB assay, FIT107-1-7b-1 was selected as lead molecule. Pharmacokinetic properties of FIT107-1-7b-1 were assessed in male Sprague-Dawley (SD) rats. FIT-Ig protein was administered to male SD rats at a single intravenous dose of 5 mg/kg. Serum samples were collected at different time points over a period of 28 days with sampling at 0, 5, 15, and 30 minutes; 1, 2, 4, 8, and 24 hours; and 2, 4, 7, 10, 14, 21, and 28 days serial bleeding via tail vein, and analyzed by general ELISAs. Briefly. ELISA plates were coated with 125 ng/well of goat anti-human IgG Fc antibody (Rockland. Cat #; 609-101-017) at 4° C. overnight, blocked with IX PBS/1% BSA/0.05% Tween-20/0.05% ProClin™ 300. All serum samples were diluted 20-fold in blocking buffer first. An additional dilution was made in 5% pooled rat serum and incubated on the plate for 60 minutes at 37° C. Detection was carried out with a goat Fab-specific anti-human IgG-peroxidase conjugated antibody (Sigma-Aldrich; Cat No. A0293), and concentrations were determined with the help of standard curves using the four-parameter logistic fit. Values for tire pharmacokinetic parameters were determined by non-compartmental model using WinNonlin software (Pharsight Corporation, Mountain View, Calif.). As demonstrated by these results shown in Table 55, the properties of FIT107-1-7b-1 are stable in vivo.

TABLE 55

Pharmacokinetic Properties of FIT107-1-7b-1

| PK parameters Antibody | CL mL/day/kg | Vss mL/kg | Beta $t_{1/2}$ day | AUC day*µg/mL | MRT day |
|---|---|---|---|---|---|
| FIT107-1-7b-1 | 9.17 | 114 | 8.82 | 436 | 12.4 |

Example 16.5; FGL1 Receptor Blocking Assay (RBA)

Figure 12:
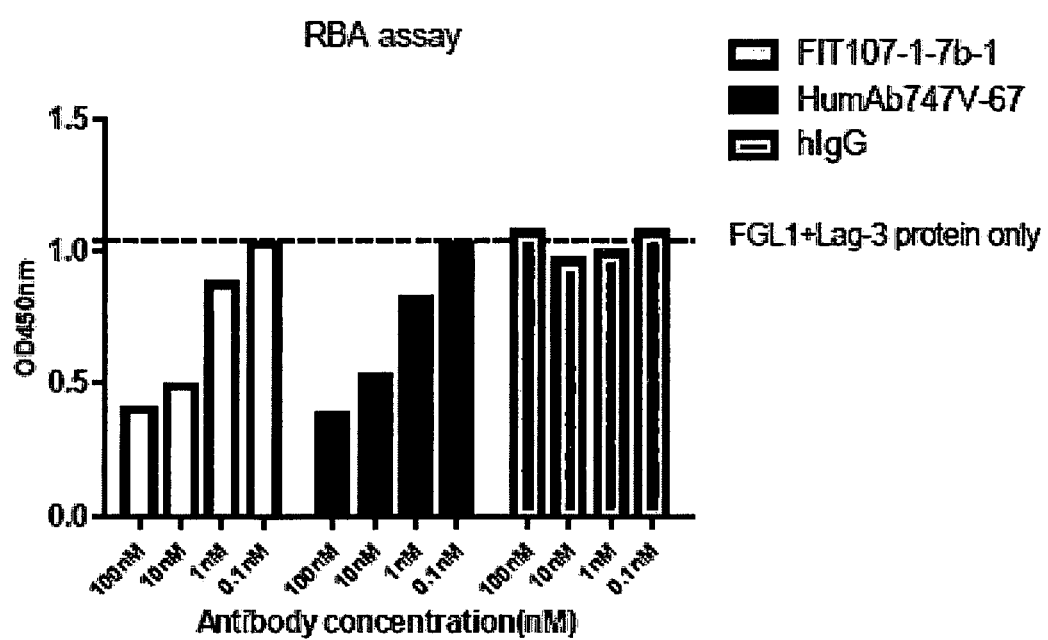
FIG. 12 is a bar graph showing the results of a receptor blocking assay showing the ability of an anti-LAG-3 antibody according to the invention (HumAb747V-67) and a PD-1/LAG-3 FIT-Ig binding protein according to the invention (FIT107-1-7b-1) to block interaction between human LAG-3 and fibrinogen-like protein 1 (FGL1). See, Example 16.5.

It was reported recently that fibrinogen-like protein. 1 (FGL1) is a major LAG-3 functional ligand independent from MHC Class II (Wang J. et al., Cell, 176(1):334-47 (2019)). Blockade of the FGL1/LAG-3 interaction by antibodies stimulates tumor immunity. To evaluate blocking activity of the anti-LAG-3 antibody or FIT-Ig, FGL1 (Wuhan USCN, Cat No. RPD022Hu01) was diluted to 5 µg/nil with Dulbecco's phosphate buffered saline and 100 µl were added into a 96-well plate and incubated at 4° C. overnight. The plate was washed three times with 300 µl/well PBS+ TWEEN 20 (PBST). HumAb747V-67, FIT107-1-7b-1, hIgG (working concentration; 100 nM. 10 nM, 1 nM and 0.1 nM) and 1 µg/ml biotinylated LAG-3 (AcroBiosystem, Cat No. H82E5) were added and incubated at room temperature for 2 hours. The plate was washed three times with 300 µl/well PBST, then read using a VARIOSKAN™ LUX microplate reader (Thermo Scientific) using the ELISA-Endpoint-TMB/HRP protocol. Results are shown in FIG. 12, The results showed that both FIT107-1-7b-1 FIT-Ig and its parental anti-LAG-3 antibody HumAb747V-67 can block human LAG-3 binding to FGL1 protein.

Example 16.6; Primary Cells Binding Activity of FIT107-1-7b-1 Protein

Figure 13:
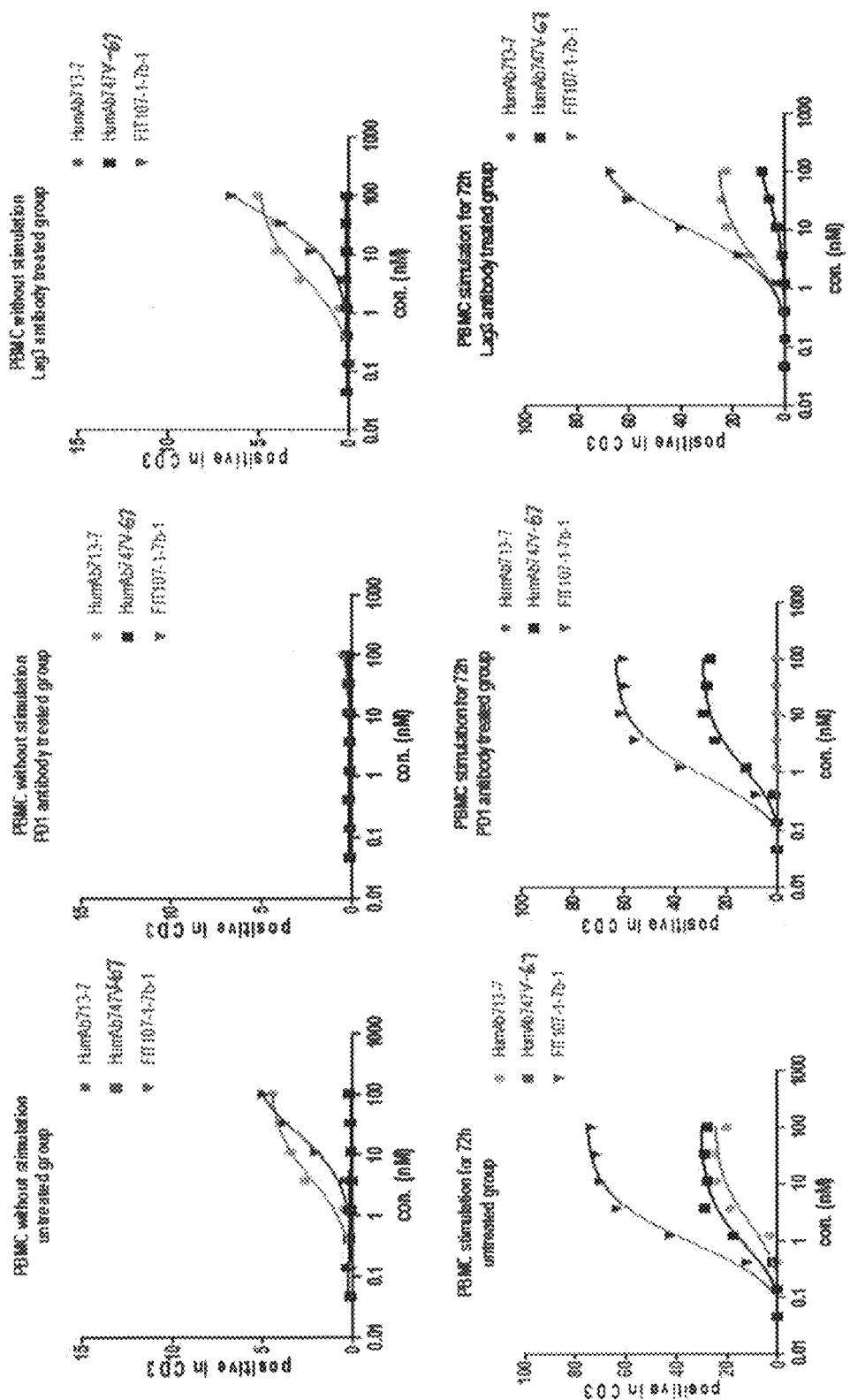
FIG. 13 is a series of graphs evaluating the cell-surface binding to PD-1 and LAG-3 expressed on T cells. The results show that the bispecific FIT-Ig protein FIT107-1-7b-1 recognizes both PD-1 and LAG-3 surface proteins on T cells.

The foregoing assays demonstrated PD-1/LAG-3 FIT-Ig proteins can bind recombinant antigen proteins. To further evaluate the cell surface binding ability of FIT107-1-7b-1, the parental antibodies HumAb713-7, HumAb747V-67, and the bispecific FIT-Ig FIT107-1-7b-1 were biotinylated with biotin reagent (Sigma, Cat. No. S3259). For PBMC without stimulation, PBMCs were re-suspended at $5 \times 10^6$ cells/mi. For PD-1 antibody (HumAb713-7) or LAG-3 antibody (HumAb747V-67) testing, 100 µg/ml of antibody were added and the reaction mixture allowed to incubate at 37° C. for 40 minutes separately, followed by two washes with FACS buffer. Then 100 µl, $5 \times 10^5$ PBMC/well (untreated group, anti-PD-1 antibody treated group and anti-LAG-3 antibody treated group) were seeded into wells of 96-well plate. Biotinylated HumAb713-7, HumAb747V-67 and FIT107-1-7b-1 were added and incubated at 37° C. for 40 minutes (final working concentration starting from 100 nM with 3-fold serial dilution) followed by washing with FACS buffer twice. FITC-streptavidin and BV421-anti human-CD3 antibody were added and the assay plate incubated at 4° C. for 30 minutes, followed by washing with FACS buffer twice. The plate was analyzed with a Beckman Coulter CytoFlex flow cytometer, PBMC stimulation groups were stimulated with anti-CD3 plus anti-CD28 antibody for 72 hours, to induce PD-1 and LAG-3 expression on T cells. HumAb713-7, HumAb747V-67 and FIT107-1-7b-1 binding were tested on stimulated PBMC with the same grouping strategy (untreated, anti-PD-1 antibody treated and anti-LAG-3 antibody treated group) as in the unstimulated PBMC experiments. The binding of test antibodies was investigated on CD3-T cells subset by FACS. The results are shown in FIG. 13. Results showed that FIT107-7b-1 exhibited a unique binding pattern indicating binding to both PD-1 and LAG-3 targets on T cells.

The contents of all references (including literature references, patents, patent applications, and websites) drat are cited throughout this application are hereby expressly incorporated by reference in their entirety. The practice of the present invention will employ, unless otherwise indicated, conventional techniques of immunology, molecular biology and cell biology, which are well known in tire art The invention may be embodied in other specific forms without departing from the essential characteristics of the invention described above. The foregoing embodiments are therefore to be considered illustrative rather than limiting of the invention described herein. The scope of the invention is indicated by the appended claims.

What is claimed is:

1. An anti-PD-1 antibody, or an antigen-binding portion thereof, capable of binding human PD-1, wherein the antibody or antigen-binding portion thereof comprises a set of six complementarity determining regions (CDRs), CDR-H1, CDR-H2, CDR-H3, CDR-L1, CDR-L2, and CDR-L3, selected from the group consisting of:

| CDR Set No. | CDR | CDR Amino Acid Sequence | SEQ ID NO |
|---|---|---|---|
| 1 | CDR-H1 | SYMMS | residues 31-35 of SEQ ID NO: 4 |
|   | CDR-H2 | SMSGGGRDTYYPDSVKG | residues 50-66 of SEQ ID NO: 4 |
|   | CDR-H3 | RGTYAMDY | residues 99-106 of SEQ ID NO: 4 |
|   | CDR-L1 | LASQTIGTWLT | residues 24-34 of SEQ ID NO: 5 |
|   | CDR-L2 | AATSLAD | residues 50-56 of SEQ ID NO: 5 |
|   | CDR-L3 | QQLYSTPWT | residues 89-97 of SEQ ID NO: 5 |
| 2 | CDR-H1 | TGYYWN | residues 31-36 of SEQ ID NO: 6 |
|   | CDR-H2 | YMSYDGNNNYNPSLKN | residues 51-66 of SEQ ID NO: 6 |
|   | CDR-H3 | DRGTTILGGTMDY | residues 99-111 of SEQ ID NO: 6 |
|   | CDR-L1 | KASQSVSNDVA | residues 24-34 of SEQ ID NO: 7 |
|   | CDR-L2 | YAFYRYT | residues 50-56 of SEQ ID NO: 7 |
|   | CDR-L3 | QQDYSSPWT | residues 89-97 of SEQ ID NO: 7 |
| 3 | CDR-H1 | FYTMS | residues 31-35 of SEQ ID NO: 8 |
|   | CDR-H2 | TISGGGRDTYYPDSVKG | residues 50-66 of SEQ ID NO: 8 |
|   | CDR-H3 | QGGNYLFAY | residues 99-107 of SEQ ID NO: 8 |
|   | CDR-L1 | KASQDVNTVVA | residues 24-34 of SEQ ID NO: 9 |
|   | CDR-L2 | WASTRHT | residues 50-56 of SEQ ID NO: 9 |
|   | CDR-L3 | QQHYTTPYT | residues 89-97 of SEQ ID NO: 9 |

-continued

| CDR Set No. | CDR | CDR Amino Acid Sequence | SEQ ID NO |
|---|---|---|---|
| 4 | CDR-H1 | DYGMH | residues 31-35 of SEQ ID NO: 10 |
|  | CDR-H2 | YISSGSYTIYYADTVKG | residues 50-66 of SEQ ID NO: 10 |
|  | CDR-H3 | RGGSSHVNVMDY | residues 99-110 of SEQ ID NO: 10 |
|  | CDR-L1 | KASDHINNWLA | residues 24-34 of SEQ ID NO: 11 |
|  | CDR-L2 | GATSLET | residues 50-56 of SEQ ID NO: 11 |
|  | CDR-L3 | QQYWSPPYT | residues 89-97 of SEQ ID NO: 11 |
| 5 | CDR-H1 | DNNVE | residues 31-35 of SEQ ID NO: 12 |
|  | CDR-H2 | DINPNNGDTLYSQYFKD | residues 50-66 of SEQ ID NO: 12 |
|  | CDR-H3 | GKSDQFDY | residues 99-106 of SEQ ID NO: 12 |
|  | CDR-L1 | LASQTIGTWLA | residues 24-34 of SEQ ID NO: 13 |
|  | CDR-L2 | AATSLAD | residues 50-56 of SEQ ID NO: 13 |
|  | CDR-L3 | QQLYSSPWT | residues 89-97 of SEQ ID NO: 13 |
| 6 | CDR-H1 | SYAMS | residues 31-35 of SEQ ID NO: 14 |
|  | CDR-H2 | TISGGGRDTYYPDSVKG | residues 50-66 of SEQ ID NO: 14 |
|  | CDR-H3 | QGGTYLFAS | residues 99-107 of SEQ ID NO: 14 |
|  | CDR-L1 | KASQDVNTAVA | residues 24-34 of SEQ ID NO: 15 |
|  | CDR-L2 | WASTRHT | residues 50-56 of SEQ ID NO: 15 |
|  | CDR-L3 | QQHYTTPYT | residues 89-97 of SEQ ID NO: 15 |
| 7 | CDR-H1 | DYEMH | residues 31-35 of SEQ ID NO: 16 |
|  | CDR-H2 | VIEPESGGTVYNQKFKG | residues 51-66 of SEQ ID NO: 16 |
|  | CDR-H3 | EGFNSDHYFDY | residues 99-109 of SEQ ID NO: 16 |
|  | CDR-L1 | RSSQNIVHSNGNTYLE | residues 24-39 of SEQ ID NO: 17 |
|  | CDR-L2 | KVFNRFS | residues 55-61 of SEQ ID NO: 17 |
|  | CDR-L3 | FQGSHVPYT | residues 94-102 of SEQ ID NO: 17 |
| 8 | CDR-H1 | SHLMS | residues 31-35 of SEQ ID NO: 18 |
|  | CDR-H2 | AISGGGADTYYPDSVKG | residues 50-66 of SEQ ID NO: 18 |
|  | CDR-H3 | QILAFDS | residues 99-105 of SEQ ID NO: 18 |
|  | CDR-L1 | HASQNIYVWLN | residues 24-34 of SEQ ID NO: 19 |
|  | CDR-L2 | KASNLHT | residues 50-56 of SEQ ID NO: 19 |
|  | CDR-L3 | QQGQSYPWT | residues 89-97 of SEQ ID NO: 19 |
| 9 | CDR-H1 | SHLMS | residues 31-35 of SEQ ID NO: 53 |
|  | CDR-H2 | AISGGGADTYYPASVKG | residues 50-66 of SEQ ID NO: 53 |
|  | CDR-H3 | QILAFDA | residues 99-105 of SEQ ID NO: 53 |
|  | CDR-L1 | HASQNIYVWLN | residues 24-34 of SEQ ID NO: 19 |

-continued

| CDR Set No. | CDR | CDR Amino Acid Sequence | SEQ ID NO |
|---|---|---|---|
|  | CDR-L2 | KASNLHT | residues 50-56 of SEQ ID NO: 19 |
|  | CDR-L3 | QQGQSYPWT | residues 89-97 of SEQ ID NO: 19 |

2. An anti-PD-1 antibody comprising a heavy chain variable domain (VH) and a light chain variable domain (VL), wherein the VH and VL comprise amino acid sequences selected from the group consisting of:

SEQ ID NO: 4 and SEQ ID NO: 5
SEQ ID NO: 8 and SEQ ID NO: 9
SEQ ID NO: 12 and SEQ ID NO: 13
SEQ ID NO: 16 and SEQ ID NO: 17
SEQ ID NO: 20 and SEQ ID NO: 23
SEQ ID NO: 22 and SEQ ID NO: 23
SEQ ID NO: 21 and SEQ ID NO: 24
SEQ ID NO: 20 and SEQ ID NO: 25
SEQ ID NO: 22 and SEQ ID NO: 25
SEQ ID NO: 21 and SEQ ID NO: 26
SEQ ID NO: 20 and SEQ ID NO: 27
SEQ ID NO: 22 and SEQ ID NO: 27
SEQ ID NO: 31 and SEQ ID NO: 34
SEQ ID NO: 33 and SEQ ID NO: 34
SEQ ID NO: 31 and SEQ ID NO: 35
SEQ ID NO: 33 and SEQ ID NO: 35
SEQ ID NO: 31 and SEQ ID NO: 36
SEQ ID NO: 33 and SEQ ID NO: 36
SEQ ID NO: 31 and SEQ ID NO: 37
SEQ ID NO: 33 and SEQ ID NO: 37
SEQ ID NO: 39 and SEQ ID NO: 43
SEQ ID NO: 41 and SEQ ID NO: 43
SEQ ID NO: 38 and SEQ ID NO: 44
SEQ ID NO: 40 and SEQ ID NO: 44
SEQ ID NO: 42 and SEQ ID NO: 44
SEQ ID NO: 39 and SEQ ID NO: 45
SEQ ID NO: 41 and SEQ ID NO: 45
SEQ ID NO: 38 and SEQ ID NO: 46
SEQ ID NO: 40 and SEQ ID NO: 46
SEQ ID NO: 42 and SEQ ID NO: 46
SEQ ID NO: 39 and SEQ ID NO: 47
SEQ ID NO: 41 and SEQ ID NO: 47
SEQ ID NO: 48 and SEQ ID NO: 55
SEQ ID NO: 50 and SEQ ID NO: 55
SEQ ID NO: 52 and SEQ ID NO: 55
SEQ ID NO: 54 and SEQ ID NO: 55
SEQ ID NO: 49 and SEQ ID NO: 56
SEQ ID NO: 51 and SEQ ID NO: 56
SEQ ID NO: 53 and SEQ ID NO: 56
SEQ ID NO: 48 and SEQ ID NO: 57
SEQ ID NO: 50 and SEQ ID NO: 57
SEQ ID NO: 52 and SEQ ID NO: 57
SEQ ID NO: 54 and SEQ ID NO: 57
SEQ ID NO: 6 and SEQ ID NO: 7
SEQ ID NO: 10 and SEQ ID NO: 11
SEQ ID NO: 14 and SEQ ID NO: 15
SEQ ID NO: 18 and SEQ ID NO: 19
SEQ ID NO: 21 and SEQ ID NO: 23
SEQ ID NO: 20 and SEQ ID NO: 24
SEQ ID NO: 22 and SEQ ID NO: 24
SEQ ID NO: 21 and SEQ ID NO: 25
SEQ ID NO: 20 and SEQ ID NO: 26
SEQ ID NO: 22 and SEQ ID NO: 26
SEQ ID NO: 21 and SEQ ID NO: 27
SEQ ID NO: 30 and SEQ ID NO: 34
SEQ ID NO: 32 and SEQ ID NO: 34
SEQ ID NO: 30 and SEQ ID NO: 35
SEQ ID NO: 32 and SEQ ID NO: 35
SEQ ID NO: 30 and SEQ ID NO: 36
SEQ ID NO: 32 and SEQ ID NO: 36
SEQ ID NO: 30 and SEQ ID NO: 37
SEQ ID NO: 32 and SEQ ID NO: 37
SEQ ID NO: 38 and SEQ ID NO: 43

-continued

SEQ ID NO: 40 and SEQ ID NO: 43
SEQ ID NO: 42 and SEQ ID NO: 43
SEQ ID NO: 39 and SEQ ID NO: 44
SEQ ID NO: 41 and SEQ ID NO: 44
SEQ ID NO: 38 and SEQ ID NO: 45
SEQ ID NO: 40 and SEQ ID NO: 45
SEQ ID NO: 42 and SEQ ID NO: 45
SEQ ID NO: 39 and SEQ ID NO: 46
SEQ ID NO: 41 and SEQ ID NO: 46
SEQ ID NO: 38 and SEQ ID NO: 47
SEQ ID NO: 40 and SEQ ID NO: 47
SEQ ID NO: 42 and SEQ ID NO: 47
SEQ ID NO: 49 and SEQ ID NO: 55
SEQ ID NO: 51 and SEQ ID NO: 55
SEQ ID NO: 53 and SEQ ID NO: 55
SEQ ID NO: 48 and SEQ ID NO: 56
SEQ ID NO: 50 and SEQ ID NO: 56
SEQ ID NO: 52 and SEQ ID NO: 56
SEQ ID NO: 54 and SEQ ID NO: 56
SEQ ID NO: 49 and SEQ ID NO: 57
SEQ ID NO: 51 and SEQ ID NO: 57
SEQ ID NO: 53 and SEQ ID NO: 57

3. An anti-LAG-3 antibody, or an antigen-binding portion thereof, capable of binding human LAG-3, wherein the antibody or antigen-binding portion thereof comprises a set of six complementarity determining regions (CDRs), CDR-H1, CDR-H2, CDR-H3, CDR-L1, CDR-L2, and CDR-L3, selected from the group consisting of:

CDR-H1 comprising DFNIKDDYMH (residues 26-35 of SEQ ID NO:114), CDR-H2 comprising WIVPENGNTEYASKFQG (residues 50-66 of SEQ ID NO:114), CDR-H3 comprising YGDY (residues 99-102 of SEQ ID NO:114), CDR-L1 comprising RASQEISGYLS (residues 24-34 of SEQ ID NO:117), CDR-L2 comprising AASTLDS (residues 50-56 of SEQ ID NO:117), and CDR-L3 comprising LQYASYPLT (residues 89-97 of SEQ ID NO:117);

CDR-H1 comprising DDYMH (residues 31-35 of SEQ ID NO:135), CDR-H2 comprising WIVPENANTVYASKFQG (SEQ ID NO:224), CDR-H3 comprising YGDY (residues 99-102 of SEQ ID NO:135), CDR-LI comprising RASQEISGYLS (residues 24-34 of SEQ ID NO:138), CDR-L2 comprising AASALDS (residues 50-56 of SEQ ID NO:138), and CDR-L3 comprising LQYASYPLT (residues 89-97 of SEQ ID NO:138);

CDR-H1 comprising DDYMH (residues 31-35 of SEQ ID NO:136), CDR-H2 comprising WIVPRNANTVYASKFQG (SEQ ID NO:225), CDR-H3 comprising YGDY (residues 99-102 of SEQ ID NO:136), CDR-LI comprising RASQEISGYLS (residues 24-34 of SEQ ID NO:139), CDR-L2 comprising AASALDL (residues 50-56 of SEQ ID NO:139), and CDR-L3 comprising LQYASYPLT (residues 89-97 of SEQ ID NO:139); and CDR-H1 comprising DDYMH (residues 31-35 of SEQ ID NO:136), CDR-H2 comprising WIVPRNANTVYASKFQG (SEQ ID NO:225), CDR-H3 comprising YGDY (residues 99-102 of SEQ ID NO:136), CDR-LI comprising RASQEISGYLS (residues 24-34 of SEQ ID NO:117), CDR-L2 comprising AASTLDS (residues 50-56 of SEQ ID NO:117), and CDR-L3 comprising LQYASYPLT (residues 89-97 of SEQ ID NO:117).

4. An anti-LAG-3 antibody comprising a heavy chain variable domain (VH) and a light chain variable domain (VL), wherein the VH and VL comprise amino acid sequences selected from the group consisting of:

SEQ ID NO: 135 and SEQ ID NO: 138
SEQ ID NO: 136 and SEQ ID NO: 117
SEQ ID NO: 227 and SEQ ID NO: 139
SEQ ID NO: 136 and SEQ ID NO: 139
SEQ ID NO: 226 and SEQ ID NO: 138
SEQ ID NO: 227 and SEQ ID NO: 117

5. A binding protein comprising first, second and third polypeptide chains,
wherein the first polypeptide chain comprises, from amino to carboxyl terminus, (i) $VL_A$-CL-$VH_B$-CH1-Fc wherein CL is directly fused to $VH_B$, or (ii) $VH_B$-CH1-$VL_A$-CL-Fc wherein CH1 is directly fused to $VL_A$; the second polypeptide chain comprises, from amino to carboxyl terminus, $VH_A$-CH1; and the third polypeptide chain comprises, from amino to carboxyl terminus, $VL_B$-CL;
wherein VL is a light chain variable domain, CL is a light chain constant domain, VH is a heavy chain variable domain, CH1 is a heavy chain constant domain, Fc is an immunoglobulin Fc region, A is an epitope of PD-1 or LAG-3 and B is an epitope of PD-1 or LAG-3, with the proviso that A and B are different, and the binding protein is bispecific and multivalent in being capable of binding to both PD-1 and LAG-3, and
wherein $VH_A$ and $VL_A$ respectively represent $VH_{LAG3}$ and $VL_{LAG3}$ when A is an epitope of LAG-3, or $VL_B$ and $VH_B$ respectively represent $VL_{LAG3}$ and $VH_{LAG3}$ when B is an epitope of LAG-3, and the $VH_{LAG3}$ and $VL_{LAG3}$ respectively comprise CDRs (CDR-H1, CDR-H2, CDR-H3, and CDR-L1, CDR-L2, CDR-L3), selected from the group consisting of:

CDR-H1 comprising DFNIKDDYMH (residues 26-35 of SEQ ID NO:114), CDR-H2 comprising WIVPENGNTEYASKFQG (residues 50-66 of SEQ ID NO:114), CDR-H3 comprising YGDY (residues 99-102 of SEQ ID NO:114), CDR-L1 comprising RASQEISGYLS (residues 24-34 of SEQ ID NO:117), CDR-L2 comprising AASTLDS (residues 50-56 of SEQ ID NO:117), and CDR-L3 comprising LQYASYPLT (residues 89-97 of SEQ ID NO:117);

CDR-H1 comprising DDYMH (residues 31-35 of SEQ ID NO:135), CDR-H2 comprising WIVPENANTVYASKFQG (SEQ ID NO:224), CDR-H3 comprising YGDY (residues 99-102 of SEQ ID NO:135), CDR-L1 comprising RASQEISGYLS (residues 24-34 of SEQ ID NO:138), CDR-L2 comprising AASALDS (residues 50-56 of SEQ ID NO:138), and CDR-L3 comprising LQYASYPLT (residues 89-97 of SEQ ID NO:138);

CDR-H1 comprising DDYMH (residues 31-35 of SEQ ID NO:136), CDR-H2 comprising WIVPRNANTVYASKFQG (SEQ ID NO:225), CDR-H3 comprising YGDY (residues 99-102 of SEQ ID NO:136), CDR-L1 comprising RASQEISGYLS (residues 24-34 of SEQ ID NO:139), CDR-L2 comprising AASALDL (residues 50-56 of SEQ ID NO:139), and CDR-L3 comprising LQYASYPLT (residues 89-97 of SEQ ID NO:139); and CDR-H1 comprising DDYMH (residues 31-35 of SEQ ID NO:136), CDR-H2 comprising WIVPRNANTVYASKFQG (SEQ ID NO:225), CDR-H3 comprising YGDY (residues 99-102 of SEQ ID NO:136), CDR-L1 comprising RASQEISGYLS (residues 24-34 of SEQ ID NO:117), CDR-L2 comprising AASTLDS (residues 50-56 of SEQ ID NO:117), and CDR-L3 comprising LQYASYPLT (residues 89-97 of SEQ ID NO:117).

6. The binding protein of claim 5, wherein the $VL_A$-CL and $VH_A$-CH1 domains are from a parental antibody capable of binding to one of the antigen targets PD-1 or LAG-3, and the $VL_B$-CL and $VH_B$-CH1 domains are from a different parental antibody capable of binding to the other of the antigen targets PD-1 or LAG-3.

7. The binding protein of claim 6, comprising first, second and third polypeptide chains, wherein the first polypeptide chain comprises, from amino to carboxyl terminus, $VL_{PD-1}$-CL-$VH_{LAG-3}$-CH1-Fc wherein CL is directly fused to $VH_{LAG-3}$; the second polypeptide chain comprises, from amino to carboxyl terminus, $VH_{PD-1}$-CH1; and the third polypeptide chain comprises, from amino to carboxyl terminus, $VL_{LAG-3}$-CL;

wherein $VL_{PD-1}$ is a light chain variable domain of an anti-PD-1 antibody, CL is a light chain constant domain, $VH_{PD-1}$ is a heavy chain variable domain of an anti-PD-1 antibody, CH1 is a heavy chain constant domain, $VL_{LAG-3}$ is a light chain variable domain of an anti-LAG-3 antibody, $VH_{LAG-3}$ is a heavy chain variable domain of an anti-LAG-3 antibody, and Fc is an immunoglobulin Fc region.

8. The binding protein of claim 7, wherein, in the first polypeptide chain, the domains $VL_{PD-1}$-CL are the same as the light chain of an anti-PD-1 parental antibody, the domains $VH_{PD-1}$-CHI are the same as the heavy chain variable and heavy chain constant domains of an anti-PD-1 parental antibody, the domains $VL_{LAG-3}$-CL are the same as the light chain of an anti-LAG-3 parental antibody, and the domains $VH_{LAG-3}$-CHI are the same as the heavy chain variable and heavy chain constant domains of an anti-LAG-3 parental antibody.

9. The binding protein of claim 6, comprising first, second and third polypeptide chains, wherein the first polypeptide chain comprises, from amino to carboxyl terminus, $VL_{LAG-3}$-CL-$VH_{PD-1}$-CH1-Fc wherein CL is directly fused to $VH_{PD-1}$; the second polypeptide chain comprises, from amino to carboxyl terminus, $VH_{LAG-3}$-CH1; and the third polypeptide chain comprises, from amino to carboxyl terminus, $VL_{PD-1}$-CL;

wherein $VL_{PD-1}$ is a light chain variable domain of an anti-PD-1 antibody, CL is a light chain constant domain, $VH_{PD-1}$ is a heavy chain variable domain of an anti-PD-1 antibody, CH1 is a heavy chain constant domain, $VL_{LAG-3}$ is a light chain variable domain of an anti-LAG-3 antibody, $VH_{LAG-3}$ is a heavy chain variable domain of an anti-LAG-3 antibody, and Fc is an immunoglobulin Fc region.

10. The binding protein of claim 9, wherein, in the first polypeptide chain, the domains $VL_{LAG-3}$-CL are the same as the light chain of an anti-LAG-3 parental antibody, the domains $VH_{LAG-3}$-CHI are the same as the heavy chain variable and heavy chain constant domains of an anti-LAG-3 parental antibody, the domains $VL_{PD-1}$-CL are the same as the light chain of an anti-PD-1 parental antibody, and the domains $VH_{PD-1}$-CHI are the same as the heavy chain variable and heavy chain constant domains of an anti-PD-1 parental antibody.

11. The binding protein of claim 5, further comprising an Fc region comprising SEQ ID NO:28.

12. The binding protein of claim 5, wherein the first polypeptide chain comprises an amino acid sequence of amino acids 23-679 of SEQ ID NO:182; the second polypeptide chain comprises the amino acid sequence of SEQ ID NO:186; and the third polypeptide chain comprises the amino acid sequence of SEQ ID NO:188;

the first polypeptide chain comprises an amino acid sequence of amino acids 23-687 of SEQ ID NO:189; the second polypeptide chain comprises the amino acid sequence of SEQ ID NO:193; and the third polypeptide chain comprises the amino acid sequence of SEQ ID NO:195;

the first polypeptide chain comprises an amino acid sequence of amino acids 23-679 of SEQ ID NO:196; the second polypeptide chain comprises the amino acid sequence of SEQ ID NO:200; and the third polypeptide chain comprises the amino acid sequence of SEQ ID NO:202;

the first polypeptide chain comprises an amino acid sequence of amino acids 23-687 of SEQ ID NO:203; the second polypeptide chain comprises the amino acid sequence of SEQ ID NO:207; and the third polypeptide chain comprises the amino acid sequence of SEQ ID NO:209;

the first polypeptide chain comprises an amino acid sequence of amino acids 23-679 of SEQ ID NO:210; the second polypeptide chain comprises the amino acid sequence of SEQ ID NO:214; and the third polypeptide chain comprises the amino acid sequence of SEQ ID NO:216; or the first polypeptide chain comprises an amino acid sequence of amino acids 23-687 of SEQ ID NO:217; the second polypeptide chain comprises the amino acid sequence of SEQ ID NO:221; and the third polypeptide chain comprises the amino acid sequence of SEQ ID NO:223.

13. A pharmaceutical composition comprising at least one anti-PD-1 antibody or antigen-binding portion thereof of claim 1, and a pharmaceutically acceptable carrier.

14. A pharmaceutical composition comprising at least one anti-LAG-3 antibody or antigen-binding portion thereof of claim 1, and a pharmaceutically acceptable carrier.

15. A pharmaceutical composition comprising at least one binding protein of claim 5, and a pharmaceutically acceptable carrier.

16. A method of treating a disorder in which PD-1-mediated and/or LAG-3-mediated activity is detrimental, comprising administering to a subject in need thereof an effective amount of a pharmaceutical composition of claim 13.

17. A method of treating a disorder in which PD-1-mediated and/or LAG-3-mediated activity is detrimental, comprising administering to a subject in need thereof an effective amount of a pharmaceutical composition of claim 14.

18. A method of treating a disorder in which PD-1-mediated and/or LAG-3-mediated activity is detrimental, comprising administering to a subject in need thereof an effective amount of a pharmaceutical composition of claim 15.

19. The method of claim 18, wherein the disorder is cancer, and the cancer is a melanoma, a renal cancer, a prostate cancer, a pancreatic adenocarcinoma, a breast cancer, a colon cancer, a lung cancer, an esophageal cancer, a squamous cell carcinoma of the head and neck, a liver cancer, an ovarian cancer, a cervical cancer, a thyroid cancer, a glioblastoma, a glioma, a leukemia, a lymphoma, or a primary bone cancer.

20. The method of claim 19, wherein the melanoma is a metastatic malignant melanoma; the renal cancer is a clear cell carcinoma; the prostate cancer is a hormone refractory prostate adenocarcinoma; the lung cancer is a non-small cell lung cancer; and/or the primary bone cancer is an osteosarcoma, Ewing sarcoma, malignant fibrous histiocytoma, or chondrosarcoma.

21. The method of claim 18, wherein the subject is a human.

\* \* \* \* \*

SEQUENCE LISTING

```
<160> NUMBER OF SEQ ID NOS: 227

<210> SEQ ID NO 1
<211> LENGTH: 380
<212> TYPE: PRT
<213> ORGANISM: Artificial Sequence
<220> FEATURE:
<223> OTHER INFORMATION: human PD-1 /Fc Fusion Protein

<400> SEQUENCE: 1

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
```

```
            20                  25                  30
Ser Asn Thr Ser Glu Ser Phe Val Leu Asn Trp Tyr Arg Met Ser Pro
            35                  40                  45

Ser Asn Gln Thr Asp Lys Leu Ala Ala Phe Pro Glu Asp Arg Ser Gln
50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Ile
        130                 135                 140

Glu Gly Arg Met Asp Pro Lys Ser Cys Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
        210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Glu Glu Met Thr Lys Asn Gln Val Ser Leu Thr Cys Leu Val Lys Gly
        290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
        370                 375                 380

<210> SEQ ID NO 2
<211> LENGTH: 380
<212> TYPE: PRT
<213> ORGANISM: artificial sequence
<220> FEATURE:
<223> OTHER INFORMATION: cynomolgus monkey PD-1 /Fc fusion protein

<400> SEQUENCE: 2

Leu Glu Ser Pro Asp Arg Pro Trp Asn Ala Pro Thr Phe Ser Pro Ala
```

```
1               5                   10                  15
Leu Leu Leu Val Thr Glu Gly Asp Asn Ala Thr Phe Thr Cys Ser Phe
            20                  25                  30

Ser Asn Ala Ser Glu Ser Phe Val Leu Asn Trp Tyr Arg Met Ser Pro
            35                  40                  45

Ser Asn Gln Thr Asp Lys Leu Ala Ala Phe Pro Glu Asp Arg Ser Gln
            50                  55                  60

Pro Gly Gln Asp Cys Arg Phe Arg Val Thr Arg Leu Pro Asn Gly Arg
 65                 70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
                100                 105                 110

Ser Leu Arg Ala Glu Leu Arg Val Thr Glu Arg Arg Ala Glu Val Pro
                115                 120                 125

Thr Ala His Pro Ser Pro Ser Pro Arg Pro Ala Gly Gln Phe Gln Ile
            130                 135                 140

Glu Gly Arg Met Asp Pro Lys Ser Cys Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
                180                 185                 190

Thr Cys Val Val Val Asp Val Ser His Glu Asp Pro Glu Val Lys Phe
            195                 200                 205

Asn Trp Tyr Val Asp Gly Val Glu Val His Asn Ala Lys Thr Lys Pro
            210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285

Glu Glu Met Thr Lys Asn Gln Val Ser Leu Thr Cys Leu Val Lys Gly
            290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 3
<211> LENGTH: 380
<212> TYPE: PRT
<213> ORGANISM: Artificial Sequence
<220> FEATURE:
<223> OTHER INFORMATION: mouse PD-1 /Fc fusion protein
```

```
<400> SEQUENCE: 3

Leu Glu Val Pro Asn Gly Pro Trp Arg Ser Leu Thr Phe Tyr Pro Ala
1               5                   10                  15

Trp Leu Thr Val Ser Glu Gly Ala Asn Ala Thr Phe Thr Cys Ser Leu
            20                  25                  30

Ser Asn Trp Ser Glu Asp Leu Met Leu Asn Trp Asn Arg Leu Ser Pro
        35                  40                  45

Ser Asn Gln Thr Glu Lys Gln Ala Ala Phe Cys Asn Gly Leu Ser Gln
    50                  55                  60

Pro Val Gln Asp Ala Arg Phe Gln Ile Ile Gln Leu Pro Asn Arg His
65                  70                  75                  80

Asp Phe His Met Asn Ile Leu Asp Thr Arg Arg Asn Asp Ser Gly Ile
                85                  90                  95

Tyr Leu Cys Gly Ala Ile Ser Leu His Pro Lys Ala Lys Ile Glu Glu
            100                 105                 110

Ser Pro Gly Ala Glu Leu Val Val Thr Glu Arg Ile Leu Glu Thr Ser
        115                 120                 125

Thr Arg Tyr Pro Ser Pro Ser Pro Lys Pro Glu Gly Arg Phe Gln Ile
    130                 135                 140

Glu Gly Arg Met Asp Pro Lys Ser Cys Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Glu Glu Met Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380

<210> SEQ ID NO 4
<211> LENGTH: 117
<212> TYPE: PRT
<213> ORGANISM: Mus musculus
```

```
<220> FEATURE:
<223> OTHER INFORMATION: VH mAb701

<400> SEQUENCE: 4

Glu Val Leu Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Met Met Ser Trp Ile Arg Gln Thr Pro Glu Arg Arg Leu Glu Trp Val
        35                  40                  45

Ala Ser Met Ser Gly Gly Gly Arg Asp Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Arg Gly Thr Tyr Ala Met Asp Tyr Trp Gly Gln Gly Thr Ser
            100                 105                 110

Val Thr Val Ser Ser
        115

<210> SEQ ID NO 5
<211> LENGTH: 107
<212> TYPE: PRT
<213> ORGANISM: Mus musculus
<220> FEATURE:
<223> OTHER INFORMATION: VL mAb701

<400> SEQUENCE: 5

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Thr Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Trp
                85                  90                  95

Thr Phe Gly Gly Gly Thr Lys Leu Glu Ile Lys
            100                 105

<210> SEQ ID NO 6
<211> LENGTH: 121
<212> TYPE: PRT
<213> ORGANISM: Mus musculus
<220> FEATURE:
<223> OTHER INFORMATION: VH mAb703

<400> SEQUENCE: 6

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Thr Gly
            20                  25                  30

Tyr Tyr Trp Asn Trp Ile Arg Gln Phe Pro Gly Asn Lys Leu Glu Trp
        35                  40                  45
```

```
Met Gly Tyr Met Ser Tyr Asp Gly Asn Asn Asn Tyr Asn Pro Ser Leu
    50                  55                  60

Lys Asn Arg Ile Ser Ile Thr Arg Asp Thr Ser Lys Asn Gln Phe Leu
65                  70                  75                  80

Leu Arg Leu Asn Ser Val Thr Thr Glu Asp Thr Ala Thr Tyr Phe Cys
                85                  90                  95

Ala Arg Asp Arg Gly Thr Thr Ile Leu Gly Gly Thr Met Asp Tyr Trp
            100                 105                 110

Gly Gln Gly Thr Ser Val Thr Val Ser
            115                 120

<210> SEQ ID NO 7
<211> LENGTH: 107
<212> TYPE: PRT
<213> ORGANISM: Mus musculus
<220> FEATURE:
<223> OTHER INFORMATION: VL mAb703

<400> SEQUENCE: 7

Ser Ile Val Met Thr Gln Thr Pro Lys Phe Leu Phe Val Ser Ala Gly
1               5                   10                  15

Asp Arg Val Thr Ile Ala Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Phe Tyr Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 8
<211> LENGTH: 118
<212> TYPE: PRT
<213> ORGANISM: Mus musculus
<220> FEATURE:
<223> OTHER INFORMATION: VH mAb709

<400> SEQUENCE: 8

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Phe Tyr
            20                  25                  30

Thr Met Ser Trp Val Arg Gln Thr Pro Glu Lys Arg Leu Glu Trp Val
        35                  40                  45

Ala Thr Ile Ser Gly Gly Gly Arg Asp Thr Tyr Tyr Pro Asp Ser Val
            50                  55                  60

Lys Gly Arg Phe Thr Ile Ser Arg Asp Asn Ala Lys Asn Thr Leu Tyr
65                  70                  75                  80

Leu His Met Ser Ser Leu Arg Ser Glu Asp Thr Ala Leu Tyr Tyr Cys
                85                  90                  95

Ala Gly Gln Gly Gly Asn Tyr Leu Phe Ala Tyr Trp Gly Gln Gly Thr
            100                 105                 110

Leu Val Thr Val Ser Ala
            115
```

<210> SEQ ID NO 9
<211> LENGTH: 107
<212> TYPE: PRT
<213> ORGANISM: Mus musculus
<220> FEATURE:
<223> OTHER INFORMATION: VL mAb709

<400> SEQUENCE: 9

```
Asp Ile Val Met Thr Gln Ser His Lys Phe Met Ser Thr Ser Val Gly
1               5                   10                  15

Asp Ser Val Thr Ile Thr Cys Lys Ala Ser Gln Asp Val Asn Thr Val
            20                  25                  30

Val Ala Trp Tyr Gln Gln Lys Pro Gly Gln Ser Leu Lys Val Leu Ile
        35                  40                  45

Ser Trp Ala Ser Thr Arg His Thr Gly Val Pro Ala Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Tyr
                85                  90                  95

Thr Phe Gly Gly Gly Thr Gln Leu Glu Ile Lys
            100                 105
```

<210> SEQ ID NO 10
<211> LENGTH: 121
<212> TYPE: PRT
<213> ORGANISM: Mus musculus
<220> FEATURE:
<223> OTHER INFORMATION: VH mAb713

<400> SEQUENCE: 10

```
Glu Val Lys Leu Val Glu Ser Gly Gly Gly Leu Val Lys Pro Gly Gly
1               5                   10                  15

Ser Leu Glu Leu Ser Cys Ala Ala Ser Gly Phe Thr Ser Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Tyr Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Lys Arg Gly Gly Ser Ser His Val Asn Val Met Asp Tyr Trp Gly
            100                 105                 110

Gln Gly Thr Ser Val Thr Val Ser Ser
        115                 120
```

<210> SEQ ID NO 11
<211> LENGTH: 107
<212> TYPE: PRT
<213> ORGANISM: Mus musculus
<220> FEATURE:
<223> OTHER INFORMATION: VL mAb713

<400> SEQUENCE: 11

```
Asp Ile Gln Met Thr Gln Ser Ser Ser Tyr Leu Ser Val Ser Leu Gly
1               5                   10                  15
```

```
Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
50                      55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Pro Pro Tyr
                    85                  90                  95

Thr Phe Gly Gly Gly Thr Lys Leu Glu Ile Lys
            100                 105
```

<210> SEQ ID NO 12
<211> LENGTH: 117
<212> TYPE: PRT
<213> ORGANISM: Mus musculus
<220> FEATURE:
<223> OTHER INFORMATION: VH mAb714

<400> SEQUENCE: 12

```
Glu Val His Leu Gln Gln Ser Gly Pro Glu Leu Val Lys Pro Gly Ala
1               5                   10                  15

Ser Val Lys Ile Phe Cys Lys Ala Ser Gly Tyr Thr Phe Thr Asp Asn
            20                  25                  30

Asn Val Glu Trp Val Lys Gln Ser His Gly Lys Ser Leu Glu Trp Ile
        35                  40                  45

Gly Asp Ile Asn Pro Asn Asn Gly Asp Thr Leu Tyr Ser Gln Tyr Phe
50                      55                  60

Lys Asp Lys Ala Thr Leu Thr Val Asp Lys Ser Ser Thr Thr Ala Tyr
65                  70                  75                  80

Met Glu Leu Arg Ser Leu Thr Ser Glu Asp Thr Gly Leu Tyr Tyr Cys
                85                  90                  95

Ala Arg Gly Lys Ser Asp Gln Phe Asp Tyr Trp Gly Gln Gly Thr Thr
            100                 105                 110

Leu Thr Val Ser Ser
        115
```

<210> SEQ ID NO 13
<211> LENGTH: 107
<212> TYPE: PRT
<213> ORGANISM: Mus musculus
<220> FEATURE:
<223> OTHER INFORMATION: VL mAb714

<400> SEQUENCE: 13

```
Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
50                      55                  60

Ser Gly Ser Gly Thr Lys Phe Ser Phe Lys Ile Ser Ser Leu Gln Gly
65                  70                  75                  80

Glu Asp Phe Val Ser Tyr Tyr Cys Gln Gln Leu Tyr Ser Ser Pro Trp
                85                  90                  95
```

```
Thr Phe Gly Gly Gly Thr Lys Leu Glu Ile Lys
            100                 105

<210> SEQ ID NO 14
<211> LENGTH: 118
<212> TYPE: PRT
<213> ORGANISM: Mus musculus
<220> FEATURE:
<223> OTHER INFORMATION: VH mAb715

<400> SEQUENCE: 14

Glu Val Met Leu Val Glu Ser Gly Gly Leu Leu Lys Pro Gly Gly
1               5                   10                  15

Ser Leu Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Thr Ile Ser Gly Gly Gly Arg Asp Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Thr Ser Leu Arg Ser Glu Asp Thr Ala Phe Tyr Tyr Cys
                85                  90                  95

Ala Gly Gln Gly Gly Thr Tyr Leu Phe Ala Ser Trp Gly Gln Gly Thr
            100                 105                 110

Leu Val Thr Val Ser Ala
        115

<210> SEQ ID NO 15
<211> LENGTH: 107
<212> TYPE: PRT
<213> ORGANISM: Artificial Sequence
<220> FEATURE:
<223> OTHER INFORMATION: VL mAb715

<400> SEQUENCE: 15

Asp Ile Val Met Thr Gln Ser His Lys Phe Met Ser Thr Ser Val Gly
1               5                   10                  15

Asp Ser Val Thr Ile Thr Cys Lys Ala Ser Gln Asp Val Asn Thr Ala
                20                  25                  30

Val Ala Trp Tyr Gln Gln Lys Pro Gly Gln Pro Pro Lys Val Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Tyr
                85                  90                  95

Thr Phe Gly Gly Gly Thr Lys Leu Glu Ile Lys
            100                 105

<210> SEQ ID NO 16
<211> LENGTH: 120
<212> TYPE: PRT
<213> ORGANISM: Mus musculus
<220> FEATURE:
<223> OTHER INFORMATION: VH mAb718

<400> SEQUENCE: 16
```

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Ala Lys Gln Thr Pro Val His Gly Leu Glu Trp Ile
        35                  40                  45

Gly Val Ile Glu Pro Glu Ser Gly Gly Thr Val Tyr Asn Gln Lys Phe
50                  55                  60

Lys Gly Lys Ala Lys Leu Thr Ala Asp Lys Ser Arg Thr Ala Tyr
65                  70                  75                  80

Met Glu Leu Arg Ser Leu Thr Ser Glu Asp Ser Ala Val Tyr Tyr Cys
            85                  90                  95

Thr Arg Glu Gly Phe Asn Ser Asp His Tyr Phe Asp Tyr Trp Gly Gln
                100                 105                 110

Gly Thr Thr Leu Thr Val Ser Ser
            115                 120

<210> SEQ ID NO 17
<211> LENGTH: 112
<212> TYPE: PRT
<213> ORGANISM: Mus musculus
<220> FEATURE:
<223> OTHER INFORMATION: VL mAb718

<400> SEQUENCE: 17

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Phe Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Tyr Thr Phe Gly Gly Gly Thr Lys Leu Glu Ile Lys
                100                 105                 110

<210> SEQ ID NO 18
<211> LENGTH: 116
<212> TYPE: PRT
<213> ORGANISM: Mus musculus
<220> FEATURE:
<223> OTHER INFORMATION: VH mAb719

<400> SEQUENCE: 18

Glu Val Lys Leu Val Glu Ser Gly Gly Gly Leu Val Lys Pro Gly Gly
1               5                   10                  15

Ser Leu Lys Leu Ser Cys Thr Ala Ser Gly Phe Ser Phe Ser Ser His
            20                  25                  30

Leu Met Ser Trp Val Arg Gln Thr Pro Glu Lys Arg Leu Glu Trp Val
        35                  40                  45

Ala Ala Ile Ser Gly Gly Gly Ala Asp Thr Tyr Tyr Pro Asp Ser Val
50                  55                  60

Lys Gly Arg Phe Thr Ile Ser Arg Asp Asn Ala Lys Asn Thr Leu Tyr
65                  70                  75                  80
```

Leu Gln Met Arg Ser Leu Arg Ser Glu Asp Thr Ala Leu Tyr Tyr Cys
                85                  90                  95

Thr Arg Gln Ile Leu Ala Phe Asp Ser Trp Gly Gln Gly Thr Thr Leu
            100                 105                 110

Thr Val Ser Ser
        115

<210> SEQ ID NO 19
<211> LENGTH: 107
<212> TYPE: PRT
<213> ORGANISM: Mus musculus
<220> FEATURE:
<223> OTHER INFORMATION: VL mAb719

<400> SEQUENCE: 19

Asp Ile Gln Met Asn Gln Ser Pro Ser Ser Leu Ser Val Ser Leu Gly
1               5                   10                  15

Asp Thr Ile Thr Ile Thr Cys His Ala Ser Gln Asn Ile Tyr Val Trp
            20                  25                  30

Leu Asn Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Gly Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys
            100                 105

<210> SEQ ID NO 20
<211> LENGTH: 118
<212> TYPE: PRT
<213> ORGANISM: Artificial Sequence
<220> FEATURE:
<223> OTHER INFORMATION: VH mAb709 VH.1

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Gly Asn Tyr Leu Phe Ala Tyr Trp Gly Gln Gly Thr
            100                 105                 110

Leu Val Thr Val Ser Ser
        115

<210> SEQ ID NO 21
<211> LENGTH: 118
<212> TYPE: PRT

<213> ORGANISM: Artificial Sequence
<220> FEATURE:
<223> OTHER INFORMATION: VH mAb709 VH.1A

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gln Gly Gly Asn Tyr Leu Phe Ala Tyr Trp Gly Gln Gly Thr
            100                 105                 110

Leu Val Thr Val Ser Ser
        115
```

<210> SEQ ID NO 22
<211> LENGTH: 118
<212> TYPE: PRT
<213> ORGANISM: Artificial Sequence
<220> FEATURE:
<223> OTHER INFORMATION: VH mAb709 VH.1B

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Arg Leu Glu Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gln Gly Gly Asn Tyr Leu Phe Ala Tyr Trp Gly Gln Gly Thr
            100                 105                 110

Leu Val Thr Val Ser Ser
        115
```

<210> SEQ ID NO 23
<211> LENGTH: 107
<212> TYPE: PRT
<213> ORGANISM: Artificial Sequence
<220> FEATURE:
<223> OTHER INFORMATION: VK mAb709 VK.1A

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Val
            20                  25                  30
```

```
Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys
                100                 105

<210> SEQ ID NO 24
<211> LENGTH: 107
<212> TYPE: PRT
<213> ORGANISM: Artificial Sequence
<220> FEATURE:
<223> OTHER INFORMATION: VK mAb709 VK.1B

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Val
                20                  25                  30

Val Ala Trp Tyr Gln Gln Lys Pro Gly Lys Ala Pro Lys Leu Leu Ile
        35                  40                  45

Ser Trp Ala Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys
                100                 105

<210> SEQ ID NO 25
<211> LENGTH: 107
<212> TYPE: PRT
<213> ORGANISM: Artificial Sequence
<220> FEATURE:
<223> OTHER INFORMATION: VK mAb709 VK.1C

<400> SEQUENCE: 25

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Val
                20                  25                  30

Val Ala Trp Tyr Gln Gln Lys Pro Gly Lys Ala Pro Lys Val Leu Ile
        35                  40                  45

Ser Trp Ala Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys
                100                 105
```

-continued

```
<210> SEQ ID NO 26
<211> LENGTH: 107
<212> TYPE: PRT
<213> ORGANISM: Artificial Sequence
<220> FEATURE:
<223> OTHER INFORMATION: VK mAb709 VK.1D

<400> SEQUENCE: 26

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Val
            20                  25                  30

Val Ala Trp Tyr Gln Gln Lys Pro Gly Lys Ala Pro Lys Val Leu Ile
        35                  40                  45

Ser Trp Ala Ser Thr Arg His Thr Gly Val Pro Ser Arg Phe Thr Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: VK mAb709 VK.1E

<400> SEQUENCE: 27

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Val
            20                  25                  30

Val Ala Trp Tyr Gln Gln Lys Pro Gly Lys Ser Leu Lys Val Leu Ile
        35                  40                  45

Ser Trp Ala Ser Thr Arg His Thr Gly Val Pro Ser Arg Phe Thr Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys
            100                 105

<210> SEQ ID NO 28
<211> LENGTH: 330
<212> TYPE: PRT
<213> ORGANISM: Homo sapiens

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
                50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 107
<212> TYPE: PRT
<213> ORGANISM: Homo sapiens

<400> SEQUENCE: 29

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
                 35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95
```

```
Pro Val Thr Lys Ser Phe Asn Arg Gly Glu Cys
            100                 105
```

<210> SEQ ID NO 30
<211> LENGTH: 121
<212> TYPE: PRT
<213> ORGANISM: Artificial Sequence
<220> FEATURE:
<223> OTHER INFORMATION: VH mAb713 VH.1

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Tyr Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Arg Gly Gly Ser Ser His Val Asn Val Met Asp Tyr Trp Gly
            100                 105                 110

Gln Gly Thr Thr Val Thr Val Ser Ser
        115                 120
```

<210> SEQ ID NO 31
<211> LENGTH: 121
<212> TYPE: PRT
<213> ORGANISM: Artificial Sequence
<220> FEATURE:
<223> OTHER INFORMATION: VH mAb713 VH.1A

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Tyr Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Lys Arg Gly Gly Ser Ser His Val Asn Val Met Asp Tyr Trp Gly
            100                 105                 110

Gln Gly Thr Thr Val Thr Val Ser Ser
        115                 120
```

<210> SEQ ID NO 32
<211> LENGTH: 121
<212> TYPE: PRT
<213> ORGANISM: Artificial Sequence
<220> FEATURE:
<223> OTHER INFORMATION: VH mAb713 VH.1B

```
<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Tyr Thr Ile Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Lys Arg Gly Gly Ser Ser His Val Asn Val Met Asp Tyr Trp Gly
            100                 105                 110

Gln Gly Thr Thr Val Thr Val Ser Ser
        115                 120

<210> SEQ ID NO 33
<211> LENGTH: 121
<212> TYPE: PRT
<213> ORGANISM: Artificial Sequence
<220> FEATURE:
<223> OTHER INFORMATION: VH mAb713 VH.1C

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Tyr Thr Ile Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Lys Arg Gly Gly Ser Ser His Val Asn Val Met Asp Tyr Trp Gly
            100                 105                 110

Gln Gly Thr Thr Val Thr Val Ser Ser
        115                 120

<210> SEQ ID NO 34
<211> LENGTH: 107
<212> TYPE: PRT
<213> ORGANISM: Artificial Sequence
<220> FEATURE:
<223> OTHER INFORMATION: VK mAb713 VK.1

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45
```

-continued

Tyr Gly Ala Thr Ser Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Trp Ser Pro Pro Tyr
                85                  90                  95

Thr Phe Gly Gly Gly Thr Lys Val Glu Ile Lys
            100                 105

<210> SEQ ID NO 35
<211> LENGTH: 107
<212> TYPE: PRT
<213> ORGANISM: Artificial Sequence
<220> FEATURE:
<223> OTHER INFORMATION: VK mAb713 VK.1A

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Ser Pro Pro Tyr
                85                  90                  95

Thr Phe Gly Gly Gly Thr Lys Val Glu Ile Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: VK mAb713 VK.1B

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Ser Pro Pro Tyr
                85                  90                  95

Thr Phe Gly Gly Gly Thr Lys Val Glu Ile Lys
            100                 105

<210> SEQ ID NO 37
<211> LENGTH: 107
<212> TYPE: PRT
<213> ORGANISM: Artificial Sequence

```
<220> FEATURE:
<223> OTHER INFORMATION: VK mAb713 VK.1C

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Gln Gln Tyr Trp Ser Pro Pro Tyr
            85                  90                  95

Thr Phe Gly Gly Gly Thr Lys Val Glu Ile Lys
        100                 105

<210> SEQ ID NO 38
<211> LENGTH: 122
<212> TYPE: PRT
<213> ORGANISM: Artificial Sequence
<220> FEATURE:
<223> OTHER INFORMATION: VH mAb703 VH.1A

<400> SEQUENCE: 38

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Thr Gly
            20                  25                  30

Tyr Tyr Trp Asn Trp Ile Arg Gln Pro Pro Gly Lys Gly Leu Glu Trp
        35                  40                  45

Ile Gly Tyr Met Ser Tyr Asp Gly Asn Asn Asn Tyr Asn Pro Ser Leu
50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Asp Arg Gly Thr Thr Ile Leu Gly Gly Thr Met Asp Tyr Trp
            100                 105                 110

Gly Gln Gly Thr Thr Val Thr Val Ser Ser
        115                 120

<210> SEQ ID NO 39
<211> LENGTH: 122
<212> TYPE: PRT
<213> ORGANISM: Artificial Sequence
<220> FEATURE:
<223> OTHER INFORMATION: VH mAb703 VH.1B

<400> SEQUENCE: 39

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Thr Gly
            20                  25                  30

Tyr Tyr Trp Asn Trp Ile Arg Gln Pro Pro Gly Lys Gly Leu Glu Trp
        35                  40                  45
```

```
Ile Gly Tyr Met Ser Tyr Asp Gly Asn Asn Asn Tyr Asn Pro Ser Leu
        50                  55                  60

Lys Asn Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Asp Arg Gly Thr Thr Ile Leu Gly Gly Thr Met Asp Tyr Trp
                100                 105                 110

Gly Gln Gly Thr Thr Val Thr Val Ser Ser
            115                 120

<210> SEQ ID NO 40
<211> LENGTH: 122
<212> TYPE: PRT
<213> ORGANISM: Artificial Sequence
<220> FEATURE:
<223> OTHER INFORMATION: VH mAb703 VH.1C

<400> SEQUENCE: 40

Glu Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser Thr Gly
                20                  25                  30

Tyr Tyr Trp Asn Trp Ile Arg Gln Pro Pro Gly Lys Gly Leu Glu Trp
            35                  40                  45

Met Gly Tyr Met Ser Tyr Asp Gly Asn Asn Asn Tyr Asn Pro Ser Leu
    50                  55                  60

Lys Asn Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Asp Arg Gly Thr Thr Ile Leu Gly Gly Thr Met Asp Tyr Trp
                100                 105                 110

Gly Gln Gly Thr Thr Val Thr Val Ser Ser
            115                 120

<210> SEQ ID NO 41
<211> LENGTH: 122
<212> TYPE: PRT
<213> ORGANISM: Artificial Sequence
<220> FEATURE:
<223> OTHER INFORMATION: VH mAb703 VH.1D

<400> SEQUENCE: 41

Glu Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr Thr Gly
                20                  25                  30

Tyr Tyr Trp Asn Trp Ile Arg Gln Pro Pro Gly Lys Gly Leu Glu Trp
            35                  40                  45

Met Gly Tyr Met Ser Tyr Asp Gly Asn Asn Asn Tyr Asn Pro Ser Leu
    50                  55                  60

Lys Asn Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Asp Arg Gly Thr Thr Ile Leu Gly Gly Thr Met Asp Tyr Trp
                100                 105                 110
```

```
Gly Gln Gly Thr Thr Val Thr Val Ser Ser
        115                 120

<210> SEQ ID NO 42
<211> LENGTH: 122
<212> TYPE: PRT
<213> ORGANISM: Artificial Sequence
<220> FEATURE:
<223> OTHER INFORMATION: VH mAb703 VH.1E

<400> SEQUENCE: 42

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Thr Gly
            20                  25                  30

Tyr Tyr Trp Asn Trp Ile Arg Gln Pro Pro Gly Lys Lys Leu Glu Trp
        35                  40                  45

Met Gly Tyr Met Ser Tyr Asp Gly Asn Asn Tyr Asn Pro Ser Leu
    50                  55                  60

Lys Asn Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Asp Arg Gly Thr Thr Ile Leu Gly Thr Met Asp Tyr Trp
            100                 105                 110

Gly Gln Gly Thr Thr Val Thr Val Ser Ser
        115                 120

<210> SEQ ID NO 43
<211> LENGTH: 107
<212> TYPE: PRT
<213> ORGANISM: Artificial Sequence
<220> FEATURE:
<223> OTHER INFORMATION: VK mAb703 VK.1

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Phe Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gly Gly Thr Lys Val Glu Ile Lys
            100                 105

<210> SEQ ID NO 44
<211> LENGTH: 107
<212> TYPE: PRT
<213> ORGANISM: Artificial Sequence
<220> FEATURE:
<223> OTHER INFORMATION: VK mAb703 VK.1A

<400> SEQUENCE: 44
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Phe Tyr Arg Tyr Thr Gly Val Pro Ser Arg Phe Ser Gly
    50                  55                  60

Ser Gly Tyr Gly Thr Asp Phe Thr Leu Thr Ile Ser Ser Leu Gln Pro
65              70                  75                  80

Glu Asp Phe Ala Thr Tyr Tyr Cys Gln Gln Asp Tyr Ser Ser Pro Trp
                85                  90                  95

Thr Phe Gly Gly Gly Thr Lys Val Glu Ile Lys
                100                 105

<210> SEQ ID NO 45
<211> LENGTH: 107
<212> TYPE: PRT
<213> ORGANISM: Artificial Sequence
<220> FEATURE:
<223> OTHER INFORMATION: VK mAb703 VK.1B

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Phe Tyr Arg Tyr Thr Gly Val Pro Asp Arg Phe Ser Gly
    50                  55                  60

Ser Gly Tyr Gly Thr Asp Phe Thr Leu Thr Ile Ser Ser Leu Gln Pro
65              70                  75                  80

Glu Asp Phe Ala Thr Tyr Tyr Cys Gln Gln Asp Tyr Ser Ser Pro Trp
                85                  90                  95

Thr Phe Gly Gly Gly Thr Lys Val Glu Ile Lys
                100                 105

<210> SEQ ID NO 46
<211> LENGTH: 107
<212> TYPE: PRT
<213> ORGANISM: Artificial Sequence
<220> FEATURE:
<223> OTHER INFORMATION: VK mAb703 VK.1C

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ser Pro Lys Leu Leu Ile
        35                  40                  45

Tyr Tyr Ala Phe Tyr Arg Tyr Thr Gly Val Pro Asp Arg Phe Ser Gly
    50                  55                  60

Ser Gly Tyr Gly Thr Asp Phe Thr Leu Thr Ile Ser Ser Leu Gln Pro
65              70                  75                  80

Glu Asp Phe Ala Thr Tyr Phe Cys Gln Gln Asp Tyr Ser Ser Pro Trp
                85                  90                  95
```

```
Thr Phe Gly Gly Gly Thr Lys Val Glu Ile Lys
            100                 105
```

<210> SEQ ID NO 47
<211> LENGTH: 107
<212> TYPE: PRT
<213> ORGANISM: Artificial Sequence
<220> FEATURE:
<223> OTHER INFORMATION: VK mAb703 VK.1D

<400> SEQUENCE: 47

```
Ser Ile Val Met Thr Gln Ser Pro Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ser Pro Lys Leu Leu Ile
        35                  40                  45

Tyr Tyr Ala Phe Tyr Arg Tyr Thr Gly Val Pro Asp Arg Phe Thr Gly
50                  55                  60

Ser Gly Tyr Gly Thr Asp Phe Thr Leu Thr Ile Ser Ser Leu Gln Pro
65                  70                  75                  80

Glu Asp Phe Ala Thr Tyr Phe Cys Gln Gln Asp Tyr Ser Ser Pro Trp
                85                  90                  95

Thr Phe Gly Gly Gly Thr Lys Val Glu Ile Lys
            100                 105
```

<210> SEQ ID NO 48
<211> LENGTH: 116
<212> TYPE: PRT
<213> ORGANISM: Artificial Sequence
<220> FEATURE:
<223> OTHER INFORMATION: VH mAb719 VH.1

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Leu Met Ser Trp Val Arg Gln Ala Pro Gly Lys Gly Leu Glu Trp Val
        35                  40                  45

Ser Ala Ile Ser Gly Gly Gly Ala Asp Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ile Leu Ala Phe Asp Ser Trp Gly Gln Gly Thr Thr Val
            100                 105                 110

Thr Val Ser Ser
        115
```

<210> SEQ ID NO 49
<211> LENGTH: 116
<212> TYPE: PRT
<213> ORGANISM: Artificial Sequence
<220> FEATURE:
<223> OTHER INFORMATION: VH mAb719 VH.1A

<400> SEQUENCE: 49

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Leu Met Ser Trp Val Arg Gln Ala Pro Gly Lys Gly Leu Glu Trp Val
        35                  40                  45

Ser Ala Ile Ser Gly Gly Gly Ala Asp Thr Tyr Tyr Pro Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Ile Leu Ala Phe Asp Ser Trp Gly Gln Gly Thr Thr Val
            100                 105                 110

Thr Val Ser Ser
        115
```

<210> SEQ ID NO 50
<211> LENGTH: 116
<212> TYPE: PRT
<213> ORGANISM: Artificial Sequence
<220> FEATURE:
<223> OTHER INFORMATION: VH mAb719 VH.1B

<400> SEQUENCE: 50

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser His
            20                  25                  30

Leu Met Ser Trp Val Arg Gln Ala Pro Gly Lys Gly Leu Glu Trp Val
        35                  40                  45

Ser Ala Ile Ser Gly Gly Gly Ala Asp Thr Tyr Tyr Pro Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Ile Leu Ala Phe Asp Ser Trp Gly Gln Gly Thr Thr Val
            100                 105                 110

Thr Val Ser Ser
        115
```

<210> SEQ ID NO 51
<211> LENGTH: 116
<212> TYPE: PRT
<213> ORGANISM: Artificial Sequence
<220> FEATURE:
<223> OTHER INFORMATION: VH mAb719 VH.1C

<400> SEQUENCE: 51

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser His
            20                  25                  30

Leu Met Ser Trp Val Arg Gln Ala Pro Gly Lys Gly Leu Glu Trp Val
        35                  40                  45

Ala Ala Ile Ser Gly Gly Gly Ala Asp Thr Tyr Tyr Pro Asp Ser Val
50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gln Ile Leu Ala Phe Asp Ser Trp Gly Gln Gly Thr Thr Val
            100                 105                 110

Thr Val Ser Ser
        115

<210> SEQ ID NO 52
<211> LENGTH: 116
<212> TYPE: PRT
<213> ORGANISM: Artificial Sequence
<220> FEATURE:
<223> OTHER INFORMATION: VH mAb719 VH.1D

<400> SEQUENCE: 52

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Phe Ser Ser His
             20                  25                  30

Leu Met Ser Trp Val Arg Gln Ala Pro Gly Lys Arg Leu Glu Trp Val
         35                  40                  45

Ala Ala Ile Ser Gly Gly Gly Ala Asp Thr Tyr Tyr Pro Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gln Ile Leu Ala Phe Asp Ser Trp Gly Gln Gly Thr Thr Val
            100                 105                 110

Thr Val Ser Ser
        115

<210> SEQ ID NO 53
<211> LENGTH: 116
<212> TYPE: PRT
<213> ORGANISM: Artificial Sequence
<220> FEATURE:
<223> OTHER INFORMATION: VH mAb719 VH.1E

<400> SEQUENCE: 53

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Phe Ser Ser His
             20                  25                  30

Leu Met Ser Trp Val Arg Gln Ala Pro Gly Lys Gly Leu Glu Trp Val
         35                  40                  45

Ala Ala Ile Ser Gly Gly Gly Ala Asp Thr Tyr Tyr Pro Ala Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gln Ile Leu Ala Phe Asp Ala Trp Gly Gln Gly Thr Thr Val
            100                 105                 110

Thr Val Ser Ser
```

```
            115

<210> SEQ ID NO 54
<211> LENGTH: 116
<212> TYPE: PRT
<213> ORGANISM: Artificial Sequence
<220> FEATURE:
<223> OTHER INFORMATION: VH mAb719 VH.1F

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser His
            20                  25                  30

Leu Met Ser Trp Val Arg Gln Ala Pro Gly Lys Arg Leu Glu Trp Val
        35                  40                  45

Ala Ala Ile Ser Gly Gly Gly Ala Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Ile Leu Ala Phe Asp Ala Trp Gly Gln Gly Thr Thr Val
            100                 105                 110

Thr Val Ser Ser
            115

<210> SEQ ID NO 55
<211> LENGTH: 107
<212> TYPE: PRT
<213> ORGANISM: Artificial Sequence
<220> FEATURE:
<223> OTHER INFORMATION: VK mAb719 VK.1

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Val Glu Ile Lys
            100                 105

<210> SEQ ID NO 56
<211> LENGTH: 107
<212> TYPE: PRT
<213> ORGANISM: Artificial Sequence
<220> FEATURE:
<223> OTHER INFORMATION: VK mAb719 VK.1A

<400> SEQUENCE: 56

Asp Ile Gln Met Asn Gln Ser Pro Ser Ser Leu Ser Ala Ser Val Gly
1               5                   10                  15
```

```
Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Gln Ser Tyr Pro Trp
                    85                  90                  95

Thr Phe Gly Gly Gly Thr Lys Val Glu Ile Lys
                100                 105

<210> SEQ ID NO 57
<211> LENGTH: 107
<212> TYPE: PRT
<213> ORGANISM: Artificial Sequence
<220> FEATURE:
<223> OTHER INFORMATION: VK mAb719 VK.1B

<400> SEQUENCE: 57

Asp Ile Gln Met Asn Gln Ser Pro Ser Ser Leu Ser Ala Ser Val Gly
 1               5                  10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ile Pro Lys Leu Leu Ile
        35                  40                  45

Tyr Lys Ala Ser Asn Leu His Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Gln Ser Tyr Pro Trp
                    85                  90                  95

Thr Phe Gly Gly Gly Thr Lys Val Glu Ile Lys
                100                 105

<210> SEQ ID NO 58
<211> LENGTH: 665
<212> TYPE: PRT
<213> ORGANISM: Artificial Sequence
<220> FEATURE:
<223> OTHER INFORMATION: human LAG-3 /Fc fusion protein

<400> SEQUENCE: 58

Leu Gln Pro Gly Ala Glu Val Pro Val Val Trp Ala Gln Glu Gly Ala
 1               5                  10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
 50                  55                  60

Ala Ala Pro Ser Ser Trp Gly Pro Arg Pro Arg Arg Tyr Thr Val Leu
 65                  70                  75                  80

Ser Val Gly Pro Gly Gly Leu Arg Ser Gly Arg Leu Pro Leu Gln Pro
                    85                  90                  95

Arg Val Gln Leu Asp Glu Arg Gly Arg Gln Arg Gly Asp Phe Ser Leu
```

```
                100                 105                 110
Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
        130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
    290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Ile Glu Gly Arg
            420                 425                 430

Met Asp Pro Lys Ser Cys Asp Lys Thr His Thr Cys Pro Pro Cys Pro
        435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525
```

```
Gln Asp Trp Leu Asn Gly Lys Glu Tyr Lys Cys Lys Val Ser Asn Lys
            530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Glu Glu Met
                565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
        595                 600                 605

Tyr Lys Thr Thr Pro Pro Val Leu Asp Ser Asp Gly Ser Phe Phe Leu
610                 615                 620

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
                645                 650                 655

Lys Ser Leu Ser Leu Ser Pro Gly Lys
            660                 665

<210> SEQ ID NO 59
<211> LENGTH: 665
<212> TYPE: PRT
<213> ORGANISM: Artificial Sequence
<220> FEATURE:
<223> OTHER INFORMATION: cynomolgus monkey LAG-3 /Fc fusion protein
<220> FEATURE:
<221> NAME/KEY: misc_feature
<222> LOCATION: (52)..(52)
<223> OTHER INFORMATION: Xaa can be any naturally occurring amino acid

<400> SEQUENCE: 59

Pro Gln Pro Gly Ala Glu Ile Ser Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Xaa Ala Pro Gly His Pro Val Pro Gly His Arg Pro
50                  55                  60

Ala Ala Pro Tyr Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
                100                 105                 110

Trp Leu Arg Pro Ala Arg Arg Ala Asp Ala Gly Glu Tyr Arg Ala Thr
            115                 120                 125

Val His Leu Arg Asp Arg Ala Leu Ser Cys Arg Leu Arg Leu Arg Val
130                 135                 140

Gly Gln Ala Ser Met Thr Ala Ser Pro Pro Gly Ser Leu Arg Thr Ser
145                 150                 155                 160

Asp Trp Val Ile Leu Asn Cys Ser Phe Ser Arg Pro Asp Arg Pro Ala
                165                 170                 175

Ser Val His Trp Phe Arg Ser Arg Gly Gln Gly Arg Val Pro Val Gln
                180                 185                 190

Gly Ser Pro His His Leu Ala Glu Ser Phe Leu Phe Leu Pro His
```

-continued

```
                195                 200                 205
    Val Gly Pro Met Asp Ser Gly Leu Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Ala Thr Pro Leu Thr Val Tyr Ala Gly Ala Gly Ser Arg Val
                    245                 250                 255

Glu Leu Pro Cys Arg Leu Pro Pro Ala Val Gly Thr Gln Ser Phe Leu
                260                 265                 270

Thr Ala Lys Trp Ala Pro Pro Gly Gly Gly Pro Asp Leu Leu Val Ala
                275                 280                 285

Gly Asp Asn Gly Asp Phe Thr Leu Arg Leu Glu Asp Val Ser Gln Ala
    290                 295                 300

Gln Ala Gly Thr Tyr Ile Cys His Ile Arg Leu Gln Gly Gln Gln Leu
305                 310                 315                 320

Asn Ala Thr Val Thr Leu Ala Ile Ile Thr Val Thr Pro Lys Ser Phe
                    325                 330                 335

Gly Ser Pro Gly Ser Leu Gly Lys Leu Leu Cys Glu Val Thr Pro Ala
                340                 345                 350

Ser Gly Gln Glu His Phe Val Trp Ser Pro Leu Asn Thr Pro Ser Gln
                355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu His Gln Gly Glu Arg Leu Leu Gly
385                 390                 395                 400

Ala Ala Val Tyr Phe Thr Glu Leu Ser Ser Pro Gly Ala Gln Arg Ser
                    405                 410                 415

Gly Arg Ala Pro Gly Ala Leu Arg Ala Gly His Leu Ile Glu Gly Arg
                420                 425                 430

Met Asp Pro Lys Ser Cys Asp Lys Thr His Thr Cys Pro Pro Cys Pro
                435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                    485                 490                 495

Val Asp Gly Val Glu Val His Asn Ala Lys Thr Lys Pro Arg Glu Glu
                500                 505                 510

Gln Tyr Asn Ser Thr Tyr Arg Val Val Ser Val Leu Thr Val Leu His
                515                 520                 525

Gln Asp Trp Leu Asn Gly Lys Glu Tyr Lys Cys Lys Val Ser Asn Lys
    530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Glu Glu Met
                    565                 570                 575

Thr Lys Asn Gln Val Ser Leu Thr Cys Leu Val Lys Gly Phe Tyr Pro
                580                 585                 590

Ser Asp Ile Ala Val Glu Trp Glu Ser Asn Gly Gln Pro Glu Asn Asn
                595                 600                 605

Tyr Lys Thr Thr Pro Pro Val Leu Asp Ser Asp Gly Ser Phe Phe Leu
    610                 615                 620
```

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
            645                 650                 655

Lys Ser Leu Ser Leu Ser Pro Gly Lys
            660                 665

<210> SEQ ID NO 60
<211> LENGTH: 113
<212> TYPE: PRT
<213> ORGANISM: Mus musculus
<220> FEATURE:
<223> OTHER INFORMATION: VH mAb746  and  VH mAb747

<400> SEQUENCE: 60

Glu Val Gln Leu Gln Gln Ser Gly Ala Glu Leu Val Arg Pro Gly Ala
1               5                   10                  15

Ser Val Lys Leu Ser Cys Thr Ala Ser Asp Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Glu Asn Gly Asn Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Val Tyr Gly Asp Tyr Trp Gly Gln Gly Thr Thr Leu Thr Val Ser
                100                 105                 110

Ser

<210> SEQ ID NO 61
<211> LENGTH: 107
<212> TYPE: PRT
<213> ORGANISM: Mus musculus
<220> FEATURE:
<223> OTHER INFORMATION: VL mAb746

<400> SEQUENCE: 61

Asp Ile Gln Met Thr Gln Ser Pro Ser Ser Leu Ser Ala Ser Leu Gly
1               5                   10                  15

Glu Arg Val Ser Leu Asn Cys Arg Ala Ser Gln Glu Ile Ser Gly Tyr
            20                  25                  30

Leu Ser Trp Leu Gln Gln Lys Ser Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
                85                  90                  95

Thr Phe Gly Ala Gly Thr Lys Leu Glu Leu Lys
                100                 105

<210> SEQ ID NO 62
<211> LENGTH: 107
<212> TYPE: PRT
<213> ORGANISM: Mus musculus
<220> FEATURE:
<223> OTHER INFORMATION: VL mAb747

<400> SEQUENCE: 62

Asp Ile Gln Met Thr Gln Ser Pro Ser Ser Leu Ser Ala Ser Leu Gly
1               5                   10                  15

Glu Arg Val Ser Leu Asn Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Ala Tyr Tyr Cys Leu Gln Tyr Ala Ser Tyr Pro Leu
                85                  90                  95

Thr Phe Gly Ala Gly Thr Lys Leu Glu Leu Lys
            100                 105

<210> SEQ ID NO 63
<211> LENGTH: 116
<212> TYPE: PRT
<213> ORGANISM: Mus musculus
<220> FEATURE:
<223> OTHER INFORMATION: VH mAb742

<400> SEQUENCE: 63

Gln Gly Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Asn Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ile Arg Trp Gly Ser Thr Val Phe Pro Tyr Trp Gly Gln Gly Thr Leu
            100                 105                 110

Val Thr Val Ser
        115

<210> SEQ ID NO 64
<211> LENGTH: 112
<212> TYPE: PRT
<213> ORGANISM: Mus musculus
<220> FEATURE:
<223> OTHER INFORMATION: VL mAb742

<400> SEQUENCE: 64

Asp Gly Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
            20                  25                  30

Asp Gly Phe Thr Tyr Leu Asp Trp Tyr Leu Gln Lys Pro Gly Gln Ser
        35                  40                  45

```
Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Trp Thr Phe Gly Gly Gly Thr Lys Leu Glu Ile Lys
                100                 105                 110

<210> SEQ ID NO 65
<211> LENGTH: 116
<212> TYPE: PRT
<213> ORGANISM: Mus musculus
<220> FEATURE:
<223> OTHER INFORMATION: VH mAb744

<400> SEQUENCE: 65

Gln Val Gln Leu Gln Gln Ser Gly Ala Glu Leu Val Arg Pro Gly Thr
1               5                   10                  15

Ser Val Thr Leu Ser Cys Lys Ala Ser Gly Tyr Thr Phe Thr Asp Tyr
                20                  25                  30

Glu Met His Trp Met Lys Gln Thr Pro Val His Gly Leu Glu Trp Ile
            35                  40                  45

Gly Ala Ile Asp Pro Ala Thr Gly Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Asp Phe Arg Ser Leu Thr Ser Glu Asp Ser Ala Val Tyr Tyr Cys
                85                  90                  95

Ile Arg Trp Gly Thr Thr Val Phe Pro Tyr Trp Gly Gln Gly Thr Leu
                100                 105                 110

Val Thr Val Ser
        115

<210> SEQ ID NO 66
<211> LENGTH: 112
<212> TYPE: PRT
<213> ORGANISM: Mus musculus
<220> FEATURE:
<223> OTHER INFORMATION: VL mAb744

<400> SEQUENCE: 66

Asp Val Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
                20                  25                  30

Asp Gly Phe Thr Tyr Leu Asp Trp Tyr Leu Gln Lys Pro Gly Gln Ser
            35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Trp Thr Phe Gly Gly Gly Thr Lys Leu Glu Ile Lys
                100                 105                 110

<210> SEQ ID NO 67
```

```
<211> LENGTH: 112
<212> TYPE: PRT
<213> ORGANISM: Mus musculus
<220> FEATURE:
<223> OTHER INFORMATION: VH mAb748

<400> SEQUENCE: 67

Glu Val Gln Met Gln Gln Ser Gly Ala Glu Leu Val Arg Pro Gly Ala
1               5                   10                  15

Ser Val Lys Leu Ser Cys Thr Val Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Thr Tyr Phe Asp Tyr Trp Gly Gln Gly Thr Thr Leu Thr Val Ser Ser
            100                 105                 110

<210> SEQ ID NO 68
<211> LENGTH: 112
<212> TYPE: PRT
<213> ORGANISM: Mus musculus
<220> FEATURE:
<223> OTHER INFORMATION: VL mAb748 and VL mAb750

<400> SEQUENCE: 68

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ser His Phe Pro Gln Thr Phe Gly Gly Gly Thr Lys Leu Glu Ile Lys
            100                 105                 110

<210> SEQ ID NO 69
<211> LENGTH: 116
<212> TYPE: PRT
<213> ORGANISM: Mus musculus
<220> FEATURE:
<223> OTHER INFORMATION: VH mAb749

<400> SEQUENCE: 69

Glu Val Gln Leu Gln Gln Ser Gly Ala Glu Leu Val Arg Pro Gly Ala
1               5                   10                  15

Ser Val Lys Val Ser Cys Thr Ala Ser Asp Phe Asn Ile Lys Asp Asp
            20                  25                  30

Tyr Val His Trp Val Lys Gln Arg Pro Glu Gln Gly Leu Glu Trp Ile
        35                  40                  45
```

```
Gly Trp Ile Asp Pro Glu Asn Gly Asp Thr Glu Tyr Ala Ser Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Phe Cys
                 85                  90                  95

Ser Thr Trp Asp Ala Glu Glu Asn Tyr Trp Gly Gln Gly Thr Thr Leu
                100                 105                 110

Ser Val Ser Ser
        115

<210> SEQ ID NO 70
<211> LENGTH: 112
<212> TYPE: PRT
<213> ORGANISM: Mus musculus
<220> FEATURE:
<223> OTHER INFORMATION: VL mAb749

<400> SEQUENCE: 70

Asp Ile Val Leu Thr Gln Ala Ala Pro Ser Val Pro Val Thr Pro Gly
 1               5                  10                  15

Glu Ser Val Ser Ile Ser Cys Arg Ser Ser Lys Ser Leu Leu His Ser
                 20                  25                  30

Asn Gly Asn Thr Tyr Leu Tyr Trp Phe Leu Gln Arg Pro Gly Gln Ser
             35                  40                  45

Pro Gln Val Leu Ile Tyr Arg Met Ser Asn Leu Ala Ser Gly Val Pro
 50                  55                  60

Val Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95

Leu Glu Tyr Pro Phe Thr Phe Gly Ser Gly Thr Lys Leu Glu Ile Lys
                100                 105                 110

<210> SEQ ID NO 71
<211> LENGTH: 116
<212> TYPE: PRT
<213> ORGANISM: Mus musculus
<220> FEATURE:
<223> OTHER INFORMATION: VH mAb750

<400> SEQUENCE: 71

Glu Val Gln Leu Gln Gln Ser Gly Ala Glu Leu Val Arg Pro Gly Ala
 1               5                  10                  15

Ser Val Lys Leu Ser Cys Thr Pro Ser Gly Leu Asn Ile Lys Asp Asp
                 20                  25                  30

Tyr Ile His Trp Val Lys Gln Arg Pro Glu Gln Gly Leu Glu Trp Ile
             35                  40                  45

Gly Trp Ile Asp Pro Glu Asn Gly Asp Thr Glu Tyr Ala Ser Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Ser Ala Val Tyr Tyr Cys
                 85                  90                  95

Cys Thr Ala Asp Tyr Arg Asn Trp Tyr Trp Gly Gln Gly Thr Thr Leu
                100                 105                 110

Thr Val Ser Ser
        115
```

```
<210> SEQ ID NO 72
<211> LENGTH: 113
<212> TYPE: PRT
<213> ORGANISM: Artificial Sequence
<220> FEATURE:
<223> OTHER INFORMATION: VH mAb747 VH.2A

<400> SEQUENCE: 72
```

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Asp
            20                  25                  30

Tyr Met His Trp Val Arg Gln Ala Pro Gly Gln Gly Leu Glu Trp Ile
        35                  40                  45

Gly Trp Ile Val Pro Glu Asn Gly Asn Thr Glu Tyr Ala Ser Lys Phe
    50                  55                  60

Gln Gly Arg Val Thr Ile Thr Ala Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser

```
<210> SEQ ID NO 73
<211> LENGTH: 113
<212> TYPE: PRT
<213> ORGANISM: Artificial Sequence
<220> FEATURE:
<223> OTHER INFORMATION: VH mAb747 VH.2B

<400> SEQUENCE: 73
```

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Asp
            20                  25                  30

Tyr Met His Trp Val Arg Gln Ala Pro Gly Gln Gly Leu Glu Trp Ile
        35                  40                  45

Gly Trp Ile Val Pro Glu Asn Gly Asn Thr Glu Tyr Ala Ser Lys Phe
    50                  55                  60

Gln Gly Lys Ala Thr Ile Thr Ala Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser

```
<210> SEQ ID NO 74
<211> LENGTH: 113
<212> TYPE: PRT
<213> ORGANISM: Artificial Sequence
<220> FEATURE:
<223> OTHER INFORMATION: VH mAb747 VH.1G

<400> SEQUENCE: 74
```

Glu Val Gln Leu Val Gln Ser Gly Ala Glu Val Lys Lys Pro Gly Ala
1               5                   10                  15

```
Thr Val Lys Ile Ser Cys Lys Ala Ser Asp Phe Asn Ile Lys Asp Asp
            20                  25                  30

Tyr Met His Trp Val Gln Gln Ala Pro Gly Lys Gly Leu Glu Trp Ile
        35                  40                  45

Gly Trp Ile Val Pro Glu Asn Gly Asn Thr Glu Tyr Ala Ser Lys Phe
50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser

<210> SEQ ID NO 75
<211> LENGTH: 107
<212> TYPE: PRT
<213> ORGANISM: Artificial Sequence
<220> FEATURE:
<223> OTHER INFORMATION: VK mAb747 VK.1E

<400> SEQUENCE: 75

Asp Ile Gln Met Thr Gln Ser Pro Ser Ser Leu Ser Ala Ser Val Gly
1               5                   10                  15

Asp Arg Val Thr Ile Asn Cys Arg Ala Ser Gln Glu Ile Ser Gly Tyr
            20                  25                  30

Leu Ser Trp Leu Gln Gln Lys Pro Gly Lys Thr Ile Lys Arg Leu Ile
        35                  40                  45

Tyr Ala Ala Ser Thr Leu Asp Ser Gly Val Pro Ser Arg Phe Ser Gly
50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys
            100                 105

<210> SEQ ID NO 76
<211> LENGTH: 107
<212> TYPE: PRT
<213> ORGANISM: Artificial Sequence
<220> FEATURE:
<223> OTHER INFORMATION: VK mAb747 VK.2A

<400> SEQUENCE: 76

Asp Ile Gln Met Thr Gln Ser Pro Ser Ser Leu Ser Ala Ser Val Gly
1               5                   10                  15

Asp Arg Val Thr Ile Asn Cys Arg Ala Ser Gln Glu Ile Ser Gly Tyr
            20                  25                  30

Leu Ser Trp Leu Gln Gln Lys Pro Glu Lys Thr Ile Lys Arg Leu Ile
        35                  40                  45

Tyr Ala Ala Ser Thr Leu Asp Ser Gly Val Pro Ser Arg Phe Ser Gly
50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95
```

```
Thr Phe Gly Gly Gly Thr Lys Val Glu Ile Lys
            100                 105

<210> SEQ ID NO 77
<211> LENGTH: 107
<212> TYPE: PRT
<213> ORGANISM: Artificial Sequence
<220> FEATURE:
<223> OTHER INFORMATION: Vk mAb747 VK.2B

<400> SEQUENCE: 77

Asp Ile Gln Met Thr Gln Ser Pro Ser Leu Ser Ala Ser Val Gly
1               5                   10                  15

Asp Arg Val Thr Ile Asn Cys Arg Ala Ser Gln Glu Ile Ser Gly Tyr
            20                  25                  30

Leu Ser Trp Leu Gln Gln Lys Pro Glu Gly Thr Ile Lys Arg Leu Ile
            35                  40                  45

Tyr Ala Ala Ser Thr Leu Asp Ser Gly Val Pro Ser Arg Phe Ser Gly
        50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys
            100                 105

<210> SEQ ID NO 78
<211> LENGTH: 679
<212> TYPE: PRT
<213> ORGANISM: Artificial Sequence
<220> FEATURE:
<223> OTHER INFORMATION: FIT107-1-2a
      FIT-Ig Polypeptide Chain #1

<400> SEQUENCE: 78

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser His Lys Phe
            20                  25                  30

Met Ser Thr Ser Val Gly Asp Ser Val Thr Ile Thr Cys Lys Ala Ser
            35                  40                  45

Gln Asp Val Asn Thr Val Val Ala Trp Tyr Gln Gln Lys Pro Gly Gln
        50                  55                  60

Ser Leu Lys Val Leu Ile Ser Trp Ala Ser Thr Arg His Thr Gly Val
65                  70                  75                  80

Pro Ala Arg Phe Thr Gly Ser Gly Ser Gly Thr Asp Tyr Thr Leu Thr
                85                  90                  95

Ile Ser Ser Val Gln Ala Glu Asp Leu Ala Leu Tyr Tyr Cys Gln Gln
            100                 105                 110

His Tyr Thr Thr Pro Tyr Thr Phe Gly Gly Gly Thr Gln Leu Glu Ile
            115                 120                 125

Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175
```

-continued

```
Gln Ser Gly Asn Ser Gln Glu Ser Val Thr Gln Asp Ser Lys Asp
                180                 185                 190
Ser Thr Tyr Ser Leu Ser Ser Thr Leu Thr Leu Ser Lys Ala Asp Tyr
            195                 200                 205
Glu Lys His Lys Val Tyr Ala Cys Glu Val Thr His Gln Gly Leu Ser
        210                 215                 220
Ser Pro Val Thr Lys Ser Phe Asn Arg Gly Glu Cys Glu Val Gln Leu
225                 230                 235                 240
Gln Gln Ser Gly Ala Glu Leu Val Arg Pro Gly Ala Ser Val Lys Leu
                245                 250                 255
Ser Cys Thr Ala Ser Asp Phe Asn Ile Lys Asp Asp Tyr Met His Trp
            260                 265                 270
Val Lys Gln Arg Pro Glu Gln Gly Leu Asp Trp Ile Gly Trp Ile Val
        275                 280                 285
Pro Glu Asn Gly Asn Thr Glu Tyr Ala Ser Lys Phe Gln Gly Lys Ala
        290                 295                 300
Thr Ile Thr Ala Asp Thr Ser Ser Asn Thr Ala Tyr Leu Gln Leu Ser
305                 310                 315                 320
Ser Leu Thr Ser Glu Asp Thr Ala Val Tyr Tyr Cys Thr Val Tyr Gly
                325                 330                 335
Asp Tyr Trp Gly Gln Gly Thr Thr Leu Thr Val Ser Ser Ala Ser Thr
            340                 345                 350
Lys Gly Pro Ser Val Phe Pro Leu Ala Pro Ser Ser Lys Ser Thr Ser
        355                 360                 365
Gly Gly Thr Ala Ala Leu Gly Cys Leu Val Lys Asp Tyr Phe Pro Glu
        370                 375                 380
Pro Val Thr Val Ser Trp Asn Ser Gly Ala Leu Thr Ser Gly Val His
385                 390                 395                 400
Thr Phe Pro Ala Val Leu Gln Ser Ser Gly Leu Tyr Ser Leu Ser Ser
                405                 410                 415
Val Val Thr Val Pro Ser Ser Ser Leu Gly Thr Gln Thr Tyr Ile Cys
            420                 425                 430
Asn Val Asn His Lys Pro Ser Asn Thr Lys Val Asp Lys Lys Val Glu
        435                 440                 445
Pro Lys Ser Cys Asp Lys Thr His Thr Cys Pro Pro Cys Pro Ala Pro
450                 455                 460
Glu Ala Ala Gly Gly Pro Ser Val Phe Leu Phe Pro Pro Lys Pro Lys
465                 470                 475                 480
Asp Thr Leu Met Ile Ser Arg Thr Pro Glu Val Thr Cys Val Val Val
                485                 490                 495
Asp Val Ser His Glu Asp Pro Glu Val Lys Phe Asn Trp Tyr Val Asp
            500                 505                 510
Gly Val Glu Val His Asn Ala Lys Thr Lys Pro Arg Glu Glu Gln Tyr
        515                 520                 525
Asn Ser Thr Tyr Arg Val Val Ser Val Leu Thr Val Leu His Gln Asp
        530                 535                 540
Trp Leu Asn Gly Lys Glu Tyr Lys Cys Lys Val Ser Asn Lys Ala Leu
545                 550                 555                 560
Pro Ala Pro Ile Glu Lys Thr Ile Ser Lys Ala Lys Gly Gln Pro Arg
                565                 570                 575
Glu Pro Gln Val Tyr Thr Leu Pro Pro Ser Arg Glu Glu Met Thr Lys
            580                 585                 590
Asn Gln Val Ser Leu Thr Cys Leu Val Lys Gly Phe Tyr Pro Ser Asp
```

-continued

```
                595                 600                 605

Ile Ala Val Glu Trp Glu Ser Asn Gly Gln Pro Glu Asn Asn Tyr Lys
    610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
                660                 665                 670

Leu Ser Leu Ser Pro Gly Lys
        675

<210> SEQ ID NO 79
<211> LENGTH: 22
<212> TYPE: PRT
<213> ORGANISM: Artificial Sequence
<220> FEATURE:
<223> OTHER INFORMATION: signal sequence

<400> SEQUENCE: 79

Met Asp Met Arg Val Pro Ala Gln Leu Leu Gly Leu Leu Leu Leu Trp
1               5                   10                  15

Phe Pro Gly Ser Arg Cys
            20

<210> SEQ ID NO 80
<211> LENGTH: 214
<212> TYPE: PRT
<213> ORGANISM: Artificial Sequence
<220> FEATURE:
<223> OTHER INFORMATION: VL-CL of mAb709

<400> SEQUENCE: 80

Asp Ile Val Met Thr Gln Ser His Lys Phe Met Ser Thr Ser Val Gly
1               5                   10                  15

Asp Ser Val Thr Ile Thr Cys Lys Ala Ser Gln Asp Val Asn Thr Val
                20                  25                  30

Val Ala Trp Tyr Gln Gln Lys Pro Gly Gln Ser Leu Lys Val Leu Ile
            35                  40                  45

Ser Trp Ala Ser Thr Arg His Thr Gly Val Pro Ala Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Tyr
                85                  90                  95

Thr Phe Gly Gly Gly Thr Gln Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 81
<211> LENGTH: 216
<212> TYPE: PRT
<213> ORGANISM: Artificial Sequence
<220> FEATURE:
<223> OTHER INFORMATION: VH-CH1 of mAb746

<400> SEQUENCE: 81

Glu Val Gln Leu Gln Gln Ser Gly Ala Glu Leu Val Arg Pro Gly Ala
1               5                   10                  15

Ser Val Lys Leu Ser Cys Thr Ala Ser Asp Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Glu Asn Gly Asn Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Val Tyr Gly Asp Tyr Trp Gly Gln Gly Thr Thr Leu Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215

<210> SEQ ID NO 82
<211> LENGTH: 227
<212> TYPE: PRT
<213> ORGANISM: Artificial Sequence
<220> FEATURE:
<223> OTHER INFORMATION: hinge-CH2-CH3 of human IgG1

<400> SEQUENCE: 82

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                      75                  80

Arg Val Val Ser Val Leu Thr Val Leu His Gln Asp Trp Leu Asn Gly
                85                      90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
            130                 135             140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 83
<211> LENGTH: 240
<212> TYPE: PRT
<213> ORGANISM: Artificial Sequence
<220> FEATURE:
<223> OTHER INFORMATION: FIT107-1-2a
      FIT-Ig Polypeptide Chain #2

<400> SEQUENCE: 83

Met Glu Phe Gly Leu Ser Trp Leu Phe Leu Val Ala Ile Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
            35                  40                  45

Ser Phe Tyr Thr Met Ser Trp Val Arg Gln Thr Pro Glu Lys Arg Leu
        50                  55                  60

Glu Trp Val Ala Thr Ile Ser Gly Gly Gly Arg Asp Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu His Met Ser Ser Leu Arg Ser Glu Asp Thr Ala Leu
            100                 105                 110

Tyr Tyr Cys Ala Gly Gln Gly Gly Asn Tyr Leu Phe Ala Tyr Trp Gly
            115                 120                 125

Gln Gly Thr Leu Val Thr Val Ser Ala Ala Ser Thr Lys Gly Pro Ser
            130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala

```
                    180                 185                 190
Val Leu Gln Ser Ser Gly Leu Tyr Ser Leu Ser Ser Val Val Thr Val
            195                 200                 205

Pro Ser Ser Leu Gly Thr Gln Thr Tyr Ile Cys Asn Val Asn His
        210                 215                 220

Lys Pro Ser Asn Thr Lys Val Asp Lys Lys Val Glu Pro Lys Ser Cys
225                 230                 235                 240

<210> SEQ ID NO 84
<211> LENGTH: 19
<212> TYPE: PRT
<213> ORGANISM: Artificial Sequence
<220> FEATURE:
<223> OTHER INFORMATION: signal sequence

<400> SEQUENCE: 84

Met Glu Phe Gly Leu Ser Trp Leu Phe Leu Val Ala Ile Leu Lys Gly
1               5                   10                  15

Val Gln Cys

<210> SEQ ID NO 85
<211> LENGTH: 221
<212> TYPE: PRT
<213> ORGANISM: Artificial Sequence
<220> FEATURE:
<223> OTHER INFORMATION: VH-CH1 of murine mAb709

<400> SEQUENCE: 85

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Phe Tyr
            20                  25                  30

Thr Met Ser Trp Val Arg Gln Thr Pro Glu Lys Arg Leu Glu Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu His Met Ser Ser Leu Arg Ser Glu Asp Thr Ala Leu Tyr Tyr Cys
            85                  90                  95

Ala Gly Gln Gly Gly Asn Tyr Leu Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220
```

```
<210> SEQ ID NO 86
<211> LENGTH: 236
<212> TYPE: PRT
<213> ORGANISM: Artificial Sequence
<220> FEATURE:
<223> OTHER INFORMATION: FIT107-1-2a
      FIT-Ig Polypeptide Chain #3

<400> SEQUENCE: 86
```

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Leu Gly Glu Arg Val Ser Leu Asn Cys Arg Ala Ser
        35                  40                  45

Gln Glu Ile Ser Gly Tyr Leu Ser Trp Leu Gln Gln Lys Ser Asp Gly
    50                  55                  60

Thr Ile Lys Arg Leu Ile Tyr Ala Ala Ser Thr Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Ala Asp Tyr Tyr Cys Leu Gln
            100                 105                 110

Tyr Ala Ser Tyr Pro Leu Thr Phe Gly Ala Gly Thr Lys Leu Glu Leu
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

```
<210> SEQ ID NO 87
<211> LENGTH: 214
<212> TYPE: PRT
<213> ORGANISM: Artificial Sequence
<220> FEATURE:
<223> OTHER INFORMATION: VL-CL of murine mAb746

<400> SEQUENCE: 87
```

Asp Ile Gln Met Thr Gln Ser Pro Ser Ser Leu Ser Ala Ser Leu Gly
1               5                   10                  15

Glu Arg Val Ser Leu Asn Cys Arg Ala Ser Gln Glu Ile Ser Gly Tyr
            20                  25                  30

Leu Ser Trp Leu Gln Gln Lys Ser Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 88
<211> LENGTH: 684
<212> TYPE: PRT
<213> ORGANISM: Artificial Sequence
<220> FEATURE:
<223> OTHER INFORMATION: FIT107-1-2b
      FIT-Ig Polypeptide Chain #1

<400> SEQUENCE: 88

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Leu Gly Glu Arg Val Ser Leu Asn Cys Arg Ala Ser
        35                  40                  45

Gln Glu Ile Ser Gly Tyr Leu Ser Trp Leu Gln Gln Lys Ser Asp Gly
    50                  55                  60

Thr Ile Lys Arg Leu Ile Tyr Ala Ala Ser Thr Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Ala Asp Tyr Tyr Cys Leu Gln
            100                 105                 110

Tyr Ala Ser Tyr Pro Leu Thr Phe Gly Ala Gly Thr Lys Leu Glu Leu
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser

```
               210                 215                 220
Ser Pro Val Thr Lys Ser Phe Asn Arg Gly Glu Cys Glu Val Lys Leu
225                 230                 235                 240

Val Glu Ser Gly Gly Gly Leu Val Lys Pro Gly Gly Ser Leu Lys Leu
                    245                 250                 255

Ser Cys Ala Ala Ser Gly Phe Thr Phe Ser Phe Tyr Thr Met Ser Trp
                260                 265                 270

Val Arg Gln Thr Pro Glu Lys Arg Leu Glu Trp Val Ala Thr Ile Ser
            275                 280                 285

Gly Gly Gly Arg Asp Thr Tyr Tyr Pro Asp Ser Val Lys Gly Arg Phe
        290                 295                 300

Thr Ile Ser Arg Asp Asn Ala Lys Asn Thr Leu Tyr Leu His Met Ser
305                 310                 315                 320

Ser Leu Arg Ser Glu Asp Thr Ala Leu Tyr Tyr Cys Ala Gly Gln Gly
                    325                 330                 335

Gly Asn Tyr Leu Phe Ala Tyr Trp Gly Gln Gly Thr Leu Val Thr Val
                340                 345                 350

Ser Ala Ala Ser Thr Lys Gly Pro Ser Val Phe Pro Leu Ala Pro Ser
            355                 360                 365

Ser Lys Ser Thr Ser Gly Gly Thr Ala Ala Leu Gly Cys Leu Val Lys
        370                 375                 380

Asp Tyr Phe Pro Glu Pro Val Thr Val Ser Trp Asn Ser Gly Ala Leu
385                 390                 395                 400

Thr Ser Gly Val His Thr Phe Pro Ala Val Leu Gln Ser Ser Gly Leu
                    405                 410                 415

Tyr Ser Leu Ser Ser Val Val Thr Val Pro Ser Ser Ser Leu Gly Thr
                420                 425                 430

Gln Thr Tyr Ile Cys Asn Val Asn His Lys Pro Ser Asn Thr Lys Val
            435                 440                 445

Asp Lys Lys Val Glu Pro Lys Ser Cys Asp Lys Thr His Thr Cys Pro
450                 455                 460

Pro Cys Pro Ala Pro Glu Ala Ala Gly Gly Pro Ser Val Phe Leu Phe
465                 470                 475                 480

Pro Pro Lys Pro Lys Asp Thr Leu Met Ile Ser Arg Thr Pro Glu Val
                485                 490                 495

Thr Cys Val Val Val Asp Val Ser His Glu Asp Pro Glu Val Lys Phe
            500                 505                 510

Asn Trp Tyr Val Asp Gly Val Glu Val His Asn Ala Lys Thr Lys Pro
        515                 520                 525

Arg Glu Glu Gln Tyr Asn Ser Thr Tyr Arg Val Val Ser Val Leu Thr
    530                 535                 540

Val Leu His Gln Asp Trp Leu Asn Gly Lys Glu Tyr Lys Cys Lys Val
545                 550                 555                 560

Ser Asn Lys Ala Leu Pro Ala Pro Ile Glu Lys Thr Ile Ser Lys Ala
                565                 570                 575

Lys Gly Gln Pro Arg Glu Pro Gln Val Tyr Thr Leu Pro Pro Ser Arg
            580                 585                 590

Glu Glu Met Thr Lys Asn Gln Val Ser Leu Thr Cys Leu Val Lys Gly
        595                 600                 605

Phe Tyr Pro Ser Asp Ile Ala Val Glu Trp Glu Ser Asn Gly Gln Pro
    610                 615                 620

Glu Asn Asn Tyr Lys Thr Thr Pro Pro Val Leu Asp Ser Asp Gly Ser
625                 630                 635                 640
```

```
Phe Phe Leu Tyr Ser Lys Leu Thr Val Asp Lys Ser Arg Trp Gln Gln
            645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
            675                 680

<210> SEQ ID NO 89
<211> LENGTH: 214
<212> TYPE: PRT
<213> ORGANISM: Artificial Sequence
<220> FEATURE:
<223> OTHER INFORMATION: VL-CL of mAb746

<400> SEQUENCE: 89

Asp Ile Gln Met Thr Gln Ser Pro Ser Ser Leu Ser Ala Ser Leu Gly
1               5                   10                  15

Glu Arg Val Ser Leu Asn Cys Arg Ala Ser Gln Glu Ile Ser Gly Tyr
            20                  25                  30

Leu Ser Trp Leu Gln Gln Lys Ser Asp Gly Thr Ile Lys Arg Leu Ile
            35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
            85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 90
<211> LENGTH: 221
<212> TYPE: PRT
<213> ORGANISM: Artificial Sequence
<220> FEATURE:
<223> OTHER INFORMATION: VH-CH1 of mAb709

<400> SEQUENCE: 90

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Phe Tyr
            20                  25                  30

Thr Met Ser Trp Val Arg Gln Thr Pro Glu Lys Arg Leu Glu Trp Val
```

```
                35                  40                  45
Ala Thr Ile Ser Gly Gly Arg Asp Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu His Met Ser Ser Leu Arg Ser Glu Asp Thr Ala Leu Tyr Tyr Cys
                 85                  90                  95

Ala Gly Gln Gly Gly Asn Tyr Leu Phe Ala Tyr Trp Gly Gln Gly Thr
                100                 105                 110

Leu Val Thr Val Ser Ala Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys
            210                 215                 220

<210> SEQ ID NO 91
<211> LENGTH: 235
<212> TYPE: PRT
<213> ORGANISM: Artificial Sequence
<220> FEATURE:
<223> OTHER INFORMATION: FIT107-1-2b FIT-Ig Polypeptide Chain #2

<400> SEQUENCE: 91

Met Glu Phe Gly Leu Ser Trp Leu Phe Leu Val Ala Ile Leu Lys Gly
 1               5                  10                  15

Val Gln Cys Glu Val Gln Leu Gln Gln Ser Gly Ala Glu Leu Val Arg
            20                  25                  30

Pro Gly Ala Ser Val Lys Leu Ser Cys Thr Ala Ser Asp Phe Asn Ile
            35                  40                  45

Lys Asp Asp Tyr Met His Trp Val Lys Gln Arg Pro Glu Gln Gly Leu
 50                  55                  60

Asp Trp Ile Gly Trp Ile Val Pro Glu Asn Gly Asn Thr Glu Tyr Ala
 65                  70                  75                  80

Ser Lys Phe Gln Gly Lys Ala Thr Ile Thr Ala Asp Thr Ser Ser Asn
                 85                  90                  95

Thr Ala Tyr Leu Gln Leu Ser Ser Leu Thr Ser Glu Asp Thr Ala Val
                100                 105                 110

Tyr Tyr Cys Thr Val Tyr Gly Asp Tyr Trp Gly Gln Gly Thr Thr Leu
            115                 120                 125

Thr Val Ser Ser Ala Ser Thr Lys Gly Pro Ser Val Phe Pro Leu Ala
            130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
```

```
              180                 185                 190
Gly Leu Tyr Ser Leu Ser Ser Val Thr Val Pro Ser Ser Leu
            195                 200                 205

Gly Thr Gln Thr Tyr Ile Cys Asn Val Asn His Lys Pro Ser Asn Thr
            210                 215                 220

Lys Val Asp Lys Lys Val Glu Pro Lys Ser Cys
225                 230                 235

<210> SEQ ID NO 92
<211> LENGTH: 216
<212> TYPE: PRT
<213> ORGANISM: Artificial Sequence
<220> FEATURE:
<223> OTHER INFORMATION: VH-CH1 of mAb746

<400> SEQUENCE: 92

Glu Val Gln Leu Gln Gln Ser Gly Ala Glu Leu Val Arg Pro Gly Ala
1               5                   10                  15

Ser Val Lys Leu Ser Cys Thr Ala Ser Asp Phe Asn Ile Lys Asp Asp
                20                  25                  30

Tyr Met His Trp Val Lys Gln Arg Pro Glu Gln Gly Leu Asp Trp Ile
            35                  40                  45

Gly Trp Ile Val Pro Glu Asn Gly Asn Thr Glu Tyr Ala Ser Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Val Tyr Gly Asp Tyr Trp Gly Gln Gly Thr Thr Leu Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215

<210> SEQ ID NO 93
<211> LENGTH: 236
<212> TYPE: PRT
<213> ORGANISM: Artificial Sequence
<220> FEATURE:
<223> OTHER INFORMATION: FIT107-1-2b FIT-Ig Polypeptide Chain #3

<400> SEQUENCE: 93

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser His Lys Phe
                20                  25                  30
```

Met Ser Thr Ser Val Gly Asp Ser Val Thr Ile Thr Cys Lys Ala Ser
            35                  40                  45

Gln Asp Val Asn Thr Val Val Ala Trp Tyr Gln Gln Lys Pro Gly Gln
 50                  55                  60

Ser Leu Lys Val Leu Ile Ser Trp Ala Ser Thr Arg His Thr Gly Val
 65                  70                  75                  80

Pro Ala Arg Phe Thr Gly Ser Gly Ser Gly Thr Asp Tyr Thr Leu Thr
                 85                  90                  95

Ile Ser Ser Val Gln Ala Glu Asp Leu Ala Leu Tyr Tyr Cys Gln Gln
                100                 105                 110

His Tyr Thr Thr Pro Tyr Thr Phe Gly Gly Gly Thr Gln Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 94
<211> LENGTH: 214
<212> TYPE: PRT
<213> ORGANISM: Artificial Sequence
<220> FEATURE:
<223> OTHER INFORMATION: VL-CL of mAb709

<400> SEQUENCE: 94

Asp Ile Val Met Thr Gln Ser His Lys Phe Met Ser Thr Ser Val Gly
 1               5                  10                  15

Asp Ser Val Thr Ile Thr Cys Lys Ala Ser Gln Asp Val Asn Thr Val
                20                  25                  30

Val Ala Trp Tyr Gln Gln Lys Pro Gly Gln Ser Leu Lys Val Leu Ile
            35                  40                  45

Ser Trp Ala Ser Thr Arg His Thr Gly Val Pro Ala Arg Phe Thr Gly
 50                  55                  60

Ser Gly Ser Gly Thr Asp Tyr Thr Leu Thr Ile Ser Ser Val Gln Ala
 65                  70                  75                  80

Glu Asp Leu Ala Leu Tyr Tyr Cys Gln Gln His Tyr Thr Thr Pro Tyr
                 85                  90                  95

Thr Phe Gly Gly Gly Thr Gln Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 95
<211> LENGTH: 679
<212> TYPE: PRT
<213> ORGANISM: Artificial Sequence
<220> FEATURE:
<223> OTHER INFORMATION: FIT107-1-5a FIT-Ig Polypeptide Chain #1

<400> SEQUENCE: 95

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Asn Thr Val Val Ala Trp Tyr Gln Gln Lys Pro Gly Lys
    50                  55                  60

Ala Pro Lys Val Leu Ile Ser Trp Ala Ser Thr Arg His Thr Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Glu Val Gln Leu
225                 230                 235                 240

Val Gln Ser Gly Ala Glu Val Lys Lys Pro Gly Ala Ser Val Lys Val
                245                 250                 255

Ser Cys Lys Ala Ser Asp Phe Asn Ile Lys Asp Asp Tyr Met His Trp
            260                 265                 270

Val Arg Gln Ala Pro Gly Gln Gly Leu Glu Trp Ile Gly Trp Ile Val
        275                 280                 285

Pro Glu Asn Gly Asn Thr Glu Tyr Ala Ser Lys Phe Gln Gly Lys Ala
    290                 295                 300
```

```
Thr Ile Thr Ala Asp Thr Ser Ile Asn Thr Ala Tyr Met Glu Leu Ser
305                 310                 315                 320

Arg Leu Arg Ser Asp Asp Thr Ala Val Tyr Tyr Cys Thr Val Tyr Gly
            325                 330                 335

Asp Tyr Trp Gly Gln Gly Thr Thr Val Thr Val Ser Ser Ala Ser Thr
        340                 345                 350

Lys Gly Pro Ser Val Phe Pro Leu Ala Pro Ser Ser Lys Ser Thr Ser
    355                 360                 365

Gly Gly Thr Ala Ala Leu Gly Cys Leu Val Lys Asp Tyr Phe Pro Glu
370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
            405                 410                 415

Val Val Thr Val Pro Ser Ser Leu Gly Thr Gln Thr Tyr Ile Cys
        420                 425                 430

Asn Val Asn His Lys Pro Ser Asn Thr Lys Val Asp Lys Lys Val Glu
            435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
            485                 490                 495

Asp Val Ser His Glu Asp Pro Glu Val Lys Phe Asn Trp Tyr Val Asp
        500                 505                 510

Gly Val Glu Val His Asn Ala Lys Thr Lys Pro Arg Glu Glu Gln Tyr
    515                 520                 525

Asn Ser Thr Tyr Arg Val Val Ser Val Leu Thr Val Leu His Gln Asp
530                 535                 540

Trp Leu Asn Gly Lys Glu Tyr Lys Cys Lys Val Ser Asn Lys Ala Leu
545                 550                 555                 560

Pro Ala Pro Ile Glu Lys Thr Ile Ser Lys Ala Lys Gly Gln Pro Arg
            565                 570                 575

Glu Pro Gln Val Tyr Thr Leu Pro Pro Ser Arg Glu Glu Met Thr Lys
        580                 585                 590

Asn Gln Val Ser Leu Thr Cys Leu Val Lys Gly Phe Tyr Pro Ser Asp
    595                 600                 605

Ile Ala Val Glu Trp Glu Ser Asn Gly Gln Pro Glu Asn Asn Tyr Lys
610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
            645                 650                 655

Cys Ser Val Met His Glu Ala Leu His Asn His Tyr Thr Gln Lys Ser
        660                 665                 670

Leu Ser Leu Ser Pro Gly Lys
        675

<210> SEQ ID NO 96
<211> LENGTH: 214
<212> TYPE: PRT
<213> ORGANISM: Artificial Sequence
<220> FEATURE:
<223> OTHER INFORMATION: VL-CL of HumAb709-8
```

<400> SEQUENCE: 96

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Val
            20                  25                  30

Val Ala Trp Tyr Gln Gln Lys Pro Gly Lys Ala Pro Lys Val Leu Ile
        35                  40                  45

Ser Trp Ala Ser Thr Arg His Thr Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 97
<211> LENGTH: 216
<212> TYPE: PRT
<213> ORGANISM: Artificial Sequence
<220> FEATURE:
<223> OTHER INFORMATION: VH-CH1 of mAb
      HumAb747-42

<400> SEQUENCE: 97

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Asp
            20                  25                  30

Tyr Met His Trp Val Arg Gln Ala Pro Gly Gln Gly Leu Glu Trp Ile
        35                  40                  45

Gly Trp Ile Val Pro Glu Asn Gly Asn Thr Glu Tyr Ala Ser Lys Phe
50                  55                  60

Gln Gly Lys Ala Thr Ile Thr Ala Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

```
Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
210                 215

<210> SEQ ID NO 98
<211> LENGTH: 240
<212> TYPE: PRT
<213> ORGANISM: Artificial Sequence
<220> FEATURE:
<223> OTHER INFORMATION: FIT107-1-5a
      FIT-Ig Polypeptide Chain #2

<400> SEQUENCE: 98

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Phe Tyr Thr Met Ser Trp Val Arg Gln Ala Pro Gly Lys Gly Leu
    50                  55                  60

Glu Trp Val Ala Thr Ile Ser Gly Gly Gly Arg Asp Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Gly Gln Gly Gly Asn Tyr Leu Phe Ala Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

<210> SEQ ID NO 99
<211> LENGTH: 221
<212> TYPE: PRT
```

<213> ORGANISM: Artificial Sequence
<220> FEATURE:
<223> OTHER INFORMATION: VH-CH1 of
      HumAb709-8

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gln Gly Gly Asn Tyr Leu Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 100
<211> LENGTH: 236
<212> TYPE: PRT
<213> ORGANISM: Artificial Sequence
<220> FEATURE:
<223> OTHER INFORMATION: FIT107-1-5a
      FIT-Ig Polypeptide Chain #3

<400> SEQUENCE: 100

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Asn Cys Arg Ala Ser
        35                  40                  45

Gln Glu Ile Ser Gly Tyr Leu Ser Trp Leu Gln Gln Lys Pro Glu Gly
    50                  55                  60

Thr Ile Lys Arg Leu Ile Tyr Ala Ala Ser Thr Leu Asp Ser Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Thr Tyr Tyr Cys Leu Gln

```
            100                 105                     110
Tyr Ala Ser Tyr Pro Leu Thr Phe Gly Gly Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 101
<211> LENGTH: 214
<212> TYPE: PRT
<213> ORGANISM: Artificial Sequence
<220> FEATURE:
<223> OTHER INFORMATION: VL-CL of
      HumAb747-42

<400> SEQUENCE: 101

Asp Ile Gln Met Thr Gln Ser Pro Ser Ser Leu Ser Ala Ser Val Gly
1               5                   10                  15

Asp Arg Val Thr Ile Asn Cys Arg Ala Ser Gln Glu Ile Ser Gly Tyr
            20                  25                  30

Leu Ser Trp Leu Gln Gln Lys Pro Glu Gly Thr Ile Lys Arg Leu Ile
        35                  40                  45

Tyr Ala Ala Ser Thr Leu Asp Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

-continued

<210> SEQ ID NO 102
<211> LENGTH: 684
<212> TYPE: PRT
<213> ORGANISM: Artificial Sequence
<220> FEATURE:
<223> OTHER INFORMATION: FIT107-1-5b FIT-Ig Polypeptide Chain #1

<400> SEQUENCE: 102

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Asn Cys Arg Ala Ser
        35                  40                  45

Gln Glu Ile Ser Gly Tyr Leu Ser Trp Leu Gln Gln Lys Pro Glu Gly
    50                  55                  60

Thr Ile Lys Arg Leu Ile Tyr Ala Ala Ser Thr Leu Asp Ser Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Thr Tyr Tyr Cys Leu Gln
            100                 105                 110

Tyr Ala Ser Tyr Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Glu Val Gln Leu
225                 230                 235                 240

Val Glu Ser Gly Gly Gly Leu Val Gln Pro Gly Gly Ser Leu Arg Leu
                245                 250                 255

Ser Cys Ala Ala Ser Gly Phe Thr Phe Ser Phe Tyr Thr Met Ser Trp
            260                 265                 270

Val Arg Gln Ala Pro Gly Lys Gly Leu Glu Trp Val Ala Thr Ile Ser
        275                 280                 285

Gly Gly Gly Arg Asp Thr Tyr Tyr Pro Asp Ser Val Lys Gly Arg Phe
    290                 295                 300

Thr Ile Ser Arg Asp Asn Ala Lys Asn Ser Leu Tyr Leu Gln Met Asn
305                 310                 315                 320

Ser Leu Arg Ala Glu Asp Thr Ala Val Tyr Tyr Cys Ala Gly Gln Gly
                325                 330                 335

Gly Asn Tyr Leu Phe Ala Tyr Trp Gly Gln Gly Thr Leu Val Thr Val
            340                 345                 350

Ser Ser Ala Ser Thr Lys Gly Pro Ser Val Phe Pro Leu Ala Pro Ser
        355                 360                 365
```

Ser Lys Ser Thr Ser Gly Gly Thr Ala Ala Leu Gly Cys Leu Val Lys
    370                 375                 380

Asp Tyr Phe Pro Glu Pro Val Thr Val Ser Trp Asn Ser Gly Ala Leu
385                 390                 395                 400

Thr Ser Gly Val His Thr Phe Pro Ala Val Leu Gln Ser Ser Gly Leu
                405                 410                 415

Tyr Ser Leu Ser Ser Val Val Thr Val Pro Ser Ser Ser Leu Gly Thr
            420                 425                 430

Gln Thr Tyr Ile Cys Asn Val Asn His Lys Pro Ser Asn Thr Lys Val
        435                 440                 445

Asp Lys Lys Val Glu Pro Lys Ser Cys Asp Lys Thr His Thr Cys Pro
    450                 455                 460

Pro Cys Pro Ala Pro Glu Ala Ala Gly Gly Pro Ser Val Phe Leu Phe
465                 470                 475                 480

Pro Pro Lys Pro Lys Asp Thr Leu Met Ile Ser Arg Thr Pro Glu Val
                485                 490                 495

Thr Cys Val Val Val Asp Val Ser His Glu Asp Pro Glu Val Lys Phe
            500                 505                 510

Asn Trp Tyr Val Asp Gly Val Glu Val His Asn Ala Lys Thr Lys Pro
        515                 520                 525

Arg Glu Glu Gln Tyr Asn Ser Thr Tyr Arg Val Val Ser Val Leu Thr
    530                 535                 540

Val Leu His Gln Asp Trp Leu Asn Gly Lys Glu Tyr Lys Cys Lys Val
545                 550                 555                 560

Ser Asn Lys Ala Leu Pro Ala Pro Ile Glu Lys Thr Ile Ser Lys Ala
                565                 570                 575

Lys Gly Gln Pro Arg Glu Pro Gln Val Tyr Thr Leu Pro Pro Ser Arg
            580                 585                 590

Glu Glu Met Thr Lys Asn Gln Val Ser Leu Thr Cys Leu Val Lys Gly
        595                 600                 605

Phe Tyr Pro Ser Asp Ile Ala Val Glu Trp Ser Asn Gly Gln Pro
    610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
        675                 680

<210> SEQ ID NO 103
<211> LENGTH: 214
<212> TYPE: PRT
<213> ORGANISM: Artificial Sequence
<220> FEATURE:
<223> OTHER INFORMATION: VL-CL of
    HumAb747-42

<400> SEQUENCE: 103

Asp Ile Gln Met Thr Gln Ser Pro Ser Ser Leu Ser Ala Ser Val Gly
1               5                   10                  15

Asp Arg Val Thr Ile Asn Cys Arg Ala Ser Gln Glu Ile Ser Gly Tyr
            20                  25                  30

Leu Ser Trp Leu Gln Gln Lys Pro Glu Gly Thr Ile Lys Arg Leu Ile
        35                  40                  45

```
Tyr Ala Ala Ser Thr Leu Asp Ser Gly Val Pro Ser Arg Phe Ser Gly
         50                  55                  60

Ser Arg Ser Gly Ser Asp Tyr Thr Leu Thr Ile Ser Ser Leu Gln Pro
 65                  70                  75                  80

Glu Asp Phe Ala Thr Tyr Tyr Cys Leu Gln Tyr Ala Ser Tyr Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
 130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
    210

<210> SEQ ID NO 104
<211> LENGTH: 221
<212> TYPE: PRT
<213> ORGANISM: Artificial Sequence
<220> FEATURE:
<223> OTHER INFORMATION: VH-CH1 of HumAb709-8

<400> SEQUENCE: 104

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Phe Tyr
             20                  25                  30

Thr Met Ser Trp Val Arg Gln Ala Pro Gly Lys Gly Leu Glu Trp Val
         35                  40                  45

Ala Thr Ile Ser Gly Gly Gly Arg Asp Thr Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Gly Gln Gly Gly Asn Tyr Leu Phe Ala Tyr Trp Gly Gln Gly Thr
             100                 105                 110

Leu Val Thr Val Ser Ser Ala Ser Thr Lys Gly Pro Ser Val Phe Pro
         115                 120                 125

Leu Ala Pro Ser Ser Lys Ser Thr Ser Gly Gly Thr Ala Ala Leu Gly
 130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
             180                 185                 190
```

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
        210                 215                 220

<210> SEQ ID NO 105
<211> LENGTH: 235
<212> TYPE: PRT
<213> ORGANISM: Artificial Sequence
<220> FEATURE:
<223> OTHER INFORMATION: FIT107-1-5b
      FIT-Ig Polypeptide Chain #2

<400> SEQUENCE: 105

Met Glu Phe Gly Leu Ser Trp Leu Phe Leu Val Ala Ile Leu Lys Gly
1               5                   10                  15

Val Gln Cys Glu Val Gln Leu Val Gln Ser Gly Ala Glu Val Lys Lys
            20                  25                  30

Pro Gly Ala Ser Val Lys Val Ser Cys Lys Ala Ser Asp Phe Asn Ile
        35                  40                  45

Lys Asp Asp Tyr Met His Trp Val Arg Gln Ala Pro Gly Gln Gly Leu
50                  55                  60

Glu Trp Ile Gly Trp Ile Val Pro Glu Asn Gly Asn Thr Glu Tyr Ala
65                  70                  75                  80

Ser Lys Phe Gln Gly Lys Ala Thr Ile Thr Ala Asp Thr Ser Ile Asn
                85                  90                  95

Thr Ala Tyr Met Glu Leu Ser Arg Leu Arg Ser Asp Asp Thr Ala Val
            100                 105                 110

Tyr Tyr Cys Thr Val Tyr Gly Asp Tyr Trp Gly Gln Gly Thr Thr Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
        210                 215                 220

Lys Val Asp Lys Lys Val Glu Pro Lys Ser Cys
225                 230                 235

<210> SEQ ID NO 106
<211> LENGTH: 216
<212> TYPE: PRT
<213> ORGANISM: Artificial Sequence
<220> FEATURE:
<223> OTHER INFORMATION: VH-CH1 of
      HumAb747-42

<400> SEQUENCE: 106

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Asp
            20                  25                  30

```
Tyr Met His Trp Val Arg Gln Ala Pro Gly Gln Gly Leu Glu Trp Ile
         35                  40                  45

Gly Trp Ile Val Pro Glu Asn Gly Asn Thr Glu Tyr Ala Ser Lys Phe
 50                  55                  60

Gln Gly Lys Ala Thr Ile Thr Ala Asp Thr Ser Ile Asn Thr Ala Tyr
 65                  70                  75                  80

Met Glu Leu Ser Arg Leu Arg Ser Asp Asp Thr Ala Val Tyr Tyr Cys
                 85                  90                  95

Thr Val Tyr Gly Asp Tyr Trp Gly Gln Gly Thr Thr Val Thr Val Ser
                100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
210                 215

<210> SEQ ID NO 107
<211> LENGTH: 236
<212> TYPE: PRT
<213> ORGANISM: Artificial Sequence
<220> FEATURE:
<223> OTHER INFORMATION: FIT107-1-5b FIT-Ig Polypeptide Chain #3

<400> SEQUENCE: 107

Met Asp Met Arg Val Pro Ala Gln Leu Leu Gly Leu Leu Leu Leu Trp
1                5                  10                  15

Phe Pro Gly Ser Arg Cys Asp Ile Val Met Thr Gln Ser Pro Ser Ser
                 20                  25                  30

Leu Ser Ala Ser Val Gly Asp Arg Val Thr Ile Thr Cys Lys Ala Ser
            35                  40                  45

Gln Asp Val Asn Thr Val Ala Trp Tyr Gln Gln Lys Pro Gly Lys
 50                  55                  60

Ala Pro Lys Val Leu Ile Ser Trp Ala Ser Thr Arg His Thr Gly Val
 65                  70                  75                  80

Pro Ser Arg Phe Ser Gly Ser Gly Ser Gly Thr Asp Tyr Thr Leu Thr
                 85                  90                  95

Ile Ser Ser Leu Gln Pro Glu Asp Phe Ala Thr Tyr Tyr Cys Gln Gln
                100                 105                 110

His Tyr Thr Thr Pro Tyr Thr Phe Gly Gly Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175
```

```
Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 108
<211> LENGTH: 214
<212> TYPE: PRT
<213> ORGANISM: Artificial Sequence
<220> FEATURE:
<223> OTHER INFORMATION: VL-CL of mAb
      HuMAb709-8

<400> SEQUENCE: 108

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Val
            20                  25                  30

Val Ala Trp Tyr Gln Gln Lys Pro Gly Lys Ala Pro Lys Val Leu Ile
        35                  40                  45

Ser Trp Ala Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 109
<211> LENGTH: 113
<212> TYPE: PRT
<213> ORGANISM: Artificial Sequence
<220> FEATURE:
<223> OTHER INFORMATION: VH for huEpi001-VHv1

<400> SEQUENCE: 109

Glu Val Gln Leu Val Gln Ser Gly Ala Glu Val Lys Lys Pro Gly Ala
1               5                   10                  15
```

```
Thr Val Lys Ile Ser Cys Lys Val Ser Asp Phe Asn Ile Lys Asp Asp
            20                  25                  30

Tyr Met His Trp Val Gln Gln Ala Pro Gly Lys Gly Leu Glu Trp Ile
            35                  40                  45

Gly Trp Ile Val Pro Glu Asn Gly Asn Thr Glu Tyr Ala Ser Lys Phe
    50                  55                  60

Gln Gly Arg Val Thr Ile Thr Ala Asp Thr Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser

<210> SEQ ID NO 110
<211> LENGTH: 113
<212> TYPE: PRT
<213> ORGANISM: Artificial Sequence
<220> FEATURE:
<223> OTHER INFORMATION: VH for huEpi001-VHv2

<400> SEQUENCE: 110

Glu Val Gln Leu Val Gln Ser Gly Ala Glu Val Lys Lys Pro Gly Ala
1               5                   10                  15

Thr Val Lys Leu Ser Cys Lys Ala Ser Asp Phe Asn Ile Lys Asp Asp
            20                  25                  30

Tyr Met His Trp Val Gln Gln Ala Pro Gly Lys Gly Leu Glu Trp Ile
            35                  40                  45

Gly Trp Ile Val Pro Glu Asn Gly Asn Thr Glu Tyr Ala Ser Lys Phe
    50                  55                  60

Gln Gly Arg Val Thr Ile Thr Ala Asp Thr Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser

<210> SEQ ID NO 111
<211> LENGTH: 113
<212> TYPE: PRT
<213> ORGANISM: Artificial Sequence
<220> FEATURE:
<223> OTHER INFORMATION: VH for huEpi001-VHv3

<400> SEQUENCE: 111

Glu Val Gln Leu Val Gln Ser Gly Ala Glu Val Lys Lys Pro Gly Ala
1               5                   10                  15

Thr Val Lys Leu Ser Cys Thr Ala Ser Asp Phe Asn Ile Lys Asp Asp
            20                  25                  30

Tyr Met His Trp Val Gln Gln Ala Pro Gly Lys Gly Leu Glu Trp Ile
            35                  40                  45

Gly Trp Ile Val Pro Glu Asn Gly Asn Thr Glu Tyr Ala Ser Lys Phe
    50                  55                  60

Gln Gly Arg Val Thr Ile Thr Ala Asp Thr Ser Thr Asp Thr Ala Tyr
65                  70                  75                  80

Leu Glu Leu Ser Ser Leu Arg Ser Glu Asp Thr Ala Val Tyr Tyr Cys
```

-continued

```
                85                  90                  95
Thr Val Tyr Gly Asp Tyr Trp Gly Gln Gly Thr Thr Val Thr Val Ser
            100                 105                 110
Ser
```

<210> SEQ ID NO 112
<211> LENGTH: 113
<212> TYPE: PRT
<213> ORGANISM: Artificial Sequence
<220> FEATURE:
<223> OTHER INFORMATION: VH for huEpi001-VHv4

<400> SEQUENCE: 112

```
Glu Val Gln Leu Val Gln Ser Gly Ala Glu Val Lys Lys Pro Gly Ala
1               5                   10                  15

Thr Val Lys Leu Ser Cys Thr Ala Ser Asp Phe Asn Ile Lys Asp Asp
            20                  25                  30

Tyr Met His Trp Val Lys Gln Ala Pro Gly Lys Gly Leu Glu Trp Ile
        35                  40                  45

Gly Trp Ile Val Pro Glu Asn Gly Asn Thr Glu Tyr Ala Ser Lys Phe
    50                  55                  60

Gln Gly Arg Ala Thr Ile Thr Ala Asp Thr Ser Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser
```

<210> SEQ ID NO 113
<211> LENGTH: 113
<212> TYPE: PRT
<213> ORGANISM: Artificial Sequence
<220> FEATURE:
<223> OTHER INFORMATION: VH for huEpi001-VHv5

<400> SEQUENCE: 113

```
Glu Val Gln Leu Val Gln Ser Gly Ala Glu Val Lys Lys Pro Gly Ala
1               5                   10                  15

Thr Val Lys Leu Ser Cys Thr Ala Ser Asp Phe Asn Ile Lys Asp Asp
            20                  25                  30

Tyr Met His Trp Val Lys Gln Arg Pro Glu Gln Gly Leu Glu Trp Ile
        35                  40                  45

Gly Trp Ile Val Pro Glu Asn Gly Asn Thr Glu Tyr Ala Ser Lys Phe
    50                  55                  60

Gln Gly Arg Ala Thr Ile Thr Ala Asp Thr Ser Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser
```

<210> SEQ ID NO 114
<211> LENGTH: 113
<212> TYPE: PRT
<213> ORGANISM: Artificial Sequence
<220> FEATURE:

<223> OTHER INFORMATION: VH for huEpi001-VHv6

<400> SEQUENCE: 114

Glu Val Gln Leu Val Gln Ser Gly Ala Glu Val Lys Lys Pro Gly Ala
1               5                   10                  15

Thr Val Lys Leu Ser Cys Thr Ala Ser Asp Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Glu Asn Gly Asn Thr Glu Tyr Ala Ser Lys Phe
    50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser

<210> SEQ ID NO 115
<211> LENGTH: 107
<212> TYPE: PRT
<213> ORGANISM: Artificial Sequence
<220> FEATURE:
<223> OTHER INFORMATION: VL for huEpi001 VLv1

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Ile Lys Ser Leu Ile
        35                  40                  45

Tyr Ala Ala Ser Thr Leu Asp Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gln Gly Thr Lys Leu Glu Ile Lys
            100                 105

<210> SEQ ID NO 116
<211> LENGTH: 107
<212> TYPE: PRT
<213> ORGANISM: Artificial Sequence
<220> FEATURE:
<223> OTHER INFORMATION: VL for huEpi001 VLv2

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Ile Lys Arg Leu Ile
        35                  40                  45

Tyr Ala Ala Ser Thr Leu Asp Ser Gly Val Pro Ser Arg Phe Ser Gly
    50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Ala Ser Tyr Pro Leu
                 85                  90                  95

Thr Phe Gly Gln Gly Thr Lys Leu Glu Ile Lys
            100                 105
```

<210> SEQ ID NO 117
<211> LENGTH: 107
<212> TYPE: PRT
<213> ORGANISM: Artificial Sequence
<220> FEATURE:
<223> OTHER INFORMATION: VL for huEpi001 VLv3

<400> SEQUENCE: 117

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Ser Gly Tyr
                20                  25                  30

Leu Ser Trp Leu Gln Gln Lys Pro Gly Gly Ala Ile Lys Arg Leu Ile
             35                  40                  45

Tyr Ala Ala Ser Thr Leu Asp Ser Gly Val Pro Ser Arg Phe Ser Gly
     50                  55                  60

Ser Arg Ser Gly Ser Asp Tyr Thr Leu Thr Ile Ser Ser Leu Gln Pro
 65                  70                  75                  80

Glu Asp Phe Ala Asp Tyr Tyr Cys Leu Gln Tyr Ala Ser Tyr Pro Leu
                 85                  90                  95

Thr Phe Gly Gln Gly Thr Lys Leu Glu Leu Lys
            100                 105
```

<210> SEQ ID NO 118
<211> LENGTH: 107
<212> TYPE: PRT
<213> ORGANISM: Artificial Sequence
<220> FEATURE:
<223> OTHER INFORMATION: VL for huEpi001 VLv4

<400> SEQUENCE: 118

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Ser Gly Tyr
                20                  25                  30

Leu Ser Trp Leu Gln Gln Lys Pro Gly Gly Ala Ile Lys Arg Leu Ile
             35                  40                  45

Tyr Ala Ala Ser Thr Leu Asp Ser Gly Val Pro Ser Arg Phe Ser Gly
     50                  55                  60

Ser Arg Ser Gly Ser Asp Tyr Thr Leu Thr Ile Ser Ser Leu Glu Pro
 65                  70                  75                  80

Glu Asp Phe Ala Asp Tyr Tyr Cys Leu Gln Tyr Ala Ser Tyr Pro Leu
                 85                  90                  95

Thr Phe Gly Gln Gly Thr Lys Leu Glu Leu Lys
            100                 105
```

<210> SEQ ID NO 119
<211> LENGTH: 113
<212> TYPE: PRT
<213> ORGANISM: Artificial Sequence
<220> FEATURE:
<223> OTHER INFORMATION: VH for Antibody B2-53

<400> SEQUENCE: 119

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Asp
            20                  25                  30

Tyr Met His Trp Val Arg Gln Ala Pro Gly Gln Gly Leu Glu Trp Ile
        35                  40                  45

Gly Trp Ile Val Pro Glu Asn Gly Asn Thr Val Tyr Ala Ser Lys Phe
    50                  55                  60

Gln Gly Arg Val Thr Ile Thr Ala Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser

<210> SEQ ID NO 120
<211> LENGTH: 107
<212> TYPE: PRT
<213> ORGANISM: Artificial Sequence
<220> FEATURE:
<223> OTHER INFORMATION: VL for Antibody B2-53

<400> SEQUENCE: 120

Asp Ile Gln Met Thr Gln Ser Pro Ser Ser Leu Ser Ala Ser Val Gly
1               5                   10                  15

Asp Arg Val Thr Ile Asn Cys Arg Ala Ser Gln Glu Ile Ser Gly Tyr
            20                  25                  30

Leu Ser Trp Leu Gln Gln Lys Pro Glu Gly Thr Ile Lys Arg Leu Ile
        35                  40                  45

Tyr Ala Ala Ser Ala Leu Asp Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys
            100                 105

<210> SEQ ID NO 121
<211> LENGTH: 113
<212> TYPE: PRT
<213> ORGANISM: Artificial Sequence
<220> FEATURE:
<223> OTHER INFORMATION: VH for Antibody B3-21

<400> SEQUENCE: 121

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Asp
            20                  25                  30

Tyr Met His Trp Val Arg Gln Ala Pro Gly Gln Gly Leu Glu Trp Ile
        35                  40                  45

Gly Trp Ile Val Pro Glu Asn Gly Asn Thr Glu Tyr Ala Ser Lys Phe
    50                  55                  60

```
Gln Gly Arg Val Thr Ile Thr Ala Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Thr Val Tyr Gly Asp Val Trp Gly Gln Gly Thr Thr Val Ser
            100                 105                 110

Ser
```

<210> SEQ ID NO 122
<211> LENGTH: 107
<212> TYPE: PRT
<213> ORGANISM: Artificial Sequence
<220> FEATURE:
<223> OTHER INFORMATION: VL for Antibody B3-21

<400> SEQUENCE: 122

```
Asp Ile Gln Met Thr Gln Ser Pro Ser Ser Leu Ser Ala Ser Val Gly
1               5                   10                  15

Asp Arg Val Thr Ile Asn Cys Arg Ala Met Gln Glu Ile Ser Gly Tyr
                20                  25                  30

Leu Ser Trp Leu Gln Gln Lys Pro Glu Gly Thr Ile Lys Arg Leu Ile
            35                  40                  45

Tyr Ala Ala Ser Thr Leu Asp Ser Gly Val Pro Ser Arg Phe Ser Gly
50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Tyr Tyr Pro Leu
                85                  90                  95

Thr Phe Gly Gly Gly Thr Lys Val Glu Ile Lys
            100                 105
```

<210> SEQ ID NO 123
<211> LENGTH: 113
<212> TYPE: PRT
<213> ORGANISM: Artificial Sequence
<220> FEATURE:
<223> OTHER INFORMATION: VH for Antibody B3-43

<400> SEQUENCE: 123

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Asp
                20                  25                  30

Tyr Met His Trp Val Cys Gln Ala Pro Gly Gln Gly Leu Glu Trp Ile
            35                  40                  45

Gly Trp Ile Val Pro Glu Asn Gly Asn Thr Glu Tyr Ala Ser Lys Phe
50                  55                  60

Gln Gly Arg Val Thr Ile Thr Ala Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser
```

<210> SEQ ID NO 124
<211> LENGTH: 107
<212> TYPE: PRT

```
<213> ORGANISM: Artificial Sequence
<220> FEATURE:
<223> OTHER INFORMATION: VL for Antibody B3-43

<400> SEQUENCE: 124

Asp Ile Gln Met Thr Gln Ser Pro Ser Leu Ser Ala Ser Val Gly
1               5                   10                  15

Asp Arg Val Thr Ile Asn Cys Arg Ala Ser Gln Glu Ile Ser Gly Tyr
            20                  25                  30

Leu Ser Trp Leu Gln Gln Lys Pro Glu Gly Thr Ile Lys Arg Leu Ile
        35                  40                  45

Tyr Ala Ala Ser His Leu Asp Ser Gly Val Pro Ser Arg Phe Ser Gly
50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys
            100                 105

<210> SEQ ID NO 125
<211> LENGTH: 113
<212> TYPE: PRT
<213> ORGANISM: Artificial Sequence
<220> FEATURE:
<223> OTHER INFORMATION: VH for Antibody B3-46

<400> SEQUENCE: 125

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Asp
            20                  25                  30

Tyr Met His Trp Val Arg Gln Ala Pro Gly Gln Gly Leu Glu Trp Ile
        35                  40                  45

Gly Trp Ile Val Pro Glu Asn Gly Leu Thr Glu Tyr Ala Ser Lys Phe
50                  55                  60

Gln Gly Arg Val Thr Ile Thr Ala Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Thr Val Tyr Gly Asp Tyr Trp Gly Gln Gly Thr Val Thr Val Ser Ser
            100                 105                 110

Ser

<210> SEQ ID NO 126
<211> LENGTH: 107
<212> TYPE: PRT
<213> ORGANISM: Artificial Sequence
<220> FEATURE:
<223> OTHER INFORMATION: VL for Antibody B3-46

<400> SEQUENCE: 126

Asp Ile Gln Met Thr Gln Ser Pro Ser Leu Ser Ala Ser Val Gly
1               5                   10                  15

Asp Arg Val Thr Ile Asn Cys Arg Ala Ser Gln Glu Ile Ser Gly Tyr
            20                  25                  30

Leu Ser Trp Leu Gln Gln Lys Pro Glu Gly Thr Ile Lys Arg Leu Ile
        35                  40                  45
```

```
Tyr Ala Thr Ser Thr Leu Asp Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys
                100                 105
```

<210> SEQ ID NO 127
<211> LENGTH: 113
<212> TYPE: PRT
<213> ORGANISM: Artificial Sequence
<220> FEATURE:
<223> OTHER INFORMATION: VH for Antibody B3-48

<400> SEQUENCE: 127

```
Glu Val Gln Leu Val Gln Ser Gly Ala Glu Val Lys Lys Pro Gly Ala
1               5                   10                  15

Ser Val Lys Val Ser Cys Lys Ala Ser Asp Phe Ser Ile Lys Asp Asp
                20                  25                  30

Tyr Met His Trp Val Arg Gln Ala Pro Gly Gln Gly Leu Glu Trp Ile
            35                  40                  45

Gly Trp Ile Val Pro Glu Asn Gly Lys Thr Glu Tyr Ala Ser Lys Phe
    50                  55                  60

Gln Gly Arg Val Thr Ile Thr Ala Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Thr Val Tyr Gly Asp Tyr Trp Gly Gln Gly Thr Thr Val Thr Val Ser
                100                 105                 110

Ser
```

<210> SEQ ID NO 128
<211> LENGTH: 107
<212> TYPE: PRT
<213> ORGANISM: Artificial Sequence
<220> FEATURE:
<223> OTHER INFORMATION: VL for Antibody B3-48

<400> SEQUENCE: 128

```
Asp Ile Gln Met Thr Gln Ser Pro Ser Ser Leu Ser Ala Ser Val Gly
1               5                   10                  15

Asp Arg Val Thr Ile Asn Cys Arg Ala Ser Gln Glu Ile Ser Gly Tyr
                20                  25                  30

Leu Ser Trp Leu Gln Gln Lys Pro Glu Gly Thr Ile Lys Arg Leu Ile
            35                  40                  45

Tyr Ala Ala Met Thr Leu Asp Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys
                100                 105
```

<210> SEQ ID NO 129
<211> LENGTH: 113

```
<212> TYPE: PRT
<213> ORGANISM: Artificial Sequence
<220> FEATURE:
<223> OTHER INFORMATION: VH for Antibody B3-69

<400> SEQUENCE: 129
```

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Asp
            20                  25                  30

Tyr Met His Trp Val Arg Gln Ala Pro Gly Gln Gly Leu Glu Trp Ile
        35                  40                  45

Gly Trp Ile Val Pro Glu Asn Gly Asn Thr His Tyr Ala Ser Lys Phe
    50                  55                  60

Gln Gly Arg Val Thr Ile Thr Ala Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Thr Val Tyr Gly Asp Tyr Trp Gly Gln Gly Thr Thr Val Thr Val Ser
                100                 105                 110

Ser

```
<210> SEQ ID NO 130
<211> LENGTH: 107
<212> TYPE: PRT
<213> ORGANISM: Artificial Sequence
<220> FEATURE:
<223> OTHER INFORMATION: VL for Antibody B3-69

<400> SEQUENCE: 130
```

Asp Ile Gln Met Thr Gln Ser Pro Ser Ser Leu Ser Ala Ser Val Gly
1               5                   10                  15

Asp Arg Val Thr Ile Asn Cys Arg Ala Ser Gln Glu Ile Ser Gly Tyr
            20                  25                  30

Leu Ser Trp Leu Gln Gln Lys Pro Glu Gly Thr Ile Lys Arg Leu Ile
        35                  40                  45

Tyr Glu Ala Ser Thr Leu Asp Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys
                100                 105

```
<210> SEQ ID NO 131
<211> LENGTH: 113
<212> TYPE: PRT
<213> ORGANISM: Artificial Sequence
<220> FEATURE:
<223> OTHER INFORMATION: VH for Antibody D1-70

<400> SEQUENCE: 131
```

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Asp
            20                  25                  30

Tyr Met His Trp Val Arg Gln Ala Pro Gly Gln Gly Leu Glu Trp Ile
        35                  40                  45

```
Gly Trp Ile Val Pro Arg Asn Gly Asn Thr Met Tyr Ala Ser Lys Phe
            50                  55                  60

Gln Gly Arg Val Thr Ile Thr Ala Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Thr Val Tyr Gly Asp Tyr Trp Gly Gln Gly Thr Val Thr Val Ser
                100                 105                 110

Ser
```

<210> SEQ ID NO 132
<211> LENGTH: 107
<212> TYPE: PRT
<213> ORGANISM: Artificial Sequence
<220> FEATURE:
<223> OTHER INFORMATION: VL for Antibody D1-70

<400> SEQUENCE: 132

```
Asp Ile Gln Met Thr Gln Ser Pro Ser Ser Leu Ser Ala Ser Val Gly
1               5                   10                  15

Asp Arg Val Thr Ile Asn Cys Arg Ala Ser Gln Glu Ile Ser Gly Tyr
                20                  25                  30

Leu Ser Trp Leu Gln Gln Lys Pro Glu Gly Thr Ile Lys Arg Leu Ile
            35                  40                  45

Tyr Ala Ala Ser Thr Leu Asp Leu Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Leu
                85                  90                  95

Thr Phe Gly Gly Gly Thr Lys Val Glu Ile Lys
                100                 105
```

<210> SEQ ID NO 133
<211> LENGTH: 113
<212> TYPE: PRT
<213> ORGANISM: Artificial Sequence
<220> FEATURE:
<223> OTHER INFORMATION: VH for huEpi001-VHv6(G55A)

<400> SEQUENCE: 133

```
Glu Val Gln Leu Val Gln Ser Gly Ala Glu Val Lys Lys Pro Gly Ala
1               5                   10                  15

Thr Val Lys Leu Ser Cys Thr Ala Ser Asp Phe Asn Ile Lys Asp Asp
                20                  25                  30

Tyr Met His Trp Val Lys Gln Arg Pro Glu Gln Gly Leu Asp Trp Ile
            35                  40                  45

Gly Trp Ile Val Pro Glu Asn Ala Asn Thr Glu Tyr Ala Ser Lys Phe
    50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Val Thr Val Ser
                100                 105                 110

Ser
```

-continued

```
<210> SEQ ID NO 134
<211> LENGTH: 113
<212> TYPE: PRT
<213> ORGANISM: Artificial Sequence
<220> FEATURE:
<223> OTHER INFORMATION: VH for huEpi001-VHv6.1

<400> SEQUENCE: 134

Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Arg Asn Gly Asn Thr Met Tyr Ala Ser Lys Phe
    50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser

<210> SEQ ID NO 135
<211> LENGTH: 113
<212> TYPE: PRT
<213> ORGANISM: Artificial Sequence
<220> FEATURE:
<223> OTHER INFORMATION: VH for huEpi001-VHv6.2

<400> SEQUENCE: 135

Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Glu Asn Gly Asn Thr Val Tyr Ala Ser Lys Phe
    50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser

<210> SEQ ID NO 136
<211> LENGTH: 113
<212> TYPE: PRT
<213> ORGANISM: Artificial Sequence
<220> FEATURE:
<223> OTHER INFORMATION: VH for huEpi001-VHv6.3

<400> SEQUENCE: 136

Glu Val Gln Leu Val Gln Ser Gly Ala Glu Val Lys Lys Pro Gly Ala
1               5                   10                  15
```

```
Thr Val Lys Leu Ser Cys Thr Ala Ser Gly Phe Asn Ile Lys Asp Asp
             20                  25                  30

Tyr Met His Trp Val Lys Gln Arg Pro Glu Gln Gly Leu Asp Trp Ile
         35                  40                  45

Gly Trp Ile Val Pro Arg Asn Gly Asn Thr Val Tyr Ala Ser Lys Phe
     50                  55                  60

Gln Gly Lys Ala Thr Ile Thr Ala Asp Thr Ser Thr Asn Thr Ala Tyr
65                   70                  75                  80

Leu Glu Leu Ser Ser Leu Arg Ser Glu Asp Thr Ala Val Tyr Tyr Cys
                 85                  90                  95

Thr Val Tyr Gly Asp Tyr Trp Gly Gln Gly Thr Thr Val Thr Val Ser
                100                 105                 110

Ser

<210> SEQ ID NO 137
<211> LENGTH: 107
<212> TYPE: PRT
<213> ORGANISM: Artificial Sequence
<220> FEATURE:
<223> OTHER INFORMATION: VL for huEpi001-VLv3.4

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
             20                  25                  30

Leu Ser Trp Leu Gln Gln Lys Pro Gly Gly Ala Ile Lys Arg Leu Ile
         35                  40                  45

Tyr Ala Ala Ser Thr Leu Asp Leu Gly Val Pro Ser Arg Phe Ser Gly
     50                  55                  60

Ser Arg Ser Gly Ser Asp Tyr Thr Leu Thr Ile Ser Ser Leu Gln Pro
65                   70                  75                  80

Glu Asp Phe Ala Asp Tyr Tyr Cys Leu Gln Tyr Ala Ser Tyr Pro Leu
                 85                  90                  95

Thr Phe Gly Gln Gly Thr Lys Leu Glu Leu Lys
                100                 105

<210> SEQ ID NO 138
<211> LENGTH: 107
<212> TYPE: PRT
<213> ORGANISM: Artificial Sequence
<220> FEATURE:
<223> OTHER INFORMATION: VL for huEpi001-VLv3.5

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
             20                  25                  30

Leu Ser Trp Leu Gln Gln Lys Pro Gly Gly Ala Ile Lys Arg Leu Ile
         35                  40                  45

Tyr Ala Ala Ser Ala Leu Asp Ser Gly Val Pro Ser Arg Phe Ser Gly
     50                  55                  60

Ser Arg Ser Gly Ser Asp Tyr Thr Leu Thr Ile Ser Ser Leu Gln Pro
65                   70                  75                  80

Glu Asp Phe Ala Asp Tyr Tyr Cys Leu Gln Tyr Ala Ser Tyr Pro Leu
                 85                  90                  95
```

Thr Phe Gly Gln Gly Thr Lys Leu Glu Leu Lys
            100                 105

<210> SEQ ID NO 139
<211> LENGTH: 107
<212> TYPE: PRT
<213> ORGANISM: Artificial Sequence
<220> FEATURE:
<223> OTHER INFORMATION: VL for huEpi001-VLv3.6

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Gly Ala Ile Lys Arg Leu Ile
        35                  40                  45

Tyr Ala Ala Ser Ala Leu Asp Leu Gly Val Pro Ser Arg Phe Ser Gly
50                  55                  60

Ser Arg Ser Gly Ser Asp Tyr Thr Leu Thr Ile Ser Ser Leu Gln Pro
65                  70                  75                  80

Glu Asp Phe Ala Asp Tyr Tyr Cys Leu Gln Tyr Ala Ser Tyr Pro Leu
                85                  90                  95

Thr Phe Gly Gln Gly Thr Lys Leu Glu Leu Lys
            100                 105

<210> SEQ ID NO 140
<211> LENGTH: 679
<212> TYPE: PRT
<213> ORGANISM: Artificial Sequence
<220> FEATURE:
<223> OTHER INFORMATION: FIT107-1-6a-1
    FIT-Ig Polypeptide Chain #1

<400> SEQUENCE: 140

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Asn Thr Val Ala Trp Tyr Gln Gln Lys Pro Gly Lys
50                  55                  60

Ala Pro Lys Val Leu Ile Ser Trp Ala Ser Thr Arg His Thr Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp

-continued

```
              180                 185                 190
Ser Thr Tyr Ser Leu Ser Ser Thr Leu Thr Leu Ser Lys Ala Asp Tyr
              195                 200                 205
Glu Lys His Lys Val Tyr Ala Cys Glu Val Thr His Gln Gly Leu Ser
              210                 215                 220
Ser Pro Val Thr Lys Ser Phe Asn Arg Gly Glu Cys Glu Val Gln Leu
225                 230                 235                 240
Val Gln Ser Gly Ala Glu Val Lys Lys Pro Gly Ala Thr Val Lys Leu
                  245                 250                 255
Ser Cys Thr Ala Ser Gly Phe Asn Ile Lys Asp Asp Tyr Met His Trp
                  260                 265                 270
Val Lys Gln Arg Pro Glu Gln Gly Leu Asp Trp Ile Gly Trp Ile Val
                  275                 280                 285
Pro Glu Asn Ala Asn Thr Val Tyr Ala Ser Lys Phe Gln Gly Lys Ala
                  290                 295                 300
Thr Ile Thr Ala Asp Thr Ser Thr Asn Thr Ala Tyr Leu Glu Leu Ser
305                 310                 315                 320
Ser Leu Arg Ser Glu Asp Thr Ala Val Tyr Tyr Cys Thr Val Tyr Gly
                  325                 330                 335
Asp Tyr Trp Gly Gln Gly Thr Thr Val Thr Val Ser Ser Ala Ser Thr
                  340                 345                 350
Lys Gly Pro Ser Val Phe Pro Leu Ala Pro Ser Ser Lys Ser Thr Ser
                  355                 360                 365
Gly Gly Thr Ala Ala Leu Gly Cys Leu Val Lys Asp Tyr Phe Pro Glu
                  370                 375                 380
Pro Val Thr Val Ser Trp Asn Ser Gly Ala Leu Thr Ser Gly Val His
385                 390                 395                 400
Thr Phe Pro Ala Val Leu Gln Ser Ser Gly Leu Tyr Ser Leu Ser Ser
                  405                 410                 415
Val Val Thr Val Pro Ser Ser Ser Leu Gly Thr Gln Thr Tyr Ile Cys
                  420                 425                 430
Asn Val Asn His Lys Pro Ser Asn Thr Lys Val Asp Lys Lys Val Glu
                  435                 440                 445
Pro Lys Ser Cys Asp Lys Thr His Thr Cys Pro Pro Cys Pro Ala Pro
                  450                 455                 460
Glu Ala Ala Gly Gly Pro Ser Val Phe Leu Phe Pro Pro Lys Pro Lys
465                 470                 475                 480
Asp Thr Leu Met Ile Ser Arg Thr Pro Glu Val Thr Cys Val Val Val
                  485                 490                 495
Asp Val Ser His Glu Asp Pro Glu Val Lys Phe Asn Trp Tyr Val Asp
                  500                 505                 510
Gly Val Glu Val His Asn Ala Lys Thr Lys Pro Arg Glu Glu Gln Tyr
                  515                 520                 525
Asn Ser Thr Tyr Arg Val Val Ser Val Leu Thr Val Leu His Gln Asp
                  530                 535                 540
Trp Leu Asn Gly Lys Glu Tyr Lys Cys Lys Val Ser Asn Lys Ala Leu
545                 550                 555                 560
Pro Ala Pro Ile Glu Lys Thr Ile Ser Lys Ala Lys Gly Gln Pro Arg
                  565                 570                 575
Glu Pro Gln Val Tyr Thr Leu Pro Pro Ser Arg Glu Glu Met Thr Lys
                  580                 585                 590
Asn Gln Val Ser Leu Thr Cys Leu Val Lys Gly Phe Tyr Pro Ser Asp
                  595                 600                 605
```

```
Ile Ala Val Glu Trp Glu Ser Asn Gly Gln Pro Glu Asn Asn Tyr Lys
        610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
                660                 665                 670

Leu Ser Leu Ser Pro Gly Lys
        675

<210> SEQ ID NO 141
<211> LENGTH: 214
<212> TYPE: PRT
<213> ORGANISM: Artificial Sequence
<220> FEATURE:
<223> OTHER INFORMATION: VL-CL of HumAb709-8

<400> SEQUENCE: 141

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Val
                20                  25                  30

Val Ala Trp Tyr Gln Gln Lys Pro Gly Lys Ala Pro Lys Val Leu Ile
            35                  40                  45

Ser Trp Ala Ser Thr Arg His Thr Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
                145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 142
<211> LENGTH: 216
<212> TYPE: PRT
<213> ORGANISM: Artificial Sequence
<220> FEATURE:
<223> OTHER INFORMATION: VH-CH1 of HumAb747V-67

<400> SEQUENCE: 142

Glu Val Gln Leu Val Gln Ser Gly Ala Glu Val Lys Lys Pro Gly Ala
```

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
            35                  40                  45

Gly Trp Ile Val Pro Glu Asn Ala Asn Thr Val Tyr Ala Ser Lys Phe
        50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys
            210                 215

<210> SEQ ID NO 143
<211> LENGTH: 240
<212> TYPE: PRT
<213> ORGANISM: Artificial Sequence
<220> FEATURE:
<223> OTHER INFORMATION: FIT107-1-6a-1
    FIT-Ig Polypeptide Chain #2

<400> SEQUENCE: 143

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Phe Tyr Thr Met Ser Trp Val Arg Gln Ala Pro Gly Lys Gly Leu
        50                  55                  60

Glu Trp Val Ala Thr Ile Ser Gly Gly Arg Asp Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Gly Gln Gly Gly Asn Tyr Leu Phe Ala Tyr Trp Gly
            115                 120                 125

Gln Gly Thr Leu Val Thr Val Ser Ser Ala Ser Thr Lys Gly Pro Ser
            130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

<210> SEQ ID NO 144
<211> LENGTH: 221
<212> TYPE: PRT
<213> ORGANISM: Artificial Sequence
<220> FEATURE:
<223> OTHER INFORMATION: VH-CH1 of
      HumAb709-8

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Gly Leu Glu Trp Val
            35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gln Gly Gly Asn Tyr Leu Phe Ala Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys
    210                 215                 220

<210> SEQ ID NO 145
<211> LENGTH: 236
<212> TYPE: PRT
<213> ORGANISM: Artificial Sequence
<220> FEATURE:
<223> OTHER INFORMATION: FIT107-1-6a-1
      FIT-Ig Polypeptide Chain #3

<400> SEQUENCE: 145

```
Met Asp Met Arg Val Pro Ala Gln Leu Leu Gly Leu Leu Leu Trp
1               5                   10                  15

Phe Pro Gly Ser Arg Cys Asp Ile Gln Met Thr Gln Ser Pro Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Leu Gln Gln Lys Pro Gly Gly
    50                  55                  60

Ala Ile Lys Arg Leu Ile Tyr Ala Ala Ser Ala Leu Asp Ser Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Asp Tyr Tyr Cys Leu Gln
            100                 105                 110

Tyr Ala Ser Tyr Pro Leu Thr Phe Gly Gln Gly Thr Lys Leu Glu Leu
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 146
<211> LENGTH: 214
<212> TYPE: PRT
<213> ORGANISM: Artificial Sequence
<220> FEATURE:
<223> OTHER INFORMATION: VL-CL of HumAb747V-67

<400> SEQUENCE: 146

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Gly Ala Ile Lys Arg Leu Ile
        35                  40                  45

Tyr Ala Ala Ser Ala Leu Asp Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Asp Tyr Tyr Cys Leu Gln Tyr Ala Ser Tyr Pro Leu
                85                  90                  95

Thr Phe Gly Gln Gly Thr Lys Leu Glu Leu Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 147
<211> LENGTH: 684
<212> TYPE: PRT
<213> ORGANISM: Artificial Sequence
<220> FEATURE:
<223> OTHER INFORMATION: FIT107-1-6b-1 FIT-Ig Polypeptide Chain #1

<400> SEQUENCE: 147

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Leu Gln Gln Lys Pro Gly Gly
    50                  55                  60

Ala Ile Lys Arg Leu Ile Tyr Ala Ala Ser Ala Leu Asp Ser Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Asp Tyr Tyr Cys Leu Gln
            100                 105                 110

Tyr Ala Ser Tyr Pro Leu Thr Phe Gly Gln Gly Thr Lys Leu Glu Leu
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Glu Val Gln Leu
225                 230                 235                 240

Val Glu Ser Gly Gly Gly Leu Val Gln Pro Gly Gly Ser Leu Arg Leu
                245                 250                 255
```

```
Ser Cys Ala Ala Ser Gly Phe Thr Phe Ser Phe Tyr Thr Met Ser Trp
            260                 265                 270

Val Arg Gln Ala Pro Gly Lys Gly Leu Glu Trp Val Ala Thr Ile Ser
        275                 280                 285

Gly Gly Gly Arg Asp Thr Tyr Tyr Pro Asp Ser Val Lys Gly Arg Phe
    290                 295                 300

Thr Ile Ser Arg Asp Asn Ala Lys Asn Ser Leu Tyr Leu Gln Met Asn
305                 310                 315                 320

Ser Leu Arg Ala Glu Asp Thr Ala Val Tyr Tyr Cys Ala Gly Gln Gly
                325                 330                 335

Gly Asn Tyr Leu Phe Ala Tyr Trp Gly Gln Gly Thr Leu Val Thr Val
            340                 345                 350

Ser Ser Ala Ser Thr Lys Gly Pro Ser Val Phe Pro Leu Ala Pro Ser
        355                 360                 365

Ser Lys Ser Thr Ser Gly Gly Thr Ala Ala Leu Gly Cys Leu Val Lys
    370                 375                 380

Asp Tyr Phe Pro Glu Pro Val Thr Val Ser Trp Asn Ser Gly Ala Leu
385                 390                 395                 400

Thr Ser Gly Val His Thr Phe Pro Ala Val Leu Gln Ser Ser Gly Leu
                405                 410                 415

Tyr Ser Leu Ser Ser Val Val Thr Val Pro Ser Ser Ser Leu Gly Thr
            420                 425                 430

Gln Thr Tyr Ile Cys Asn Val Asn His Lys Pro Ser Asn Thr Lys Val
        435                 440                 445

Asp Lys Lys Val Glu Pro Lys Ser Cys Asp Lys Thr His Thr Cys Pro
    450                 455                 460

Pro Cys Pro Ala Pro Glu Ala Ala Gly Gly Pro Ser Val Phe Leu Phe
465                 470                 475                 480

Pro Pro Lys Pro Lys Asp Thr Leu Met Ile Ser Arg Thr Pro Glu Val
                485                 490                 495

Thr Cys Val Val Val Asp Val Ser His Glu Asp Pro Glu Val Lys Phe
            500                 505                 510

Asn Trp Tyr Val Asp Gly Val Glu Val His Asn Ala Lys Thr Lys Pro
        515                 520                 525

Arg Glu Glu Gln Tyr Asn Ser Thr Tyr Arg Val Val Ser Val Leu Thr
    530                 535                 540

Val Leu His Gln Asp Trp Leu Asn Gly Lys Glu Tyr Lys Cys Lys Val
545                 550                 555                 560

Ser Asn Lys Ala Leu Pro Ala Pro Ile Glu Lys Thr Ile Ser Lys Ala
                565                 570                 575

Lys Gly Gln Pro Arg Glu Pro Gln Val Tyr Thr Leu Pro Pro Ser Arg
            580                 585                 590

Glu Glu Met Thr Lys Asn Gln Val Ser Leu Thr Cys Leu Val Lys Gly
        595                 600                 605

Phe Tyr Pro Ser Asp Ile Ala Val Glu Trp Ser Asn Gly Gln Pro
    610                 615                 620

Glu Asn Asn Tyr Lys Thr Thr Pro Val Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
```

<210> SEQ ID NO 148
<211> LENGTH: 214
<212> TYPE: PRT
<213> ORGANISM: Artificial Sequence
<220> FEATURE:
<223> OTHER INFORMATION: VL-CL of HumAb747V-67

<400> SEQUENCE: 148

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Gly Ala Ile Lys Arg Leu Ile
        35                  40                  45

Tyr Ala Ala Ser Ala Leu Asp Ser Gly Val Pro Ser Arg Phe Ser Gly
50                  55                  60

Ser Arg Ser Gly Ser Asp Tyr Thr Leu Thr Ile Ser Ser Leu Gln Pro
65                  70                  75                  80

Glu Asp Phe Ala Asp Tyr Tyr Cys Leu Gln Tyr Ala Ser Tyr Pro Leu
                85                  90                  95

Thr Phe Gly Gln Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 149
<211> LENGTH: 221
<212> TYPE: PRT
<213> ORGANISM: Artificial Sequence
<220> FEATURE:
<223> OTHER INFORMATION: VH-CH1 of HumAb709-8

<400> SEQUENCE: 149

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                 85                  90                  95

Ala Gly Gln Gly Gly Asn Tyr Leu Phe Ala Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys
            210                 215                 220

<210> SEQ ID NO 150
<211> LENGTH: 235
<212> TYPE: PRT
<213> ORGANISM: Artificial Sequence
<220> FEATURE:
<223> OTHER INFORMATION: FIT107-1-6b-1
      FIT-Ig Polypeptide Chain #2

<400> SEQUENCE: 150

Met Glu Phe Gly Leu Ser Trp Leu Phe Leu Val Ala Ile Leu Lys Gly
1               5                   10                  15

Val Gln Cys Glu Val Gln Leu Val Gln Ser Gly Ala Glu Val Lys Lys
            20                  25                  30

Pro Gly Ala Thr Val Lys Leu Ser Cys Thr Ala Ser Gly Phe Asn Ile
            35                  40                  45

Lys Asp Asp Tyr Met His Trp Val Lys Gln Arg Pro Glu Gln Gly Leu
50                  55                  60

Asp Trp Ile Gly Trp Ile Val Pro Glu Asn Ala Asn Thr Val Tyr Ala
65                  70                  75                  80

Ser Lys Phe Gln Gly Lys Ala Thr Ile Thr Ala Asp Thr Ser Thr Asn
                85                  90                  95

Thr Ala Tyr Leu Glu Leu Ser Ser Leu Arg Ser Glu Asp Thr Ala Val
            100                 105                 110

Tyr Tyr Cys Thr Val Tyr Gly Asp Tyr Trp Gly Gln Gly Thr Thr Val
            115                 120                 125

Thr Val Ser Ser Ala Ser Thr Lys Gly Pro Ser Val Phe Pro Leu Ala
            130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220
```

```
Lys Val Asp Lys Lys Val Glu Pro Lys Ser Cys
225                 230                 235
```

<210> SEQ ID NO 151
<211> LENGTH: 216
<212> TYPE: PRT
<213> ORGANISM: Artificial Sequence
<220> FEATURE:
<223> OTHER INFORMATION: VH-CH1 of HumAb747V-67

<400> SEQUENCE: 151

```
Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Glu Asn Ala Asn Thr Val Tyr Ala Ser Lys Phe
    50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215
```

<210> SEQ ID NO 152
<211> LENGTH: 236
<212> TYPE: PRT
<213> ORGANISM: Artificial Sequence
<220> FEATURE:
<223> OTHER INFORMATION: FIT107-1-6b-1
      FIT-Ig Polypeptide Chain #3

<400> SEQUENCE: 152

```
Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Asn Thr Val Val Ala Trp Tyr Gln Gln Lys Pro Gly Lys
    50                  55                  60
```

```
Ala Pro Lys Val Leu Ile Ser Trp Ala Ser Thr Arg His Thr Gly Val
 65                  70                  75                  80

Pro Ser Arg Phe Ser Gly Ser Gly Ser Gly Thr Asp Tyr Thr Leu Thr
                 85                  90                  95

Ile Ser Ser Leu Gln Pro Glu Asp Phe Ala Thr Tyr Tyr Cys Gln Gln
            100                 105                 110

His Tyr Thr Thr Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 153
<211> LENGTH: 214
<212> TYPE: PRT
<213> ORGANISM: Artificial Sequence
<220> FEATURE:
<223> OTHER INFORMATION: VL-CL of HumAb709-8

<400> SEQUENCE: 153

Asp Ile Val Met Thr Gln Ser Pro Ser Leu Ser Ala Ser Val Gly
  1               5                  10                  15

Asp Arg Val Thr Ile Thr Cys Lys Ala Ser Gln Asp Val Asn Thr Val
                 20                  25                  30

Val Ala Trp Tyr Gln Gln Lys Pro Gly Lys Ala Pro Lys Val Leu Ile
             35                  40                  45

Ser Trp Ala Ser Thr Arg His Thr Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln His Tyr Thr Thr Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
            210

<210> SEQ ID NO 154
<211> LENGTH: 679
<212> TYPE: PRT
<213> ORGANISM: Artificial Sequence
<220> FEATURE:
<223> OTHER INFORMATION: FIT107-1-6a-2
      FIT-Ig Polypeptide Chain #1

<400> SEQUENCE: 154

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Asn Thr Val Val Ala Trp Tyr Gln Gln Lys Pro Gly Lys
    50                  55                  60

Ala Pro Lys Val Leu Ile Ser Trp Ala Ser Thr Arg His Thr Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Glu Val Gln Leu
225                 230                 235                 240

Val Gln Ser Gly Ala Glu Val Lys Lys Pro Gly Ala Thr Val Lys Leu
                245                 250                 255

Ser Cys Thr Ala Ser Gly Phe Asn Ile Lys Asp Asp Tyr Met His Trp
            260                 265                 270

Val Lys Gln Arg Pro Glu Gln Gly Leu Asp Trp Ile Gly Trp Ile Val
        275                 280                 285

Pro Arg Asn Ala Asn Thr Val Tyr Ala Ser Lys Phe Gln Gly Lys Ala
    290                 295                 300

Thr Ile Thr Ala Asp Thr Ser Thr Asn Thr Ala Tyr Leu Glu Leu Ser
305                 310                 315                 320

Ser Leu Arg Ser Glu Asp Thr Ala Val Tyr Tyr Cys Thr Val Tyr Gly
                325                 330                 335
```

Asp Tyr Trp Gly Gln Gly Thr Thr Val Thr Val Ser Ser Ala Ser Thr
                    340                 345                 350

Lys Gly Pro Ser Val Phe Pro Leu Ala Pro Ser Ser Lys Ser Thr Ser
            355                 360                 365

Gly Gly Thr Ala Ala Leu Gly Cys Leu Val Lys Asp Tyr Phe Pro Glu
        370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Lys Lys Val Glu
        435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
        515                 520                 525

Asn Ser Thr Tyr Arg Val Val Ser Val Leu Thr Val Leu His Gln Asp
        530                 535                 540

Trp Leu Asn Gly Lys Glu Tyr Lys Cys Lys Val Ser Asn Lys Ala Leu
545                 550                 555                 560

Pro Ala Pro Ile Glu Lys Thr Ile Ser Lys Ala Lys Gly Gln Pro Arg
                565                 570                 575

Glu Pro Gln Val Tyr Thr Leu Pro Pro Ser Arg Glu Glu Met Thr Lys
            580                 585                 590

Asn Gln Val Ser Leu Thr Cys Leu Val Lys Gly Phe Tyr Pro Ser Asp
        595                 600                 605

Ile Ala Val Glu Trp Glu Ser Asn Gly Gln Pro Glu Asn Asn Tyr Lys
        610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro Gly Lys
            675

<210> SEQ ID NO 155
<211> LENGTH: 214
<212> TYPE: PRT
<213> ORGANISM: Artificial Sequence
<220> FEATURE:
<223> OTHER INFORMATION: VL-CL of HumAb709-8

<400> SEQUENCE: 155

Asp Ile Val Met Thr Gln Ser Pro Ser Ser Leu Ser Ala Ser Val Gly
1               5                   10                  15

```
Asp Arg Val Thr Ile Thr Cys Lys Ala Ser Gln Asp Val Asn Thr Val
         20                  25                  30

Val Ala Trp Tyr Gln Gln Lys Pro Gly Lys Ala Pro Lys Val Leu Ile
             35                  40                  45

Ser Trp Ala Ser Thr Arg His Thr Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln His Tyr Thr Thr Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 156
<211> LENGTH: 216
<212> TYPE: PRT
<213> ORGANISM: Artificial Sequence
<220> FEATURE:
<223> OTHER INFORMATION: VH-CH1 of HumAb747V-72

<400> SEQUENCE: 156

Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
             35                  40                  45

Gly Trp Ile Val Pro Arg Asn Ala Asn Thr Val Tyr Ala Ser Lys Phe
 50                  55                  60

Gln Gly Lys Ala Thr Ile Thr Ala Asp Thr Ser Thr Asn Thr Ala Tyr
 65                  70                  75                  80

Leu Glu Leu Ser Ser Leu Arg Ser Glu Asp Thr Ala Val Tyr Tyr Cys
                 85                  90                  95

Thr Val Tyr Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160
```

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys
    210                 215

<210> SEQ ID NO 157
<211> LENGTH: 240
<212> TYPE: PRT
<213> ORGANISM: Artificial Sequence
<220> FEATURE:
<223> OTHER INFORMATION: FIT107-1-6a-2
    FIT-Ig Polypeptide Chain #2

<400> SEQUENCE: 157

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Phe Tyr Thr Met Ser Trp Val Arg Gln Ala Pro Gly Lys Gly Leu
    50                  55                  60

Glu Trp Val Ala Thr Ile Ser Gly Gly Gly Arg Asp Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Gly Gln Gly Gly Asn Tyr Leu Phe Ala Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

<210> SEQ ID NO 158
<211> LENGTH: 221
<212> TYPE: PRT
<213> ORGANISM: Artificial Sequence
<220> FEATURE:
<223> OTHER INFORMATION: VH-CH1 of HumAb709-8

<400> SEQUENCE: 158

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Gly Leu Glu Trp Val
        35                  40                  45

Ala Thr Ile Ser Gly Gly Arg Asp Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gln Gly Gly Asn Tyr Leu Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 159
<211> LENGTH: 236
<212> TYPE: PRT
<213> ORGANISM: Artificial Sequence
<220> FEATURE:
<223> OTHER INFORMATION: FIT107-1-6a-2
    FIT-Ig Polypeptide Chain #3

<400> SEQUENCE: 159

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Leu Gln Gln Lys Pro Gly Gly
    50                  55                  60

Ala Ile Lys Arg Leu Ile Tyr Ala Ala Ser Ala Leu Asp Leu Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Asp Tyr Tyr Cys Leu Gln
            100                 105                 110

Tyr Ala Ser Tyr Pro Leu Thr Phe Gly Gln Gly Thr Lys Leu Glu Leu
        115                 120                 125

Lys Arg Thr Val Ala Ala Pro Ser Val Phe Ile Phe Pro Pro Ser Asp
        130                 135                 140
```

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 160
<211> LENGTH: 214
<212> TYPE: PRT
<213> ORGANISM: Artificial Sequence
<220> FEATURE:
<223> OTHER INFORMATION: VL-CL of HumAb747V-72

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Gly Ala Ile Lys Arg Leu Ile
        35                  40                  45

Tyr Ala Ala Ser Ala Leu Asp Leu Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Asp Tyr Tyr Cys Leu Gln Tyr Ala Ser Tyr Pro Leu
                85                  90                  95

Thr Phe Gly Gln Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 161
<211> LENGTH: 684
<212> TYPE: PRT
<213> ORGANISM: Artificial Sequence
<220> FEATURE:
<223> OTHER INFORMATION: FIT107-1-6b-2
      FIT-Ig Polypeptide Chain #1
```

<400> SEQUENCE: 161

Met Asp Met Arg Val Pro Ala Gln Leu Gly Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Leu Gln Gln Lys Pro Gly Gly
    50                  55                  60

Ala Ile Lys Arg Leu Ile Tyr Ala Ala Ser Ala Leu Asp Leu Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Asp Tyr Tyr Cys Leu Gln
            100                 105                 110

Tyr Ala Ser Tyr Pro Leu Thr Phe Gly Gln Gly Thr Lys Leu Glu Leu
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Glu Val Gln Leu
225                 230                 235                 240

Val Glu Ser Gly Gly Gly Leu Val Gln Pro Gly Gly Ser Leu Arg Leu
                245                 250                 255

Ser Cys Ala Ala Ser Gly Phe Thr Phe Ser Tyr Thr Met Ser Trp
            260                 265                 270

Val Arg Gln Ala Pro Gly Lys Gly Leu Glu Trp Val Ala Thr Ile Ser
        275                 280                 285

Gly Gly Gly Arg Asp Thr Tyr Tyr Pro Asp Ser Val Lys Gly Arg Phe
290                 295                 300

Thr Ile Ser Arg Asp Asn Ala Lys Asn Ser Leu Tyr Leu Gln Met Asn
305                 310                 315                 320

Ser Leu Arg Ala Glu Asp Thr Ala Val Tyr Tyr Cys Ala Gly Gln Gly
                325                 330                 335

Gly Asn Tyr Leu Phe Ala Tyr Trp Gly Gln Gly Thr Leu Val Thr Val
            340                 345                 350

Ser Ser Ala Ser Thr Lys Gly Pro Ser Val Phe Pro Leu Ala Pro Ser
        355                 360                 365

Ser Lys Ser Thr Ser Gly Gly Thr Ala Ala Leu Gly Cys Leu Val Lys
    370                 375                 380

Asp Tyr Phe Pro Glu Pro Val Thr Val Ser Trp Asn Ser Gly Ala Leu
385                 390                 395                 400

Thr Ser Gly Val His Thr Phe Pro Ala Val Leu Gln Ser Ser Gly Leu 405                 410                 415
Tyr Ser Leu Ser Ser Val Val Thr Val Pro Ser Ser Leu Gly Thr
            420                 425                 430

Gln Thr Tyr Ile Cys Asn Val Asn His Lys Pro Ser Asn Thr Lys Val
            435                 440                 445

Asp Lys Lys Val Glu Pro Lys Ser Cys Asp Lys Thr His Thr Cys Pro
450                 455                 460

Pro Cys Pro Ala Pro Glu Ala Ala Gly Gly Pro Ser Val Phe Leu Phe
465                 470                 475                 480

Pro Pro Lys Pro Lys Asp Thr Leu Met Ile Ser Arg Thr Pro Glu Val
            485                 490                 495

Thr Cys Val Val Val Asp Val Ser His Glu Asp Pro Glu Val Lys Phe
            500                 505                 510

Asn Trp Tyr Val Asp Gly Val Glu Val His Asn Ala Lys Thr Lys Pro
            515                 520                 525

Arg Glu Glu Gln Tyr Asn Ser Thr Tyr Arg Val Val Ser Val Leu Thr
530                 535                 540

Val Leu His Gln Asp Trp Leu Asn Gly Lys Glu Tyr Lys Cys Lys Val
545                 550                 555                 560

Ser Asn Lys Ala Leu Pro Ala Pro Ile Glu Lys Thr Ile Ser Lys Ala
            565                 570                 575

Lys Gly Gln Pro Arg Glu Pro Gln Val Tyr Thr Leu Pro Pro Ser Arg
            580                 585                 590

Glu Glu Met Thr Lys Asn Gln Val Ser Leu Thr Cys Leu Val Lys Gly
            595                 600                 605

Phe Tyr Pro Ser Asp Ile Ala Val Glu Trp Glu Ser Asn Gly Gln Pro
610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
            645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
            675                 680

<210> SEQ ID NO 162
<211> LENGTH: 214
<212> TYPE: PRT
<213> ORGANISM: Artificial Sequence
<220> FEATURE:
<223> OTHER INFORMATION: VL-CL of HumAb747V-72

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Gly Ala Ile Lys Arg Leu Ile
        35                  40                  45

Tyr Ala Ala Ser Ala Leu Asp Leu Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Asp Tyr Tyr Cys Leu Gln Tyr Ala Ser Tyr Pro Leu

```
                85                  90                  95
Thr Phe Gly Gln Gly Thr Lys Leu Glu Leu Lys Arg Thr Val Ala Ala
               100                 105                 110

Pro Ser Val Phe Ile Phe Pro Pro Ser Asp Glu Gln Leu Lys Ser Gly
               115                 120                 125

Thr Ala Ser Val Val Cys Leu Leu Asn Asn Phe Tyr Pro Arg Glu Ala
               130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
               165                 170                 175

Ser Thr Leu Thr Leu Ser Lys Ala Asp Tyr Glu Lys His Lys Val Tyr
               180                 185                 190

Ala Cys Glu Val Thr His Gln Gly Leu Ser Ser Pro Val Thr Lys Ser
               195                 200                 205

Phe Asn Arg Gly Glu Cys
               210

<210> SEQ ID NO 163
<211> LENGTH: 221
<212> TYPE: PRT
<213> ORGANISM: Artificial Sequence
<220> FEATURE:
<223> OTHER INFORMATION: VH-CH1 of HumAb709-8

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
               20                  25                  30

Thr Met Ser Trp Val Arg Gln Ala Pro Gly Lys Gly Leu Glu Trp Val
               35                  40                  45

Ala Thr Ile Ser Gly Gly Gly Arg Asp Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
               85                  90                  95

Ala Gly Gln Gly Gly Asn Tyr Leu Phe Ala Tyr Trp Gly Gln Gly Thr
               100                 105                 110

Leu Val Thr Val Ser Ser Ala Ser Thr Lys Gly Pro Ser Val Phe Pro
               115                 120                 125

Leu Ala Pro Ser Ser Lys Ser Thr Ser Gly Gly Thr Ala Ala Leu Gly
               130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
               165                 170                 175

Ser Ser Gly Leu Tyr Ser Leu Ser Ser Val Val Thr Val Pro Ser Ser
               180                 185                 190

Ser Leu Gly Thr Gln Thr Tyr Ile Cys Asn Val Asn His Lys Pro Ser
               195                 200                 205

Asn Thr Lys Val Asp Lys Lys Val Glu Pro Lys Ser Cys
210                 215                 220
```

```
<210> SEQ ID NO 164
<211> LENGTH: 235
<212> TYPE: PRT
<213> ORGANISM: Artificial Sequence
<220> FEATURE:
<223> OTHER INFORMATION: FIT107-1-6b-2 FIT-Ig Polypeptide Chain #2

<400> SEQUENCE: 164

Met Glu Phe Gly Leu Ser Trp Leu Phe Leu Val Ala Ile Leu Lys Gly
1               5                   10                  15

Val Gln Cys Glu Val Gln Leu Val Gln Ser Gly Ala Glu Val Lys Lys
            20                  25                  30

Pro Gly Ala Thr Val Lys Leu Ser Cys Thr Ala Ser Gly Phe Asn Ile
        35                  40                  45

Lys Asp Asp Tyr Met His Trp Val Lys Gln Arg Pro Glu Gln Gly Leu
    50                  55                  60

Asp Trp Ile Gly Trp Ile Val Pro Arg Asn Ala Asn Thr Val Tyr Ala
65                  70                  75                  80

Ser Lys Phe Gln Gly Lys Ala Thr Ile Thr Ala Asp Thr Ser Thr Asn
                85                  90                  95

Thr Ala Tyr Leu Glu Leu Ser Ser Leu Arg Ser Glu Asp Thr Ala Val
            100                 105                 110

Tyr Tyr Cys Thr Val Tyr Gly Asp Tyr Trp Gly Gln Gly Thr Thr Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys
225                 230                 235

<210> SEQ ID NO 165
<211> LENGTH: 216
<212> TYPE: PRT
<213> ORGANISM: Artificial Sequence
<220> FEATURE:
<223> OTHER INFORMATION: VH-CH1 of HumAb747V-72

<400> SEQUENCE: 165

Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Arg Asn Ala Asn Thr Val Tyr Ala Ser Lys Phe
    50                  55                  60

Gln Gly Lys Ala Thr Ile Thr Ala Asp Thr Ser Thr Asn Thr Ala Tyr
65                  70                  75                  80
```

```
Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215

<210> SEQ ID NO 166
<211> LENGTH: 236
<212> TYPE: PRT
<213> ORGANISM: Artificial Sequence
<220> FEATURE:
<223> OTHER INFORMATION: FIT107-1-6b-2
      FIT-Ig Polypeptide Chain #3

<400> SEQUENCE: 166

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Asn Thr Val Val Ala Trp Tyr Gln Gln Lys Pro Gly Lys
    50                  55                  60

Ala Pro Lys Val Leu Ile Ser Trp Ala Ser Thr Arg His Thr Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220
```

Ser Pro Val Thr Lys Ser Phe Asn Arg Gly Glu Cys
225                 230                 235

<210> SEQ ID NO 167
<211> LENGTH: 214
<212> TYPE: PRT
<213> ORGANISM: Artificial Sequence
<220> FEATURE:
<223> OTHER INFORMATION: VL-CL of HumAb709-8

<400> SEQUENCE: 167

Asp Ile Val Met Thr Gln Ser Pro Ser Leu Ser Ala Ser Val Gly
1               5                   10                  15

Asp Arg Val Thr Ile Thr Cys Lys Ala Ser Gln Asp Val Asn Thr Val
            20                  25                  30

Val Ala Trp Tyr Gln Gln Lys Pro Gly Lys Ala Pro Lys Val Leu Ile
        35                  40                  45

Ser Trp Ala Ser Thr Arg His Thr Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 168
<211> LENGTH: 679
<212> TYPE: PRT
<213> ORGANISM: Artificial Sequence
<220> FEATURE:
<223> OTHER INFORMATION: FIT107-1-6a-3
    FIT-Ig Polypeptide Chain #1

<400> SEQUENCE: 168

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Asn Thr Val Val Ala Trp Tyr Gln Gln Lys Pro Gly Lys
50                  55                  60

```
Ala Pro Lys Val Leu Ile Ser Trp Ala Ser Thr Arg His Thr Gly Val
 65                  70                  75                  80

Pro Ser Arg Phe Ser Gly Ser Gly Ser Gly Thr Asp Tyr Thr Leu Thr
                 85                  90                  95

Ile Ser Ser Leu Gln Pro Glu Asp Phe Ala Thr Tyr Tyr Cys Gln Gln
            100                 105                 110

His Tyr Thr Thr Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Glu Val Gln Leu
225                 230                 235                 240

Val Gln Ser Gly Ala Glu Val Lys Lys Pro Gly Ala Thr Val Lys Leu
                245                 250                 255

Ser Cys Thr Ala Ser Gly Phe Asn Ile Lys Asp Asp Tyr Met His Trp
            260                 265                 270

Val Lys Gln Arg Pro Glu Gln Gly Leu Asp Trp Ile Gly Trp Ile Val
        275                 280                 285

Pro Arg Asn Ala Asn Thr Val Tyr Ala Ser Lys Phe Gln Gly Lys Ala
    290                 295                 300

Thr Ile Thr Ala Asp Thr Ser Asn Thr Ala Tyr Leu Glu Leu Ser Ser
305                 310                 315                 320

Ser Leu Arg Ser Glu Asp Thr Ala Val Tyr Tyr Cys Thr Val Tyr Gly
                325                 330                 335

Asp Tyr Trp Gly Gln Gly Thr Thr Val Thr Val Ser Ser Ala Ser Thr
            340                 345                 350

Lys Gly Pro Ser Val Phe Pro Leu Ala Pro Ser Ser Lys Ser Thr Ser
        355                 360                 365

Gly Gly Thr Ala Ala Leu Gly Cys Leu Val Lys Asp Tyr Phe Pro Glu
    370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Lys Lys Val Glu
        435                 440                 445

Pro Lys Ser Cys Asp Lys Thr His Thr Cys Pro Pro Cys Pro Ala Pro
    450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
```

```
                485                 490                 495
Asp Val Ser His Glu Asp Pro Glu Val Lys Phe Asn Trp Tyr Val Asp
                500                 505                 510

Gly Val Glu Val His Asn Ala Lys Thr Lys Pro Arg Glu Glu Gln Tyr
                515                 520                 525

Asn Ser Thr Tyr Arg Val Val Ser Val Leu Thr Val Leu His Gln Asp
                530                 535                 540

Trp Leu Asn Gly Lys Glu Tyr Lys Cys Lys Val Ser Asn Lys Ala Leu
545                 550                 555                 560

Pro Ala Pro Ile Glu Lys Thr Ile Ser Lys Ala Lys Gly Gln Pro Arg
                565                 570                 575

Glu Pro Gln Val Tyr Thr Leu Pro Pro Ser Arg Glu Glu Met Thr Lys
                580                 585                 590

Asn Gln Val Ser Leu Thr Cys Leu Val Lys Gly Phe Tyr Pro Ser Asp
                595                 600                 605

Ile Ala Val Glu Trp Glu Ser Asn Gly Gln Pro Glu Asn Asn Tyr Lys
                610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                    645                 650                 655

Cys Ser Val Met His Glu Ala Leu His Asn His Tyr Thr Gln Lys Ser
                    660                 665                 670

Leu Ser Leu Ser Pro Gly Lys
                675

<210> SEQ ID NO 169
<211> LENGTH: 214
<212> TYPE: PRT
<213> ORGANISM: Artificial Sequence
<220> FEATURE:
<223> OTHER INFORMATION: VL-CL of HumAb709-8

<400> SEQUENCE: 169

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Val
                20                  25                  30

Val Ala Trp Tyr Gln Gln Lys Pro Gly Lys Ala Pro Lys Val Leu Ile
                35                  40                  45

Ser Trp Ala Ser Thr Arg His Thr Gly Val Pro Ser Arg Phe Ser Gly
            50                  55                  60

Ser Gly Ser Gly Thr Asp Tyr Thr Leu Thr Ile Ser Ser Leu Gln Pro
65              70                  75                  80

Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

-continued

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 170
<211> LENGTH: 216
<212> TYPE: PRT
<213> ORGANISM: Artificial Sequence
<220> FEATURE:
<223> OTHER INFORMATION: VH-CH1 of HumAb747V-73

<400> SEQUENCE: 170

Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Arg Asn Ala Asn Thr Val Tyr Ala Ser Lys Phe
    50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215

<210> SEQ ID NO 171
<211> LENGTH: 240
<212> TYPE: PRT
<213> ORGANISM: Artificial Sequence
<220> FEATURE:
<223> OTHER INFORMATION: FIT107-1-6a-3
      FIT-Ig Polypeptide Chain #2

<400> SEQUENCE: 171

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30
```

```
Pro Gly Gly Ser Leu Arg Leu Ser Cys Ala Ala Ser Gly Phe Thr Phe
        35                  40                  45

Ser Phe Tyr Thr Met Ser Trp Val Arg Gln Ala Pro Gly Lys Gly Leu
    50                  55                  60

Glu Trp Val Ala Thr Ile Ser Gly Gly Arg Asp Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
                100                 105                 110

Tyr Tyr Cys Ala Gly Gln Gly Gly Asn Tyr Leu Phe Ala Tyr Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Leu Gly Thr Gln Thr Tyr Ile Cys Asn Val Asn His
        210                 215                 220

Lys Pro Ser Asn Thr Lys Val Asp Lys Val Glu Pro Lys Ser Cys
225                 230                 235                 240

<210> SEQ ID NO 172
<211> LENGTH: 221
<212> TYPE: PRT
<213> ORGANISM: Artificial Sequence
<220> FEATURE:
<223> OTHER INFORMATION: VH-CH1 of HumAb709-8

<400> SEQUENCE: 172

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Gly Leu Glu Trp Val
        35                  40                  45

Ala Thr Ile Ser Gly Gly Arg Asp Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gln Gly Gly Asn Tyr Leu Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys
        210                 215                 220

<210> SEQ ID NO 173
<211> LENGTH: 236
<212> TYPE: PRT
<213> ORGANISM: Artificial Sequence
<220> FEATURE:
<223> OTHER INFORMATION: FIT107-1-6a-3
     FIT-Ig Polypeptide Chain #3

<400> SEQUENCE: 173

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Glu Ile Ser Gly Tyr Leu Ser Trp Leu Gln Gln Lys Pro Gly Gly
    50                  55                  60

Ala Ile Lys Arg Leu Ile Tyr Ala Ala Ser Thr Leu Asp Ser Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Asp Tyr Tyr Cys Leu Gln
            100                 105                 110

Tyr Ala Ser Tyr Pro Leu Thr Phe Gly Gln Gly Thr Lys Leu Glu Leu
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 174
<211> LENGTH: 214
<212> TYPE: PRT
<213> ORGANISM: Artificial Sequence
<220> FEATURE:
<223> OTHER INFORMATION: VL-CL of HumAb747V-73

<400> SEQUENCE: 174

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Glu Ile Ser Gly Tyr
             20                  25                  30

Leu Ser Trp Leu Gln Gln Lys Pro Gly Gly Ala Ile Lys Arg Leu Ile
             35                  40                  45

Tyr Ala Ala Ser Thr Leu Asp Ser Gly Val Pro Ser Arg Phe Ser Gly
 50                  55                  60

Ser Arg Ser Gly Ser Asp Tyr Thr Leu Thr Ile Ser Ser Leu Gln Pro
 65                  70                  75                  80

Glu Asp Phe Ala Asp Tyr Tyr Cys Leu Gln Tyr Ala Ser Tyr Pro Leu
             85                  90                  95

Thr Phe Gly Gln Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 175
<211> LENGTH: 684
<212> TYPE: PRT
<213> ORGANISM: Artificial Sequence
<220> FEATURE:
<223> OTHER INFORMATION: FIT107-1-6b-3
      FIT-Ig Polypeptide Chain #1

<400> SEQUENCE: 175

Met Asp Met Arg Val Pro Ala Gln Leu Leu Gly Leu Leu Leu Leu Trp
  1               5                  10                  15

Phe Pro Gly Ser Arg Cys Asp Ile Gln Met Thr Gln Ser Pro Ser Ser
             20                  25                  30

Leu Ser Ala Ser Val Gly Asp Arg Val Thr Ile Thr Cys Arg Ala Ser
             35                  40                  45

Gln Glu Ile Ser Gly Tyr Leu Ser Trp Leu Gln Gln Lys Pro Gly Gly
 50                  55                  60

Ala Ile Lys Arg Leu Ile Tyr Ala Ala Ser Thr Leu Asp Ser Gly Val
 65                  70                  75                  80

Pro Ser Arg Phe Ser Gly Ser Arg Ser Gly Ser Asp Tyr Thr Leu Thr
             85                  90                  95

Ile Ser Ser Leu Gln Pro Glu Asp Phe Ala Asp Tyr Tyr Cys Leu Gln
            100                 105                 110

Tyr Ala Ser Tyr Pro Leu Thr Phe Gly Gln Gly Thr Lys Leu Glu Leu
            115                 120                 125

Lys Arg Thr Val Ala Ala Pro Ser Val Phe Ile Phe Pro Pro Ser Asp
130                 135                 140
```

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Glu Val Gln Leu
225                 230                 235                 240

Val Glu Ser Gly Gly Gly Leu Val Gln Pro Gly Gly Ser Leu Arg Leu
                245                 250                 255

Ser Cys Ala Ala Ser Gly Phe Thr Phe Ser Phe Tyr Thr Met Ser Trp
                260                 265                 270

Val Arg Gln Ala Pro Gly Lys Gly Leu Glu Trp Val Ala Thr Ile Ser
                275                 280                 285

Gly Gly Gly Arg Asp Thr Tyr Tyr Pro Asp Ser Val Lys Gly Arg Phe
290                 295                 300

Thr Ile Ser Arg Asp Asn Ala Lys Asn Ser Leu Tyr Leu Gln Met Asn
305                 310                 315                 320

Ser Leu Arg Ala Glu Asp Thr Ala Val Tyr Tyr Cys Ala Gly Gln Gly
                325                 330                 335

Gly Asn Tyr Leu Phe Ala Tyr Trp Gly Gln Gly Thr Leu Val Thr Val
                340                 345                 350

Ser Ser Ala Ser Thr Lys Gly Pro Ser Val Phe Pro Leu Ala Pro Ser
                355                 360                 365

Ser Lys Ser Thr Ser Gly Gly Thr Ala Ala Leu Gly Cys Leu Val Lys
370                 375                 380

Asp Tyr Phe Pro Glu Pro Val Thr Val Ser Trp Asn Ser Gly Ala Leu
385                 390                 395                 400

Thr Ser Gly Val His Thr Phe Pro Ala Val Leu Gln Ser Ser Gly Leu
                405                 410                 415

Tyr Ser Leu Ser Ser Val Val Thr Val Pro Ser Ser Ser Leu Gly Thr
                420                 425                 430

Gln Thr Tyr Ile Cys Asn Val Asn His Lys Pro Ser Asn Thr Lys Val
                435                 440                 445

Asp Lys Lys Val Glu Pro Lys Ser Cys Asp Lys Thr His Thr Cys Pro
450                 455                 460

Pro Cys Pro Ala Pro Glu Ala Ala Gly Gly Pro Ser Val Phe Leu Phe
465                 470                 475                 480

Pro Pro Lys Pro Lys Asp Thr Leu Met Ile Ser Arg Thr Pro Glu Val
                485                 490                 495

Thr Cys Val Val Val Asp Val Ser His Glu Asp Pro Glu Val Lys Phe
                500                 505                 510

Asn Trp Tyr Val Asp Gly Val Glu Val His Asn Ala Lys Thr Lys Pro
                515                 520                 525

Arg Glu Glu Gln Tyr Asn Ser Thr Tyr Arg Val Val Ser Val Leu Thr
                530                 535                 540

Val Leu His Gln Asp Trp Leu Asn Gly Lys Glu Tyr Lys Cys Lys Val
545                 550                 555                 560
```

```
Ser Asn Lys Ala Leu Pro Ala Pro Ile Glu Lys Thr Ile Ser Lys Ala
                565             570             575

Lys Gly Gln Pro Arg Glu Pro Gln Val Tyr Thr Leu Pro Pro Ser Arg
            580             585             590

Glu Glu Met Thr Lys Asn Gln Val Ser Leu Thr Cys Leu Val Lys Gly
            595             600             605

Phe Tyr Pro Ser Asp Ile Ala Val Glu Trp Glu Ser Asn Gly Gln Pro
            610             615             620

Glu Asn Asn Tyr Lys Thr Thr Pro Pro Val Leu Asp Ser Asp Gly Ser
625             630             635             640

Phe Phe Leu Tyr Ser Lys Leu Thr Val Asp Lys Ser Arg Trp Gln Gln
            645             650             655

Gly Asn Val Phe Ser Cys Ser Val Met His Glu Ala Leu His Asn His
            660             665             670

Tyr Thr Gln Lys Ser Leu Ser Leu Ser Pro Gly Lys
            675             680
```

<210> SEQ ID NO 176
<211> LENGTH: 214
<212> TYPE: PRT
<213> ORGANISM: Artificial Sequence
<220> FEATURE:
<223> OTHER INFORMATION: VL-CL of HumAb747V-73

<400> SEQUENCE: 176

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Gly Ala Ile Lys Arg Leu Ile
        35                  40                  45

Tyr Ala Ala Ser Thr Leu Asp Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Asp Tyr Tyr Cys Leu Gln Tyr Ala Ser Tyr Pro Leu
                85                  90                  95

Thr Phe Gly Gln Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 177
<211> LENGTH: 221

```
<212> TYPE: PRT
<213> ORGANISM: Artificial Sequence
<220> FEATURE:
<223> OTHER INFORMATION: VH-CH1 of HumAb709-8

<400> SEQUENCE: 177
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Thr Met Ser Trp Val Arg Gln Ala Pro Gly Lys Gly Leu Glu Trp Val
        35                  40                  45

Ala Thr Ile Ser Gly Gly Arg Asp Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gln Gly Gly Asn Tyr Leu Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
210                 215                 220

```
<210> SEQ ID NO 178
<211> LENGTH: 235
<212> TYPE: PRT
<213> ORGANISM: Artificial Sequence
<220> FEATURE:
<223> OTHER INFORMATION: FIT107-1-6b-3
      FIT-Ig Polypeptide Chain #2

<400> SEQUENCE: 178
```

Met Glu Phe Gly Leu Ser Trp Leu Phe Leu Val Ala Ile Leu Lys Gly
1               5                   10                  15

Val Gln Cys Glu Val Gln Leu Val Gln Ser Gly Ala Glu Val Lys Lys
            20                  25                  30

Pro Gly Ala Thr Val Lys Leu Ser Cys Thr Ala Ser Gly Phe Asn Ile
        35                  40                  45

Lys Asp Asp Tyr Met His Trp Val Lys Gln Arg Pro Glu Gln Gly Leu
50                  55                  60

Asp Trp Ile Gly Trp Ile Val Pro Arg Asn Ala Asn Thr Val Tyr Ala
65                  70                  75                  80

Ser Lys Phe Gln Gly Lys Ala Thr Ile Thr Ala Asp Thr Ser Thr Asn
                85                  90                  95

Thr Ala Tyr Leu Glu Leu Ser Ser Leu Arg Ser Glu Asp Thr Ala Val

```
                  100                 105                 110
Tyr Tyr Cys Thr Val Tyr Gly Asp Tyr Trp Gly Gln Gly Thr Thr Val
            115                 120                 125
Thr Val Ser Ser Ala Ser Thr Lys Gly Pro Ser Val Phe Pro Leu Ala
130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
            165                 170                 175
Ala Leu Thr Ser Gly Val His Thr Phe Pro Ala Val Leu Gln Ser Ser
        180                 185                 190
Gly Leu Tyr Ser Leu Ser Ser Val Val Thr Val Pro Ser Ser Ser Leu
            195                 200                 205
Gly Thr Gln Thr Tyr Ile Cys Asn Val Asn His Lys Pro Ser Asn Thr
        210                 215                 220
Lys Val Asp Lys Lys Val Glu Pro Lys Ser Cys
225                 230                 235

<210> SEQ ID NO 179
<211> LENGTH: 216
<212> TYPE: PRT
<213> ORGANISM: Artificial Sequence
<220> FEATURE:
<223> OTHER INFORMATION: VH-CH1 of HumAb747V-73

<400> SEQUENCE: 179

Glu Val Gln Leu Val Gln Ser Gly Ala Glu Val Lys Lys Pro Gly Ala
1               5                   10                  15
Thr Val Lys Leu Ser Cys Thr Ala Ser Gly Phe Asn Ile Lys Asp Asp
            20                  25                  30
Tyr Met His Trp Val Lys Gln Arg Pro Glu Gln Gly Leu Asp Trp Ile
        35                  40                  45
Gly Trp Ile Val Pro Arg Asn Ala Asn Thr Val Tyr Ala Ser Lys Phe
    50                  55                  60
Gln Gly Lys Ala Thr Ile Thr Ala Asp Thr Ser Thr Asn Thr Ala Tyr
65                  70                  75                  80
Leu Glu Leu Ser Ser Leu Arg Ser Glu Asp Thr Ala Val Tyr Tyr Cys
                85                  90                  95
Thr Val Tyr Gly Asp Tyr Trp Gly Gln Gly Thr Thr Val Thr Val Ser
            100                 105                 110
Ser Ala Ser Thr Lys Gly Pro Ser Val Phe Pro Leu Ala Pro Ser Ser
        115                 120                 125
Lys Ser Thr Ser Gly Gly Thr Ala Ala Leu Gly Cys Leu Val Lys Asp
    130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Gln
            180                 185                 190
Thr Tyr Ile Cys Asn Val Asn His Lys Pro Ser Asn Thr Lys Val Asp
        195                 200                 205
Lys Lys Val Glu Pro Lys Ser Cys
    210                 215
```

```
<210> SEQ ID NO 180
<211> LENGTH: 236
<212> TYPE: PRT
<213> ORGANISM: Artificial Sequence
<220> FEATURE:
<223> OTHER INFORMATION: FIT107-1-6b-3 FIT-Ig Polypeptide Chain #3

<400> SEQUENCE: 180

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Asn Thr Val Val Ala Trp Tyr Gln Gln Lys Pro Gly Lys
    50                  55                  60

Ala Pro Lys Val Leu Ile Ser Trp Ala Ser Thr Arg His Thr Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 181
<211> LENGTH: 214
<212> TYPE: PRT
<213> ORGANISM: Artificial Sequence
<220> FEATURE:
<223> OTHER INFORMATION: VL-CL of HumAb709-8

<400> SEQUENCE: 181

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Val
            20                  25                  30

Val Ala Trp Tyr Gln Gln Lys Pro Gly Lys Ala Pro Lys Val Leu Ile
        35                  40                  45

Ser Trp Ala Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

```
Glu Asp Phe Ala Thr Tyr Tyr Cys Gln Gln His Tyr Thr Thr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 182
<211> LENGTH: 679
<212> TYPE: PRT
<213> ORGANISM: Artificial Sequence
<220> FEATURE:
<223> OTHER INFORMATION: FIT107-1-7a-1
      FIT-Ig Polypeptide Chain #1

<400> SEQUENCE: 182

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
            35                  40                  45

Asp His Ile Asn Asn Trp Leu Ala Trp Tyr Gln Gln Lys Pro Gly Lys
        50                  55                  60

Ala Pro Lys Leu Leu Ile Tyr Gly Ala Thr Ser Leu Glu Thr Gly Val
65                  70                  75                  80

Pro Ser Arg Phe Ser Gly Ser Gly Ser Gly Thr Asp Tyr Thr Phe Thr
                85                  90                  95

Ile Ser Ser Leu Gln Pro Glu Asp Ile Ala Thr Tyr Tyr Cys Gln Gln
            100                 105                 110

Tyr Trp Ser Pro Pro Tyr Thr Phe Gly Gly Gly Thr Lys Val Glu Ile
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220
```

```
Ser Pro Val Thr Lys Ser Phe Asn Arg Gly Glu Cys Glu Val Gln Leu
225                 230                 235                 240

Val Gln Ser Gly Ala Glu Val Lys Lys Pro Gly Ala Thr Val Lys Leu
            245                 250                 255

Ser Cys Thr Ala Ser Gly Phe Asn Ile Lys Asp Asp Tyr Met His Trp
            260                 265                 270

Val Lys Gln Arg Pro Glu Gln Gly Leu Asp Trp Ile Gly Trp Ile Val
            275                 280                 285

Pro Glu Asn Ala Asn Thr Val Tyr Ala Ser Lys Phe Gln Gly Lys Ala
            290                 295                 300

Thr Ile Thr Ala Asp Thr Ser Thr Asn Thr Ala Tyr Leu Glu Leu Ser
305                 310                 315                 320

Ser Leu Arg Ser Glu Asp Thr Ala Val Tyr Tyr Cys Thr Val Tyr Gly
            325                 330                 335

Asp Tyr Trp Gly Gln Gly Thr Thr Val Thr Val Ser Ser Ala Ser Thr
            340                 345                 350

Lys Gly Pro Ser Val Phe Pro Leu Ala Pro Ser Ser Lys Ser Thr Ser
            355                 360                 365

Gly Gly Thr Ala Ala Leu Gly Cys Leu Val Lys Asp Tyr Phe Pro Glu
370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
            405                 410                 415

Val Val Thr Val Pro Ser Ser Leu Gly Thr Gln Thr Tyr Ile Cys
            420                 425                 430

Asn Val Asn His Lys Pro Ser Asn Thr Lys Val Asp Lys Lys Val Glu
            435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
            485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
            515                 520                 525

Asn Ser Thr Tyr Arg Val Val Ser Val Leu Thr Val Leu His Gln Asp
            530                 535                 540

Trp Leu Asn Gly Lys Glu Tyr Lys Cys Lys Val Ser Asn Lys Ala Leu
545                 550                 555                 560

Pro Ala Pro Ile Glu Lys Thr Ile Ser Lys Ala Lys Gly Gln Pro Arg
            565                 570                 575

Glu Pro Gln Val Tyr Thr Leu Pro Pro Ser Arg Glu Glu Met Thr Lys
            580                 585                 590

Asn Gln Val Ser Leu Thr Cys Leu Val Lys Gly Phe Tyr Pro Ser Asp
            595                 600                 605

Ile Ala Val Glu Trp Glu Ser Asn Gly Gln Pro Glu Asn Asn Tyr Lys
            610                 615                 620

Thr Thr Pro Pro Val Leu Asp Ser Asp Gly Ser Phe Phe Leu Tyr Ser
625                 630                 635                 640
```

```
Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro Gly Lys
        675
```

<210> SEQ ID NO 183
<211> LENGTH: 214
<212> TYPE: PRT
<213> ORGANISM: Artificial Sequence
<220> FEATURE:
<223> OTHER INFORMATION: VL-CL of mAb HumAb713-7

<400> SEQUENCE: 183

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Ser Pro Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 184
<211> LENGTH: 216
<212> TYPE: PRT
<213> ORGANISM: Artificial Sequence
<220> FEATURE:
<223> OTHER INFORMATION: VH-CH1 of HumAb747V-67

<400> SEQUENCE: 184

```
Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
        35                  40                  45
```

```
Gly Trp Ile Val Pro Glu Asn Ala Asn Thr Val Tyr Ala Ser Lys Phe
            50                  55                  60

Gln Gly Lys Ala Thr Ile Thr Ala Asp Thr Ser Asn Thr Ala Tyr
 65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
                100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
                195                 200                 205

Lys Lys Val Glu Pro Lys Ser Cys
    210                 215

<210> SEQ ID NO 185
<211> LENGTH: 243
<212> TYPE: PRT
<213> ORGANISM: Artificial Sequence
<220> FEATURE:
<223> OTHER INFORMATION: FIT107-1-7a-1
    FIT-Ig Polypeptide Chain #2

<400> SEQUENCE: 185

Met Glu Phe Gly Leu Ser Trp Leu Phe Leu Val Ala Ile Leu Lys Gly
 1               5                  10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Ser
            35                  40                  45

Ser Asp Tyr Gly Met His Trp Val Arg Gln Ala Pro Gly Lys Gly Leu
 50                  55                  60

Glu Trp Val Ser Tyr Ile Ser Ser Gly Ser Tyr Thr Ile Tyr Tyr Ala
 65                  70                  75                  80

Asp Thr Val Lys Gly Arg Phe Thr Ile Ser Arg Asp Asn Ala Lys Asn
                85                  90                  95

Ser Leu Tyr Leu Gln Met Asn Ser Leu Arg Asp Glu Asp Thr Ala Val
                100                 105                 110

Tyr Tyr Cys Ala Lys Arg Gly Gly Ser His Val Asn Val Met Asp
                115                 120                 125

Tyr Trp Gly Gln Gly Thr Thr Val Thr Val Ser Ser Ala Ser Thr Lys
130                 135                 140

Gly Pro Ser Val Phe Pro Leu Ala Pro Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
```

```
                    180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys

<210> SEQ ID NO 186
<211> LENGTH: 224
<212> TYPE: PRT
<213> ORGANISM: Artificial Sequence
<220> FEATURE:
<223> OTHER INFORMATION: VH-CH1 of HumAb713-7

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Tyr Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Lys Arg Gly Gly Ser Ser His Val Asn Val Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 187
<211> LENGTH: 236
<212> TYPE: PRT
<213> ORGANISM: Artificial Sequence
<220> FEATURE:
<223> OTHER INFORMATION: FIT107-1-7a-1
      FIT-Ig Polypeptide Chain #3

<400> SEQUENCE: 187

Met Asp Met Arg Val Pro Ala Gln Leu Leu Gly Leu Leu Leu Leu Trp
1               5                   10                  15
```

```
Phe Pro Gly Ser Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Glu Ile Ser Gly Tyr Leu Ser Trp Leu Gln Gln Lys Pro Gly Gly
        50                  55                  60

Ala Ile Lys Arg Leu Ile Tyr Ala Ala Ser Ala Leu Asp Ser Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Asp Tyr Tyr Cys Leu Gln
            100                 105                 110

Tyr Ala Ser Tyr Pro Leu Thr Phe Gly Gln Gly Thr Lys Leu Glu Leu
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 188
<211> LENGTH: 214
<212> TYPE: PRT
<213> ORGANISM: Artificial Sequence
<220> FEATURE:
<223> OTHER INFORMATION: VL-CL of HumAb747V-67

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Gly Ala Ile Lys Arg Leu Ile
        35                  40                  45

Tyr Ala Ala Ser Ala Leu Asp Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Asp Tyr Tyr Cys Leu Gln Tyr Ala Ser Tyr Pro Leu
                85                  90                  95

Thr Phe Gly Gln Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 189
<211> LENGTH: 687
<212> TYPE: PRT
<213> ORGANISM: Artificial Sequence
<220> FEATURE:
<223> OTHER INFORMATION: FIT107-1-7b-1
      FIT-Ig Polypeptide Chain #1

<400> SEQUENCE: 189

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Glu Ile Ser Gly Tyr Leu Ser Trp Leu Gln Gln Lys Pro Gly Gly
        50                  55                  60

Ala Ile Lys Arg Leu Ile Tyr Ala Ala Ser Ala Leu Asp Ser Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Asp Tyr Tyr Cys Leu Gln
                100                 105                 110

Tyr Ala Ser Tyr Pro Leu Thr Phe Gly Gln Gly Thr Lys Leu Glu Leu
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Glu Val Gln Leu
225                 230                 235                 240

Val Glu Ser Gly Gly Gly Leu Val Gln Pro Gly Gly Ser Leu Arg Leu
                245                 250                 255

Ser Cys Ala Ala Ser Gly Phe Thr Ser Ser Asp Tyr Gly Met His Trp
            260                 265                 270

Val Arg Gln Ala Pro Gly Lys Gly Leu Glu Trp Val Ser Tyr Ile Ser
        275                 280                 285

```
Ser Gly Ser Tyr Thr Ile Tyr Ala Asp Thr Val Lys Gly Arg Phe
        290                 295                 300

Thr Ile Ser Arg Asp Asn Ala Lys Asn Ser Leu Tyr Leu Gln Met Asn
305                 310                 315                 320

Ser Leu Arg Asp Glu Asp Thr Ala Val Tyr Tyr Cys Ala Lys Arg Gly
                325                 330                 335

Gly Ser Ser His Val Asn Val Met Asp Tyr Trp Gly Gln Gly Thr Thr
            340                 345                 350

Val Thr Val Ser Ser Ala Ser Thr Lys Gly Pro Ser Val Phe Pro Leu
        355                 360                 365

Ala Pro Ser Ser Lys Ser Thr Ser Gly Gly Thr Ala Ala Leu Gly Cys
370                 375                 380

Leu Val Lys Asp Tyr Phe Pro Glu Pro Val Thr Val Ser Trp Asn Ser
385                 390                 395                 400

Gly Ala Leu Thr Ser Gly Val His Thr Phe Pro Ala Val Leu Gln Ser
                405                 410                 415

Ser Gly Leu Tyr Ser Leu Ser Ser Val Val Thr Val Pro Ser Ser Ser
            420                 425                 430

Leu Gly Thr Gln Thr Tyr Ile Cys Asn Val Asn His Lys Pro Ser Asn
        435                 440                 445

Thr Lys Val Asp Lys Lys Val Glu Pro Lys Ser Cys Asp Lys Thr His
450                 455                 460

Thr Cys Pro Pro Cys Pro Ala Pro Glu Ala Ala Gly Gly Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser His Glu Asp Pro Glu
            500                 505                 510

Val Lys Phe Asn Trp Tyr Val Asp Gly Val Glu Val His Asn Ala Lys
        515                 520                 525

Thr Lys Pro Arg Glu Glu Gln Tyr Asn Ser Thr Tyr Arg Val Val Ser
530                 535                 540

Val Leu Thr Val Leu His Gln Asp Trp Leu Asn Gly Lys Glu Tyr Lys
545                 550                 555                 560

Cys Lys Val Ser Asn Lys Ala Leu Pro Ala Pro Ile Glu Lys Thr Ile
                565                 570                 575

Ser Lys Ala Lys Gly Gln Pro Arg Glu Pro Gln Val Tyr Thr Leu Pro
            580                 585                 590

Pro Ser Arg Glu Glu Met Thr Lys Asn Gln Val Ser Leu Thr Cys Leu
        595                 600                 605

Val Lys Gly Phe Tyr Pro Ser Asp Ile Ala Val Glu Trp Glu Ser Asn
610                 615                 620

Gly Gln Pro Glu Asn Asn Tyr Lys Thr Thr Pro Pro Val Leu Asp Ser
625                 630                 635                 640

Asp Gly Ser Phe Phe Leu Tyr Ser Lys Leu Thr Val Asp Lys Ser Arg
                645                 650                 655

Trp Gln Gln Gly Asn Val Phe Ser Cys Ser Val Met His Glu Ala Leu
            660                 665                 670

His Asn His Tyr Thr Gln Lys Ser Leu Ser Leu Ser Pro Gly Lys
        675                 680                 685

<210> SEQ ID NO 190
<211> LENGTH: 214
```

```
<212> TYPE: PRT
<213> ORGANISM: Artificial Sequence
<220> FEATURE:
<223> OTHER INFORMATION: VL-CL of HumAb747V-67

<400> SEQUENCE: 190
```

| | | | | | | | | | | | | | | |
|---|---|---|---|---|---|---|---|---|---|---|---|---|---|---|
| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |

| Asp | Arg | Val | Thr | Ile | Thr | Cys | Arg | Ala | Ser | Gln | Glu | Ile | Ser | Gly | Tyr |
| | | | 20 | | | | | 25 | | | | | 30 | | |

| Leu | Ser | Trp | Leu | Gln | Gln | Lys | Pro | Gly | Gly | Ala | Ile | Lys | Arg | Leu | Ile |
| | | | 35 | | | | | 40 | | | | | 45 | | |

| Tyr | Ala | Ala | Ser | Ala | Leu | Asp | Ser | Gly | Val | Pro | Ser | Arg | Phe | Ser | Gly |
| | 50 | | | | | 55 | | | | | 60 | | | | |

| Ser | Arg | Ser | Gly | Ser | Asp | Tyr | Thr | Leu | Thr | Ile | Ser | Ser | Leu | Gln | Pro |
| 65 | | | | | 70 | | | | | 75 | | | | | 80 |

| Glu | Asp | Phe | Ala | Asp | Tyr | Tyr | Cys | Leu | Gln | Tyr | Ala | Ser | Tyr | Pro | Leu |
| | | | | 85 | | | | | 90 | | | | | 95 | |

| Thr | Phe | Gly | Gln | Gly | Thr | Lys | Leu | Glu | Leu | Lys | Arg | Thr | Val | Ala | Ala |
| | | | 100 | | | | | 105 | | | | | 110 | | |

| Pro | Ser | Val | Phe | Ile | Phe | Pro | Pro | Ser | Asp | Glu | Gln | Leu | Lys | Ser | Gly |
| | | | 115 | | | | | 120 | | | | | 125 | | |

| Thr | Ala | Ser | Val | Val | Cys | Leu | Leu | Asn | Asn | Phe | Tyr | Pro | Arg | Glu | Ala |
| | | 130 | | | | | 135 | | | | | 140 | | | |

| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |

| Glu | Ser | Val | Thr | Glu | Gln | Asp | Ser | Lys | Asp | Ser | Thr | Tyr | Ser | Leu | Ser |
| | | | | 165 | | | | | 170 | | | | | 175 | |

| Ser | Thr | Leu | Thr | Leu | Ser | Lys | Ala | Asp | Tyr | Glu | Lys | His | Lys | Val | Tyr |
| | | | 180 | | | | | 185 | | | | | 190 | | |

| Ala | Cys | Glu | Val | Thr | His | Gln | Gly | Leu | Ser | Ser | Pro | Val | Thr | Lys | Ser |
| | | | 195 | | | | | 200 | | | | | 205 | | |

| Phe | Asn | Arg | Gly | Glu | Cys |
| | | 210 | | | |

```
<210> SEQ ID NO 191
<211> LENGTH: 224
<212> TYPE: PRT
<213> ORGANISM: Artificial Sequence
<220> FEATURE:
<223> OTHER INFORMATION: VH-CH1 of HumAb713-7

<400> SEQUENCE: 191
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Ser | Ser | Asp | Tyr |
| | | | 20 | | | | | 25 | | | | | 30 | | |

| Gly | Met | His | Trp | Val | Arg | Gln | Ala | Pro | Gly | Lys | Gly | Leu | Glu | Trp | Val |
| | | | 35 | | | | | 40 | | | | | 45 | | |

| Ser | Tyr | Ile | Ser | Ser | Gly | Ser | Tyr | Thr | Ile | Tyr | Tyr | Ala | Asp | Thr | Val |
| | 50 | | | | | 55 | | | | | 60 | | | | |

| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |

| Leu | Gln | Met | Asn | Ser | Leu | Arg | Asp | Glu | Asp | Thr | Ala | Val | Tyr | Tyr | Cys |
| | | | | 85 | | | | | 90 | | | | | 95 | |

| Ala | Lys | Arg | Gly | Gly | Ser | Ser | His | Val | Asn | Val | Met | Asp | Tyr | Trp | Gly |
| | | | 100 | | | | | 105 | | | | | 110 | | |

```
Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 192
<211> LENGTH: 235
<212> TYPE: PRT
<213> ORGANISM: Artificial Sequence
<220> FEATURE:
<223> OTHER INFORMATION: FIT107-1-7b-1
    FIT-Ig Polypeptide Chain #2

<400> SEQUENCE: 192

```
Met Glu Phe Gly Leu Ser Trp Leu Phe Leu Val Ala Ile Leu Lys Gly
1               5                   10                  15

Val Gln Cys Glu Val Gln Leu Val Gln Ser Gly Ala Glu Val Lys Lys
            20                  25                  30

Pro Gly Ala Thr Val Lys Leu Ser Cys Thr Ala Ser Gly Phe Asn Ile
        35                  40                  45

Lys Asp Asp Tyr Met His Trp Val Lys Gln Arg Pro Glu Gln Gly Leu
    50                  55                  60

Asp Trp Ile Gly Trp Ile Val Pro Glu Asn Ala Asn Thr Val Tyr Ala
65                  70                  75                  80

Ser Lys Phe Gln Gly Lys Ala Thr Ile Thr Ala Asp Thr Ser Thr Asn
                85                  90                  95

Thr Ala Tyr Leu Glu Leu Ser Ser Leu Arg Ser Glu Asp Thr Ala Val
            100                 105                 110

Tyr Tyr Cys Thr Val Tyr Gly Asp Tyr Trp Gly Gln Gly Thr Thr Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys
225                 230                 235
```

<210> SEQ ID NO 193
<211> LENGTH: 216
<212> TYPE: PRT
<213> ORGANISM: Artificial Sequence
<220> FEATURE:
<223> OTHER INFORMATION: VH-CH1 of HumAb747V-67

<400> SEQUENCE: 193

```
Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Glu Asn Ala Asn Thr Val Tyr Ala Ser Lys Phe
    50                  55                  60

Gln Gly Lys Ala Thr Ile Thr Ala Asp Thr Ser Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215
```

<210> SEQ ID NO 194
<211> LENGTH: 236
<212> TYPE: PRT
<213> ORGANISM: Artificial Sequence
<220> FEATURE:
<223> OTHER INFORMATION: FIT107-1-7b-1
    FIT-Ig Polypeptide Chain #3

<400> SEQUENCE: 194

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Asp His Ile Asn Asn Trp Leu Ala Trp Tyr Gln Gln Lys Pro Gly Lys
    50                  55                  60

Ala Pro Lys Leu Leu Ile Tyr Gly Ala Thr Ser Leu Glu Thr Gly Val
65                  70                  75                  80

Pro Ser Arg Phe Ser Gly Ser Gly Ser Gly Thr Asp Tyr Thr Phe Thr
                85                  90                  95
```

```
Ile Ser Ser Leu Gln Pro Glu Asp Ile Ala Thr Tyr Tyr Cys Gln Gln
            100                 105                 110

Tyr Trp Ser Pro Pro Tyr Thr Phe Gly Gly Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 195
<211> LENGTH: 214
<212> TYPE: PRT
<213> ORGANISM: Artificial Sequence
<220> FEATURE:
<223> OTHER INFORMATION: VL-CL of HumAb713-7

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Ser Pro Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 196
<211> LENGTH: 679
<212> TYPE: PRT
<213> ORGANISM: Artificial Sequence
<220> FEATURE:
<223> OTHER INFORMATION: FIT107-1-7a-2
       FIT-Ig Polypeptide Chain #1

<400> SEQUENCE: 196

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Asp His Ile Asn Asn Trp Leu Ala Trp Tyr Gln Gln Lys Pro Gly Lys
    50                  55                  60

Ala Pro Lys Leu Leu Ile Tyr Gly Ala Thr Ser Leu Glu Thr Gly Val
65                  70                  75                  80

Pro Ser Arg Phe Ser Gly Ser Gly Ser Gly Thr Asp Tyr Thr Phe Thr
                85                  90                  95

Ile Ser Ser Leu Gln Pro Glu Asp Ile Ala Thr Tyr Tyr Cys Gln Gln
            100                 105                 110

Tyr Trp Ser Pro Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Glu Val Gln Leu
225                 230                 235                 240

Val Gln Ser Gly Ala Glu Val Lys Lys Pro Gly Ala Thr Val Lys Leu
                245                 250                 255

Ser Cys Thr Ala Ser Gly Phe Asn Ile Lys Asp Asp Tyr Met His Trp
            260                 265                 270

Val Lys Gln Arg Pro Glu Gln Gly Leu Asp Trp Ile Gly Trp Ile Val
        275                 280                 285

Pro Arg Asn Ala Asn Thr Val Tyr Ala Ser Lys Phe Gln Gly Lys Ala
290                 295                 300

Thr Ile Thr Ala Asp Thr Ser Thr Asn Thr Ala Tyr Leu Glu Leu Ser
305                 310                 315                 320

Ser Leu Arg Ser Glu Asp Thr Ala Val Tyr Tyr Cys Val Tyr Gly
                325                 330                 335

Asp Tyr Trp Gly Gln Gly Thr Thr Val Thr Val Ser Ser Ala Ser Thr
            340                 345                 350

Lys Gly Pro Ser Val Phe Pro Leu Ala Pro Ser Ser Lys Ser Thr Ser
```

```
            355                 360                 365
Gly Gly Thr Ala Ala Leu Gly Cys Leu Val Lys Asp Tyr Phe Pro Glu
            370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Lys Lys Val Glu
            435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
            515                 520                 525

Asn Ser Thr Tyr Arg Val Val Ser Val Leu Thr Val Leu His Gln Asp
530                 535                 540

Trp Leu Asn Gly Lys Glu Tyr Lys Cys Lys Val Ser Asn Lys Ala Leu
545                 550                 555                 560

Pro Ala Pro Ile Glu Lys Thr Ile Ser Lys Ala Lys Gly Gln Pro Arg
                565                 570                 575

Glu Pro Gln Val Tyr Thr Leu Pro Pro Ser Arg Glu Glu Met Thr Lys
            580                 585                 590

Asn Gln Val Ser Leu Thr Cys Leu Val Lys Gly Phe Tyr Pro Ser Asp
            595                 600                 605

Ile Ala Val Glu Trp Glu Ser Asn Gly Gln Pro Glu Asn Asn Tyr Lys
            610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro Gly Lys
            675

<210> SEQ ID NO 197
<211> LENGTH: 214
<212> TYPE: PRT
<213> ORGANISM: Artificial Sequence
<220> FEATURE:
<223> OTHER INFORMATION: VL-CL of HumAb713-7

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
```

```
               35                  40                  45
Tyr Gly Ala Thr Ser Leu Glu Thr Gly Val Pro Ser Arg Phe Ser Gly
            50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Ser Pro Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 198
<211> LENGTH: 216
<212> TYPE: PRT
<213> ORGANISM: Artificial Sequence
<220> FEATURE:
<223> OTHER INFORMATION: VH-CH1 of HumAb747V-72

<400> SEQUENCE: 198

Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
            35                  40                  45

Gly Trp Ile Val Pro Arg Asn Ala Asn Thr Val Tyr Ala Ser Lys Phe
        50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
```

```
              180             185             190
Thr Tyr Ile Cys Asn Val Asn His Lys Pro Ser Asn Thr Lys Val Asp
        195                 200                 205

Lys Lys Val Glu Pro Lys Ser Cys
    210             215
```

<210> SEQ ID NO 199
<211> LENGTH: 243
<212> TYPE: PRT
<213> ORGANISM: Artificial Sequence
<220> FEATURE:
<223> OTHER INFORMATION: FIT107-1-7a-2
        FIT-Ig Polypeptide Chain #2

<400> SEQUENCE: 199

```
Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Ser
        35                  40                  45

Ser Asp Tyr Gly Met His Trp Val Arg Gln Ala Pro Gly Lys Gly Leu
    50                  55                  60

Glu Trp Val Ser Tyr Ile Ser Ser Gly Ser Tyr Thr Ile Tyr Tyr Ala
65                  70                  75                  80

Asp Thr Val Lys Gly Arg Phe Thr Ile Ser Arg Asp Asn Ala Lys Asn
                85                  90                  95

Ser Leu Tyr Leu Gln Met Asn Ser Leu Arg Asp Glu Asp Thr Ala Val
            100                 105                 110

Tyr Tyr Cys Ala Lys Arg Gly Gly Ser Ser His Val Asn Val Met Asp
        115                 120                 125

Tyr Trp Gly Gln Gly Thr Thr Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys
```

<210> SEQ ID NO 200
<211> LENGTH: 224
<212> TYPE: PRT
<213> ORGANISM: Artificial Sequence
<220> FEATURE:
<223> OTHER INFORMATION: VH-CH1 of HumAb713-7

<400> SEQUENCE: 200

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Ser Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Tyr Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Lys Arg Gly Gly Ser Ser His Val Asn Val Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

<210> SEQ ID NO 201
<211> LENGTH: 236
<212> TYPE: PRT
<213> ORGANISM: Artificial Sequence
<220> FEATURE:
<223> OTHER INFORMATION: FIT107-1-7a-2
    FIT-Ig Polypeptide Chain #3

<400> SEQUENCE: 201

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Leu Gln Gln Lys Pro Gly Gly
    50                  55                  60

Ala Ile Lys Arg Leu Ile Tyr Ala Ala Ser Ala Leu Asp Leu Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Asp Tyr Tyr Cys Leu Gln
            100                 105                 110

Tyr Ala Ser Tyr Pro Leu Thr Phe Gly Gln Gly Thr Lys Leu Glu Leu
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

```
Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 202
<211> LENGTH: 214
<212> TYPE: PRT
<213> ORGANISM: Artificial Sequence
<220> FEATURE:
<223> OTHER INFORMATION: VL-CL of HumAb747V-72

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Gly Ala Ile Lys Arg Leu Ile
        35                  40                  45

Tyr Ala Ala Ser Ala Leu Asp Leu Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Asp Tyr Tyr Cys Leu Gln Tyr Ala Ser Tyr Pro Leu
                85                  90                  95

Thr Phe Gly Gln Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 203
<211> LENGTH: 687
<212> TYPE: PRT
<213> ORGANISM: Artificial Sequence
<220> FEATURE:
<223> OTHER INFORMATION: FIT107-1-7b-2
      FIT-Ig Polypeptide Chain #1

<400> SEQUENCE: 203
```

```
Met Asp Met Arg Val Pro Ala Gln Leu Leu Gly Leu Leu Leu Leu Trp
1               5                   10                  15
Phe Pro Gly Ser Arg Cys Asp Ile Gln Met Thr Gln Ser Pro Ser Ser
            20                  25                  30
Leu Ser Ala Ser Val Gly Asp Arg Val Thr Ile Thr Cys Arg Ala Ser
        35                  40                  45
Gln Glu Ile Ser Gly Tyr Leu Ser Trp Leu Gln Gln Lys Pro Gly Gly
50                  55                  60
Ala Ile Lys Arg Leu Ile Tyr Ala Ala Ser Ala Leu Asp Leu Gly Val
65                  70                  75                  80
Pro Ser Arg Phe Ser Gly Ser Arg Ser Gly Ser Asp Tyr Thr Leu Thr
                85                  90                  95
Ile Ser Ser Leu Gln Pro Glu Asp Phe Ala Asp Tyr Tyr Cys Leu Gln
            100                 105                 110
Tyr Ala Ser Tyr Pro Leu Thr Phe Gly Gln Gly Thr Lys Leu Glu Leu
        115                 120                 125
Lys Arg Thr Val Ala Ala Pro Ser Val Phe Ile Phe Pro Pro Ser Asp
130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
210                 215                 220
Ser Pro Val Thr Lys Ser Phe Asn Arg Gly Glu Cys Glu Val Gln Leu
225                 230                 235                 240
Val Glu Ser Gly Gly Gly Leu Val Gln Pro Gly Gly Ser Leu Arg Leu
                245                 250                 255
Ser Cys Ala Ala Ser Gly Phe Thr Ser Ser Asp Tyr Gly Met His Trp
            260                 265                 270
Val Arg Gln Ala Pro Gly Lys Gly Leu Glu Trp Val Ser Tyr Ile Ser
        275                 280                 285
Ser Gly Ser Tyr Thr Ile Tyr Tyr Ala Asp Thr Val Lys Gly Arg Phe
290                 295                 300
Thr Ile Ser Arg Asp Asn Ala Lys Asn Ser Leu Tyr Leu Gln Met Asn
305                 310                 315                 320
Ser Leu Arg Asp Glu Asp Thr Ala Val Tyr Tyr Cys Ala Lys Arg Gly
                325                 330                 335
Gly Ser Ser His Val Asn Val Met Asp Tyr Trp Gly Gln Gly Thr Thr
            340                 345                 350
Val Thr Val Ser Ser Ala Ser Thr Lys Gly Pro Ser Val Phe Pro Leu
        355                 360                 365
Ala Pro Ser Ser Lys Ser Thr Ser Gly Gly Thr Ala Ala Leu Gly Cys
370                 375                 380
Leu Val Lys Asp Tyr Phe Pro Glu Pro Val Thr Val Ser Trp Asn Ser
385                 390                 395                 400
Gly Ala Leu Thr Ser Gly Val His Thr Phe Pro Ala Val Leu Gln Ser
                405                 410                 415
Ser Gly Leu Tyr Ser Leu Ser Ser Val Val Thr Val Pro Ser Ser Ser
```

```
                    420                 425                 430
Leu Gly Thr Gln Thr Tyr Ile Cys Asn Val Asn His Lys Pro Ser Asn
                435                 440                 445

Thr Lys Val Asp Lys Val Glu Pro Lys Ser Cys Asp Lys Thr His
    450                 455                 460

Thr Cys Pro Pro Cys Pro Ala Pro Glu Ala Ala Gly Gly Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser His Glu Asp Pro Glu
                500                 505                 510

Val Lys Phe Asn Trp Tyr Val Asp Gly Val Glu Val His Asn Ala Lys
                515                 520                 525

Thr Lys Pro Arg Glu Glu Gln Tyr Asn Ser Thr Tyr Arg Val Val Ser
                530                 535                 540

Val Leu Thr Val Leu His Gln Asp Trp Leu Asn Gly Lys Glu Tyr Lys
545                 550                 555                 560

Cys Lys Val Ser Asn Lys Ala Leu Pro Ala Pro Ile Glu Lys Thr Ile
                565                 570                 575

Ser Lys Ala Lys Gly Gln Pro Arg Glu Pro Gln Val Tyr Thr Leu Pro
                580                 585                 590

Pro Ser Arg Glu Glu Met Thr Lys Asn Gln Val Ser Leu Thr Cys Leu
                595                 600                 605

Val Lys Gly Phe Tyr Pro Ser Asp Ile Ala Val Glu Trp Glu Ser Asn
                610                 615                 620

Gly Gln Pro Glu Asn Asn Tyr Lys Thr Thr Pro Pro Val Leu Asp Ser
625                 630                 635                 640

Asp Gly Ser Phe Phe Leu Tyr Ser Lys Leu Thr Val Asp Lys Ser Arg
                645                 650                 655

Trp Gln Gln Gly Asn Val Phe Ser Cys Ser Val Met His Glu Ala Leu
                660                 665                 670

His Asn His Tyr Thr Gln Lys Ser Leu Ser Leu Ser Pro Gly Lys
                675                 680                 685

<210> SEQ ID NO 204
<211> LENGTH: 214
<212> TYPE: PRT
<213> ORGANISM: Artificial Sequence
<220> FEATURE:
<223> OTHER INFORMATION: VL-CL of mAb HumAb747V-72

<400> SEQUENCE: 204

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
                20                  25                  30

Leu Ser Trp Leu Gln Gln Lys Pro Gly Gly Ala Ile Lys Arg Leu Ile
            35                  40                  45

Tyr Ala Ala Ser Ala Leu Asp Leu Gly Val Pro Ser Arg Phe Ser Gly
        50                  55                  60

Ser Arg Ser Gly Ser Asp Tyr Thr Leu Thr Ile Ser Ser Leu Gln Pro
65                  70                  75                  80

Glu Asp Phe Ala Asp Tyr Tyr Cys Leu Gln Tyr Ala Ser Tyr Pro Leu
                85                  90                  95

Thr Phe Gly Gln Gly Thr Lys Leu Glu Leu Lys Arg Thr Val Ala Ala
```

```
                100             105              110
Pro Ser Val Phe Ile Phe Pro Ser Asp Glu Gln Leu Lys Ser Gly
        115                 120             125

Thr Ala Ser Val Val Cys Leu Leu Asn Asn Phe Tyr Pro Arg Glu Ala
    130                 135             140

Lys Val Gln Trp Lys Val Asp Asn Ala Leu Gln Ser Gly Asn Ser Gln
145                 150             155                 160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210

<210> SEQ ID NO 205
<211> LENGTH: 224
<212> TYPE: PRT
<213> ORGANISM: Artificial Sequence
<220> FEATURE:
<223> OTHER INFORMATION: VH-CH1 of HumAb713-7

<400> SEQUENCE: 205

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Tyr Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Lys Arg Gly Gly Ser Ser His Val Asn Val Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 206
<211> LENGTH: 235
<212> TYPE: PRT
```

<213> ORGANISM: Artificial Sequence
<220> FEATURE:
<223> OTHER INFORMATION: FIT107-1-7b-2 FIT-Ig Polypeptide Chain #2

<400> SEQUENCE: 206

Met Glu Phe Gly Leu Ser Trp Leu Phe Leu Val Ala Ile Leu Lys Gly
1               5                   10                  15

Val Gln Cys Glu Val Gln Leu Val Gln Ser Gly Ala Glu Val Lys Lys
            20                  25                  30

Pro Gly Ala Thr Val Lys Leu Ser Cys Thr Ala Ser Gly Phe Asn Ile
        35                  40                  45

Lys Asp Asp Tyr Met His Trp Val Lys Gln Arg Pro Glu Gln Gly Leu
    50                  55                  60

Asp Trp Ile Gly Trp Ile Val Pro Arg Asn Ala Asn Thr Val Tyr Ala
65                  70                  75                  80

Ser Lys Phe Gln Gly Lys Ala Thr Ile Thr Ala Asp Thr Ser Thr Asn
                85                  90                  95

Thr Ala Tyr Leu Glu Leu Ser Ser Leu Arg Ser Glu Asp Thr Ala Val
            100                 105                 110

Tyr Tyr Cys Thr Val Tyr Gly Asp Tyr Trp Gly Gln Gly Thr Thr Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys
225                 230                 235

<210> SEQ ID NO 207
<211> LENGTH: 216
<212> TYPE: PRT
<213> ORGANISM: Artificial Sequence
<220> FEATURE:
<223> OTHER INFORMATION: VH-CH1 of HumAb747V-72

<400> SEQUENCE: 207

Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Arg Asn Ala Asn Thr Val Tyr Ala Ser Lys Phe
    50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

```
Thr Val Tyr Gly Asp Tyr Trp Gly Gln Gly Thr Val Thr Val Ser
                100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
    195                 200                 205

Lys Lys Val Glu Pro Lys Ser Cys
    210                 215
```

<210> SEQ ID NO 208
<211> LENGTH: 236
<212> TYPE: PRT
<213> ORGANISM: Artificial Sequence
<220> FEATURE:
<223> OTHER INFORMATION: FIT107-1-7b-2
      FIT-Ig Polypeptide Chain #3

<400> SEQUENCE: 208

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Asp His Ile Asn Asn Trp Leu Ala Trp Tyr Gln Gln Lys Pro Gly Lys
50                  55                  60

Ala Pro Lys Leu Leu Ile Tyr Gly Ala Thr Ser Leu Glu Thr Gly Val
65                  70                  75                  80

Pro Ser Arg Phe Ser Gly Ser Gly Ser Gly Thr Asp Tyr Thr Phe Thr
                85                  90                  95

Ile Ser Ser Leu Gln Pro Glu Asp Ile Ala Thr Tyr Tyr Cys Gln Gln
            100                 105                 110

Tyr Trp Ser Pro Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

<210> SEQ ID NO 209
<211> LENGTH: 214
<212> TYPE: PRT
<213> ORGANISM: Artificial Sequence
<220> FEATURE:
<223> OTHER INFORMATION: VL-CL of HumAb713-7

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Ser Pro Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 210
<211> LENGTH: 679
<212> TYPE: PRT
<213> ORGANISM: Artificial Sequence
<220> FEATURE:
<223> OTHER INFORMATION: FIT107-1-7a-3
      FIT-Ig Polypeptide Chain #1

<400> SEQUENCE: 210

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Asp His Ile Asn Asn Trp Leu Ala Trp Tyr Gln Gln Lys Pro Gly Lys
50                  55                  60

Ala Pro Lys Leu Leu Ile Tyr Gly Ala Thr Ser Leu Glu Thr Gly Val
65                  70                  75                  80

-continued

```
Pro Ser Arg Phe Ser Gly Ser Gly Ser Gly Thr Asp Tyr Thr Phe Thr
                85                  90                  95

Ile Ser Ser Leu Gln Pro Glu Asp Ile Ala Thr Tyr Tyr Cys Gln Gln
            100                 105                 110

Tyr Trp Ser Pro Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Glu Val Gln Leu
225                 230                 235                 240

Val Gln Ser Gly Ala Glu Val Lys Lys Pro Gly Ala Thr Val Lys Leu
                245                 250                 255

Ser Cys Thr Ala Ser Gly Phe Asn Ile Lys Asp Asp Tyr Met His Trp
            260                 265                 270

Val Lys Gln Arg Pro Glu Gln Gly Leu Asp Trp Ile Gly Trp Ile Val
        275                 280                 285

Pro Arg Asn Ala Asn Thr Val Tyr Ala Ser Lys Phe Gln Gly Lys Ala
290                 295                 300

Thr Ile Thr Ala Asp Thr Ser Thr Asn Thr Ala Tyr Leu Glu Leu Ser
305                 310                 315                 320

Ser Leu Arg Ser Glu Asp Thr Ala Val Tyr Tyr Cys Thr Val Tyr Gly
                325                 330                 335

Asp Tyr Trp Gly Gln Gly Thr Thr Val Thr Val Ser Ser Ala Ser Thr
            340                 345                 350

Lys Gly Pro Ser Val Phe Pro Leu Ala Pro Ser Ser Lys Ser Thr Ser
        355                 360                 365

Gly Gly Thr Ala Ala Leu Gly Cys Leu Val Lys Asp Tyr Phe Pro Glu
370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Lys Lys Val Glu
        435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
```

```
                500                 505                 510
Gly Val Glu Val His Asn Ala Lys Thr Lys Pro Arg Glu Glu Gln Tyr
            515                 520                 525

Asn Ser Thr Tyr Arg Val Val Ser Val Leu Thr Val Leu His Gln Asp
        530                 535                 540

Trp Leu Asn Gly Lys Glu Tyr Lys Cys Lys Val Ser Asn Lys Ala Leu
545                 550                 555                 560

Pro Ala Pro Ile Glu Lys Thr Ile Ser Lys Ala Lys Gly Gln Pro Arg
                565                 570                 575

Glu Pro Gln Val Tyr Thr Leu Pro Pro Ser Arg Glu Glu Met Thr Lys
            580                 585                 590

Asn Gln Val Ser Leu Thr Cys Leu Val Lys Gly Phe Tyr Pro Ser Asp
        595                 600                 605

Ile Ala Val Glu Trp Glu Ser Asn Gly Gln Pro Glu Asn Asn Tyr Lys
    610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro Gly Lys
            675

<210> SEQ ID NO 211
<211> LENGTH: 214
<212> TYPE: PRT
<213> ORGANISM: Artificial Sequence
<220> FEATURE:
<223> OTHER INFORMATION: VL-CL of HumAb713-7

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Ser Pro Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

-continued

```
                180                 185                 190
Ala Cys Glu Val Thr His Gln Gly Leu Ser Ser Pro Val Thr Lys Ser
            195                 200                 205

Phe Asn Arg Gly Glu Cys
    210

<210> SEQ ID NO 212
<211> LENGTH: 216
<212> TYPE: PRT
<213> ORGANISM: Artificial Sequence
<220> FEATURE:
<223> OTHER INFORMATION: VH-CH1 of HumAb747V-73

<400> SEQUENCE: 212

Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
        35                  40                  45

Gly Trp Ile Val Pro Arg Asn Ala Asn Thr Val Tyr Ala Ser Lys Phe
    50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215

<210> SEQ ID NO 213
<211> LENGTH: 243
<212> TYPE: PRT
<213> ORGANISM: Artificial Sequence
<220> FEATURE:
<223> OTHER INFORMATION: FIT107-1-7a-3
     FIT-Ig Polypeptide Chain #2

<400> SEQUENCE: 213

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Ser
        35                  40                  45
```

Ser Asp Tyr Gly Met His Trp Val Arg Gln Ala Pro Gly Lys Gly Leu
50                  55                  60

Glu Trp Val Ser Tyr Ile Ser Ser Gly Ser Tyr Thr Ile Tyr Tyr Ala
65                  70                  75                  80

Asp Thr Val Lys Gly Arg Phe Thr Ile Ser Arg Asp Asn Ala Lys Asn
                85                  90                  95

Ser Leu Tyr Leu Gln Met Asn Ser Leu Arg Asp Glu Asp Thr Ala Val
                100                 105                 110

Tyr Tyr Cys Ala Lys Arg Gly Gly Ser Ser His Val Asn Val Met Asp
                115                 120                 125

Tyr Trp Gly Gln Gly Thr Thr Val Thr Val Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
                210                 215                 220

Val Asn His Lys Pro Ser Asn Thr Lys Val Asp Lys Lys Val Glu Pro
225                 230                 235                 240

Lys Ser Cys

<210> SEQ ID NO 214
<211> LENGTH: 224
<212> TYPE: PRT
<213> ORGANISM: Artificial Sequence
<220> FEATURE:
<223> OTHER INFORMATION: VH-CH1 of HumAb713-7

<400> SEQUENCE: 214

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Asp Tyr
                20                  25                  30

Gly Met His Trp Val Arg Gln Ala Pro Gly Lys Gly Leu Glu Trp Val
                35                  40                  45

Ser Tyr Ile Ser Ser Gly Ser Tyr Thr Ile Tyr Tyr Ala Asp Thr Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Lys Arg Gly Gly Ser Ser His Val Asn Val Met Asp Tyr Trp Gly
                100                 105                 110

Gln Gly Thr Thr Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

<210> SEQ ID NO 215
<211> LENGTH: 236
<212> TYPE: PRT
<213> ORGANISM: Artificial Sequence
<220> FEATURE:
<223> OTHER INFORMATION: FIT107-1-7a-3
    FIT-Ig Polypeptide Chain #3

<400> SEQUENCE: 215

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
            35                  40                  45

Gln Glu Ile Ser Gly Tyr Leu Ser Trp Leu Gln Gln Lys Pro Gly Gly
        50                  55                  60

Ala Ile Lys Arg Leu Ile Tyr Ala Ala Ser Thr Leu Asp Ser Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Asp Tyr Tyr Cys Leu Gln
            100                 105                 110

Tyr Ala Ser Tyr Pro Leu Thr Phe Gly Gln Gly Thr Lys Leu Glu Leu
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 216
<211> LENGTH: 214
<212> TYPE: PRT
<213> ORGANISM: Artificial Sequence
<220> FEATURE:
<223> OTHER INFORMATION: VL-CL of HumAb747V-73

<400> SEQUENCE: 216

Asp Ile Gln Met Thr Gln Ser Pro Ser Ser Leu Ser Ala Ser Val Gly

```
                1               5                  10                    15
        Asp Arg Val Thr Ile Thr Cys Arg Ala Ser Gln Glu Ile Ser Gly Tyr
                       20                  25                  30

Leu Ser Trp Leu Gln Gln Lys Pro Gly Gly Ala Ile Lys Arg Leu Ile
                       35                  40                  45

Tyr Ala Ala Ser Thr Leu Asp Ser Gly Val Pro Ser Arg Phe Ser Gly
                       50                  55                  60

Ser Arg Gly Ser Asp Tyr Thr Leu Thr Ile Ser Ser Leu Gln Pro
        65                  70                  75                  80

Glu Asp Phe Ala Asp Tyr Tyr Cys Leu Gln Tyr Ala Ser Tyr Pro Leu
                            85                  90                  95

Thr Phe Gly Gln Gly Thr Lys Leu Glu Leu Lys Arg Thr Val Ala Ala
                       100                 105                 110

Pro Ser Val Phe Ile Phe Pro Pro Ser Asp Glu Gln Leu Lys Ser Gly
                       115                 120                 125

Thr Ala Ser Val Val Cys Leu Leu Asn Asn Phe Tyr Pro Arg Glu Ala
                       130                 135                 140

Lys Val Gln Trp Lys Val Asp Asn Ala Leu Gln Ser Gly Asn Ser Gln
        145                 150                 155                 160

Glu Ser Val Thr Glu Gln Asp Ser Lys Asp Ser Thr Tyr Ser Leu Ser
                       165                 170                 175

Ser Thr Leu Thr Leu Ser Lys Ala Asp Tyr Glu Lys His Lys Val Tyr
                       180                 185                 190

Ala Cys Glu Val Thr His Gln Gly Leu Ser Ser Pro Val Thr Lys Ser
                       195                 200                 205

Phe Asn Arg Gly Glu Cys
                       210

<210> SEQ ID NO 217
<211> LENGTH: 687
<212> TYPE: PRT
<213> ORGANISM: Artificial Sequence
<220> FEATURE:
<223> OTHER INFORMATION: FIT107-1-7b-3
        FIT-Ig Polypeptide Chain #1

<400> SEQUENCE: 217

Met Asp Met Arg Val Pro Ala Gln Leu Leu Gly Leu Leu Leu Leu Trp
        1               5                   10                  15

Phe Pro Gly Ser Arg Cys Asp Ile Gln Met Thr Gln Ser Pro Ser Ser
                       20                  25                  30

Leu Ser Ala Ser Val Gly Asp Arg Val Thr Ile Thr Cys Arg Ala Ser
                       35                  40                  45

Gln Glu Ile Ser Gly Tyr Leu Ser Trp Leu Gln Gln Lys Pro Gly Gly
        50                  55                  60

Ala Ile Lys Arg Leu Ile Tyr Ala Ala Ser Thr Leu Asp Ser Gly Val
        65                  70                  75                  80

Pro Ser Arg Phe Ser Gly Ser Arg Ser Gly Ser Asp Tyr Thr Leu Thr
                       85                  90                  95

Ile Ser Ser Leu Gln Pro Glu Asp Phe Ala Asp Tyr Tyr Cys Leu Gln
                       100                 105                 110

Tyr Ala Ser Tyr Pro Leu Thr Phe Gly Gln Gly Thr Lys Leu Glu Leu
                       115                 120                 125

Lys Arg Thr Val Ala Ala Pro Ser Val Phe Ile Phe Pro Pro Ser Asp
        130                 135                 140
```

-continued

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Glu Val Gln Leu
225                 230                 235                 240

Val Glu Ser Gly Gly Gly Leu Val Gln Pro Gly Gly Ser Leu Arg Leu
                245                 250                 255

Ser Cys Ala Ala Ser Gly Phe Thr Ser Ser Asp Tyr Gly Met His Trp
            260                 265                 270

Val Arg Gln Ala Pro Gly Lys Gly Leu Glu Trp Val Ser Tyr Ile Ser
        275                 280                 285

Ser Gly Ser Tyr Thr Ile Tyr Tyr Ala Asp Thr Val Lys Gly Arg Phe
    290                 295                 300

Thr Ile Ser Arg Asp Asn Ala Lys Asn Ser Leu Tyr Leu Gln Met Asn
305                 310                 315                 320

Ser Leu Arg Asp Glu Asp Thr Ala Val Tyr Tyr Cys Ala Lys Arg Gly
                325                 330                 335

Gly Ser Ser His Val Asn Val Met Asp Tyr Trp Gly Gln Gly Thr Thr
            340                 345                 350

Val Thr Val Ser Ser Ala Ser Thr Lys Gly Pro Ser Val Phe Pro Leu
        355                 360                 365

Ala Pro Ser Ser Lys Ser Thr Ser Gly Gly Thr Ala Ala Leu Gly Cys
    370                 375                 380

Leu Val Lys Asp Tyr Phe Pro Glu Pro Val Thr Val Ser Trp Asn Ser
385                 390                 395                 400

Gly Ala Leu Thr Ser Gly Val His Thr Phe Pro Ala Val Leu Gln Ser
                405                 410                 415

Ser Gly Leu Tyr Ser Leu Ser Ser Val Val Thr Val Pro Ser Ser Ser
            420                 425                 430

Leu Gly Thr Gln Thr Tyr Ile Cys Asn Val Asn His Lys Pro Ser Asn
        435                 440                 445

Thr Lys Val Asp Lys Lys Val Glu Pro Lys Ser Cys Asp Lys Thr His
    450                 455                 460

Thr Cys Pro Pro Cys Pro Ala Pro Glu Ala Ala Gly Gly Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser His Glu Asp Pro Glu
            500                 505                 510

Val Lys Phe Asn Trp Tyr Val Asp Gly Val Glu Val His Asn Ala Lys
        515                 520                 525

Thr Lys Pro Arg Glu Glu Gln Tyr Asn Ser Thr Tyr Arg Val Val Ser
    530                 535                 540

Val Leu Thr Val Leu His Gln Asp Trp Leu Asn Gly Lys Glu Tyr Lys
545                 550                 555                 560

Cys Lys Val Ser Asn Lys Ala Leu Pro Ala Pro Ile Glu Lys Thr Ile
```

565                 570                 575

Ser Lys Ala Lys Gly Gln Pro Arg Glu Pro Gln Val Tyr Thr Leu Pro
                580                 585                 590

Pro Ser Arg Glu Glu Met Thr Lys Asn Gln Val Ser Leu Thr Cys Leu
                595                 600                 605

Val Lys Gly Phe Tyr Pro Ser Asp Ile Ala Val Glu Trp Glu Ser Asn
            610                 615                 620

Gly Gln Pro Glu Asn Asn Tyr Lys Thr Thr Pro Pro Val Leu Asp Ser
625                 630                 635                 640

Asp Gly Ser Phe Phe Leu Tyr Ser Lys Leu Thr Val Asp Lys Ser Arg
                645                 650                 655

Trp Gln Gln Gly Asn Val Phe Ser Cys Ser Val Met His Glu Ala Leu
                660                 665                 670

His Asn His Tyr Thr Gln Lys Ser Leu Ser Leu Ser Pro Gly Lys
            675                 680                 685

<210> SEQ ID NO 218
<211> LENGTH: 214
<212> TYPE: PRT
<213> ORGANISM: Artificial Sequence
<220> FEATURE:
<223> OTHER INFORMATION: VL-CL of HumAb747V-73

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Gly Ala Ile Lys Arg Leu Ile
        35                  40                  45

Tyr Ala Ala Ser Thr Leu Asp Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Asp Tyr Tyr Cys Leu Gln Tyr Ala Ser Tyr Pro Leu
                85                  90                  95

Thr Phe Gly Gln Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 219
<211> LENGTH: 224
<212> TYPE: PRT

<213> ORGANISM: Artificial Sequence
<220> FEATURE:
<223> OTHER INFORMATION: VH-CH1 of HumAb713-7

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Tyr Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Lys Arg Gly Gly Ser Ser His Val Asn Val Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 220
<211> LENGTH: 235
<212> TYPE: PRT
<213> ORGANISM: Artificial Sequence
<220> FEATURE:
<223> OTHER INFORMATION: FIT107-1-7b-3
       FIT-Ig Polypeptide Chain #2

<400> SEQUENCE: 220

Met Glu Phe Gly Leu Ser Trp Leu Phe Leu Val Ala Ile Leu Lys Gly
1               5                   10                  15

Val Gln Cys Glu Val Gln Leu Val Gln Ser Gly Ala Glu Val Lys Lys
            20                  25                  30

Pro Gly Ala Thr Val Lys Leu Ser Cys Thr Ala Ser Gly Phe Asn Ile
        35                  40                  45

Lys Asp Asp Tyr Met His Trp Val Lys Gln Arg Pro Glu Gln Gly Leu
    50                  55                  60

Asp Trp Ile Gly Trp Ile Val Pro Arg Asn Ala Asn Thr Val Tyr Ala
65                  70                  75                  80

Ser Lys Phe Gln Gly Lys Ala Thr Ile Thr Ala Asp Thr Ser Thr Asn
                85                  90                  95

Thr Ala Tyr Leu Glu Leu Ser Ser Leu Arg Ser Glu Asp Thr Ala Val
            100                 105                 110

```
Tyr Tyr Cys Thr Val Tyr Gly Asp Tyr Trp Gly Gln Gly Thr Thr Val
            115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220

Lys Val Asp Lys Lys Val Glu Pro Lys Ser Cys
225                 230                 235
```

<210> SEQ ID NO 221
<211> LENGTH: 216
<212> TYPE: PRT
<213> ORGANISM: Artificial Sequence
<220> FEATURE:
<223> OTHER INFORMATION: VH-CH1 of HumAb747V-73

<400> SEQUENCE: 221

```
Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
                20                  25                  30

Tyr Met His Trp Val Lys Gln Arg Pro Glu Gln Gly Leu Asp Trp Ile
            35                  40                  45

Gly Trp Ile Val Pro Arg Asn Ala Asn Thr Val Tyr Ala Ser Lys Phe
        50                  55                  60

Gln Gly Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Thr Val Tyr Gly Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215
```

<210> SEQ ID NO 222

```
<211> LENGTH: 236
<212> TYPE: PRT
<213> ORGANISM: Artificial Sequence
<220> FEATURE:
<223> OTHER INFORMATION: FIT107-1-7b-3
      FIT-Ig Polypeptide Chain #3

<400> SEQUENCE: 222

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Asp His Ile Asn Asn Trp Leu Ala Trp Tyr Gln Gln Lys Pro Gly Lys
    50                  55                  60

Ala Pro Lys Leu Leu Ile Tyr Gly Ala Thr Ser Leu Glu Thr Gly Val
65                  70                  75                  80

Pro Ser Arg Phe Ser Gly Ser Gly Ser Gly Thr Asp Tyr Thr Phe Thr
                85                  90                  95

Ile Ser Ser Leu Gln Pro Glu Asp Ile Ala Thr Tyr Tyr Cys Gln Gln
            100                 105                 110

Tyr Trp Ser Pro Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 223
<211> LENGTH: 214
<212> TYPE: PRT
<213> ORGANISM: Artificial Sequence
<220> FEATURE:
<223> OTHER INFORMATION: VL-CL of HumAb713-7

<400> SEQUENCE: 223

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80
```

```
Glu Asp Ile Ala Thr Tyr Tyr Cys Gln Gln Tyr Trp Ser Pro Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 224
<211> LENGTH: 17
<212> TYPE: PRT
<213> ORGANISM: Artificial Sequence
<220> FEATURE:
<223> OTHER INFORMATION: CDR-H2 of anti-LAG-3 antibody HumAb747V-67,
      with G55A substituion by Kabat numbering

<400> SEQUENCE: 224

Trp Ile Val Pro Glu Asn Ala Asn Thr Val Tyr Ala Ser Lys Phe Gln
1               5                   10                  15

Gly

<210> SEQ ID NO 225
<211> LENGTH: 17
<212> TYPE: PRT
<213> ORGANISM: Artificial Sequence
<220> FEATURE:
<223> OTHER INFORMATION: CDR-H2 of anti-LAG-3 antibody HumAb747V-72 or
      HumAb747V-73, with G55A substituion by Kabat numbering

<400> SEQUENCE: 225

Trp Ile Val Pro Arg Asn Ala Asn Thr Val Tyr Ala Ser Lys Phe Gln
1               5                   10                  15

Gly

<210> SEQ ID NO 226
<211> LENGTH: 113
<212> TYPE: PRT
<213> ORGANISM: Artificial Sequence
<220> FEATURE:
<223> OTHER INFORMATION: VH with G55A substituion by Kabat numbering

<400> SEQUENCE: 226

Glu Val Gln Leu Val Gln Ser Gly Ala Glu Val Lys Lys Pro Gly Ala
1               5                   10                  15

Thr Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Asp Trp Ile
            35                  40                  45

Gly Trp Ile Val Pro Glu Asn Ala Asn Thr Val Tyr Ala Ser Lys Phe
```

```
                50               55                60
Gln Gly Lys Ala Thr Ile Thr Ala Asp Thr Ser Thr Asn Thr Ala Tyr
 65                  70                   75                 80

Leu Glu Leu Ser Ser Leu Arg Ser Glu Asp Thr Ala Val Tyr Tyr Cys
                 85                  90                  95

Thr Val Tyr Gly Asp Tyr Trp Gly Gln Gly Thr Thr Val Thr Val Ser
                100                 105                 110

Ser

<210> SEQ ID NO 227
<211> LENGTH: 113
<212> TYPE: PRT
<213> ORGANISM: Artificial Sequence
<220> FEATURE:
<223> OTHER INFORMATION: VH with G55A substituion by Kabat numbering

<400> SEQUENCE: 227

Glu Val Gln Leu Val Gln Ser Gly Ala Glu Val Lys Lys Pro Gly Ala
 1               5                  10                  15

Thr Val Lys Leu Ser Cys Thr Ala Ser Gly Phe Asn Ile Lys Asp Asp
                20                  25                  30

Tyr Met His Trp Val Lys Gln Arg Pro Glu Gln Gly Leu Asp Trp Ile
                35                  40                  45

Gly Trp Ile Val Pro Arg Asn Ala Asn Thr Val Tyr Ala Ser Lys Phe
 50                  55                  60

Gln Gly Lys Ala Thr Ile Thr Ala Asp Thr Ser Thr Asn Thr Ala Tyr
 65                  70                  75                  80

Leu Glu Leu Ser Ser Leu Arg Ser Glu Asp Thr Ala Val Tyr Tyr Cys
                 85                  90                  95

Thr Val Tyr Gly Asp Tyr Trp Gly Gln Gly Thr Thr Val Thr Val Ser
                100                 105                 110

Ser
```